United States Patent
Ushio et al.

(10) Patent No.: US 7,015,218 B1
(45) Date of Patent: Mar. 21, 2006

(54) AMIDE COMPOUNDS AND MEDICINAL USE THEREOF

(75) Inventors: Hiroyuki Ushio, Fukuoka (JP); Seigo Ishibuchi, Osaka (JP); Youichiro Naito, Fukuoka (JP); Naoki Sugiyama, Saitama (JP); Takafumi Kawaguchi, Iruma (JP); Kenji Chiba, Iruma (JP); Makio Ohtsuki, Iruma (JP); Yoichi Naka, Hirakata (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 09/913,260

(22) PCT Filed: Feb. 10, 2000

(86) PCT No.: PCT/JP00/00767

§ 371 (c)(1),
(2), (4) Date: Nov. 19, 2001

(87) PCT Pub. No.: WO00/47558

PCT Pub. Date: Aug. 17, 2000

(30) Foreign Application Priority Data

Feb. 10, 1999 (JP) .................................. 11-033367
Jul. 13, 1999 (JP) .................................. 11-198473

(51) Int. Cl.
- A61K 31/541 (2006.01)
- A61K 31/5375 (2006.01)
- A61K 31/496 (2006.01)
- A61K 31/454 (2006.01)
- A61K 31/4545 (2006.01)

(52) U.S. Cl. ............. 514/227.8; 514/235.8; 514/253.09; 514/316; 514/326; 544/60; 544/130; 544/364; 546/187; 546/230

(58) Field of Classification Search ............... 546/230, 546/187; 514/326, 227.8, 235.8, 253.09, 514/316; 544/130, 60, 364

See application file for complete search history.

(56) References Cited

U.S. PATENT DOCUMENTS

| | | | |
|---|---|---|---|
| 4,046,775 A | 9/1977 | Bailey | |
| 4,134,987 A | 1/1979 | Huppatz | |
| 5,368,854 A | * | 11/1994 | Rennick .................... 424/85.2 |

FOREIGN PATENT DOCUMENTS

| | | |
|---|---|---|
| EP | 0 459 887 | 12/1991 |
| NZ | 226679 | 10/1991 |
| NZ | 255757 | 11/1997 |
| WO | 94/04180 | 3/1994 |
| WO | 95/24918 | 9/1995 |
| WO | 97/11690 | 4/1997 |

OTHER PUBLICATIONS

Khoury et al., Cellular Immunology, 131, 302-310 (1990).*
Mannie et al., Cellular Immunology, 153, 312-328 (1994).*
Di marco et al., Clin. Exp. Immunol., 1996, 105: 338-343.*
O'Driscoll et al., J. CLin. Invest., vol. 100, No. 3, Aug. 1997, 678-684.*
Liu et al., The Journal of Immunology, 2000, 164: 3608-3615.*
Annovazzi et al., Diabetes Metab REs REv. Nov.-Dec. 2003; 19(6):464-8.*
Villadsen et al., The Journal fo Clinical Investigation, Nov. 2003, vol. 112, No. 10.*
Sakai et al., Gastroenterology 1998, 114, pp. 1237-1243.*
Kirman et al., The American Journal of Gastroenterology, vol. 91., No. 9, 1996, pp. 1789-1794.*
Lampert, Clin Exp Immunol. 1984, 57(1), pp. 93-100, abstract only.*
Onuma S., J Dermatol. 1994, 21(4):223-32.*
Reidalova, L.I., et al. "Growth-regulating properties of substituted pyrazole-4-(thio)carboxylic acids and their analogs", Fiziol. Akt. Veshchestva, vol. 23 (1991), pp. 82-87.

(Continued)

Primary Examiner—Kamal A. Saeed
Assistant Examiner—Rebecca Anderson
(74) Attorney, Agent, or Firm—Wenderoth, Lind & Ponack, L.L.P.

(57) ABSTRACT

The present invention relates to a compound of the formula

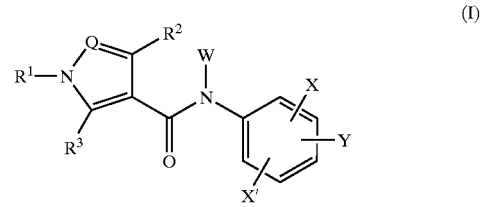

(I)

wherein $R^1$ is substituted aryl, heteroaryl and the like, $R^2$ and $R^3$ are hydrogen, alkyl, halogen, hydroxyl group and the like, Q is N, CH and the like, W is hydrogen, alkyl, hydroxycarbonylalkyl and the like, X is halogen, cyano, nitro, amino and the like, X' is hydrogen, halogen, cyano, nitro, and Y is alkyl, hydroxyl group, alkoxy, mercapto and the like and a salt thereof, and a medicine containing the said compound. The compound of the present invention shows a superior inhibitory effect on activated lymphocytes proliferation and is useful as an agent for the prophylaxis or treatment of various autoimmune diseases.

18 Claims, No Drawings

OTHER PUBLICATIONS

Luo. H., et al. "Anti-CD28 antibody- and IL-4-induced human T cell proliferation is sensitive to rapamycin", Clin. Exp. Immunol., vol. 94 (1993), pp. 371-376.

Wang, A.X., et al. "Synthesis and immunosuppressant activity of pyrazole carboxamides", Bioorg. Med. Chem. Lett., vol. 8, No. 19, P. 2787-2792 (1998).

Brian S. Andrews et al., "Spontaneous Murine Lupus-Like Syndromes", J. Exp. Med., vol. 148, pp. 1198-1215, 1978.

Philip L. Cohen, "Lpr and gld: Single Gene Models of Systemic Autoimmunity and Lymphoproliferative Disease", Annual Review of Immunology, vol. 9, pp. 243-269, 1991.

* cited by examiner

AMIDE COMPOUNDS AND MEDICINAL USE THEREOF

This application is 371 application of PCT/JP00/00767 filed Feb. 10, 2000.

TECHNICAL FIELD OF THE INVENTION

The present invention relates to an amide compound useful as a medicine, particularly as an agent for the prophylaxis or treatment of autoimmune disease, and its use as a medicine.

BACKGROUND

Autoimmune diseases are considered to be induced by autoreactivity acquired by lymphocytes that originally does not respond to themselves, or by incomplete removal of autoreactivated lymphocytes in the thymus and the like. In particular, rheumatoid arthritis (RA) is considered to be induced by immune response of lymphocytes, particularly T cells and B cells, against type II collagen that mostly exists in one's own joints. The disease gets serious because it accompanies infiltration of T cells and B cells into the joints, activation and proliferation of these cells in the joints and, when it advances, abnormal proliferation of synoviocytes in the joints to result in articular destruction. Because a number of activated lymphocytes infiltrate into articular tissues of RA patients, activated lymphocytes are considered to play an important role in the formation and advance of the disease state of RA.

In general terms, it is known that when lymphocytes are activated by antigen, type 1 helper T cells (Th1 cell) in the lymphocytes produces cytokines such as interleukin 2 (IL-2), interferon γ (IFN-γ) and the like, and the produced IL-2 and IFN-γ cause growth and division of lymphocytes, particularly T cells. Despite the presence of a great number of activated lymphocytes in the articular tissues of RA patients, IL-2 level is extremely low, which has produced a presumption that a lymphocyte growth factor should be present besides IL-2 (Journal of Experimental Medicine, vol. 168, p. 1573, 1988).

Recently, interleukin 15 (IL-15) was cloned as a new cytokine that promotes growth and differentiation of lymphocytes (T cells or B cells) (Science, vol. 264, p 965, 1994). The IL-15 receptor has been clarified to consist of α chain specific to IL-15, β chain common to IL-15 and IL-2, and γ chain common to the receptors of IL-15, IL-2, IL- 4, IL-7, IL-9 and IL-13 (EMBO Journal, vol. 13, p. 2822, 1994; EMBO Journal, vol. 14, p. 3654, 1995). The presence of a signal transduction pathway via tyrosin kinase (represented by JAK1 and JAK3) in the downstream of β chain and γ chain has been also uncovered (Science, vol. 266, p. 1782, 1994). It is expected, therefore, that the pharmacological activity induced by the binding of IL-15 and IL-15 receptor is the promotion of proliferation of lymphocytes, and is almost of the same nature as the binding of IL-2 and IL-2 receptor. It has been reported that the IL-2, IL-9-producing cells are T cells, particularly helper T cells activated by antigen, the IL-7-producing cells are mostly stroma cells, and IL-15-producing cells are macrophages, dendritic cells, synoviocytes and the like (Science, vol. 264, p. 965, 1994). A recent report has documented that synovial fluid of RA patients has a markedly high concentration of IL-15, which suggests the important role of IL-15 as a growth factor for the proliferation of activated lymphocytes in the joints in RA. In addition, there is a report on many activities of IL-15 besides promotion of proliferation of the activated lymphocytes, such as promotion of migration of T cells toward inflammatory sites, activation of memory T cells, promotion of production of inflammatory cytokines such as tumor necrosis factor (TNF)-α and the like, and other activities (Nature medicine, vol. 3, p. 189, 1997). It is being elucidated that IL-15 plays an important role in the onset and development of various autoimmune diseases such as Crohn's diseases, lupus-nephritis in systemic lupus erythematosus and the like.

From the foregoing, it is considered that, for the improvement of symptoms of autoimmune diseases represented by RA, inhibition of proliferation of IL-15-dependent activated lymphocytes is particularly effective.

Conventionally, a therapeutic agent for autoimmune diseases, particularly RA, has been a gold compound, penicillamine, bucillamine, azathioprine, cyclophosphamide, methotrexate and the like. These inhibit proliferation of synoviocytes in the joints. Due to their antagonistic inhibitory action in nucleic acid metabolism, however, the long-term use of the agent is associated with highly frequent occurrence of side effects, such as hematopoietic injury, digestive system disorder and the like. Combined with easy infectivity and the like caused by the agents, they are not therapeutically satisfactory. While corticosteroid is effective for these diseases, it is associated with serious side effects, such as moon face, hypoadrenalism, osteonecrosis of femoral head and the like. Furthermore, leflunomide approved as an antirheumatic drug in the US has been reported to show a long half-life of blood disappearance despite its superior therapeutic effect, causing side effects such as digestive system disorder, liver disorder, eruption and the like (The Lancet, vol. 353, pp. 259–266, 1999), and a clinically more superior therapeutic agent is desired.

Thus, there is a strong demand for a therapeutic agent for autoimmune diseases such as RA and the like, which shows a superior therapeutic effect as compared to conventional pharmaceutical agents and which causes less side effects.

As mentioned above, the proliferation of activated lymphocytes in articular tissue is deeply involved in the progress of arthritis in RA, and IL-15 is suggested to be responsible for the proliferation of activated lymphocytes. Therefore, a compound that inhibits signal transduction via tyrosine kinase originated from IL-15 receptor (γ chain common to IL-2, IL-4, IL-7, IL-9, IL-13 and IL-15) is considered to show a superior effect for the prophylaxis or treatment of autoimmune diseases such as rheumatoid arthritis and the like. In addition to the aforementioned effect, a compound that inhibits production of IL-15 itself or production of inflammatory cytokines, such as TNF-α and the like, which is derived by IL-15, is likely to show a superior effect for the prophylaxis or treatment of autoimmune diseases such as rheumatoid arthritis and the like. However, there is no report taking note of IL-15, which concerns a compound having an inhibitory effect on the proliferation of activated lymphocytes as a therapeutic agent for autoimmune diseases or as a therapeutic agent for RA.

Bioorganic and Medicinal Chemistry Letters, vol. 8, pp. 2787–2792, 1998 discloses a pyrazolecarboxamide compound useful as an immunosuppressant agent. As phenylpyrazolecarboxamide having similar structure, JP-A-52-87168 discloses a compound as an antimicrobial agent, WO97/11690 discloses a compound for treating bacterial infection in which a therapeutically effective amount of an inhibitor of global regulator of pathogenic gene is administered to mammals. Veshchestva, vol. 23, pp. 82–87, 1991 discloses a compound as an agricultural chemical to inhibit growth of plants. However, an inhibitory effect on the proliferation of activated lymphocytes taking note of IL-15 on these compounds is not disclosed at all.

In view of the above, the present inventors have conducted intensive studies and found that an amide compound of the following formula and a pharmaceutically acceptable salt thereof suppress cytokine response that may induce proliferation, differentiation and the like of various cells responsible for immunity, such as lymphocytes (T cells, B cells), macrophages and the like, by the addition of a cytokine, such as IL-2, IL-4, IL-7, IL-9, IL-13, IL-15 and the like, in the presence or absence of an antigen or mitogen. In particular, they have found that the above compound and its salt inhibit IL-15-dependent proliferation of activated lymphocytes and production of inflammatory cytokine derived by IL-15, namely, IL-1, IL-6, IL-12, IL-15, IL-18, TNF-α and the like, which resulted in the completion of the present invention.

DISCLOSURE OF THE INVENTION

Accordingly, the present invention provides the following.

[1] An amide compound of the formula

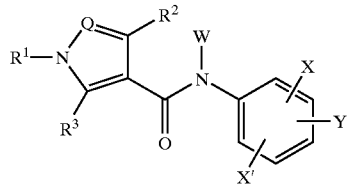

(I)

wherein
$R^1$ is substituted aryl, arylalkyl, optionally substituted heteroaryl, heteroarylalkyl or cycloalkyl,
$R^2$ and $R^3$ are the same or different and each is hydrogen, alkyl, halogen, hydroxyl group, alkoxy, optionally substituted amino or phenyl,
Q is nitrogen atom or a group C—$R^4$ (wherein $R^4$ is hydrogen, alkyl, halogen or optionally substituted amino),
W is hydrogen, alkyl, hydroxyalkyl, acyloxyalkyl, aminoalkyl, hydroxycarbonylalkyl or alkoxycarbonylalkyl,
X is halogen, cyano, nitro, amino, alkyl, alkoxy, carboxy, alkoxycarbonyl, carbamoyl, alkenyl, alkynyl or haloalkyl,
X' is hydrogen, halogen, cyano or nitro, and
Y is alkyl, hydroxyalkyl, hydroxycarbonylalkyl, optionally substituted aminoalkyl, hydroxyl group, alkoxy, haloalkoxy, aryloxy, cycloalkyloxy, hydroxyalkoxy, hydroxycarbonylalkoxy, optionally substituted aminoalkoxy, mercapto, alkylthio, hydroxyalkylthio, hydroxycarbonylalkylthio, optionally substituted aminoalkylthio, a group O-Het (wherein Het is optionally substituted saturated heterocycle having hetero atom selected from oxygen atom and nitrogen atom) or a group N($Z^2$) ($Z^3$) (wherein $Z^2$ and $Z^3$ are the same or different and each is hydrogen, alkyl, hydroxyalkyl or aminoalkyl, or $Z^2$ and $Z^3$ form, together with the adjacent nitrogen atom, cyclic amine optionally having one or two atoms from oxygen atom, sulfur atom and nitrogen atom in the ring), or a pharmaceutically acceptable salt thereof.

[2] The amide compound of the above-mentioned [1], which has the formula

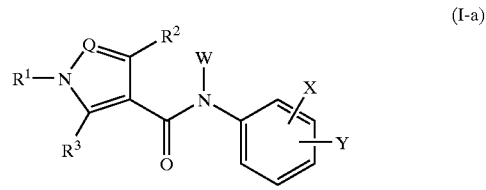

(I-a)

wherein
$R^1$ is substituted aryl, arylalkyl, optionally substituted heteroaryl, heteroarylalkyl or cycloalkyl,
$R^2$ and $R^3$ are the same or different and each is hydrogen, alkyl, halogen, hydroxyl group, alkoxy, optionally substituted amino or phenyl,
Q is nitrogen atom or a group C—$R^4$ (wherein $R^4$ is hydrogen, alkyl, halogen or optionally substituted amino),
W is hydrogen, alkyl, hydroxyalkyl, acyloxyalkyl, aminoalkyl, hydroxycarbonylalkyl or alkoxycarbonylalkyl,
X is halogen, cyano, nitro, amino, alkyl, alkoxy, carboxy, alkoxycarbonyl, carbamoyl, alkenyl, alkynyl or haloalkyl,
Y is alkyl, hydroxyalkyl, hydroxycarbonylalkyl, optionally substituted aminoalkyl, hydroxyl group, alkoxy, haloalkoxy, aryloxy, cycloalkyloxy, hydroxyalkoxy, hydroxycarbonylalkoxy, optionally substituted aminoalkoxy, mercapto, alkylthio, hydroxyalkylthio, hydroxycarbonylalkylthio, optionally substituted aminoalkylthio, a group O-Het (wherein Het is optionally substituted saturated heterocycle having hetero atom selected from oxygen atom and nitrogen atom) or a group N($Z^2$)($Z^3$) (wherein $Z^2$ and $Z^3$ are the same or different and each is hydrogen, alkyl, hydroxyalkyl or aminoalkyl, or $Z^2$ and $Z^3$ form, together with the adjacent nitrogen atom, cyclic amine optionally having one or two atoms from oxygen atom, sulfur atom and nitrogen atom in the ring), or a pharmaceutically acceptable salt thereof.

[3] The amide compound of the above-mentioned [2], which has the formula

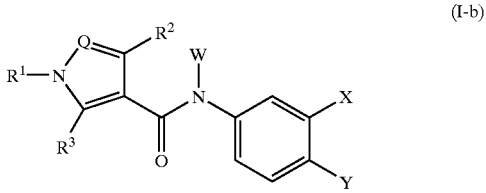

(I-b)

wherein
$R^1$ is substituted aryl, arylalkyl, optionally substituted heteroaryl, heteroarylalkyl or cycloalkyl,
$R^2$ and $R^3$ are the same or different and each is hydrogen, alkyl, halogen, hydroxyl group, alkoxy, optionally substituted amino or phenyl,
Q is nitrogen atom or a group C—$R^4$ (wherein $R^4$ is hydrogen, alkyl, halogen or optionally substituted amino), W is hydrogen, alkyl, hydroxyalkyl, acyloxyalkyl, aminoalkyl, hydroxycarbonylalkyl or alkoxycarbonylalkyl, X is halogen, cyano, nitro, amino, alkyl, alkoxy, carboxy, alkoxycarbonyl, carbamoyl, alkenyl, alkynyl or haloalkyl, and Y is alkyl, hydroxyalkyl, hydroxycarbonylalkyl, optionally substituted aminoalkyl, hydroxyl group, alkoxy, haloalkoxy, aryloxy, cycloalkyloxy, hydroxyalkoxy, hydroxycarbonylalkoxy, optionally substituted aminoalkoxy, mercapto, alkylthio, hydroxyalkylthio, hydroxycarbonylalkylthio, optionally substituted aminoalkylthio, a group O-Het (wherein Het is optionally substituted saturated heterocycle having hetero atom selected from oxygen atom and nitrogen atom) or a group $N(Z^2)(Z^3)$ (wherein $Z^2$ and $Z^3$ are the same or different and each is hydrogen, alkyl, hydroxyalkyl or aminoalkyl, or $Z^2$ and $Z^3$ form, together with the adjacent nitrogen atom, cyclic amine optionally having one or two atoms from oxygen atom, sulfur atom and nitrogen atom in the ring), or a pharmaceutically acceptable salt thereof.

[4] The amide compound of the above-mentioned [3], which has the formula

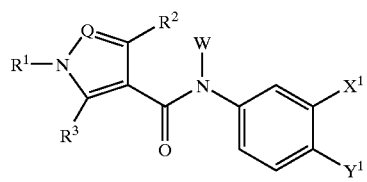

(I-c)

wherein $R^1$ is substituted aryl, arylalkyl, optionally substituted heteroaryl, heteroarylalkyl or cycloalkyl, $R^2$ and $R^3$ are the same or different and each is hydrogen, alkyl, halogen, hydroxyl group, alkoxy, optionally substituted amino or phenyl, Q is nitrogen atom or a group C—$R^4$ (wherein $R^4$ is hydrogen, alkyl, halogen or optionally substituted amino), W is hydrogen, alkyl, hydroxyalkyl, acyloxyalkyl, aminoalkyl, hydroxycarbonylalkyl or alkoxycarbonylalkyl, $X^1$ is halogen, cyano, nitro, carboxy, alkoxycarbonyl or alkynyl, and $Y^1$ is alkoxy, haloalkoxy, aryloxy, cycloalkyloxy, hydroxyalkoxy, optionally substituted aminoalkoxy, optionally substituted aminoalkylthio, a group O-Het (wherein Het is optionally substituted saturated heterocycle having hetero atom selected from oxygen atom and nitrogen atom) or a group $N(Z^2)(Z^3)$ (wherein $Z^2$ and $Z^3$ are the same or different and each is hydrogen, alkyl, hydroxyalkyl or aminoalkyl, or $Z^2$ and $Z^3$ form, together with the adjacent nitrogen atom, cyclic amine optionally having one or two atoms from oxygen atom, sulfur atom and nitrogen atom in the ring), or a pharmaceutically acceptable salt thereof.

[5] The amide compound of the above-mentioned [4], which has the formula

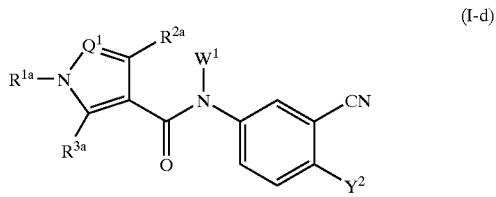

(I-d)

wherein $R^{1a}$ is substituted aryl, arylalkyl or optionally substituted heteroaryl, $R^{1a}$ and $R^{3a}$ are the same or different and each is hydrogen or alkyl, $Q^1$ is nitrogen atom or a group C—$R^{4a}$ (wherein $R^{4a}$ is hydrogen or alkyl), $W^1$ is hydrogen, alkyl, hydroxycarbonylalkyl or alkoxycarbonylalkyl, and $Y^2$ is alkoxy, optionally substituted aminoalkoxy, optionally substituted aminoalkylthio or a group $N(Z^{2a})(Z^{3a})$ (wherein $Z^{2a}$ and $Z^{3a}$ form, together with the adjacent nitrogen atom, cyclic amine optionally having one or two atoms from oxygen atom, sulfur atom and nitrogen atom in the ring), or a pharmaceutically acceptable salt thereof.

[6] The amide compound of [1] above, which is a member selected from the group consisting of (1) N-(3-cyano-4-neopentyloxyphenyl)-1-(4-fluorophenyl)-3-methylpyrazole-4-carboxamide, (2) N-(3-cyano-4-neopentyloxyphenyl)-1-(4-fluorophenyl)-5-methylpyrazole-4-carboxamide, (3) N-(3-cyano-4-neopentyloxyphenyl)-1-(4-fluorophenyl)-3,5-dimethylpyrazole-4-carboxamide, (4) N-(3-cyano-4-neopentyloxyphenyl)-1-(4-fluorophenyl)-N,3-dimethylpyrazole-4-carboxamide, (5) N-(3-cyano-4-neopentyloxyphenyl)-5-chloro-1-(4-fluorophenyl)pyrazole-4-carboxamide, (6) N-(3-cyano-4-neopentyloxyphenyl)-N-[1-(4-fluorophenyl)-3-methylpyrazol-4-ylcarbonyl]glycine, (7) 4-[N-(3-cyano-4-neopentyloxyphenyl)-N-[1-(4-fluorophenyl)-3-methylpyrazol-4-ylcarbonyl]amino]butyric acid, (8) N-(3-cyano-4-piperidinophenyl)-1-(4-fluorophenyl)-5-methylpyrazole-4-carboxamide, (9) N-[3-cyano-4-(4-hydroxypiperidino)phenyl]-1-(4-fluorophenyl)-5-methylpyrazole-4-carboxamide,

(10) N-{3-cyano-4-[4-(2-hydroxyethyl)piperazin-1-yl]phenyl}-1-(4-fluorophenyl)pyrazole-4-carboxamide,

(11) N-{3-cyano-4-[4-(2-hydroxyethyl)piperazin-1-yl]phenyl}-1-(4-fluorophenyl)-3-methylpyrazole-4-carboxamide,

(12) N-{3-cyano-4-[4-(2-hydroxyethyl)piperazin-1-yl]phenyl}-1-(4-fluorophenyl)-5-methylpyrazole-4-carboxamide,

(13) N-{3-cyano-4-[4-(2-hydroxyethyl)piperazin-1-yl]phenyl}-1-(4-chlorophenyl)-5-methylpyrazole-4-carboxamide,

(14) N-{3-cyano-4-[4-(2-hydroxyethyl)piperazin-1-yl]phenyl}-1-(4-methylphenyl)-5-methylpyrazole-4-carboxamide,

(15) N-{3-cyano-4-[4-(2-hydroxyethyl)piperazin-1-yl]phenyl}-1-(4-fluorophenyl)-3,5-dimethylpyrazole-4-carboxamide,
(16) N-{3-cyano-4-[4-(2-hydroxyethyl)piperazin-1-yl]phenyl}-1-(3-trifluoromethylphenyl)-5-methylpyrazole-4-carboxamide,
(17) N-{3-cyano-4-[4-(2-hydroxyethyl)piperazin-1-yl]phenyl}-1-(2,4-difluorophenyl)-5-methylpyrazole-4-carboxamide,
(18) N-{3-cyano-4-[4-(2-hydroxyethyl)homopiperazin-1-yl]phenyl}-1-(4-fluorophenyl)-5-methylpyrazole-4-carboxamide,
(19) N-{3-cyano-4-[4-(3-hydroxypropyl)piperazin-1-yl]phenyl}-1-(4-fluorophenyl)-5-methylpyrazole-4-carboxamide,
(20) N-{3-cyano-4-[4-(2-hydroxyethyl)piperazin-1-yl]phenyl}-1-(4-fluorophenyl)pyrrole-3-carboxamide,
(21) 1-(4-bromophenyl)-N-{3-cyano-4-[4-(2-hydroxyethyl)piperazin-1-yl]phenyl}-5-methylpyrazole-4-carboxamide,
(22) N-{3-cyano-4-[4-(2-hydroxyethyl)piperazin-1-yl]phenyl}-1-(4-iodophenyl)-5-methylpyrazole-4-carboxamide,
(23) 1-(4-chlorophenyl)-N-(3-cyano-4-piperidinophenyl)-5-methylpyrazole-4-carboxamide,
(24) 1-(4-chlorophenyl)-N-[3-cyano-4-(4-hydroxypiperidin-1-yl)phenyl]5-methylpyrazole-4-carboxamide,
(25) 1-(4-chlorophenyl)-N-[3-cyano-4-(4-morpholinopiperidin-1-yl)phenyl]-5-methylpyrazole-4-carboxamide,
(26) N-{4-(4-[bis(2-hydroxyethyl)amino]piperidin-1-yl}-3-cyanophenyl)-1-(4-chlorophenyl)-5-methylpyrazole-4-carboxamide,
(27) 1-(3,4-dichlorophenyl)-N-[3-cyano-4-(4-morpholinopiperidin-1-yl)phenyl]-5-methylpyrazole-4-carboxamide,
(28) N-[3-cyano-4-(4-morpholinopiperidin-1-yl)phenyl]-1-(3,4-difluorophenyl)-5-methylpyrazole-4-carboxamide,
(29) 1-(3-chloro-4-fluorophenyl)-N-[3-cyano-4-(4-morpholinopiperidin-1-yl)phenyl]-5-methylpyrazole-4-carboxamide,
(30) N-{3-cyano-4-[4-(2-hydroxyethyl)piperazin-1-yl]phenyl}-1-(4-trifluoromethylphenyl)-5-methylpyrazole-4-carboxamide,
(31) N-[3-cyano-4-(4-morpholinopiperidin-1-yl)phenyl]-1-(4-trifluoromethylphenyl)-5-methylpyrazole-4-carboxamide,
(32) N-{4-[4-bis(2-methoxyethyl)aminopiperidin-1-yl]-3-cyanophenyl}-1-(4-chlorophenyl)-5-methylpyrazole-4-carboxamide
(33) 1-(4-chlorophenyl)-N-[3-cyano-(4-morpholinopiperidin-1-yl)phenyl]pyrrole-3-carboxamide,
(34) N-[3-bromo-4-(4-morpholinopiperidin-1-yl)phenyl]-1-(4-chlorophenyl)-5-methylpyrazole-4-carboxamide,
(35) N-[3-bromo-4-(4-morpholinopiperidin-1-yl)phenyl]-5-methyl-1-(4-trifluoromethylphenyl)pyrazole-4-carboxamide,
(36) 1-(4-chlorophenyl)-N-{3-cyano-4-[4-(3,4,5,6-tetrahydro-2H-pyran-4-yl)piperazin-1-yl]phenyl}-5-methylpyrazole-4-carboxamide,
(37) N-{3-cyano-4-[4-(3,4,5,6-tetrahydro-2H-pyran-4-yl)piperazin-1-yl]phenyl}-5-methyl-1-(4-trifluoromethylphenyl)pyrazole-4-carboxamide,
(38) N-{3-cyano-4-[4-(3,4,5,6-tetrahydro-2H-pyran-4-yl)piperazin-1-yl]phenyl}-1-(4-fluorophenyl)-5-methylpyrazole-4-carboxamide,
(39) N-{3-cyano-4-[4-(3,4,5,6-tetrahydro-2H-pyran-4-yl)piperazin-1-yl]phenyl}-1-(4-fluorophenyl)pyrrole-3-carboxamide,
(40) 1-(4-chlorophenyl)-N-{3-cyano-4-[4-(3,4,5,6-tetrahydro-2H-pyran-4-yl) piperazin-1-yl]phenyl}pyrrole-3-carboxamide,
(41) 1-(3,4-dichlorophenyl)-N-{3-cyano-4-[4-(3,4,5,6-tetrahydro-2H-pyran-4-yl)piperazin-1-yl]phenyl}-5-methylpyrazole-4-carboxamide,
(42) 1-(4-chlorophenyl)-N-{3-cyano-4-[4-(3-hydroxypropyl)piperazin-1-yl]phenyl}-5-methylpyrazole-4-carboxamide,
(43) 1-(3,4-dichlorophenyl)-N-{3-cyano-4-[4-(2-hydroxyethyl)piperazin-1-yl]phenyl}-5-methylpyrazole-4-carboxamide,
(44) 1-(4-chlorophenyl)-N-{3-cyano-4-[4-(2-hydroxyethyl)piperidin-1-yl]phenyl}-5-methylpyrazole-4-carboxamide,
(45) 1-(4-chlorophenyl)-N-(3-cyano-4-{4-[2-(2-hydroxyethoxy)ethyl]piperazin-1-yl}phenyl)-5-methylpyrazole-4-carboxamide,
(46) 1-(4-chlorophenyl)-N-[3-cyano-4-(1,4-dioxa-8-azaspiro[4,5]deca-8-yl)phenyl]-5-methylpyrazole-4-carboxamide,
(47) 1-(4-bromophenyl)-N-[3-cyano-4-(4-morpholinopiperidino)phenyl]-5-methylpyrazole-4-carboxamide,
(48) N-[3-cyano-4-(4-morpholinopiperidino)phenyl]-1-(4-fluorophenyl)-5-methylpyrazole-4-carboxamide,
(49) N-[3-cyano-4-(4-morpholinopiperidino)phenyl]-1-(4-fluorophenyl)pyrrole-3-carboxamide,
(50) N-[3-cyano-4-(4-morpholinopiperidin-1-yl)phenyl]-1-(4-methylphenyl)-5-methylpyrazole-4-carboxamide,
(51) N-[3-cyano-4-(4-morpholinopiperidin-1-yl)phenyl]-1-(4-iodophenyl)-5-methylpyrazole-4-carboxamide,
(52) N-[3-cyano-4-(4-morpholinopiperidin-1-yl)phenyl]-1-(4-methoxyphenyl)-5-methylpyrazole-4-carboxamide,
(53) 1-(4-chlorophenyl)-N-[3-cyano-4-(4-thiomorpholinopiperidin-1-yl)phenyl]-5-methylpyrazole-4-carboxamide,
(54) 1-(4-chlorophenyl)-5-methyl-N-[4-(4-morpholinopiperidin-1-yl)-3-nitrophenyl]pyrazole-4-carboxamide,
(55) 5-methyl-N-[4-(4-morpholinopiperidin-1-yl)-3-nitrophenyl]-1-(4-trifluoromethylphenyl)pyrazole-4-carboxamide,
(56) N-[3-chloro-4-(4-morpholinopiperidin-1-yl)phenyl]-5-methyl-1-(4-trifluoromethylphenyl)pyrazole-4-carboxamide,
(57) 1-(4-chlorophenyl)-N-[3-ethynyl-4-(4-morpholinopiperidin-1-yl)phenyl]-5-methylpyrazole-4-carboxamide,
(58) N-[3-cyano-4-(4-morpholinopiperidin-1-yl)phenyl]-5-methyl-1-(2-phenylethyl)pyrazole-4-carboxamide,
(59) 1-(4-chlorophenyl)-N-[3-cyano-4-(4-methoxymethoxypiperidin-1-yl)phenyl]-5-methylpyrazole-4-carboxamide,
(60) 1-(4-chlorophenyl)-N-[3-cyano-4-[4-(2-methoxyethoxy)piperidin-1-yl]phenyl]-5-methylpyrazole-4-carboxamide,
(61) N-{3-cyano-4-[4-(2-hydroxyethyl)piperidin-1-yl]phenyl}-1-(4-fluorophenyl)-5-methylpyrazole-4-carboxamide,
(62) N-[3-cyano-(4-morpholinopiperidin-1-yl)phenyl]-5-methyl-1-(4-nitrophenyl) pyrazole-4-carboxamide,
(63) 1-(4-bromophenyl)-N-{3-cyano-4-[4-(3,4,5,6-tetrahydro-2H-pyran-4-yl)piperazin-1-yl]phenyl}-5-methylpyrazole-4-carboxamide,
(64) N-{3-cyano-4-[4-(3,4,5,6-tetrahydro-2H-pyran-4-yl)piperazin-1-yl]phenyl}-1-(3,4-difluorophenyl)-5-methylpyrazole-4-carboxamide,

(65) 1-(3-chlorophenyl)-N-{3-cyano-4-[4-(3,4,5,6-tetrahydro-2H-pyran-4-yl)piperazin-1-yl]phenyl}-5-methylpyrazole-4-carboxamide,
(66) N-{3-cyano-4-[4-(3,4,5,6-tetrahydro-2H-pyran-4-yl)piperazin-1 -yl]phenyl}-5-methyl-1-(4-methylphenyl) pyrazole-4-carboxamide,
(67) 1-(3-chlorophenyl)-N-[3-cyano-4-(4-morpholinopiperidino)phenyl]-5-methylpyrazole-4-carboxamide,
(68) 1-(4-chlorophenyl)-N-[3-chloro-4-(4-morpholinopiperidin-1-yl)phenyl]-5-methylpyrazole-4-carboxamide,
(69) N-{3-cyano-4-[4-(3,4,5,6-tetrahydro-2H-pyran-4-yl)piperazin-1-yl]phenyl}-1-(4-trifluoromethylphenyl)pyrrole-3-carboxamide,
(70) N-[3-cyano-4-(4-morpholinopiperidin-1-yl)phenyl]-1-(4-trifluoromethylphenyl)pyrrole-3-carboxamide,
(71) N-{3-cyano-4-[4-(3,4,5,6-tetrahydro-2H-pyran-4-yl)piperazin-1-yl]phenyl}-1-(3,4-dichlorophenyl)pyrrole-3-carboxamide,
(72) N-[3-cyano-4-(4-morpholinopiperidin-1-yl)phenyl]-1-(3,4-dichlorophenyl)pyrrole-3-carboxamide,
(73) 1-(4-chlorophenyl)-N-{3-ethynyl-4-[4-(3,4,5,6-tetrahydro-2H-pyran-4-yl)piperazin-1-yl]phenyl}-5-methylpyrazole-4-carboxamide,
(74) 1-(4-chlorophenyl)-5-methyl-N-{3-(1-propyne)-4-[4-(3,4,5,6-tetrahydro-2H-pyran-4-yl)piperazin-1-yl]phenyl}pyrazole-4-carboxamide,
(75) 1-(4-chlorophenyl)-5-methyl-N-[3-(1-propyne)-4-(4-morpholinopiperidin-1-yl)phenyl]pyrazole-4-carboxamide,
(76) 1-(4-chlorophenyl)-N-{3-ethenyl-4-[4-(3,4,5,6-tetrahydro-2H-pyran-4-yl)piperazin-1-yl]phenyl}-5-methylpyrazole-4-carboxamide,
(77) 1-(4-chlorophenyl)-N-[3-ethenyl-4-(4-morpholinopiperidin-1-yl)phenyl]-5-methylpyrazole-4-carboxamide,
(78) 1-(4-chlorophenyl)-N-[3-iodo-4-(4-morpholinopiperidin-1-yl)phenyl]-5-methylpyrazole-4-carboxamide,
(79) N-{3-bromo-4-[4-(3,4,5,6-tetrahydro-2H-pyran-4-yl)piperazin-1-yl]phenyl}-1-(4-chlorophenyl)-5-methylpyrazole-4-carboxamide,
(80) N-{3-chloro-4-[4-(3,4,5,6-tetrahydro-2H-pyran-4-yl)piperazin-1-yl]phenyl}-1-(4-chlorophenyl)-5-methylpyrazole-4-carboxamide,
(81) N-{3-chloro-4-[4-(3,4,5,6-tetrahydro-2H-pyran-4-yl)piperazin-1-yl]phenyl}-1-(4-chlorophenyl) pyrrole-3-carboxamide,
(82) N-{3-bromo-4-[4-(3,4,5,6-tetrahydro-2H-pyran-4-yl)piperazin-1-yl]phenyl}-1-(4-chlorophenyl)pyrrole-3-carboxamide,
(83) 1-(4-chlorophenyl)-N-[3-cyano-4-(5-morpholinopentyloxy)phenyl]-5-methylpyrazole-4-carboxamide,
(84) 1-(4-chlorophenyl)-N-[3-cyano-4-(5-morpholinopentyloxy)phenyl]pyrrole-3-carboxamide,
(85) 1-(4-chlorophenyl)-N-[3-cyano-4-(5-morpholinopentylthio)phenyl]-5-methylpyrazole-4-carboxamide,
(86) 1-(4-chlorophenyl)-N-[3-cyano-4-(5-morpholinopentylthio)phenyl]pyrrole-3-carboxamide,
(87) N-[3-cyano-4-(4-morpholinopiperidin-1-yl)phenyl]-1-(3,4-methylenedioxyphenyl)-5-methylpyrazole-4-carboxamide,
(88) N-[3-cyano-4-(4-morpholinopiperidin-1-yl)phenyl]-1-(3,4-methylenedioxyphenyl)pyrrole-3-carboxamide,
(89) N-{3-cyano-4-[4-(3,4,5,6-tetrahydro-2H-pyran-4-yl)piperazin-1-yl]phenyl}-1-(3,4-methylenedioxyphenyl)-5-methylpyrazole-4-carboxamide,
(90) N-{3-cyano-4-[4-(3,4,5,6-tetrahydro-2H-pyran-4-yl)piperazin-1-yl]phenyl}-1-(3,4-methylenedioxyphenyl) pyrrole-3-carboxamide,
(91) 1-(4-chlorophenyl)-N-[3-cyano-4-(2,2-dimethyl-3-morpholinopropoxy)phenyl]-5-methylpyrazole-4-carboxamide,
(92) 1-(4-chlorophenyl)-N-[3-cyano-4-(2,2-dimethyl-3-morpholinopropoxy)phenyl]pyrrole-3-carboxamide,
(93) N-[3-cyano-4-(2,2-dimethyl-3-morpholinopropoxy)phenyl]-5-methyl-1-(3,4-methylenedioxyphenyl)pyrazole-4-carboxamide,
(94) N-[3-cyano-4-(2,2-dimethyl-3-morpholinopropoxy)phenyl]-2,5-dimethyl-1-(3,4-methylenedioxyphenyl)pyrrole-3-carboxamide,
(95) N-[3-cyano-4-(4-morpholinopiperidin-1-yl)phenyl]-2,5-dimethyl-1-(3,4-methylenedioxyphenyl)pyrrole-3-carboxamide,
(96) N-[3-cyano-4-(4-morpholinopiperidin-1-yl)phenyl]-5-methyl-1-(3,4-methylenedioxyphenyl)pyrrole-3-carboxamide,
(97) N-[3-cyano-4-[4-(3,4,5,6-tetrahydro-2H-pyran-4-yl)piperazin-1-yl]phenyl]-2,5-dimethyl-1-(3,4-methylenedioxyphenyl)pyrrole-3-carboxamide,
(98) N-[3-chloro-4-(4-morpholinopiperidin-1-yl)phenyl]-2,5-dimethyl-1-(3,4-methylenedioxyphenyl)pyrrole-3-carboxamide,
(99) N-[3-cyano-4-(4-morpholinopiperidin-1-yl)phenyl]-1-(3,4-dimethoxyphenyl)-5-methylpyrazole-4-carboxamide,
(100) N-[3-cyano-4-(4-morpholinopiperidin-1-yl)phenyl]-1-(3,4-dimethoxyphenyl)pyrrole-3-carboxamide,
(101) N-[3-cyano-4-(4-morpholinopiperidin-1-yl)phenyl]-1-(3,4-dimethoxyphenyl)-2,5-dimethylpyrrole-3-carboxamide,
(102) 1-(4-chlorophenyl)-N-[3-cyano-4-(2,2-dimethyl-3-morpholinopropoxy)phenyl]-2,5-dimethylpyrrole-3-carboxamide, and
(103) 1-(4-chlorophenyl)-N-[3-cyano-4-(4-morpholinopiperazin-1-yl)phenyl]-2,5-dimethylpyrrole-3-carboxamide or a pharmaceutically acceptable salt thereof.

[7] A pharmaceutical composition comprising the amide compound of the above-mentioned [1] to [6] or a pharmaceutically acceptable salt thereof, and a pharmaceutically acceptable carrier.

[8] A pharmaceutical agent comprising the amide compound of the above-mentioned [1] to [6] or a pharmaceutically acceptable salt thereof.

[9] An inhibitor on the proliferation of activated lymphocytes comprising, as an active ingredient, an amide compound of the formula

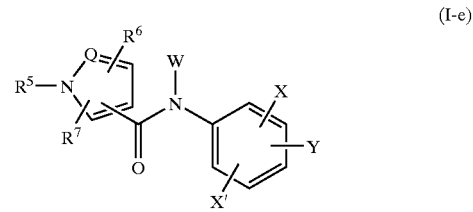

(I-e)

wherein
R$^5$ is hydrogen, optionally substituted alkyl, hydroxyalkyl, aminoalkyl, optionally substituted aryl, arylalkyl, optionally substituted heteroaryl, heteroarylalkyl or cycloalkyl,
R$^6$ and R$^7$ are the same or different and each is hydrogen, alkyl, halogen, hydroxyl group, alkoxy, optionally substituted amino or phenyl, Q is nitrogen atom or a group C—$R^8$ (wherein $R^8$ is hydrogen, alkyl, halogen or optionally substituted amino), W is hydrogen, alkyl, hydroxyalkyl, acyloxyalkyl, aminoalkyl, hydroxycarbonylalkyl or alkoxycarbonylalkyl, X is halogen, cyano, nitro, amino, alkyl, alkoxy, carboxy, alkoxycarbonyl, carbamoyl, alkenyl, alkynyl or haloalkyl, X' is hydrogen, halogen, cyano or nitro, and Y is alkyl, hydroxyalkyl, hydroxycarbonylalkyl, optionally substituted aminoalkyl, hydroxyl group, alkoxy, haloalkoxy, aryloxy, cycloalkyloxy, hydroxyalkoxy, hydroxycarbonylalkoxy, optionally substituted aminoalkoxy, mercapto, alkylthio, hydroxyalkylthio, hydroxycarbonylalkylthio, optionally substituted aminoalkylthio, a group O-Het (wherein Het is optionally substituted saturated heterocycle having hetero atom selected from oxygen atom and nitrogen atom) or a group $N(Z^2)(Z^3)$ (wherein $Z^2$ and $Z^3$ are the same or different and each is hydrogen, alkyl, hydroxyalkyl or aminoalkyl, or $Z^2$ and $Z^3$ form, together with the adjacent nitrogen atom, cyclic amine optionally having one or two atoms from oxygen atom, sulfur atom and nitrogen atom in the ring), or a pharmaceutically acceptable salt thereof.

[10] An inhibitor on the proliferation of activated lymphocytes comprising the amide compound of the above-mentioned [1]–[6] or a pharmaceutically acceptable salt thereof as an active ingredient.

[11] The inhibitor on the proliferation of activated lymphocytes of the above-mentioned [9] or [10], which is dependent on IL-2, IL-4, IL-7, IL-9, IL-13 or IL-15.

[12] A phosphorylation inhibitor of tyrosine kinase involved in the signal transduction in the downstream of a common β chain that is a receptor subunit common to IL-15 and IL-2 and/or a common γ chain that is a receptor subunit common to IL-2, IL-4, IL-7, IL-9, IL-13 and IL-15, which inhibitor comprises the amide compound of the above-mentioned [1]–[6] or a pharmaceutically acceptable salt thereof as an active ingredient.

[13] The cytokine production inhibitor, which comprises the amide compound of the above-mentioned [1]–[6] or a pharmaceutically acceptable salt thereof as an active ingredient.

[14] An IL-2, IL-4, IL-13 or IFN-γ production inhibitor, which comprises the amide compound of the above-mentioned [1]–[6] or a pharmaceutically acceptable salt thereof as an active ingredient.

[15] An IL-1, IL-6, IL-12, IL-15, IL-18 or TNF-α production inhibitor, which comprises the amide compound of the above-mentioned [1]–[6] or a pharmaceutically acceptable salt thereof as an active ingredient.

[16] A pharmaceutical agent comprising a synthesized low molecular compound having inhibitory effect on activated lymphocytes proliferation dependent on IL-2, IL-4, IL-7, IL-9, IL-13 or IL-15.

[17] An agent for the prophylaxis or treatment of diseases caused by proliferation of lymphocytes, which agent comprises, as an active ingredient, a synthesized low molecular compound having inhibitory effect on activated lymphocytes proliferation dependent on IL-2, IL-4, IL-7, IL-9, IL-13 or IL-15.

[18] An agent for the prophylaxis or treatment of diseases caused by proliferation of lymphocytes, which comprises the amide compound of the above-mentioned [1]–[6] or a pharmaceutically acceptable salt thereof as an active ingredient.

[19] An agent for the prophylaxis or treatment of autoimmune diseases, which comprises, as an active ingredient, a synthesized low molecular compound having inhibitory effect on activated lymphocytes proliferation dependent on IL-2, IL-4, IL-7, IL-9, IL-13 or IL-15.

[20] An agent for the prophylaxis or treatment of autoimmune diseases, which comprises, as an active ingredient, the amide compound of the above-mentioned [1]–[6] or a pharmaceutically acceptable salt thereof.

[21] An agent for the prophylaxis or treatment of rheumatoid arthritis, which comprises, as an active ingredient, the amide compound of the above-mentioned [1]–[6] or a pharmaceutically acceptable salt thereof.

[22] A combination composition comprising the amide compound of the formula

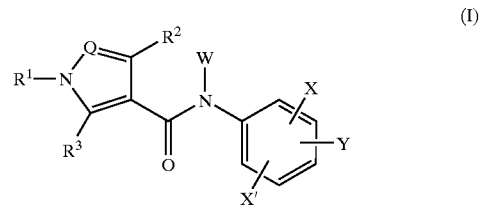

(I)

wherein $R^1$ is substituted aryl, arylalkyl, optionally substituted heteroaryl, heteroarylalkyl or cycloalkyl, $R^2$ and $R^3$ are the same or different and each is hydrogen, alkyl, halogen, hydroxyl group, alkoxy, optionally substituted amino or phenyl, Q is nitrogen atom or a group C—$R^4$ (wherein $R^4$ is hydrogen, alkyl, halogen or optionally substituted amino), W is hydrogen, alkyl, hydroxyalkyl, acyloxyalkyl, aminoalkyl, hydroxycarbonylalkyl or alkoxycarbonylalkyl, X is halogen, cyano, nitro, amino, alkyl, alkoxy, carboxy, alkoxycarbonyl, carbamoyl, alkenyl, alkynyl or haloalkyl, X' is hydrogen, halogen, cyano or nitro, and Y is alkyl, hydroxyalkyl, hydroxycarbonylalkyl, optionally substituted aminoalkyl, hydroxyl group, optionally substituted alkoxy, aryloxy, cycloalkyloxy, hydroxyalkoxy, hydroxycarbonylalkoxy, optionally substituted aminoalkoxy, mercapto, alkylthio, hydroxyalkylthio, hydroxycarbonylalkylthio, optionally substituted aminoalkylthio, a group O-Het (wherein Het is optionally substituted saturated heterocycle having hetero atom selected from oxygen atom and nitrogen atom) or a group $N(Z^2)(Z^3)$ (wherein $Z^2$ and $Z^3$ are the same or different and each is hydrogen, alkyl, hydroxyalkyl or aminoalkyl, or $Z^2$ and $Z^3$ form, together with the adjacent nitrogen atom, cyclic amine optionally having one or two atoms from oxygen atom, sulfur atom and nitrogen atom in the ring), or a pharmaceutically acceptable salt thereof, and one or more pharmaceutical agents selected from an antirheumatic drug, an immunosuppressive agent, a steroidal drug and a nonsteroidal anti-inflammatory drug.

[23] The combination composition of the above-mentioned [22], wherein the antirheumatic drug is selected from a gold compound, penicillamine, bucillamine, lobenzarit, actarit and salazosulfapyridine.

[24] The combination composition of the above-mentioned [22], wherein the immunosuppressive agent is selected from azathioprine, cyclophosphamide, methotrexate, brequinar sodium, deoxyspergualin, mizoribine, 2-morpholinoethyl mycophenolate, cyclosporin, rapamycin, tacrolimus hydrate, leflunomide, OKT-3, anti TNF-α antibody, anti IL-6 antibody and FTY720.

[25] The combination composition of the above-mentioned [22], wherein the steroidal drug is selected from prednisolone, methylprednisolone, dexamethasone and hydrocortisone.

[26] The combination composition of the above-mentioned [22], wherein the nonsteroidal anti-inflammatory drug is selected from aspirin, indomethacin, indomethacin farnesil, diclofenac sodium, alclofenac, amfenac sodium, ibuprofen, ketoprofen, loxoprofen sodium, naproxen, pranoprofen, zaltoprofen, mefenamic acid, flufenamic acid, tolufenamic acid, phenylbutazone, ketophenylbutazone, piroxicam, tenoxicam and ampiroxicam.

[27] An effect enhancer of one or more pharmaceutical agents selected from an antirheumatic drug, an immunosuppressive agent, a steroidal drug and a nonsteroidal anti-inflammatory drug, which enhancer comprises an amide compound of the formula

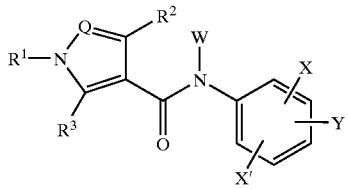

wherein
$R^1$ is substituted aryl, arylalkyl, optionally substituted heteroaryl, heteroarylalkyl or cycloalkyl,
$R^2$ and $R^3$ are the same or different and each is hydrogen, alkyl, halogen, hydroxyl group, alkoxy, optionally-substituted amino or phenyl,
Q is nitrogen atom or a group C—$R^4$ (wherein $R^1$ is hydrogen, alkyl, halogen or optionally substituted amino),
W is hydrogen, alkyl, hydroxyalkyl, acyloxyalkyl, aminoalkyl, hydroxycarbonylalkyl or alkoxycarbonylalkyl,
X is halogen, cyano, nitro, amino, alkyl, alkoxy, carboxy, alkoxycarbonyl, carbamoyl, alkenyl, alkynyl or haloalkyl,
X' is hydrogen, halogen, cyano or nitro, and
Y is alkyl, hydroxyalkyl, hydroxycarbonylalkyl, optionally substituted aminoalkyl, hydroxyl group, optionally substituted alkoxy, aryloxy, cycloalkyloxy, hydroxyalkoxy, hydroxycarbonylalkoxy, optionally substituted aminoalkoxy, mercapto, alkylthio, hydroxyalkylthio, hydroxycarbonylalkylthio, optionally substituted aminoalkylthio, a group O-Het (wherein Het is optionally substituted saturated heterocycle having hetero atom selected from oxygen atom and nitrogen atom) or a group N($Z^2$)($Z^3$) (wherein $Z^2$ and $Z^3$ are the same or different and each is hydrogen, alkyl, hydroxyalkyl or aminoalkyl, or $Z^2$ and $Z^3$ form, together with the adjacent nitrogen atom, cyclic amine optionally having one or two atoms from oxygen atom, sulfur atom and nitrogen atom in the ring), or a pharmaceutically acceptable salt thereof.

[28] The effect enhancer of the above-mentioned [27], wherein the antirheumatic drug is selected from a gold compound, penicillamine, bucillamine, lobenzarit, actarit and salazosulfapyridine.

[29] The effect enhancer of the above-mentioned [27], wherein the immunosuppressive agent is selected from azathioprine, cyclophosphamide, methotrexate, brequinar sodium, deoxyspergualin, mizoribine, 2-morpholinoethyl mycophenolate, cyclosporin, rapamycin, tacrolimus hydrate, leflunomide, OKT-3, anti TNF-α antibody, anti IL-6 antibody and FTY720.

[30] The effect enhancer of the above-mentioned [27], wherein the steroidal drug is selected from prednisolone, methylprednisolone, dexamethasone and hydrocortisone.

[31] The effect enhancer of the above-mentioned [27], wherein the nonsteroidal anti-inflammatory drug is selected from aspirin, indomethacin, indomethacin farnesil, diclofenac sodium, alclofenac, amfenac sodium, ibuprofen, ketoprofen, loxoprofen sodium, naproxen, pranoprofen, zaltoprofen, mefenamic acid, flufenamic acid, tolufenamic acid, phenylbutazone, ketophenylbutazone, piroxicam, tenoxicam and ampiroxicam.

The present invention aims at providing a synthesized low molecular compound having an inhibitory effect on the proliferation of activated lymphocytes taking note of IL-15. The inhibitory effect on the proliferation of activated lymphocytes taking note of IL-15 means inhibitory effect on activated lymphocytes proliferation dependent on IL-15, and embraces an inhibitory effect on the activated lymphocytes proliferation dependent on IL-2, IL-4, IL-7, IL-9 and IL-13 which are cytokines closely related to IL-15. The present invention also aims at providing a compound which inhibits signal transduction from an IL-15 receptor (β chain common to IL-15 and IL-2, and γ chain common to IL-2, IL-4, IL-7, IL-9, IL-13 and IL-15), inhibits a path via tyrosine kinase during the process of the signal transduction, and which inhibits production of IL-15 and inflammatory cytokines (IL-1, IL-6, IL-12, IL-15, IL-18, TNF-α and the like) derived by IL-15. In addition, the synthesized low molecular compound is able to produce by using a low molecular weight organic compound to a method known in the field of organic synthetic chemistry. The preferable compounds in the present invention are compound (I) and compound (I-e), more preferably the compound (I-a)- compound (I-d). The particularly preferable compounds are as follows.

(1) N-(3-cyano-4-neopentyloxyphenyl)-1-(4-fluorophenyl)-3-methylpyrazole-4-carboxamide,
(2) N-(3-cyano-4-neopentyloxyphenyl)-1-(4-fluorophenyl)-5-methylpyrazole-4-carboxamide,
(3) N-(3-cyano-4-neopentyloxyphenyl)-1-(4-fluorophenyl)-3,5-dimethylpyrazole-4-carboxamide,
(4) N-(3-cyano-4-neopentyloxyphenyl)-1-(4-fluorophenyl)-N,3-dimethylpyrazole-4-carboxamide,
(5) N-(3-cyano-4-neopentyloxyphenyl)-5-chloro-1-(4-fluorophenyl)pyrazole-4-carboxamide,
(6) N-(3-cyano-4-neopentyloxyphenyl)-N-[1-(4-fluorophenyl)-3-methylpyrazol-4-ylcarbonyl]glycine,
(7) 4-[N-(3-cyano-4-neopentyloxyphenyl)-N-[1-(4-fluorophenyl)-3-methylpyrazol-4-ylcarbonyl]amino]butyric acid,
(8) N-(3-cyano-4-piperidinophenyl)-1-(4-fluorophenyl)-5-methylpyrazole-4-carboxamide,
(9) N-[3-cyano-4-(4-hydroxypiperidino)phenyl]-1-(4-fluorophenyl)-5-methylpyrazole-4-carboxamide,
(10) N-{3-cyano-4-[4-(2-hydroxyethyl)piperazin-1-yl]phenyl}-1-(4-fluorophenyl)pyrazole-4-carboxamide,
(11) N-{3-cyano-4-[4-(2-hydroxyethyl)piperazin-1-yl]phenyl}-1-(4-fluorophenyl)-3-methylpyrazole-4-carboxamide,

(12) N-{3-cyano-4-[4-(2-hydroxyethyl)piperazin-1-yl]phenyl}-1-(4-fluorophenyl)-5-methylpyrazole-4-carboxamide,
(13) N-{3-cyano-4-[4-(2-hydroxyethyl)piperazin-1-yl]phenyl)-1-(4-chlorophenyl)-5-methylpyrazole-4-carboxamide,
(14) N-{3-cyano-4-[4-(2-hydroxyethyl)piperazin-1-yl]phenyl}-1-(4-methylphenyl)-5-methylpyrazole-4-carboxamide,
(15) N-{3-cyano-4-[4-(2-hydroxyethyl)piperazin-1-yl]phenyl}-1-(4-fluorophenyl)-3,5-dimethylpyrazole-4-carboxamide,
(16) N-{3-cyano-4-[4-(2-hydroxyethyl)piperazin-1-yl]phenyl}-1-(3-trifluoromethylphenyl)-5-methylpyrazole-4-carboxamide,
(17) N-{3-cyano-4-[4-(2-hydroxyethyl)piperazin-1-yl]phenyl}-1-(2,4-difluorophenyl)-5-methylpyrazole-4-carboxamide,
(18) N-{3-cyano-4-[4-(2-hydroxyethyl)homopiperazin-1-yl]phenyl}-1-(4-fluorophenyl)-5-methylpyrazole-4-carboxamide,
(19) N-{3-cyano-4-[4-(3-hydroxypropyl)piperazin-1-yl]phenyl}-1-(4-fluorophenyl)-5-methylpyrazole-4-carboxamide,
(20) N-{3-cyano-4-[4-(2-hydroxyethyl)piperazin-1-yl]phenyl}-1-(4-fluorophenyl)pyrrole-3-carboxamide,
(21) 1-(4-bromophenyl)-N-{3-cyano-4-[4-(2-hydroxyethyl)piperazin-1-yl]phenyl}-5-methylpyrazole-4-carboxamide,
(22) N-{3-cyano-4-[4-(2-hydroxyethyl)piperazin-1-yl]phenyl}-1-(4-iodophenyl)-5-methylpyrazole-4-carboxamide,
(23) 1-(4-chlorophenyl)-N-(3-cyano-4-piperidinophenyl)-5-methylpyrazole-4-carboxamide,
(24) 1-(4-chlorophenyl)-N-[3-cyano-4-(4-hydroxypiperidin-1-yl)phenyl]-5-methylpyrazole-4-carboxamide,
(25) 1-(4-chlorophenyl)-N-[3-cyano-4-(4-morpholinopiperidin-1 -yl)phenyl]-5-methylpyrazole-4-carboxamide,
(26) N-(4-{4-[bis(2-hydroxyethyl)amino]piperidin-1-yl}-3-cyanophenyl)-1-(4-chlorophenyl)-5-methylpyrazole-4-carboxamide,
(27) 1-(3,4-dichlorophenyl)-N-[3-cyano-4-(4-morpholinopiperidin-1-yl) phenyl]-5-methylpyrazole-4-carboxamide,
(28) N-[3-cyano-4-(4-morpholinopiperidin-1-yl)phenyl]-1-(3,4-difluorophenyl)-5-methylpyrazole-4-carboxamide,
(29) 1-(3-chloro-4-fluorophenyl)-N-[3-cyano-4-(4-morpholinopiperidin-1-yl)phenyl]-5-methylpyrazole-4-carboxamide,
(30) N-{3-cyano-4-[4-(2-hydroxyethyl)piperazin-1-yl]phenyl}-1-(4-trifluoromethylphenyl)-5-methylpyrazole-4-carboxamide,
(31) N-[3-cyano-4-(4-morpholinopiperidin-1-yl)phenyl]-1-(4-trifluoromethylphenyl)-5-methylpyrazole-4-carboxamide,
(32) N-{4-[4-bis(2-methoxyethyl)aminopiperidin-1-yl]-3-cyanophenyl}-1-(4-chlorophenyl)-5-methylpyrazole-4-carboxamide
(33) 1-(4-chlorophenyl)-N-[3-cyano-(4-morpholinopiperidin-1-yl)phenyl]pyrrole-3-carboxamide,
(34) N-[3-bromo-4-(4-morpholinopiperidin-1-yl)phenyl]-1-(4-chlorophenyl)-5-methylpyrazole-4-carboxamide,
(35) N-[3-bromo-4-(4-morpholinopiperidin-1-yl)phenyl]-5-methyl-1-(4-trifluoromethylphenyl)pyrazole-4-carboxamide,
(36) 1-(4-chlorophenyl)-N-{3-cyano-4-[4-(3,4,5,6-tetrahydro-2H-pyran-4-yl)piperazin-1-yl]phenyl}-5-methylpyrazole-4-carboxamide,
(37) N-{3-cyano-4-[4-(3,4,5,6-tetrahydro-2H-pyran-4-yl)piperazin-1-yl]phenyl}-5-methyl-1-(4-trifluoromethylphenyl)pyrazole-4-carboxamide,
(38) N-{3-cyano-4-[4-(3,4,5,6-tetrahydro-2H-pyran-4-yl)piperazin-1-yl]phenyl}-1-(4-fluorophenyl)-5-methylpyrazole-4-carboxamide,
(39) N-{3-cyano-4-[4-(3,4,5,6-tetrahydro-2H-pyran-4-yl)piperazin-1-yl]phenyl}-1-(4-fluorophenyl)pyrrole-3-carboxamide,
(40) 1-(4-chlorophenyl)-N-{3-cyano-4-[4-(3,4,5,6-tetrahydro-2H-pyran-4-yl)piperazin-1-yl]phenyl}pyrrole-3-carboxamide,
(41) 1-(3,4-dichlorophenyl)-N-{3-cyano-4-[4-(3,4,5,6-tetrahydro-2H-pyran-4-yl)piperazin-1-yl]phenyl}-5-methylpyrazole-4-carboxamide,
(42) 1-(4-chlorophenyl)-N-{3-cyano-4-[4-(3-hydroxypropyl)piperazin-1-yl]phenyl}-5-methylpyrazole-4-carboxamide,
(43) 1-(3,4-dichlorophenyl)-N-{3-cyano-4-[4-(2-hydroxyethyl)piperazin-1-yl]phenyl}-5-methylpyrazole-4-carboxamide,
(44) 1-(4-chlorophenyl)-N-{3-cyano-4-[4-(2-hydroxyethyl)piperidin-1-yl]phenyl}-5-methylpyrazole-4-carboxamide,
(45) 1-(4-chlorophenyl)-N-(3-cyano-4-{4-[2-(2-hydroxyethoxy)ethyl]piperazin-1-yl}phenyl)-5-methylpyrazole-4-carboxamide,
(46) 1-(4-chlorophenyl)-N-[3-cyano-4-(1,4-dioxa-8-azaspiro[4,5]deca-8-yl)phenyl]-5-methylpyrazole-4-carboxamide,
(47) 1-(4-bromophenyl)-N-[3-cyano-4-(4-morpholinopiperidino)phenyl]-5-methylpyrazole-4-carboxamide,
(48) N-[3-cyano-4-(4-morpholinopiperidino)phenyl]-1-(4-fluorophenyl)-5-methylpyrazole-4-carboxamide,
(49) N-[3-cyano-4-(4-morpholinopiperidino)phenyl]-1-(4-fluorophenyl)pyrrole-3-carboxamide,
(50) N-[3-cyano-4-(4-morpholinopiperidin-1-yl)phenyl]-1-(4-methylphenyl)-5-methylpyrazole-4-carboxamide,
(51) N-[3-cyano-4-(4-morpholinopiperidin-1-yl)phenyl]-1-(4-iodophenyl)-5-methylpyrazole-4-carboxamide,
(52) N-[3-cyano-4-(4-morpholinopiperidin-1-yl)phenyl]-1-(4-methoxyphenyl)-5-methylpyrazole-4-carboxamide,
(53) 1-(4-chlorophenyl)-N-[3-cyano-4-(4-thiomorpholinopiperidin-1-yl)phenyl]-5-methylpyrazole-4-carboxamide,
(54) 1-(4-chlorophenyl)-5-methyl-N-[4-(4-morpholinopiperidin-1-yl)-3-nitrophenyl]pyrazole-4-carboxamide
(55) 5-methyl-N-[4-(4-morpholinopiperidin-1-yl)-3-nitrophenyl]-1-(4-trifluoromethylphenyl)pyrazole-4-carboxamide,
(56) N-[3-chloro-4-(4-morpholinopiperidin-1-yl)phenyl]-5-methyl-1-(4-trifluoromethylphenyl)pyrazole-4-carboxamide,
(57) 1-(4-chlorophenyl)-N-[3-ethynyl-4-(4-morpholinopiperidin-1-yl)phenyl]-5-methylpyrazole-4-carboxamide,
(58) N-[3-cyano-4-(4-morpholinopiperidin-1-yl)phenyl]-5-methyl-1-(2-phenylethyl)pyrazole-4-carboxamide,
(59) 1-(4-chlorophenyl)-N-[3-cyano-4-(4-methoxymethoxypiperidin-1-yl) phenyl]-5-methylpyrazole-4-carboxamide,
(60) 1-(4-chlorophenyl)-N-[3-cyano-4-[4-(2-methoxyethoxy)piperidin-1-yl]phenyl}-5-methylpyrazole-4-carboxamide,
(61) N-{3-cyano-4-[4-(2-hydroxyethyl)piperidin-1-yl]phenyl}-1-(4-fluorophenyl)-5-methylpyrazole-4-carboxamide,

(62) N-[3-cyano-(4-morpholinopiperidin-1-yl)phenyl]-5-methyl-1-(4-nitrophenyl)pyrazole-4-carboxamide,
(63) 1-(4-bromophenyl)-N-{3-cyano-4-[4-(3,4,5,6-tetrahydro-2H-pyran-4-yl)piperazin-1-yl]phenyl}-5-methylpyrazole-4-carboxamide,
(64) N-{3-cyano-4-[4-(3,4,5,6-tetrahydro-2H-pyran-4-yl)piperazin-1-yl]phenyl}-1-(3,4-difluorophenyl)-5-methylpyrazole-4-carboxamide,
(65) 1-(3-chlorophenyl)-N-{3-cyano-4-[4-(3,4,5,6-tetrahydro-2H-pyran-4-yl)piperazin-1-yl]phenyl}-5-methylpyrazole-4-carboxamide,
(66) N-{3-cyano-4-[4-(3,4,5,6-tetrahydro-2H-pyran-4-yl)piperazin-1-yl]phenyl}-5-methyl-1-(4-methylphenyl)pyrazole-4-carboxamide,
(67) 1-(3-chlorophenyl)-N-[3-cyano-4-(4-morpholinopiperidino)phenyl]-5-methylpyrazole-4-carboxamide,
(68) 1-(4-chlorophenyl)-N-[3-chloro-4-(4-morpholinopiperidin-1-yl)phenyl]-5-methylpyrazole-4-carboxamide,
(69) N-{3-cyano-4-[4-(3,4,5,6-tetrahydro-2H-pyran-4-yl)piperazin-1-yl]phenyl}-1-(4-trifluoromethylphenyl)pyrrole-3-carboxamide,
(70) N-[3-cyano-4-(4-morpholinopiperidin-1-yl)phenyl]-1-(4-trifluoromethylphenyl)pyrrole-3-carboxamide,
(71) N-{3-cyano-4-[4-(3,4,5,6-tetrahydro-2H-pyran-4-yl)piperazin-1-yl]phenyl}-1-(3,4-dichlorophenyl)pyrrole-3-carboxamide,
(72) N-[3-cyano-4-(4-morpholinopiperidin-1-yl)phenyl]-1-(3,4-dichlorophenyl)pyrrole-3-carboxamide,
(73) 1-(4-chlorophenyl)-N-{3-ethynyl-4-[4-(3,4,5,6-tetrahydro-2H-pyran-4-yl)piperazin-1-yl]phenyl}-5-methylpyrazole-4-carboxamide,
(74) 1-(4-chlorophenyl)-5-methyl-N-{3-(1-propyne)-4-[4-(3,4,5,6-tetrahydro-2H-pyran-4-yl)piperazin-1-yl]phenyl}pyrazole-4-carboxamide,
(75) 1-(4-chlorophenyl)-5-methyl-N-[3-(1-propyne)-4-(4-morpholinopiperidin-1-yl)phenyl]pyrazole-4-carboxamide,
(76) 1-(4-chlorophenyl)-N-{3-ethenyl-4-[4-(3,4,5,6-tetrahydro-2H-pyran-4-yl)piperazin-1-yl]phenyl}-5-methylpyrazole-4-carboxamide,
(77) 1-(4-chlorophenyl)-N-[3-ethenyl-4-(4-morpholinopiperidin-1-yl)phenyl]-5-methylpyrazole-4-carboxamide,
(78) 1-(4-chlorophenyl)-N-[3-iodo-4-(4-morpholinopiperidin-1-yl)phenyl]-5-methylpyrazole-4-carboxamide,
(79) N-{3-bromo-4-[4-(3,4,5,6-tetrahydro-2H-pyran-4-yl)piperazin-1-yl]phenyl}-1-(4-chlorophenyl)-5-methylpyrazole-4-carboxamide,
(80) N-{3-chloro-4-[4-(3,4,5,6-tetrahydro-2H-pyran-4-yl)piperazin-1-yl]phenyl}-1-(4-chlorophenyl)-5-methylpyrazole-4-carboxamide,
(81) N-{3-chloro-4-[4-(3,4,5,6-tetrahydro-2H-pyran-4-yl)piperazin-1-yl]phenyl}-1-(4-chlorophenyl)pyrrole-3-carboxamide,
(82) N-{3-bromo-4-[4-(3,4,5,6-tetrahydro-2H-pyran-4-yl)piperazin-1-yl]phenyl}-1-(4-chlorophenyl)pyrrole-3-carboxamide,
(83) 1-(4-chlorophenyl)-N-[3-cyano-4-(5-morpholinopentyloxy)phenyl]-5-methylpyrazole-4-carboxamide,
(84) 1-(4-chlorophenyl)-N-[3-cyano-4-(5-morpholinopentyloxy)phenyl]pyrrole-3-carboxamide,
(85) 1-(4-chlorophenyl)-N-[3-cyano-4-(5-morpholinopentylthio)phenyl]-5-methylpyrazole-4-carboxamide,
(86) 1-(4-chlorophenyl)-N-[3-cyano-4-(5-morpholinopentylthio)phenyl]pyrrole-3-carboxamide,
(87) N-[3-cyano-4-(4-morpholinopiperidin-1-yl)phenyl]-1-(3,4-methylenedioxyphenyl)-5-methylpyrazole-4-carboxamide,
(88) N-[3-cyano-4-(4-morpholinopiperidin-1-yl)phenyl]-1-(3,4-methylenedioxyphenyl)pyrrole-3-carboxamide,
(89) N-{3-cyano-4-[4-(3,4,5,6-tetrahydro-2H-pyran-4-yl)piperazin-1-yl]phenyl}-1-(3,4-methylenedioxyphenyl)-5-methylpyrazole-4-carboxamide,
(90) N-{3-cyano-4-[4-(3,4,5,6-tetrahydro-2H-pyran-4-yl)piperazin-1-yl]phenyl}-1-(3,4-methylenedioxyphenyl)pyrrole-3-carboxamide,
(91) 1-(4-chlorophenyl)-N-[3-cyano-4-(2,2-dimethyl-3-morpholinopropoxy)phenyl]-5-methylpyrazole-4-carboxamide,
(92) 1-(4-chlorophenyl)-N-[3-cyano-4-(2,2-dimethyl-3-morpholinopropoxy)phenyl]pyrrole-3-carboxamide,
(93) N-[3-cyano-4-(2,2-dimethyl-3-morpholinopropoxy)phenyl]-5-methyl-1-(3,4-methylenedioxyphenyl)pyrazole-4-carboxamide,
(94) N-[3-cyano-4-(2,2-dimethyl-3-morpholinopropoxy)phenyl]-2,5-dimethyl-1-(3,4-methylenedioxyphenyl)pyrrole-3-carboxamide,
(95) N-[3-cyano-4-(4-morpholinopiperidin-1-yl)phenyl]-2,5-dimethyl-1-(3,4-methylenedioxyphenyl)pyrrole-3-carboxamide,
(96) N-[3-cyano-4-(4-morpholinopiperidin-1-yl)phenyl]-5-methyl-1-(3,4-methylenedioxyphenyl) pyrrole-3-carboxamide,
(97) N-[3-cyano-4-[4-(3,4,5,6-tetrahydro-2H-pyran-4-yl)piperazin-1-yl]phenyl]-2,5-dimethyl-1-(3,4-methylenedioxyphenyl)pyrrole-3-carboxamide,
(98) N-[3-chloro-4-(4-morpholinopiperidin-1-yl)phenyl]-2,5-dimethyl-1-(3,4-methylenedioxyphenyl)pyrrole-3-carboxamide,
(99) N-[3-cyano-4-(4-morpholinopiperidin-1-yl)phenyl]-1-(3,4-dimethoxyphenyl)-5-methylpyrazole-4-carboxamide,
(100) N-[3-cyano-4-(4-morpholinopiperidin-1-yl)phenyl]-1-(3,4-dimethoxyphenyl)pyrrole-3-carboxamide,
(101) N-[3-cyano-4-(4-morpholinopiperidin-1-yl)phenyl]-1-(3,4-dimethoxyphenyl)-2,5-dimethylpyrrole-3-carboxamide,
(102) 1-(4-chlorophenyl)-N-[3-cyano-4-(2,2-dimethyl-3-morpholinopropoxy)phenyl]-2,5-dimethylpyrrole-3-carboxamide, and
(103) 1-(4-chlorophenyl)-N-[3-cyano-4-(4-morpholinopiperazin-1-yl)phenyl]-2,5-dimethylpyrrole-3-carboxamide.

The substituents represented by each symbol in the present specification are explained in the following.

The aryl of substituted aryl at $R^1$, $R^{1a}$ and $R^5$ means phenyl, naphthyl and the like, wherein the substituent is 1 to 3 groups selected from halogen (fluorine, chlorine, bromine, iodine), alkyl having 1 to 4 carbon atoms (methyl, ethyl, propyl, isopropyl, butyl and the like), alkoxy having 1 to 4 carbon atoms (methoxy, ethoxy, propoxy, isopropoxy, butoxy and the like), cyano, nitro, carboxy, alkylenedioxy having 1 to 4 carbon atoms (methylenedioxy, ethylenedioxy, propylenedioxy, 1,1-dimethylmethylenedioxy and the like) and haloalkyl having 1 to 4 carbon atoms (fluoromethyl, chloromethyl, trifluoromethyl, 2,2,2-trifluoroethyl and the like). The preferable substituent is exemplified by halogen, alkyl, alkoxy, haloalkyl, alkylenedioxy and nitro. Examples of substituted aryl include 4-chlorophenyl, 3-chlorophenyl, 2-chlorophenyl, 3,4-dichlorophenyl, 4-fluorophenyl, 2,4-difluorophenyl, 3,4-difluorophenyl, 3-chloro-4-fluorophenyl, 4-bromophenyl, 4-iodophenyl, 4-methylphenyl, 4-methoxyphenyl, 4-ethoxyphenyl, 3,4-dimethoxyphenyl, 3,4-diethoxyphenyl, 4-cyanophenyl, 4-carboxyphenyl, 4-trifluoromethylphenyl, 3-trifluoromethylphenyl, 2-chloro-5- trifluoromethylphenyl, 4-nitrophenyl, 3,4-methylenedioxyphenyl, 3,4-ethylenedioxyphenyl and the like.

The arylalkyl at $R^1$, $R^{1a}$ and $R^5$ is aryl (phenyl, naphthyl and the like) substituted with alkyl having 1 to 4 carbon atoms, and is exemplified by phenylmethyl, 2-phenylethyl, 1-phenylethyl, 3-phenylpropyl, 4-phenylbutyl and the like.

The heteroaryl of optionally substituted heteroaryl at $R^1$, $R^{1a}$ and $R^5$ is a 5 or 6-membered heteroaryl ring having 1 or 2 substituents selected from hetero atoms of nitrogen atom, sulfur atom and oxygen atom. As the substituent, alkyl having 1 to 4 carbon atoms, halogen (fluorine, chlorine, bromine and the like) and the like are exemplified. Examples thereof include pyrimidyl, 4,6-dimethylpyrimidyl, pyridazinyl, 6-chloropyridazinyl, thienyl, 5-methylthienyl, 5-chlorothienyl, pyridyl and the like.

The heteroarylalkyl at $R^1$ and $R^5$ is a 5 or 6-membered heteroaryl ring substituted with 1 or 2 hetero atoms selected from nitrogen atom, sulfur atom and oxygen atom (as defined above), which is substituted with alkyl having 1 to 4 carbon atoms. Examples thereof include 2-thienylmethyl, 2-(2-thienyl)ethyl, 3-(2-thienyl)propyl, 2-pyridylmethyl, 3-pyridylmethyl, 4-pyridylmethyl and the like.

The cycloalkyl at $R^1$ and $R^5$ is a cycloalkyl having 3 to 6 carbon atoms, such as cyclopropyl, cyclobutyl, cyclopentyl, cyclohexyl and the like.

The alkyl at $R^2$, $R^{2a}$, $R^3$, $R^{3a}$, $R^{4a}$, $R^6$ and $R^7$ is a linear or branched chain alkyl having 1 to 4 carbon atoms, and is exemplified by methyl, ethyl, propyl, isopropyl, butyl, isobutyl, tert-butyl and the like, preferably methyl.

The halogen at $R^2$, $R^3$, $R^6$ and $R^7$ is fluorine, chlorine, bromine or iodine.

The alkoxy at $R^2$, $R^3$, $R^6$ and $R^7$ is a linear or branched chain alkoxy having 1 to 4 carbon atoms, and is exemplified by methoxy, ethoxy, propoxy, isopropoxy, butoxy, tert-butoxy and the like.

The optionally substituted amino at $R^2$, $R^3$, $R^6$ and $R^7$ may be mono or di-substituted with a substituent selected from alkyl having 1 to 4 carbon atoms (as defined above), acyl having 1 to 4 carbon atoms (formyl, acetyl, propionyl and the like) and benzoyl. Examples thereof include amino, methylamino, dimethylamino, ethylamino, diethylamino, formylamino, acetylamino, propionylamino and benzoylamino.

The alkyl, halogen and optionally substituted amino at $R^4$ and $R^8$ are as defined for alkyl, halogen and optionally substituted amino at $R^2$, $R^3$, $R^6$ and $R^7$.

The alkyl of optionally substituted alkyl at $R^5$ is a linear or branched chain alkyl having 1 to 6 carbon atoms, and is exemplified by methyl, ethyl, propyl, isopropyl, butyl, isobutyl, tert-butyl, pentyl, isopentyl, neopentyl, hexyl and the like. Examples of the substituent include halogen (fluorine, chlorine, bromine, iodine), alkoxycarbonyl wherein the alkoxy moiety has 1 to 4 carbon atoms (C1–C4 alkoxy moiety is as defined above) and carboxyl group, and specific examples thereof include fluoromethyl, chloromethyl, 2,2,2-trifluoroethyl, 2,2,2-trichloroethyl, methoxycarbonylmethyl, ethoxycarbonylmethyl, 2-(methoxycarbonyl)ethyl, carboxymethyl, 2-carboxyethyl and the like.

The hydroxyalkyl at $R^5$ is a linear or branched chain alkyl having 1 to 4 carbon atoms (as defined above), which is substituted with hydroxyl group. Examples thereof include hydroxymethyl, 2-hydroxyethyl, 3-hydroxypropyl, 4-hydroxybutyl and the like, preferably 2-hydroxyethyl.

The aminoalkyl at $R^5$ is a linear or branched chain alkyl having 1 to 4 carbon atoms (as defined above), which is substituted with amino. The amino may be substituted with a substituent selected from alkyl having 1 to 4 carbon atoms (as defined above), acyl having 1 to 4 carbon atoms (as defined above) and benzoyl. Examples thereof include aminomethyl, 2-aminoethyl, 3-aminopropyl, 4-aminobutyl, dimethylaminomethyl, diethylaminomethyl, dipropylaminomethyl, dibutylaminomethyl, 2-dimethylaminoethyl, formylaminomethyl, 2-formylaminoethyl, acetylaminomethyl, 2-acetylaminoethyl, benzoylaminomethyl, 2-benzoylaminoethyl and the like.

The alkyl at W and $W^1$ is a linear or branched chain alkyl having 1 to 4 carbon atoms, and is exemplified by methyl, ethyl, propyl, isopropyl, butyl and the like, preferably methyl or ethyl.

The hydroxyalkyl at W is an alkyl having 1 to 4 carbon atoms (as defined above) which is substituted with hydroxyl group, and is exemplified by hydroxymethyl, 2-hydroxyethyl, 3-hydroxypropyl, 4-hydroxybutyl and the like.

The acyloxyalkyl at W is a C1–C4 alkyl (as defined above) substituted with acyloxy having 1 to 4 carbon atoms (formyloxy, acetyloxy, propionyloxy, butyryloxy and the like). Examples thereof include formyloxymethyl, 2-formyloxyethyl, acetyloxymethyl, 2-acetyloxyethyl, 3-acetyloxypropyl, 4-acetyloxybutyl, propionyloxymethyl and the like, preferably 2-acetyloxyethyl.

The aminoalkyl at W is a C1–C4 alkyl (as defined above) substituted with amino. Examples thereof include aminomethyl, aminoethyl, dimethylaminomethyl, diethylaminomethyl and the like.

The hydroxycarbonylalkyl at W and $W^1$ is C1–C4 alkyl (as defined above) substituted with hydroxycarbonyl. Examples thereof include hydroxycarbonylmethyl, 2-hydroxycarbonylethyl, 3-hydroxycarbonylpropyl, 4-hydroxycarbonylbutyl and the like, preferably hydroxycarbonylmethyl and 3-hydroxycarbonylpropyl.

The alkoxycarbonylalkyl at W, $W^1$ is a C1–C4 alkyl (as defined above) substituted with alkoxycarbonyl, wherein the alkoxy moiety has 1 to 4 carbon atoms (as defined above). Examples thereof include methoxycarbonylmethyl, methoxycarbonylethyl, methoxycarbonylpropyl, methoxycarbonylbutyl, ethoxycarbonylmethyl, propoxycarbonylmethyl, isopropoxycarbonylmethyl, butoxycarbonylmethyl and the like, preferably ethoxycarbonylmethyl.

The halogen at X and $X^1$ is fluorine, chlorine, bromine or iodine, preferably chlorine or bromine The alkyl at X is a linear or branched chain alkyl having 1 to 6 carbon atoms, and is exemplified by methyl, ethyl, propyl, isopropyl, butyl, isobutyl, tert-butyl, pentyl, isopentyl, neopentyl, hexyl and the like, preferably alkyl having 1 to 3 carbon atoms, particularly preferably methyl.

The alkoxy at X is a linear or branched chain alkoxy having 1 to 6 carbon atoms, and is exemplified by methoxy, ethoxy, propoxy, isopropoxy, butoxy, isobutoxy, tert-butoxy, pentyloxy, isopentyloxy, neopentyloxy, hexyloxy and the like, particularly preferably alkoxy having 1 to 3 carbon atoms.

The alkenyl at X is a linear or branched chain alkenyl having 2 to 4 carbon atoms, and is exemplified by ethenyl, 1-propenyl, 1-butenyl and the like, particularly preferably ethenyl.

The haloalkyl at X is a linear or branched chain haloalkyl having 1 to 4 carbon atoms, and is exemplified by fluoromethyl, chloromethyl, bromomethyl, trifluoromethyl, 2-fluoroethyl, 2-chloromethyl, 2,2,2-trifluoroethyl and the like, particularly preferably trifluoromethyl.

The alkoxycarbonyl at X and $X^1$ is an alkoxycarbonyl, wherein the alkoxy moiety has 1 to 4 carbon atoms (as defined above). Examples thereof include methoxycarbonyl, ethoxycarbonyl, propoxycarbonyl, isopropoxycarbonyl, butoxycarbonyl, tert-butoxycarbonyl and the like.

The alkynyl at X and $X^1$ is a linear or branched chain alkynyl having 1 to 4 carbon atoms, and is exemplified by ethynyl, 1-propynyl, 1-butynyl and the like, particularly preferably ethynyl.

The halogen at X' is fluorine, chlorine, bromine or iodine, preferably chlorine.

The alkyl at Y is a linear or branched chain alkyl having 1 to 6 carbon atoms, and is exemplified by methyl, ethyl, propyl, isopropyl, butyl, isobutyl, tert-butyl, pentyl, isopentyl, neopentyl, hexyl, isohexyl, neohexyl and the like, particularly preferably alkyl having 4 to 6 carbon atoms.

The hydroxyalkyl at Y is a linear or branched chain C1–C4 alkyl (as defined above) substituted with hydroxyl group. Examples thereof include hydroxymethyl, 2-hydroxyethyl, 3-hydroxypropyl, 4-hydroxybutyl and the like.

The hydroxycarbonylalkyl at Y is C1–C4 alkyl (as defined above) substituted with hydroxycarbonyl. Examples thereof include hydroxycarbonylmethyl, 2-hydroxycarbonylethyl, 3-hydroxycarbonylpropyl, 4-hydroxycarbonylbutyl and the like.

The optionally substituted aminoalkyl at Y is C1–C4 alkyl (as defined above) substituted with amino, wherein the amino may be mono or di-substituted with alkyl having 1 to 4 carbon atoms (as defined above), acyl having 1 to 4 carbon atoms (as defined above) and benzoyl and the like. Examples thereof include aminomethyl, 2-aminoethyl, dimethylaminomethyl, 2-diethylaminomethyl, formylaminomethyl, acetylaminomethyl, 2-formylaminoethyl, 2-acetylaminoethyl, benzoylaminomethyl and the like. The said amino may form cyclic amine, which may have one or two atoms from oxygen atom, sulfur atom and nitrogen atom in the ring. Examples thereof include pyrrolidine, optionally substituted piperidine, homopiperidine, optionally substituted piperazine, optionally substituted homopiperazine, morpholine and thiomorpholine and the like. Specific examples thereof include piperidinomethyl, 2-piperidinoethyl, morpholinomethyl, 2-morpholinoethyl, thiomorpholinomethyl, piperazinomethyl, (4-morpholinopiperidin-1-yl)methyl and the like.

The alkoxy at Y, $Y^1$ and $Y^2$ is a linear or branched chain alkoxy having 1 to 6 carbon atoms, and is exemplified by methoxy, ethoxy, propoxy, isopropoxy, butoxy, isobutoxy, tert-butoxy, pentyloxy, isopentyloxy, neopentyloxy, hexyloxy, isohexyloxy, neohexyloxy and the like, preferably alkoxy having 4 to 6 carbon atoms.

The haloalkoxy at Y and $Y^1$ is a C1–C4 alkoxy (as defined above) substituted with halogen (as defined above). Examples thereof include fluoromethoxy, chloromethoxy, 2-fluoroethoxy, 2,2,2-trifluoroethoxy and the like, preferably 2,2,2-trifluoroethoxy.

The aryloxy at Y and $Y^1$ is phenyloxy, naphthyloxy and the like, preferably phenyloxy.

The cycloalkyloxy at Y and $Y^1$ is a cycloalkyloxy having 3 to 6 carbon atoms, and is exemplified by cyclopentyloxy, cyclohexyloxy and the like, preferably cyclohexyloxy.

The hydroxyalkoxy at Y and $Y^1$ is a linear or branched chain C3–C6 alkoxy substituted with hydroxy. Examples thereof include 3-hydroxypropoxy, 1-methyl-1-hydroxyethoxy, 4-hydroxybutoxy, 5-hydroxypentyloxy and 6-hydroxyhexyloxy.

The hydroxycarbonylalkoxy at Y is a linear or branched chain C1–C4 alkoxy substituted with hydroxycarbonyl. Examples thereof include hydroxycarbonylmethoxy, 2-hydroxycarbonylethoxy, 3-hydroxycarbonylpropoxy and 4-hydroxycarbonylbutoxy.

The optionally substituted aminoalkoxy at Y, $Y^1$ and $Y^2$ is a linear or branched chain C1–C6 alkoxy (as defined above) substituted with amino. The said amino may have a substituent such as alkyl having 1 to 4 carbon atoms (as defined above), acyl having 1 to 4 carbon atoms (as defined above) and benzoyl. The said amino may form cyclic amine which may have one or two atoms from oxygen atom, sulfur atom and nitrogen atom in the ring. Examples thereof include pyrrolidine, optionally substituted piperidine, homopiperidine, optionally substituted piperazine, optionally substituted homopiperazine, morpholine and thiomorpholine and the like. Examples thereof include aminomethoxy, aminoethoxy, aminopropoxy, methylaminomethoxy, dimethylaminomethoxy, 2-dimethylaminoethoxy, formylaminomethoxy, acetylaminomethoxy, propionylaminomethoxy, benzoylaminomethoxy, morpholinomethoxy, 2-morpholinoethoxy, 3-morpholinopropoxy, 2,2-dimethyl-3-morpholinopropoxy, 4-morpholinobutoxy, 5-morpholinopentyloxy, 6-morpholinohexyloxy, thiomorpholinomethoxy, 2-thiomorpholinoethoxy, 3-thiomorpholinopropoxy, 2,2-dimethyl-3-thiomorpholinopropoxy, 4-thiomorpholinobutoxy, 5-thiomorpholinopentyloxy, 6-thiomorpholinohexyloxy, piperidinomethoxy, 2-piperidinoethoxy, 3-piperidinopropoxy, 2,2-dimethyl-3-piperidinopropoxy, 4-piperidinobutoxy, 5-piperidinopentyloxy, 6-piperidinohexyloxy, piperazinomethoxy, 2-piperazinoethoxy, 3-piperazinopropoxy, 2,2-dimethyl-3-piperazinopropoxy, 4-piperazinobutoxy, 5-piperazinopentyloxy, 6-piperazinohexyloxy, 2-pyrrolidinoethoxy, 3-pyrrolidinopropoxy and the like. Of these, 2-dimethylaminoethoxy, 4-morpholinobutoxy, 3-morpholinopropoxy, 2-morpholinoethoxy, morpholinomethoxy and 2,2-dimethyl-3-morpholinopropoxy are preferable.

The alkylthio at Y is that wherein the alkyl moiety has 1 to 6 carbon atoms, and is exemplified by methylthio, ethylthio, propylthio, n-butylthio, pentylthio, neopentylthio, hexylthio and the like.

The hydroxyalkylthio at Y is that wherein the alkyl moiety has 1 to 6 carbon atoms. Examples thereof include hydroxymethylthio, 2-hydroxyethylthio, 3-hydroxypropylthio, 4-hydroxybutylthio, 5-hydroxypentylthio and 6-hydroxyhexylthio.

The hydroxycarbonylalkylthio at Y is that wherein the alkyl moiety has 1 to 4 carbon atoms. Examples thereof include hydroxycarbonylmethylthio, 2-hydroxycarbonylethylthio, 3-hydroxycarbonylpropylthio and 4-hydroxycarbonylbutylthio.

The optionally substituted aminoalkylthio at Y, $Y^1$, $Y^2$ is that wherein the alkyl moiety has a linear or branched chain alkyl having 1 to 6 carbon atoms (as defined above). The said amino is optionally substituted with alkyl having 1 to 4 carbon atoms (as defined above), acyl having 1 to 4 carbon atoms (as defined above) or benzoyl as a substituent. The said amino may form cyclic amine which may have one or two atoms from oxygen atom, sulfur atom and nitrogen atom in the ring. Examples thereof include pyrrolidine, optionally substituted piperidine, homopiperidine, optionally substituted piperazine, optionally substituted homopiperazine, morpholine and thiomorpholine and the like. Specific examples thereof include aminomethylthio, 2-aminoethylthio, 3-aminopropylthio, 4-aminobutylthio, dimethylaminomethylthio, diethylaminomethylthio, 2-dimethylaminoethylthio, dimethylaminoethylthio, 3-dimethylaminopropylthio, 4-dimethylaminobutylthio, formylaminomethylthio, 2-formylaminoethylthio, acetylaminomethylthio, 2-acetylaminoethylthio, benzoylaminomethylthio, 2-benzoylaminoethylthio, morpholinomethylthio, 2-morpholinoethylthio, 3-morpholinopropylthio, 4-morpholinobutylthio, 5-morpholinopentylthio, 6-morpholinohexylthio, thiomorpholinomethylthio, 2-thiomorpholinoethylthio, 3-thiomorpholinopropylthio, 4-thiomorpholinobutylthio, 5-thiomorpholinopentylthio, 6-thiomorpholinohexylthio, piperidinomethylthio, 2-piperidinoethylthio, 3-piperidinopropylthio, 4-piperidinobutylthio, 5-piperidinopentylthio, 6-piperidinohexylthio, piperazinomethylthio, 2-piperazinoethylthio, 3-piperazinopropylthio, 4-piperazinobutylthio, 5-piperazinopentylthio, 6-piperazinohexylthio, 2-pyrrolidinoethylthio and 3-pyrrolidinopropylthio.

The alkyl at $Z^2$ and $Z^3$ is an alkyl having 1 to 4 carbon atoms (as defined above). Examples thereof include methyl, ethyl, propyl, isopropyl, butyl, isobutyl, tert-butyl and the like, preferably ethyl.

The hydroxyalkyl at $Z^2$ and $Z^3$ is a C1–C4 alkyl (as defined above) substituted with hydroxyl group. Examples thereof include hydroxymethyl, 2-hydroxyethyl, 3-hydroxypropyl, 4-hydroxybutyl and the like, preferably 2-hydroxyethyl.

The aminoalkyl at $Z^2$ and $Z^3$ is a C1–C4 alkyl (as defined above) substituted with amino. The amino may be substituted with alkyl having 1 to 4 carbon atoms (as defined above), acyl having 1 to 4 carbon atoms (as defined above) or benzoyl. Examples thereof include aminomethyl, aminoethyl, dimethylaminomethyl, diethylaminomethyl, formylaminomethyl, 2-formylaminoethyl, acetylaminomethyl, 2-acetylaminoethyl, benzoylaminomethyl and the like.

The group at $Z^2$, $Z^3$, $Z^{2a}$ and $Z^{3a}$ that forms, together with the adjacent nitrogen atom, cyclic amine which may have one or two atoms from oxygen atom, sulfur atom and nitrogen atom in the ring is cyclic amine selected from pyrrolidine, optionally substituted piperidine, homopiperidine, optionally substituted piperazine, optionally substituted homopiperazine, morpholine and thiomorpholine.

The substituent of the aforementioned optionally substituted got piperidine is exemplified by hydroxy; carboxy; alkoxycarbonyl wherein the alkoxy moiety has 1 to 4 carbon atoms (as defined above); hydroxyalkyl having 1 to 4 carbon atoms (as defined above); alkoxyalkoxy wherein the alkoxy moiety has 1 to 4 carbon atoms (methoxymethoxy, ethoxymethoxy, propoxymethoxy, butoxymethoxy, 2-methoxyethoxy, 3-methoxypropoxy, 4-methoxybutoxy and the like); carboxyalkylcarbonyloxy wherein the alkyl moiety has 1 to 4 carbon atoms (carboxymethylcarbonyloxy, 2-carboxyethylcarbonyloxy and the like); acyloxy having 1 to 4 carbon atoms (as defined above); benzoyloxy; phenyl; alkylenedioxy having 1 to 4 carbon atoms (methylenedioxy, ethylenedioxy and the like); oxo; amino optionally mono or di-substituted with alkyl having 1 to 4 carbon atoms (as defined above), alkoxyalkyl wherein the alkoxy moiety and alkyl moiety each have 1 to 4 carbon atoms (methoxymethyl, ethoxymethyl, 2-methoxyethyl, 2-ethoxyethyl and the like) or hydroxyalkyl having 1 to 4 carbon atoms (as defined above); cyclic amine selected from piperidine optionally having a substituent (hydroxy, alkoxy having 1 to 4 carbon atoms, oxo and the like), morpholine, thiomorpholine, piperazine optionally having a substituent (alkyl having 1 to 4 carbon atoms, acyl having 1 to 4 carbon atoms and the like) and the like (the said cyclic amine may be N-oxide); morpholinomethyl and the like. Examples thereof include piperidin-1-yl, 4-hydroxypiperidin-1-yl, 4-carboxypiperidin-1-yl, 4-methoxycarbonylpiperidin-1-yl, 4-ethoxycarbonylpiperidin-1-yl, 4-((2-carboxyethyl)carbonyloxy)piperidin-1-yl, 4-benzoyloxypiperidin-1-yl, 4-piperidinopiperidin-1-yl, 4-morpholinopiperidin-1-yl, 4-thiomorpholinopiperidin-1-yl, 4-(N-oxidomorpholino)piperidin-1-yl, 4,4-ethylenedioxypiperidin-1-yl, 4-oxopiperidin-1-yl, 4-aminopiperidin-1-yl, 4-dimethylaminopiperidin-1-yl, 4-(N-(2-hydroxyethyl)amino)piperidin-1-yl, 4-(N,N-bis(2-hydroxyethyl)amino)piperidin-1-yl, 4-(N-(2-hydroxyethyl)-N-methylamino)piperidin-1-yl, 4-(4-methylpiperazin-1-yl)piperidin-1-yl, 4-(N-(2-hydroxyethyl)amino)piperidin-1-yl, 4-(piperazin-1-yl)piperidin-1-yl, 4-(4-(4-acetylpiperazin-1-yl)piperidine)-1-yl, 4-phenylpiperidin-1-yl, 4-(N-(2-methoxyethyl)amino)piperidin-1-yl, 4-(N-(2-methoxyethyl)-N-methylamino)piperidin-1-yl, 4-(N,N-bis(2-methoxyethyl)amino)piperidin-1-yl, 4-methoxymethoxypiperidin-1-yl, 4-(2-methoxyethyl)oxypiperidin-lyl, 4-(2-hydroxyethyl)piperidin-1-yl, 4-(4-hydroxypiperidin-1-yl) piperidin-1-yl, 4-(4-morpholinomethyl)piperidin-1-yl, 4-(4-methoxypiperidin-1-yl)piperidin-1-yl, 4-(4-oxopiperidin-1-yl)piperidin-1-yl and the like.

The substituent of the aforementioned optionally substituted piperazine is exemplified by alkyl having 1 to 4 carbon atoms (as defined above); carboxyalkyl wherein the alkyl moiety has 1 to 4 carbon atoms (carboxylmethyl, carboxyethyl and the like); hydroxyalkyl having 1 to 4 carbon atoms (as defined above); alkoxyalkyl wherein the alkyl moiety and alkoxy moiety have 1 to 4 carbon atoms (as defined above); hydroxyalkoxyalkyl wherein the alkoxy moiety and alkyl moiety each have 1 to 4 carbon atoms (hydroxymethoxymethyl, hydroxyethoxyethyl and the like); carboxy; alkoxycarbonyl wherein the alkoxy moiety has 1 to 4 carbon atoms (as defined above); alkoxycarbonylalkyl wherein the alkoxy moiety and alkyl moiety each have 1 to 4 carbon atoms (as defined above); acyl having 1 to 4 carbon atoms (as defined above); acyloxyalkyl wherein the acyl moiety and alkyl moiety have 1 to 4 carbon atoms (as defined above); optionally substituted aminoalkyl having 1 to 4 carbon atoms (as defined above); carboxyalkylcarbonyloxy wherein the alkyl moiety has 1 to 4 carbon atoms (carboxymethylcarbonyloxy, (2-carboxyethyl)carbonyloxy and the like); heteroaralkyl (C1–C4 alkyl substituted with heteroaryl such as pyridyl, thienyl, furyl and the like); phenyl substituted with a substituent selected from halogen (as defined above), alkyl having 1 to 4 carbon atoms (as defined above) and alkoxy having 1 to 4 carbon atoms (as defined above); 3,4,5,6-tetrahydro-2H-pyran-4-yl; 3,4,5,6-tetrahydro-2H-thiopyran-4-yl; 5-methylisoxazole-4-ylcarbonyl; 2-cyano-3-hydroxyisocrotonoyl and the like. Examples thereof include piperazin-1-yl, 4-methylpiperazin-1-yl, 4-ethylpiperazin-1-yl, 4-hydroxymethylpiperazin-1-yl, 4-(2-hydroxyethyl)piperazin-1-yl, 4-(3-hydroxypropyl)piperazin-1-yl, 4-(tert-butoxycarbonyl)piperazin-1-yl, 4-(ethoxycarbonylmethyl) piperazin-1-yl, 4-(2-ethoxycarbonylethyl)piperazin-1-yl, 4-(3-methoxycarbonylpropyl)piperazin-1-yl, 4-(carboxymethyl)piperazin-1-yl, 4-(2-carboxyethyl)piperazin-1-yl, 4-(3-carboxypropyl)piperazin-1-yl, 4-((2-carboxyethyl)carbonyloxy)piperazin-1-yl, 4-(5-methylisoxazole-4-ylcarbonyl)piperazin-1-yl, 4-(2-cyano-3-hydroxyisocrotonoyl)piperazin-1-yl, 4-(dimethylaminomethyl)piperazin-1-yl, 4-(2-dimethylaminoethyl)piperazin-1-yl, 3,5-dimethyl-4-ethoxycarbonylmethylpiperazin-1-yl, 3,5-dimethyl-4-carboxymethylpiperazin-1-yl, 4-(3-(3-pyridyl)propyl)piperazin-1-yl, 4-(2-(2-hydroxyethoxy)ethyl)piperazin-1-yl, 4-(2-acetyloxyethyl)piperazin-1-yl, 4-(3,4,5,6-tetrahydro-2H-pyran-4-yl)piperazin-1-yl, 4-(3,4,5,6-tetrahydro-2H-thiopyran-4-yl)piperazin-1-yl, 4-(4-chlorophenyl)piperazin-1-yl, 4-(4-fluorophenyl)piperazin-1-yl, 4-(4-methylphenyl)piperazin-1-yl, 4-(4-methoxyphenyl)piperazin-1-yl, 4-methoxymethylpiperazin-1-yl, 4-(2-methoxyethyl)piperazin-1-yl, 4-(3-methoxypropyl)piperazin-1-yl and the like.

The above-mentioned optionally substituted homopiperazine may be substituted with alkyl having 1 to 4 carbon atoms (as defined above) or hydroxyalkyl having 1 to 4 carbon atoms (as defined above). Examples thereof include homopiperazine, 4-(hydroxymethyl)homopiperazin-1-yl, 4-(2-hydroxyethyl)homopiperazin-1-yl, 4-methylhomopiperazin-1-yl and the like.

The optionally substituted saturated heterocycle at Het which contains a hetero atom selected from oxygen atom and nitrogen atom is a 5 or 6-membered ring. The substituent of the said heterocycle is exemplified by alkyl having 1 to 4 carbon atoms (as defined above), arylalkyl (as defined above) and the like. Examples thereof include piperidin-4-yl, 1-methylpiperidin-4-yl, 1-ethylpiperidin-4-yl, 1-benzylpiperidin-4-yl, pyrrolidin-3-yl, 1-methylpyrrolidin-3-yl, 1-ethylpyrrolidin-3-yl, 1-benzylpyrrolidin-3-yl, 3,4,5,6-tetrahydro-2H-pyran-4-yl, 2,3,4,5-tetrahydrofuran-3-yl and the like.

The pharmaceutically acceptable salt of the compound of the present invention is exemplified by salts with inorganic acid such as hydrochloride, hydrobromate, sulfate, phosphate, nitrate and the like, salts with organic acid such as acetate, propionate, succinate, maleate, fumarate, benzoate, citrate, malate, methanesulfonate, benzenesulfonate, p-toluenesulfonate and the like, metal salts such as sodium salt, potassium salt, calcium salt, aluminum salt, magnesium salt and the like when carboxyl group is contained, salts with amine such as triethylamine and the like, and salts with dibasic amino acid such as lysine and the like. In addition, the compound of the present invention encompasses hydrate (1 hydrate, ½ hydrate, ¾ hydrate, ¼ hydrate and the like), solvates and the like. The compound of the present invention further encompasses N-oxide compound.

When the compound of the present invention has a geometric isomer, the present invention encompasses cis compound, trans compound and mixtures thereof. When the present invention contains one or more asymmetric centers in a molecule, various optical isomers exist. The present invention also encompasses optical isomers, racemates, diastereomers and mixtures thereof.

The compound of the present invention can be produced by the following methods.

Method 1: The compound (I) of the present invention can be produced by the following method.

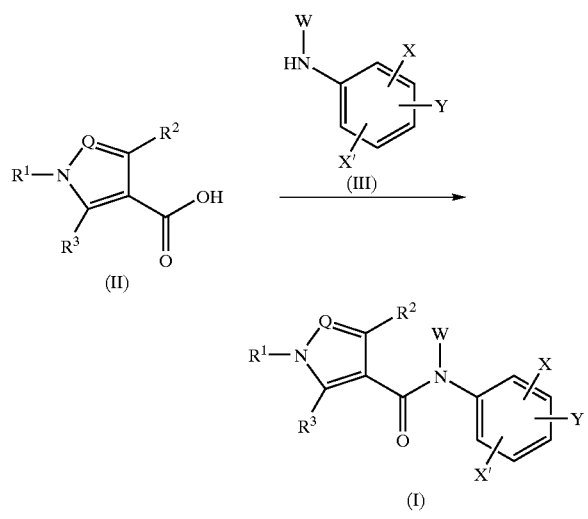

wherein each symbol is as defined above.

The compound (II) and compound (III) are condensed by the following three methods.

(1) The compound (II) is converted to acid halide by a conventional method using a halogenating agent such as thionyl chloride and the like. The acid halide is condensed with compound (III) in a suitable solvent (dichloromethane, dichloroethane, chloroform and the like) in the presence of a base (triethylamine, pyridine, sodium methoxide, sodium ethoxide, sodium hydroxide, potassium hydroxide, sodium acetate and the like) at a temperature of from −20° C. to the refluxing temperature of a solvent for 30 min to 12 h to give compound (I). In this reaction, the base to be used can be used as a solvent.

(2) The compound (II) is condensed with compound (III) as necessary in a suitable solvent (dimethylformamide, dimethyl sulfoxide, methanol, ethanol, isopropyl alcohol, butanol and the like) in the presence of a condensing agent (1,3-dicyclohexylcarbodiimide, 1-ethyl-3-(3-dimethylaminopropyl)carbodiimide, carbonyldiimidazole and the like) or condensed with compound (III) in a suitable solvent (dimethylformamide, dimethyl sulfoxide and the like) in the presence of phosphoric acid ester such as diethyl cyanophosphate and the like and base (triethylamine, pyridine and the like) to give compound (I). The reaction temperature is generally from 0° C. to 100° C. and the reaction time is generally from 30 min to 24 h. The reaction using a condensing agent can be carried out in the presence of 1-hydroxybenztriazole and the like as necessary.

(3) The compound (II) is converted to lower alcohol ester (methyl ester, ethyl ester and the like) or carbonate (mixed acid anhydride with methyl chlorocarbonate, ethyl chlorocarbonate and the like), and condensed with compound (III) in a suitable solvent (methanol, ethanol, isopropyl alcohol, butanol, ethylene glycol, tetrahydrofuran, toluene, nitrobenzene or a mixed solvent thereof and the like) or without solvent in the presence of a base (triethylamine, pyridine, sodium methoxide, sodium ethoxide, sodium hydroxide, potassium hydroxide and the like) at a temperature of from roan temperature to the refluxing temperature of a solvent for 1–24 h to give compound (I).

When W of compound (III) is hydrogen in this reaction, a protecting group generally used in the organic synthetic chemistry, such as tert-butoxycarbonyl group, 9-fluorenylmethoxycarbonyl group, benzyloxycarbonyl group and the like, can be also used for the reaction.

Method 2: A compound (I) wherein W is hydroxyalkyl, alkyl, acyloxyalkyl, aminoalkyl, hydroxycarbonylalkyl or alkoxycarbonylalkyl [compound (I-2)] can be produced by the following method.

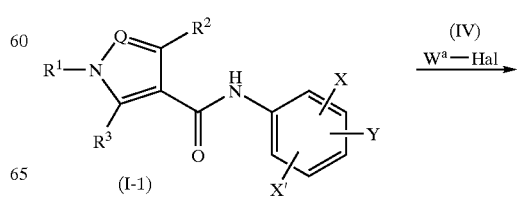

-continued

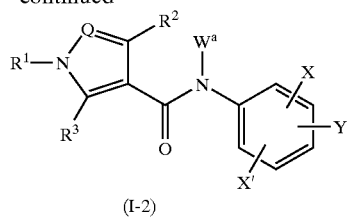

(I-2)

wherein $W^a$ is alkyl, hydroxyalkyl, acyloxyalkyl, aminoalkyl, hydroxycarbonylalkyl or alkoxycarbonylalkyl, Hal is halogen such as chlorine, bromine, iodine and the like, and other symbols are as defined above.

The compound (I-2) can be obtained by reacting compound (I-1) with compound (IV) in a suitable solvent (dimethylformamide, dimethyl sulfoxide, benzene, toluene, xylene, hexane, tetrahydrofuran, diethyl ether, methanol, ethanol, isopropyl alcohol, tert-butyl alcohol and the like) in the presence of a base (sodium hydride, sodium hydroxide, potassium hydroxide, potassium carbonate, sodium carbonate, sodium methoxide, sodium ethoxide, triethylamine and the like) at a temperature of from −20° C. to 100° C. for 30 min to 24 h.

Method 3: A compound (I) wherein $R^1$ is arylalkyl, heteroarylalkyl or cycloalkyl [compound (I-4)] can be produced by the following method.

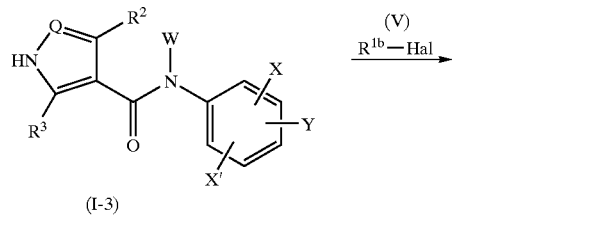

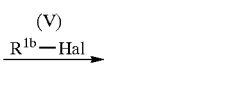

(I-3)

(I-4)

wherein $R^{1b}$ is arylalkyl (same as arylalkyl at $R^1$), heteroarylalkyl (same as heteroarylalkyl at $R^1$) or cycloalkyl (same as cycloalkyl at $R^1$) and other symbols are as defined above.

The compound (I-3) is reacted with compound (V) in a suitable solvent (dimethylformamide, dimethyl sulfoxide, benzene, toluene, xylene, tetrahydrofuran, diethyl ether, methanol, ethanol, isopropyl alcohol, tert-butyl alcohol and the like) in the presence of a base (sodium hydride, sodium hydroxide, potassium hydroxide, potassium carbonate, sodium carbonate, sodium methoxide, sodium ethoxide, triethylamine and the like) at a temperature of from −20° C. to 100° C. for 30 min to 24 h to give compound (I-4).

Method 4: A compound (I) wherein Y is optionally substituted alkoxy, aryloxy, cycloalkyloxy, hydroxyalkoxy, hydroxycarbonylalkoxy, optionally substituted aminoalkoxy, alkylthio, hydroxyalkylthio, hydroxycarbonylalkylthio, optionally substituted aminoalkylthio or a group $N(Z^2)(Z^3)$ [compound (I-6)] can be produced by the following method.

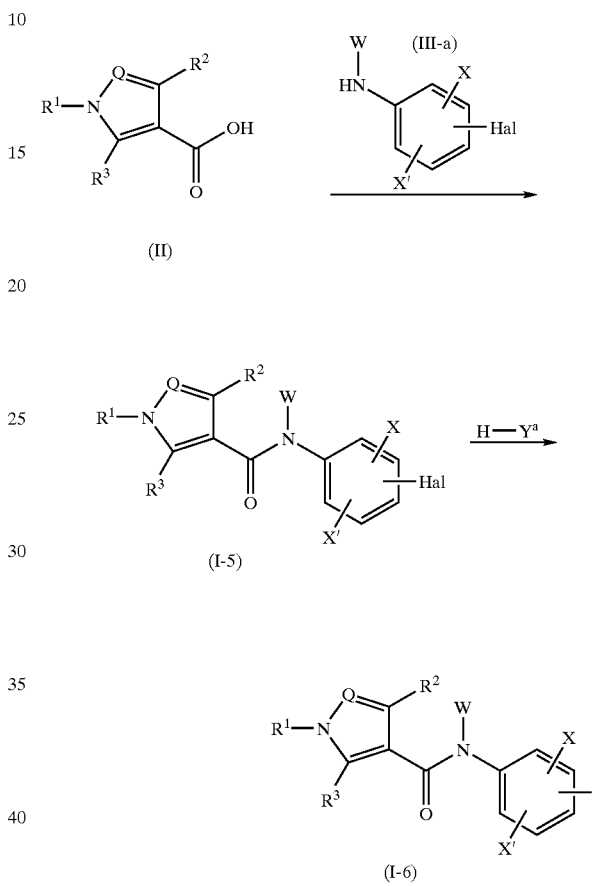

wherein $Y^a$ is optionally substituted alkoxy, aryloxy, cycloalkyloxy, hydroxyalkoxy, hydroxycarbonylalkoxy, optionally substituted aminoalkoxy, alkylthio, hydroxyalkylthio, hydroxycarbonylalkylthio, optionally substituted aminoalkylthio or a group $N(Z^2)(Z^3)$ (wherein $Z^2$ and $Z^3$ are the same or different and each is hydrogen, alkyl, hydroxyalkyl or aminoalkyl, or form cyclic amine together with the adjacent nitrogen atom) and other symbols are as defined above.

The compound (I-5) can be obtained by reacting and treating compound (II) and compound (III-a) in the same manner as in Method 1.

The compound (I-5) is reacted with H—$Y^a$ in a suitable solvent (dimethyl sulfoxide, dimethylformamide, dichloromethane, chloroform and the like) in the presence of a base (triethylamine, pyridine and the like) at a temperature of from 0° C. to the refluxing temperature of the solvent to be used for 30 min to 24 h to give compound (I-6). It is possible to use an excess H—$Y^a$ instead of the base for the reaction.

Method 5: A compound (I) wherein X is alkenyl or alkynyl [compound (I-8)] can be also produced by the following method.

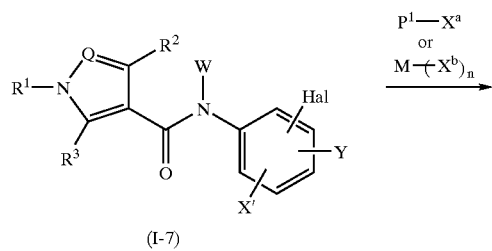

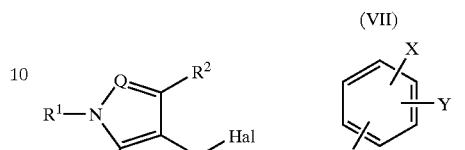

Method 6: A compound (I) wherein W is hydrogen [compound (I-1)] can be also produced by the following method.

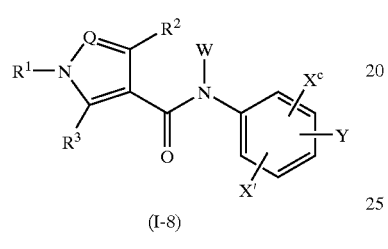

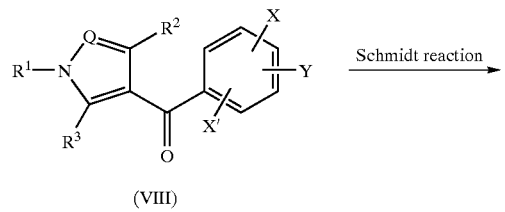

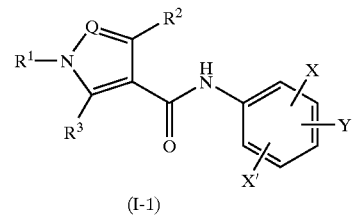

wherein $P^1$ is a protecting group of triple bond such as trimethylsilyl and the like, $X^a$ is alkynyl such as acetylene and the like, M is metal such as tin and the like or boron, $X^b$ is alkenyl such as vinyl and the like, n is an integer of 3 or 4, $X^c$ is alkynyl such as acetylene and the like or alkenyl such as vinyl and the like, and other symbols are as defined above.

The compound (I-7) is subjected to Sonogashira coupling reaction in the presence of a palladium catalyst (bis(triphenylphosphine)palladium dichloride or tetrakis(triphenylphosphine)palladium and the like) using alkyne such as trimethylsilylacetylene and the like, Suzuki coupling reaction using alkenylborane (vinylborane and the like) or Stille coupling reaction using alkenyltin (tetravinyltin and the like) to give compound (I-8). In the Sonogashira coupling reaction, compound (I-7) and compound $P^1$—$X^a$ can be reacted in the presence of a tetrakis(triphenylphosphine)palladium or bis(triphenylphosphine)palladium dichloride and cuprous iodide as a catalyst, wherein the solvent to be used is exemplified by triethylamine, diethylamine, piperidine and the like. The reaction temperature is generally from room temperature to the refluxing temperature of the solvent, and the reaction time is generally 1–24 h. After the Sonogashira coupling reaction, by reacting under moderate alkaline conditions using potassium carbonate, sodium hydroxide and the like in an alcohol solvent such as methanol and the like at a temperature of from room temperature to the refluxing temperature of a solvent for 1–24 h, a compound (I-8) wherein $X^c$ is alkynyl (acetylene and the like) can be obtained.

In the Stille coupling reaction, compound (I-7) is reacted with alkenyltin (tetravinyltin and the like) using tetrakis(triphenylphosphine)palladium and the like as a catalyst to give compound (I-8) wherein $X^c$ is alkenyl (vinyl and the like). The solvent to be used is benzene, toluene, tetrahydrofuran, dimethylformamide, N-methylpyrrolidone and the like. Where necessary, an additive such as lithium chloride and the like, or a base such as triethylamine, diisopropylethylamine and the like is used. The reaction temperature is generally from room temperature to the refluxing temperature of a solvent, and the reaction time is generally 1–24 h.

wherein each symbol is as defined above.

The compound (VI) and compound (VII) are subjected to Friedel-Craft reaction in a suitable solvent (tetrahydrofuran, diethyl ether, ethylene glycol dimethyl ether, dimethylformamide, dimethyl sulfoxide, methylene chloride, chloroform, dichloroethane, acetonitrile, nitromethane, carbon disulfide and the like) or without solvent where necessary in the presence of an acid catalyst (aluminum chloride, aluminum bromide, titanium tetrachloride and the like) at a temperature of from −20° C. to 100° C. for 30 min to 24 h to give compound (VIII). The compound (VIII) is subjected to Schmidt reaction in a suitable solvent (benzene, toluene, xylene and the like, preferably benzene) using a strong acid (sulfuric acid, trifluoroacetic acid and the like) and sodium azide at a temperature of from −20° C. to the refluxing temperature of the solvent for 1–24 h to give compound (I-1).

Method 7: The compound (I-1) can be also produced by the following method.

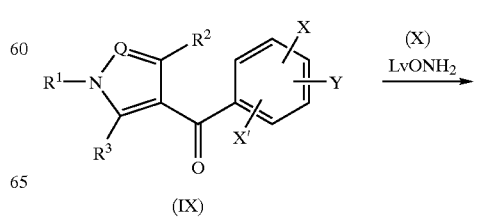

-continued

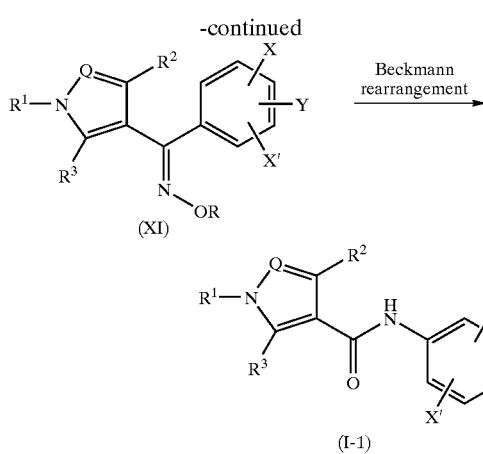

wherein Lv is hydrogen or arylsulfonyl group such as benzenesulfonyl and the like, and other symbols are as defined above.

The compound (IX) and compound (X) are reacted in a suitable solvent (water, methanol, ethanol or a mixed solvent thereof and the like) in the presence of a base (sodium carbonate, potassium carbonate, sodium hydroxide, potassium hydroxide, sodium acetate, triethylamine and the like) at a temperature of from −20° C. to 100° C. for 1–24 h to give compound (XI). The compound (XI) is subjected to Beckmann rearrangement reaction in a suitable solvent (water, dimethyl sulfoxide, dimethylformamide, benzene, toluene, xylene or a mixed solvent thereof and the like) at a temperature of from room temperature to the refluxing temperature of a solvent for 1–24 h to give compound (I-1).

Method 8: When the compound of the present invention has a hydroxyl group, the corresponding ester compound can be obtained by subjecting the compound to condensation generally used in the field of organic synthetic chemistry with a carboxylic acid compound, an acid halide compound or an acid anhydride compound. When the compound of the present invention has a carboxyl group, the corresponding ester compound can be obtained by subjecting the compound to condensation generally used in the field of organic synthetic chemistry with an alcohol compound or phenol compound. Furthermore, when the compound of the present invention has an ester group, the corresponding carboxylic acid compound can be obtained by subjecting the compound to hydrolysis by a conventional method with an acid (hydrochloric acid, sulfuric acid and the like) or a base (sodium hydroxide, potassium hydroxide and the like). When the compound of the present invention has an amino group, the compound can be N-alkylated or N-acylated by a conventional method in the presence of a base (triethylamine, pyridine and the like) using an alkyl halide or acyl halide. When the compound of the present invention has a hydroxyl group, the compound can be converted to carbonyl group or aldehyde group by oxidation known in the field of organic synthetic chemistry using chromic acid-sulfuric acid, chromium oxide (VI)-sulfuric acid-acetone (Jones reagent), chromium oxide (VI)-pyridine complex (Collins reagent), dichromate (sodium dichromate, potassium dichromate and the like)-sulfuric acid, pyridinium chlorochromate (PCC), manganese dioxide, dimethyl sulfoxide-electrophilic activating reagent (dicyclohexylcarbodiimide, acetic anhydride, phosphorus pentaoxide, sulfur trioxide-pyridine complex, anhydrous trifluoroacetic acid, oxalyl chloride, halogen), sodium hypochlorite, potassium hypochlorite, sodium bromite and the like.

Method 9: A compound (II) having a pyrazole ring wherein Q is nitrogen atom, which ring is substituted with alkyl at the 3-position, with hydrogen or alkyl at the 5-posiiton and with carboxy group at the 4-position [compound (II-1)] can be produced by the following method.

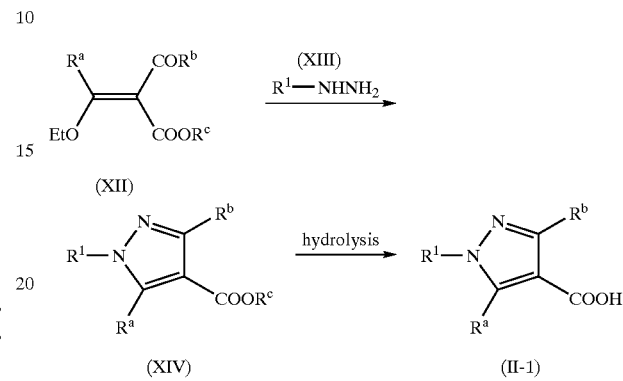

wherein $R^a$ is hydrogen or alkyl having 1 to 4 carbon atoms, $R^b$ and $R^c$ are each alkyl having 1 to 4 carbon atoms, and other symbols are as defined above.

The compound (XII) and compound (XIII) are reacted in a suitable solvent (water, methanol, ethanol, isopropyl alcohol, butanol, ethylene glycol or a mixed solvent thereof) at a temperature of from room temperature to the refluxing temperature of a solvent for 1–24 h to give compound (XIV).

The compound (XIV) is reacted in a suitable solvent (water, methanol, ethanol or a mixed solvent thereof) using an acid (hydrochloric acid, sulfuric acid and the like) or an alkali (sodium hydroxide, potassium hydroxide and the like) at a temperature of from room temperature to the refluxing temperature of a solvent for 1–12 h to give compound (II-1).

The compound (XII) can be produced according to J. Chem. Soc. Perkin Trans I), p. 1875 (1988).

Method 10: A compound (II) having a pyrazole ring wherein Q is nitrogen atom, which ring is substituted with hydrogen or an alkyl at the 3-position, with carboxyl group at the 4-position, and with amino at the 5-position [compound (II-3)] can be produced by the following method.

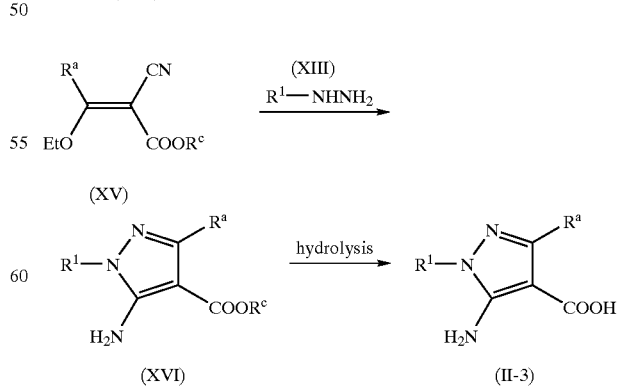

wherein each symbol is as defined above.

The reaction of compound (XV) and compound (XIII) and hydrolysis of compound (XVI) can be conducted under the same reaction condition as in Method 9.

Method 11: A compound (II) having a pyrazole ring wherein Q is nitrogen atom, which ring is substituted with alkyl at the 3-position, with carboxyl group at the 4-position, and with amino at the 5-position [compound (II-2)] can be produced by the following method.

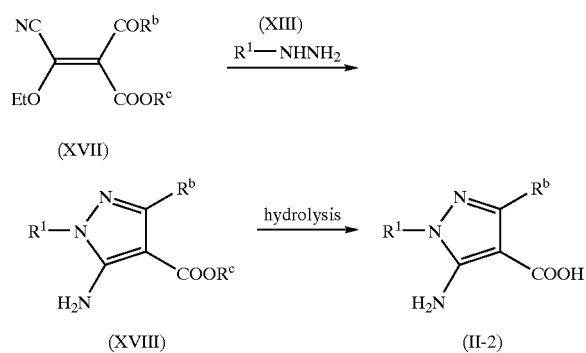

wherein each symbol is as defined above.

The reaction of compound (XVII) and compound (XIII) and hydrolysis of compound (XVIII) can be conducted under the same reaction condition as in Method 9.

Method 12: A compound (II) having a pyrazole ring wherein Q is nitrogen atom, which ring is substituted with hydrogen or alkyl at the 3-position, with carboxyl group at the 4-position, and with hydroxyl group at the 5-position [compound (II-4)] can be produced by the following method.

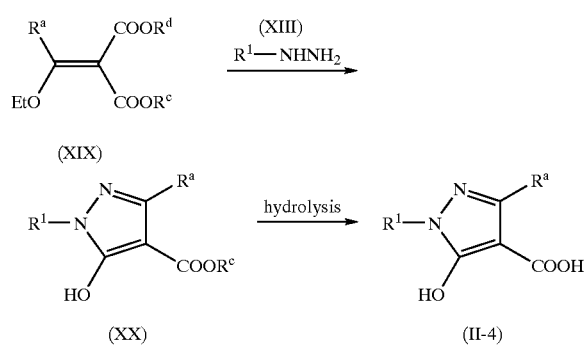

wherein $R^d$ is alkyl having 1 to 4 carbon atoms and other symbols are as defined above.

The reaction of compound (XIX) and compound (XIII) and hydrolysis of compound (XX) can be conducted under the same reaction condition as in Method 9.

Method 13: A compound (II) having a pyrazole ring wherein Q is nitrogen atom, which ring is substituted with hydrogen or alkyl at the 3-position, with alkyl at the 5-position, and with carboxyl group at the 4-position [compound (II-5)] can be produced by the following method.

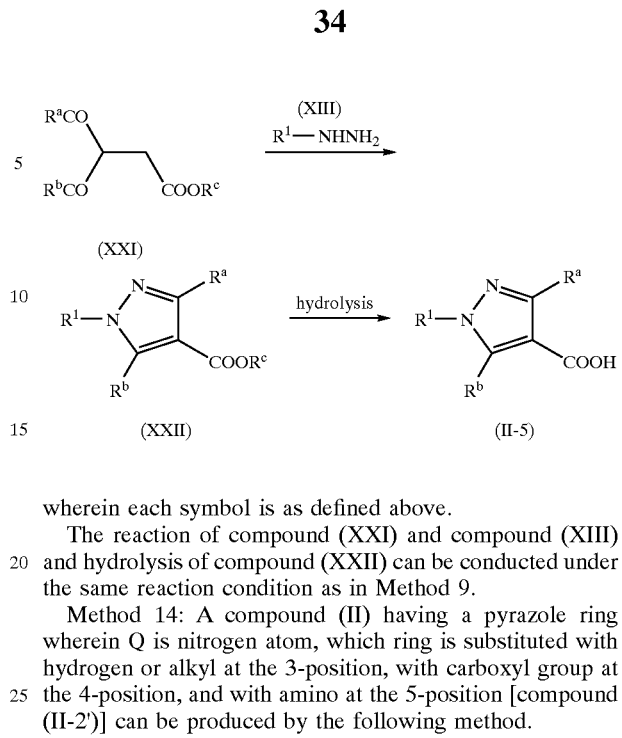

wherein each symbol is as defined above.

The reaction of compound (XXI) and compound (XIII) and hydrolysis of compound (XXII) can be conducted under the same reaction condition as in Method 9.

Method 14: A compound (II) having a pyrazole ring wherein Q is nitrogen atom, which ring is substituted with hydrogen or alkyl at the 3-position, with carboxyl group at the 4-position, and with amino at the 5-position [compound (II-2')] can be produced by the following method.

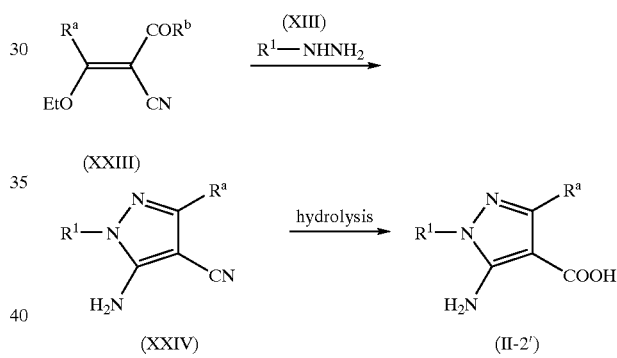

wherein each symbol is as defined above.

The compound (XXIII) and compound (XIII) are reacted in a suitable solvent (water, methanol, ethanol, propanol, butanol, ethylene glycol or a mixed solvent thereof) at a temperature of from room temperature to the refluxing temperature of a solvent for 1–24 h to give compound (XXIV) and the compound (XXIV) is treated by a conventional method with an acid (hydrochloric acid, sulfuric acid and the like) or an alkali (sodium hydroxide, potassium hydroxide and the like) in a suitable solvent (water, methanol, ethanol or a mixed solvent thereof) to give compound (II-2').

Method 15: A compound (II) having substituted amino can be obtained as follows. The carboxyl group of compound (II-2) is protected with a suitable protecting group and reacted with halogenated alkyl in the presence of a base (triethylamine, pyridine and the like), or subjected to reductive N-alkylation with alkylaldehyde in an organic acid (preferably formic acid), followed by deprotection to give a compound having mono or di-substituted amino. The compound (II-2) can be also obtained by hydrolysis after the above-mentioned N-alkylation of compound (XXIV).

Method 16: A compound (II) having a pyrazole ring wherein Q is nitrogen atom, which ring is substituted with chlorine at the 5-position, with hydrogen or alkyl at the 3-position, and with carboxyl group at the 4-position [compound (II-6)] can be produced by the following method.

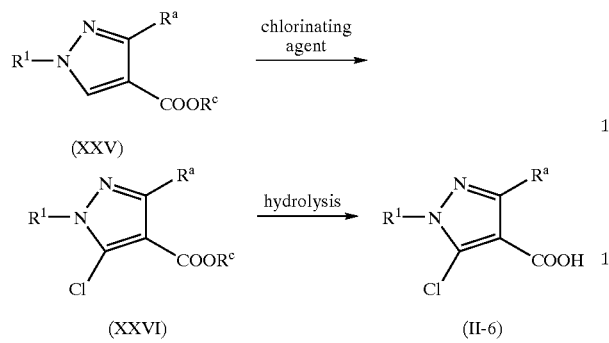

wherein each symbol is as defined above.

The compound (XXV) is reacted with chlorinating agent (sulfuryl chloride and the like) in a suitable solvent (toluene, benzene, n-hexane or a mixed solvent thereof), at a temperature of from room temperature to the refluxing temperature of a solvent for 1–24 h to give compound (XXVI). The compound (XXVI) is hydrolyzed according to a conventional method using an acid (hydrochloric acid, sulfuric acid and the like) or an alkali (sodium hydroxide, potassium hydroxide and the like) to give compound (II-6).

Method 17: A compound (II) wherein $R^1$ is arylalkyl, heteroarylalkyl or cycloalkyl [compound (II-7)] can be produced by the following method.

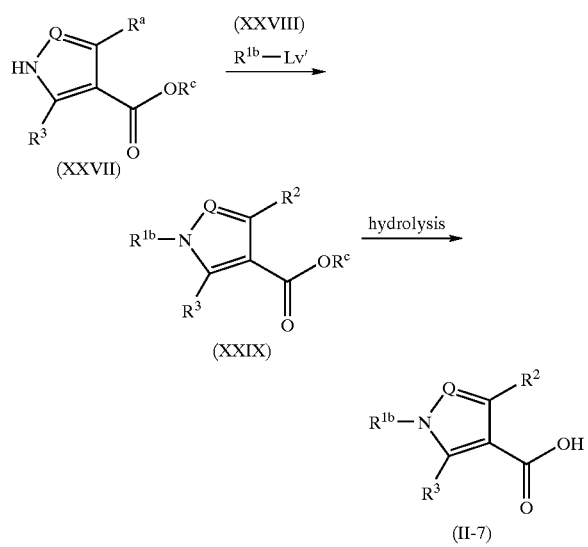

wherein Lv' is a leaving group such as halogen (chlorine, bromine, iodine and the like), methanesulfonyloxy, p-toluenesulfonyloxy and the like, and other symbols are as defined above.

The compound (XXVII) and compound (XXVIII) are reacted in a suitable solvent (dimethylformamide, dimethyl sulfoxide, benzene, toluene, xylene, methylene chloride, chloroform and the like) in the presence of, where necessary, a metal catalyst (copper powder, copper chloride, copper sulfate, silver carbonate, silver nitrate and the like) in a base (potassium carbonate, barium carbonate, sodium hydride and the like) at a temperature of from −20° C. to 100° C. for 1–24 h to give compound (XXIX). The compound (XXIX) is hydrolyzed according to a conventional method using an acid (hydrochloric acid, sulfuric acid and the like) or an alkali (sodium hydroxide, potassium hydroxide and the like) to give compound (II-7).

Method 18: The compound (II-1) can be also produced by the following method.

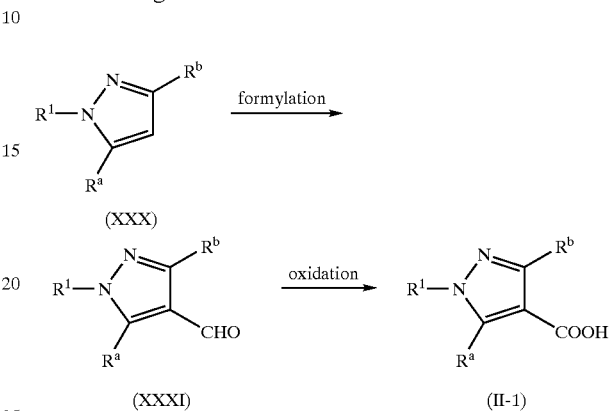

wherein each symbol is as defined above.

The compound (XXX) is subjected to Vilsmeier reaction using phosphorus oxychloride in the presence of N,N-dimethylformamide or N-methylformanilide at a temperature of from room temperature to 100° C. for 1–24 h to give compound (XXXI). The compound (XXXI) is subjected to oxidation with an oxidizing agent (manganese dioxide, potassium permanganate, peroxidate (hydrogen peroxide, m-chloroperbenzoic acid etc.) and the like) in a suitable solvent (water, diethyl ether, tetrahydrofuran, dioxane, acetone, tert-butyl alcohol, methylene chloride, chloroform, hexane, benzene, toluene or a mixed solvent thereof) to give compound (II-1). The compound (XXX) can be obtained according to the method described in Bull. Soc. Chim. France, p. 1346, 1970.

Method 19: The compound (II-1) can be also produced by the following method.

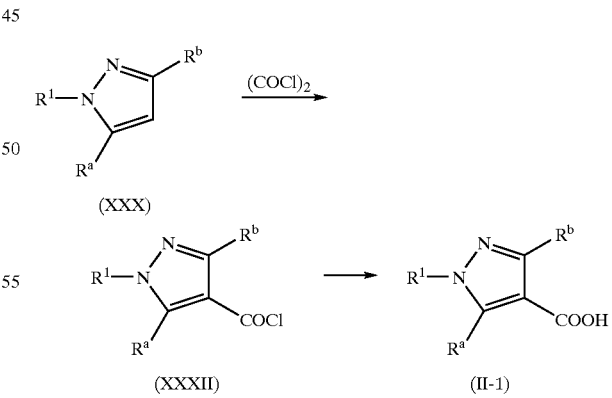

wherein each symbol is as defined above.

The compound (XXX) and oxalyl chloride are reacted at a temperature of from room temperature to the refluxing temperature of a solvent for 1–24 h to give compound (XXXII). The compound (XXXII) is reacted in an aqueous solution for 1–24 h to give compound (II-1).

Method 20: A compound (II) having a pyrrole ring wherein Q is C—R⁴ where R⁴ is hydrogen, which ring is substituted with carboxyl group at the 3-position, and unsubstituted at the 2- and 4-positions [compound (II-8)] can be produced by the following method.

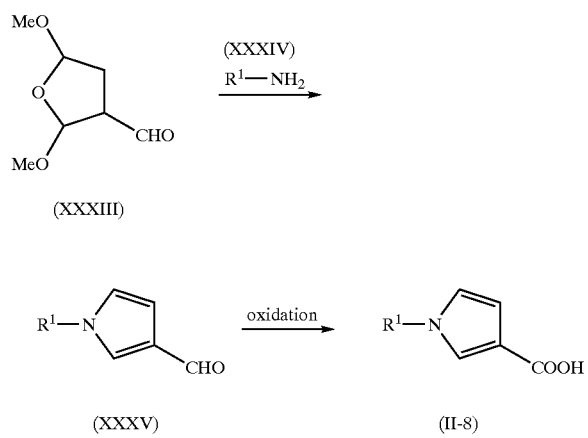

wherein each symbol is as defined above.

The compound (XXXIII) and compound (XXXIV) are reacted in a suitable solvent (diethyl ether, dimethyl ether, n-hexane or a mixed solvent thereof) at a temperature of from room temperature to the refluxing temperature of a solvent for 1–24 h to give compound (XXXV). The compound (XXXV) is subjected to oxidation with an oxidizing agent (manganese dioxide, potassium permanganate, peroxidate (hydrogen peroxide, m-chloroperbenzoic acid etc.) and the like) in the presence of a base (sodium hydroxide, potassium hydroxide, triethylamine, pyridine and the like) to give compound (II-8).

The compound (XXXIII) can be also obtained according to the method described in Synthetic Communications, vol. 13, No. 9, pp. 741–744 (1983). The compound (XXXV) can be also obtained according to the method described in Synthetic Communications, vol. 24, No. 13, p. 1855 (1994).

Method 21: The compound (XXXV) can be also produced by the following method.

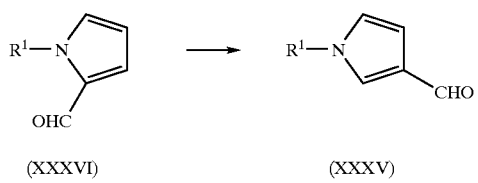

wherein each symbol is as defined above.

The compound (XXXVI) is reacted with trifluoromethanesulfonic acid in a suitable solvent (methylene chloride, chloroform, dichloroethane, benzene, toluene, xylene and the like) at a temperature of from room temperature to the refluxing temperature of a solvent for 1–24 h to give compound (XXXV).

Method 22: The compound (XXXVI) can be produced by the following method.

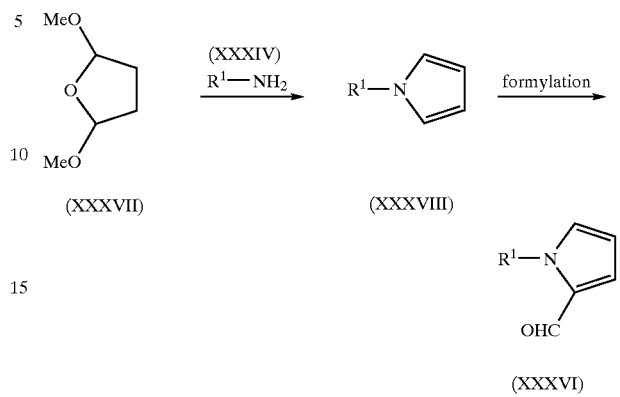

wherein each symbol is as defined above.

The compound (XXXVII) and compound (XXXIV) are reacted in a suitable solvent (diethyl ether, dimethyl ether, n-hexane or a mixed solvent thereof) at a temperature of from room temperature to the refluxing temperature of a solvent for 1–24 h to give compound (XXXVIII). The compound (XXXVIII) is reacted with phosphorus oxychloride using Vilsmeier reaction in the presence of N,N-dimethylformamide or in the presence of N-methylformanilide at a temperature of from room temperature to 100° C. for 1–24 h to give compound (XXXVI).

Method 23: A compound (II) having a pyrrole ring wherein Q is C—Rᵉ, which ring is substituted with alkyl at both the 2- and 5-positions, carboxyl group at the 3-position, and unsubstituted at the 4-position [compound (II-9)] can be produced by the following method.

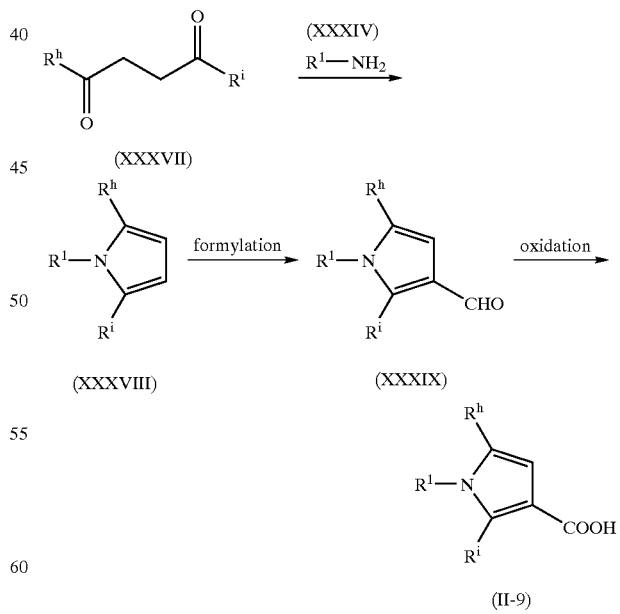

wherein $R^h$ and $R^i$ are each alkyl having 1 to 4 carbon atoms and other symbols are as defined above.

Utilizing the pyrrole synthetic method of Paal-Knorr, compound (XXXVII) and compound (XXXIV) are condensed in N,N-dimethylformamide or without solvent in the presence of an acid catalyst (hydrochloric acid, sulfuric acid and the like) where necessary at a temperature of from 20° C. to 100° C. for 1–24 h to give compound (XXXVIII). The formylation of compound (XXXVIII) and oxidation of compound (XXXIX) can be conducted under the same reaction condition as in Method 20.

Method 24: The compound (II-9) can be also produced by the following method.

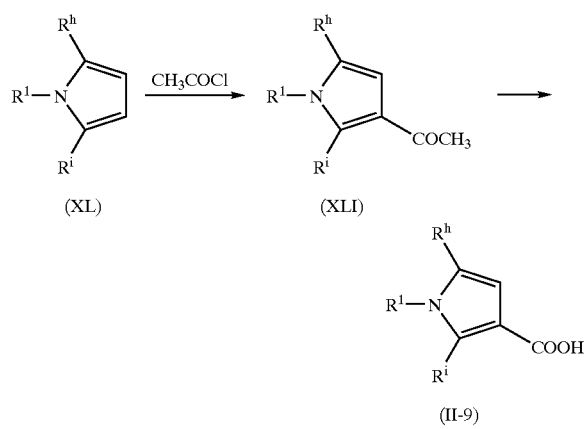

wherein each symbol is as defined above.

The compound (XL) is subjected to Friedel-Craft reaction in a suitable solvent (tetrahydrofuran, dioxane, diethyl ether, dichloromethane, dichloroethane, chloroform, ethylene glycol dimethyl ether, acetonitrile, nitromethane, carbon disulfide or a mixture thereof) or without solvent in the presence of an acid catalyst (aluminum chloride, aluminum bromide, titanium chloride and the like) at a temperature of from −20° C. to 100° C. for 30 min to 24 h to give compound (XLI). Utilizing the Haloform reaction, the compound (XLI) is treated with an alkali (sodium hydroxide, potassium hydroxide and the like) and a halogenating agent (bromine, chlorine, sodium (potassium) hypochlorite, sodium (potassium) hypobromite and the like) in a suitable solvent (water, methanol, ethanol, 1-propanol, 2-propanol, tert-butyl alcohol, tetrahydrofuran, dioxane or a mixture thereof and the like) at a temperature of from −20° C. to 100° C. for 30 min to 24 h to give compound (II-9).

Method 25: A compound (III) wherein W is hydrogen [compound (III-1)] can be produced by the following method.

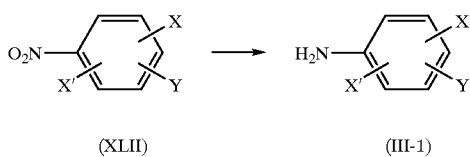

wherein each symbol is as defined above.

The compound (XLII) is subjected to reduction generally used in the field of organic synthetic chemistry, such as a method comprising treating with dilute hydrochloric acid or a catalytic amount of ammonium chloride in a suitable solvent (water, methanol, ethanol, propanol, butanol, ethylene glycol or a mixed solvent thereof and the like) using iron powder or tin chloride as a catalyst; a method comprising treating with a catalytic amount of iron chloride and hydrazine; catalytic reduction by hydrogenation in the presence of a catalyst such as nickel, palladium, platinum and the like; Birch reduction using alkali metal such as sodium, lithium and the like in liquid ammonia, and the like to give compound (III-1). The reaction temperature is generally from room temperature to the refluxing temperature of a solvent and the reaction time is generally 1–24 h.

Method 26: The compound (III-1) can be also produced by the following method.

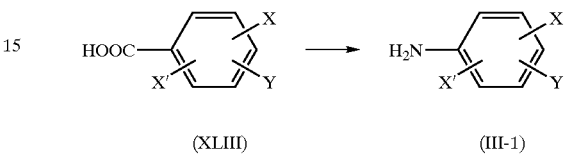

wherein each symbol is as defined above.

Utilizing the Schmidt reaction, compound (XLIII) is treated with sodium azide and a strong acid (sulfuric acid, trifluoroacetic acid and the like) in a suitable solvent (water, methanol, ethanol, propanol, butanol, tert-butyl alcohol, ethylene glycol, benzene, toluene or xylene, preferably benzene) at a temperature of from room temperature to the refluxing temperature of a solvent for 1–24 h, or reacted with triethylamine and diphenylphosphonyl azide in a suitable solvent (methanol, ethanol, isopropyl alcohol, butanol or tert-butanol, preferably tert-butanol) at a temperature of from room temperature to the refluxing temperature of a solvent for 1–24 h, followed by treatment with an acid (hydrochloric acid, sulfuric acid and the like) to give compound (III-1).

Method 27: A compound (XLII) wherein X' is hydrogen, X is halogen substituted at the 3-position, and Y is alkoxy substituted at the 4-position can be produced by the following method.

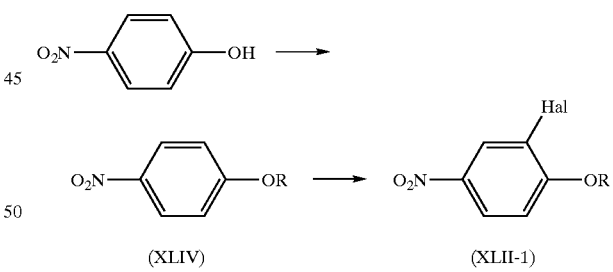

wherein R is alkyl having 1 to 6 carbon atoms and other symbols are as defined above.

4-Nitrophenol is reacted with haloalkyl in a suitable solvent (water, dimethyl sulfoxide, dimethylformamide, toluene, methanol, ethanol, tetrahydrofuran or a mixed solvent thereof and the like) in the presence of a base (sodium hydroxide, sodium hydride, sodium methoxide, sodium ethoxide, butyllithium, butylmagnesium chloride and the like) at a temperature of from −20° C. to the refluxing temperature of a solvent for 1–24 h to give compound (XLIV). The compound (XLIV) is reacted with halogen (chlorine, bromine and the like) at a temperature of from −20° C. to room temperature for 1–24 h to give compound (XLII-1). The compound (XLII-1) can be also obtained by halogenating 4-nitrophenol, followed by alkylation under the above-mentioned reaction conditions.

Method 28: A compound (XLII) wherein X' is hydrogen, X is cyano substituted at the 3-position, and Y is halogen substituted at the 4-position can be produced by the following method.

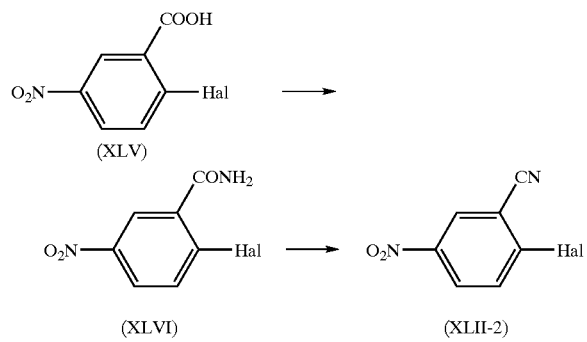

wherein each symbol is as defined above.

The compound (XLV) is treated with a halogenating agent (thionyl chloride and the like) to convert to an acid halide, and reacted with aqueous ammonia at a temperature of from −20° C. to room temperature for 30 min to 24 h to give compound (XLVI). The compound (XLVI) is reacted with toluenesulfonic chloride in the mixed solvent of pyridine-dimethylformamide at a temperature of from room temperature to 100° C. for 1–24 h to give compound (XLII-2).

The compound (XLII-2) can be also produced by reacting compound (XLV) in the presence of a phosphorus pentachloride and toluenesulfonamide at a temperature of from room temperature to 200° C. for 30 min to 12 h and treating with a base such as pyridine and the like at a temperature of from 0° C. to 40° C. for 1–24 h.

Method 29: A compound (XLII) wherein Y is alkoxy, hydroxyalkoxy, hydroxycarbonylalkoxy, optionally substituted aminoalkoxy, alkylthio, hydroxyalkylthio, hydroxycarbonylalkylthio, optionally substituted aminoalkylthio or a group $N(Z^2)(Z^3)$ can be produced by the following method.

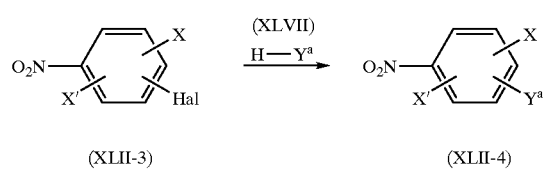

wherein $Y^a$ is alkoxy, hydroxyalkoxy, hydroxycarbonylalkoxy, optionally substituted aminoalkoxy, alkylthio, hydroxyalkylthio, hydroxycarbonylalkylthio, optionally substituted aminoalkylthio or a group $N(Z^2)$ $(Z^3)$, and other symbols are as defined above.

The compound (XLII-3) is reacted with compound (XLVII) in a suitable solvent (chloroform, acetonitrile, water, methanol, ethanol, tetrahydrofuran, diethyl ether, dimethylformamide, dimethyl sulfoxide or a mixed solvent thereof and the like) or without solvent in the presence of a base (sodium hydroxide, sodium methoxide, sodium ethoxide, sodium hydride, butyllithium and the like) at a temperature of from −20° C. to 100° C. for 1–24 h to give compound (XLII-4).

A compound (XLII-4) wherein $Y^a$ is hydroxyalkoxy or hydroxyalkylthio, which is obtained by this method, can be converted to compound (XLII-4) wherein $Y^a$ is aminoalkoxy or aminoalkylthio by treating its hydroxyl group with a halogenating agent such as thionyl chloride and the like, methanesulfonyl chloride or p-toluenesulfonyl chloride etc. to give the corresponding halogenated compound or sulfonyl compound, which is then subjected to the same reaction and treatment with $HN(Z^2)$ $(Z^3)$ as in the above-mentioned method.

Method 30: A compound (XLII) or compound (XLIII) wherein X is cyano can be produced by the following method.

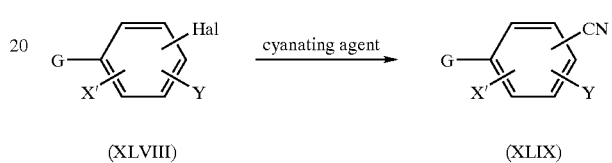

wherein G is nitro or carboxy and other symbols are as defined above.

The compound (XLVIII) is reacted with a cyanide agent (sodium cyanide, potassium cyanide, cuprous cyanide and the like) in a suitable solvent (water, methanol, ethanol, propanol, ethylene glycol, dimethyl sulfoxide, dimethylformamide or a mixed solvent thereof and the like) at a temperature of from room temperature to 100° C. for 1–24 h to give compound (XLIX). The compound (XLIX) can be also produced by using a tetrakis(phenylphosphine)palladium catalyst and a cyanating agent such as zinc cyanide and the like.

Method 31: A compound (III) wherein W is alkyl, hydroxyalkyl, acyloxyalkyl, aminoalkyl, hydroxycarbonylalkyl or alkoxycarbonylalkyl [compound (III-2)] can be produced by the following method.

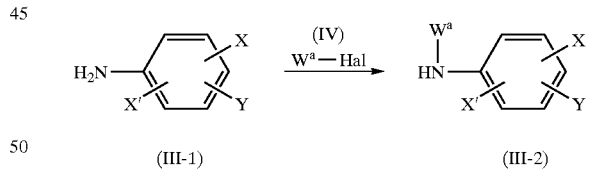

wherein each symbol is as defined above.

The compound (III-1) is reacted with compound (IV) in the presence of sodium acetate without solvent or in a suitable solvent (tetrahydrofuran, diethyl ether, dimethylformamide, dimethyl sulfoxide and the like) at a temperature of from room temperature to 60° C. for 1–24 h to give compound (III-2).

The compound (III-2) can be also obtained by protecting compound (III-1) by a conventional method with tert-butoxycarbonyl and the like conventionally used generally as an amino-protecting group, reacting with compound (IV) in the presence of metal sodium, sodium hydride, sodium amide and the like and then deprotecting by a conventional method.

Method 32: The compound (I-c) can be produced according to the above-mentioned Methods 1–31. The starting compound for the production of compound (I-c), which is the compound of the formula

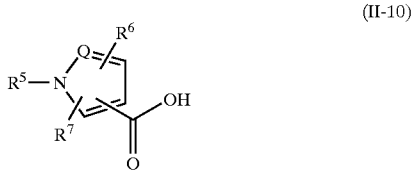

(II-10)

wherein each symbol is as defined above, having a pyrazole ring wherein Q is nitrogen atom, and having carboxyl group at the 3- or 5-position, can be produced by the following method.

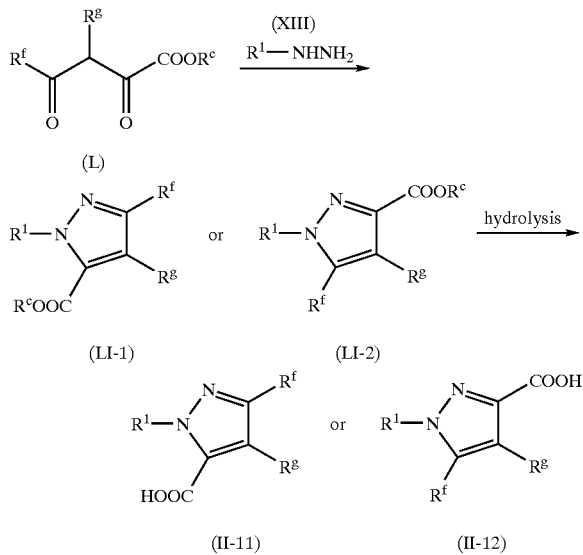

wherein $R^f$ is alkyl having 1 to 4 carbon atoms, $R^g$ is hydrogen or alkyl having 1 to 4 carbon atoms, and other symbols are as defined above.

The reaction of compound (L) and compound (XIII) and hydrolysis of compounds (LI-1) and (LI-2) can be conducted under the same reaction condition as in Method 9.

A compound having a pyrrole ring wherein Q is C—$R^4$ where $R^4$ is hydrogen, which ring having carboxyl group at the 2-position can be produced by the following method

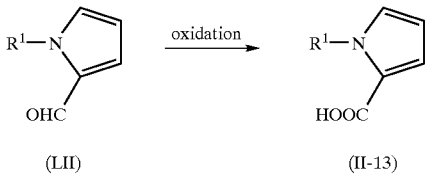

wherein each symbol is as defined above.

The oxidation of compound (LII) can be conducted under the same reaction condition as in Method 20.

The compound of the present invention can be converted to an acid addition salt by treating the compound with an acid (inorganic acid such as hydrochloric acid, hydrobromic acid, sulfuric acid, phosphoric acid, nitric acid and the like, or organic acid such as acetic acid, propionic acid, succinic acid, maleic acid, fumaric acid, benzoic acid, citric acid, malic acid, methanesulfonic acid, benzenesulfonic acid and the like) in, where necessary, a suitable solvent (water, methanol, ethanol, propanol, isopropyl alcohol, diethyl ether, tetrahydrofuran, dioxane and the like). When the obtained compound has a carboxyl group, the compound can be treated with sodium hydroxide, potassium hydroxide, calcium hydroxide, aluminum hydroxide, magnesium hydroxide, sodium alcoholate and the like to give the corresponding metal salt, and treated with amine, such as triethylamine and the like, or a dibasic amino acid, such as lysine and the like, in, where necessary, a suitable solvent to give the corresponding salt. In addition, when crystal of the compound of the present invention is anhydride, it can be treated with water, hydrous solvent or other solvent to give a hydrate (1 hydrate, ½ hydrate, ¾ hydrate, ¼ hydrate and the like) or a solvate. Moreover, the compound of the present invention can be converted to an N-oxide compound by treating it with an oxidizing agent, such as hydrogen peroxide, m-chloroperbenzoic acid and the like, according to a conventional method.

The compound of the present invention thus obtained can be isolated and purified by a method known in the field of organic synthetic chemistry, such as recrystallization, column chromatography and the like. When the obtained product is a racemate, it can be resolved into a desired optically active compound by, for example, fractional crystallization into a salt with an optically active acid or base, or passing through a column packed with an optically active carrier. These can be also produced by using an optically active starting compound and the like.

Because the compound of the present invention and a pharmaceutically acceptable salt thereof have been clarified to show a superior inhibitory effect on the proliferation of activated lymphocytes, particularly inhibitory effect on lymphocyte proliferation dependent on IL-2, IL-4, IL-7, IL-9, IL-13 or IL-15, and inhibit the production of IL-15 as well as inflammatory cytokines (IL-1, IL-6, IL-12, IL-15, IL-18, TNF-a and the like) derived by IL-15, and also inhibit the phosphorylation of tyrosine kinase represented by JAK1, JAK3 and the like, which are present in the signal transduction path involved in the proliferation of lymphocytes derived by IL-15, they can be used for the prophylaxis or treatment of various autoimmune diseases. More particularly, the compound of the present invention and a pharmaceutically acceptable salt thereof can be used for the treatment and prophylaxis of the diseases caused by lymphocyte proliferation, particularly autoimmune diseases such as rheumatoid arthritis, systemic lupus erythematosus, nephrotic syndrome lupus, Hashimoto's struma, multiple sclerosis, myasthenia gravis, type I diabetes, type II adult onset type diabetes mellitus, uveitis, nephrotic syndrome, steroid-dependent and steroid resistant nephrosis, pustulosis palmoplantaris, allergic encephalomyelitis, glomerular nephritis and the like, as well as for infection with pathogenic microorganisms. Moreover, they can be used for the treatment of inflammatory, proliferative and superproliferative dermatosis, onset on the skin of immunity-mediated diseases, such as psoriasis, psoriatic arthritis, atopic eczema (atopic dermatitis), contact dermatitis, eczematous dermatitis, seborrheic dermatitis, lichen planus, pemphigus, bullous pemphigoid, epidermolysis bullosa, urticaria, vascular edema, angitis, erythema, eosinophilic increase of skin, acne, alopecia areata, eosinophilic fasciitis and atherosclerosis. The compound of the present invention more specifically prevents epilation, forms hair germ and/or produces and grows hair, and can be used for recovery of hair by treating female or male pattern alopecia and senile alopecia.

The compound of the present invention is also applicable to respiratory diseases, such as sarcoidosis, fibroid lung, idiopathic interstitial pneumonia and reversible obstructive airway diseases, and to the treatment of symptoms such as asthma including bronchial asthma, infantile asthma, allergic asthma, intrinsic asthma, extrinsic asthma and dust asthma, particularly chronic and intractable asthma (e.g., late asthma and airway irritation), bronchitis and the like. The compound of the present invention can be used for the treatment of liver disorders related to ischemia. It is also effective for particular eye diseases such as conjunctivitis, keratoconjunctivitis, keratitis, vernal conjunctivitis, Behcet disease-related uveitis, herpetic keratitis, keratoconus, corneal epithelial degeneration, keratoleukoma, ocular pemphigus, Mooren's ulcer, scleritis, Graves, disease, severe intraocular inflammation and the like.

The compound of the present invention can be used for the prophylaxis or treatment of mucosal or vascular inflammation [e.g., leukotriene B4-mediated disease, gastric ulcer, vascular injury caused by thrombosis and ischemic disease, ischemic intestinal disease, inflammatory bowel disease (e.g., Crohn's disease and ulcerative colitis), necrotizing enterocolitis] and bowel injury relating to thermal burn. The composition of the present invention can be also used for the prophylaxis or treatment of renal diseases such as interstitial nephritis, Goodpasture's syndrome, hemolytic uremic syndrome and diabetic nephropathy; nervous disease selected from multiple myositis, Guillain-Barre syndrome, Meniere's disease and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, granulocytopenia and anerythroplasia; diseases of bone such as osteoporosis; respiratory diseases such as sarcoidosis, fibroid lung and idiopathic interstitial pneumonia; dermatosis such as dermatomyositis, leukoderma vulgaris, ichthyosis vulgaris, photoallergic sensitivity and skin T-cell lymphoma; circulatory diseases such as arteriosclerosis, aortitis, polyarteritis nodosa and myocardiopathy; collagen diseases such as scleroderma, Wegener's granulomatosis and Sjögren's syndrome; adiposis; eosinophilic fasciitis; periodontal disease; nephrotic syndrome; hemolytic uremic syndrome; and muscular dystrophy.

The compound of the present invention is suitable for the prophylaxis or treatment of bowel inflammation/allergy, such as Coeliac disease, proctitis, eosinophilic gastroenteritis, mastocytosis, Crohn's disease and ulcerative colitis; and allergic diseases related to food, which shows symptoms directly unrelated to the gastrointestinal tract, such as migraine, rhinitis and eczema. Due to the liver regeneration activity and/or hepatocyte hypertrophy and hyperplasia promoting activity, the compound of the present invention can be used for the prophylaxis or treatment of liver diseases such as immunogenic diseases (e.g., chronic autoimmune liver diseases including autoimmune hepatitis, primary biliary cirrhosis and sclerosing cholangitis), partial hepatic resection, acute liver necrosis (necrosis due to toxin, viral hepatitis, shock or oxygen deficiency), viral hepatitis type B, non-A non-B viral hepatitis and cirrhosis.

Where the case demands, the compound of the present invention can be also used for the prophylaxis or treatment of malignant rheumatoid arthritis, amyloidosis, fulminant hepatitis, Shy-Drager syndrome, pustular psoriasis, Behcet's disease, systemic lupus erythematodes, endocrine ophthalmopathy, progressive systemic sclerosis, mixed connective tissue disease, aortitis syndrome, Wegener's granulomatosis, active chronic hepatitis, Evans syndrome, pollinosis, idiopathic hypoparathyroidism, Addison's disease (autoimmune adrenalitis), autoimmune orchitis, autoimmune oophoritis, cold hemagglutinin disease, paroxysmal cold hemoglobinuria, pernicious anemia, adult T cells leukemia, autoimmune atrophic gastritis, lupoid hepatitis, tubulointerstitial nephritis, membranous nephropathy, amyotrophic lateral sclerosis, rheumatic fever, postmyocardial infarction syndrome and sympathetic ophthalmia.

Where the case demands, the compound of the present invention or a pharmaceutically acceptable salt thereof can be used along with other antirheumatic drug (gold compound, penicillamine, bucillamine, lobenzarit, actarit, salazosulfapyridine and the like), immunosuppressive agent, steroidal drug (prednisolone, methylprednisolone, dexamethasone, hydrocortisone and the like) or nonsteroidal anti-inflammatory drug and the like. The immunosuppressive agent is particularly preferably the one selected from azathioprine, cyclophosphamide, methotrexate, brequinar sodium, deoxyspergualin, mizoribine, 2-morpholinoethyl mycophenolate, cyclosporin, rapamycin, tacrolimus hydrate, leflunomide, OKT-3, anti TNF-α antibody, anti IL-6 antibody and FTY720 (EP627406-B1). The nonsteroidal anti-inflammatory drug is exemplified by aspirin, indomethacin, indomethacin farnesil, diclofenac sodium, alclofenac, amfenac sodium, ibuprofen, ketoprofen, loxoprofen sodium, naproxen, pranoprofen, zaltoprofen, mefenamic acid, flufenamic acid, tolufenamic acid, phenylbutazone, ketophenylbutazone, piroxicam, tenoxicam, ampiroxicam and the like.

As mentioned above, the compound of the present invention and a pharmaceutically acceptable salt thereof have a novel action mechanism, which is different from that of existing antirheumatic drugs, immunosuppressive agents, steroidal drugs, nonsteroidal anti-inflammatory drugs and the like used for the treatment of various autoimmune diseases. Thus, they are expected to show a synergistic action when combined with the above-mentioned existing pharmaceutical agents.

When the compound of the present invention or a pharmaceutically salt thereof is used as a pharmaceutical agent, the inventive compound is admixed with a pharmaceutically acceptable carrier (e.g., excipient, binder, disintegrator, corrective, corrigent, emulsifier, diluent, solubilizer and the like) to give a pharmaceutical composition or pharmaceutical preparation, which is formulated into tablet, pill, capsule, granule, powder, syrup, emulsion, elixir, suspension, solution, injection, infusion, eye drop, eye ointment, suppository, ointment, lotion and the like and administered orally or parenterally.

A pharmaceutical composition can be formulated according to a typical method. In the present specification, the "parenteral" includes subcutaneous injection, intravenous injection, intramuscular injection, intraperitoneal injection, drip, instillation and the like. A preparation for injection such as sterile aqueous suspension for injection and oily suspension for injection can be prepared according to the method known in this field using a suitable dispersing agent, moisturizing agent or suspending agent. The sterile preparation for injection may be a sterile injectable solution or suspension in a nontoxic, parenterally administrable diluent or solvent such as an aqueous solution and the like. Examples of usable vehicle and solvent include water, Ringer solution, isotonic brine and the like. It is also possible to use sterile nonvolatile oil as a typical solvent or suspending solvent. Any nonvolatile oil or fatty acid can be used for this end, which may be natural, synthetic or semi-synthetic fatty oil or fatty acid, or natural, synthetic or semi-synthetic mono, di or tri-glycerides. When an injection is prepared, a suitable suspending agent, nonionic surfactant, solubilizer and the like may be combined as necessary. Suppositories for intrarectal administration can be produced by admixing a drug with a suitable nonirritative excipient, such as cocoa butter and polyethylene glycols, and the like that are solid at normal temperature but become liquid at the temperature in the intestine and melt in rectum to release the drug. The solid dosage form for oral administration includes the abovementioned powder, granule, tablet, pill, capsule and the like. In such a dosage form, the active ingredient compound can contain at least one additive such as sucrose, lactose, cellulose sugar, mannitol, maltitol, dextran, starches, agar, arginates, chitins, chitosans, pectines, tragacanth, gum arabic, gelatins, collagens, casein, albumin, synthetic or semi-synthetic polymers and glycerides. Such dosage product can generally contain other additives such as inert diluent, lubricants such as magnesium stearate, preservatives such as parabens, sorbins and the like, antioxidant such as ascorbic acid, α-tocopherol, cysteine and the like, disintegrators, binders, thickeners, buffer agent, sweetener, flavors, perfumes and the like. Tablets and pills may be further entericcoated. A liquid agent for oral administration may be those approved as medicines, such as emulsion, syrup, elixir, suspension, solution and the like, which may contain an inert diluent generally used in this field, such as water and the like. When preparing an eye drop, an aqueous liquid or aqueous solution, particularly a sterile injectable aqueous solution is used. Such liquid for instillation may contain various additives as appropriate, such as buffer, isotonicity agent, solubilizer, preservative, thickener, chelating agent, pH adjusting agent, flavor and the like. When an ointment is prepared, an oleaginous base, an emulsion base, a water-soluble base, a suspension base and the like are used, and a dissolution/absorption accelerator can be also added as appropriate. When a lotion is prepared, the compound is dispersed in a liquid medium or partially dissolved therein and admixed with emulsifier, dissolution/absorption accelerator, thickener and stabilizer as appropriate.

Moreover, by combining the compound of the formula (I) of the present invention or a pharmaceutically acceptable salt thereof with one or more pharmaceutical agents selected from an antirheumatic drug, an immunosuppressive agent, a steroidal drug and a nonsteroidal anti-inflammatory drug, a superior therapeutic effect can be expected. As used herein, by the "combination" is meant a combination composition of the compound of the present invention or a pharmaceutically acceptable salt thereof, with one or more pharmaceutical agents selected from an antirheumatic drug, an immunosuppressive agent, a steroidal drug and a nonsteroidal anti-inflammatory drug, and the use as an enhancer of the effect of one or more pharmaceutical agents selected from an antirheumatic drug, an immunosuppressive agent, a steroidal drug and a nonsteroidal anti-inflammatory drug, which enhancer contains the compound of the present invention or a pharmaceutically acceptable salt thereof. It also includes simultaneous or time interval use of two or more active ingredient compounds upon mixing or without mixing, as well as use upon combination and the combination. The medicine of the present invention characterized by the combination of the above-mentioned compound of the formula (I) or a pharmaceutically acceptable salt thereof with one or more pharmaceutical agents selected from an antirheumatic drug, an immunosuppressive agent, a steroidal drug and a nonsteroidal anti-inflammatory drug is free of any particular limitation as long as the compound of the formula (I) of the present invention or a pharmaceutically acceptable salt thereof is combined with one or more pharmaceutical agents selected from an antirheumatic drug, an immunosuppressive agent, a steroidal drug and a nonsteroidal anti-inflammatory drug. For example, (A) a compound of the formula (I) or a pharmaceutically acceptable salt thereof, and (B) one or more pharmaceutical agents selected from an antirheumatic drug, an immunosuppressive agent, a steroidal drug and a nonsteroidal anti-inflammatory drug may be set to give a preparation for general administration, or they may be admixed in advance to give a composition. The combination medicine of the present invention may be obtained by, for example, mixing a compound of the formula (I) or a pharmaceutically acceptable salt thereof and one or more pharmaceutical agents selected from an antirheumatic drug, an immunosuppressive agent, a steroidal drug and a nonsteroidal anti-inflammatory drug according to a known production method for producing a pharmaceutical preparation, while using a pharmaceutically acceptable diluent, excipient and the like, to give a single preparation. Alternatively, they may be respectively prepared into a preparation using a pharmaceutically acceptable diluent, excipient and the like on demand, or into a combined preparation (set, kit, pack) containing respective agents prepared separately in one container. For example, the combination medicine of the present invention may be (1) a combination preparation wherein a preparation, which may be independent or in combination, containing a compound of the formula (I) or a pharmaceutically acceptable salt thereof, and one or more pharmaceutical agents selected from an antirheumatic drug, an immunosuppressive agent, a steroidal drug and a nonsteroidal anti-inflammatory drug are packaged, or (2) a composition containing a compound of the formula (I) or a pharmaceutically acceptable salt thereof and one or more pharmaceutical agents selected from an antirheumatic drug, an immunosuppressive agent, a steroidal drug and a nonsteroidal anti-inflammatory drug.

The administration route of the combination medicine of the present invention is the same as the administration route of the above-mentioned medicine containing the compound of the present invention, which may be an oral administration or parenteral administration and determined in consideration of concrete target disease site and the like. When the compound of the present invention or a pharmaceutically acceptable salt thereof and one or more pharmaceutical agents selected from an antirheumatic drug, an immunosuppressive agent, a steroidal drug and a nonsteroidal anti-inflammatory drug are prepared separately, these may be administered separately, simultaneously or at time intervals to a single subject via the same route or different routes. When the combination medicine of the present invention is administered, the compound of the present invention or a pharmaceutically acceptable salt thereof, and one or more pharmaceutical agents selected from an antirheumatic drug, an immunosuppressive agent, a steroidal drug and a nonsteroidal anti-inflammatory drug are each prepared by the above-mentioned conventional method and used for administration.

When the compound of the present invention or a pharmaceutically acceptable salt thereof is used as a medicine or a combination medicine, the dose is determined in consideration of the age, body weight, general health condition, sex, diet, administration time, administration method, clearance rate, combination of drugs, level of disease for which the patient is under treatment and other factors.

The compound of the present invention and pharmaceutically acceptable salts thereof are low toxic and can be used safely. When the compound or a pharmaceutically acceptable salt thereof is used alone, the daily dose varies depending on the conditions and body weight of patients, the kind of the compound, administration route and the like. In the case of parenteral use, it is about 0.01–100 mg/person/day, preferably 0.01–500 mg/person/day for subcutaneous injection, intravenous injection, intramuscular injection and intrarectal injection, and in case of oral use, it is about 0.01–1000 mg/person/day, preferably 0.01–500 mg/person/day.

When the compound of the present invention or a pharmaceutically acceptable salt thereof is used as a combination medicine, the daily dose varies depending on the condition and body weight of patients, the kind of the compound, administration route and the like. For example, it is administered parenterally in a dose of about 0.01–100 mg/person/day, preferably 0.01–10 mg/person/day, subcutaneously, intravenously, intramuscularly or intrarectally, or orally in a dose of about 0.01–1000 mg/person/day, preferably 0.01–100 mg/person/day. When an antirheumatic drug, an immunosuppressive agent, a steroidal drug or a nonsteroidal anti-inflammatory drug is used as a combination medicine, the daily dose varies depending on the condition and body weight of patients, the kind of the compound, administration route and the like. For example, it is administered parenterally in a dose of about 0.001–500 mg/person/day, preferably 0.001–50 mg/person/day, subcutaneously, intravenously, intramuscularly or intrarectally, or orally in a dose of about 0.001–5000 mg/person/day, preferably 0.001–500 mg/person/day.

BEST MODE OF EMBODIMENT OF THE INVENTION

The present invention is explained in more detail in the following by way of Starting Material Synthesis Examples, Examples, Formulation Example and Experimental Examples that do not limit the present invention in any way. In the Examples, Me means methyl, Et means ethyl, iPr means isopropyl, tBu means tert-butyl, TBDMS means tert-butyldimethylsilyl and DMF means dimethylformamide.

Starting Material Synthesis Example 1

1-(4-Fluorophenyl)-5-methylpyrazole-4-carboxylic acid

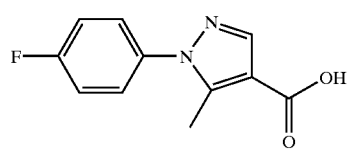

4-Fluorophenylhydrazine (15.5 g) and ethyl 2-ethoxymethyleneacetoacetate (22.9 g) synthesized according to the method described in J. Chem. Soc. Perkin trans. I, p. 1875, 1988 were stirred in ethanol (200 ml) at a refluxing temperature for 2 h. After the evaporation of the solvent, the residue was recrystallized from a mixed solvent of ethyl acetate-n-hexane to give ethyl 1-(4-fluorophenyl)-5-methylpyrazole-4-carboxylate (17.7 g), melting point: 48–49° C.

Then, ethyl 1-(4-fluorophenyl)-5-methylpyrazole-4-carboxylate (17.7 g) and sodium hydroxide (3.5 g) were added to a mixed solvent of ethanol (80 ml)-water (80 ml), and the mixture was stirred at a refluxing temperature for 2 h. After the reaction, ethanol was evaporated and dilute hydrochloric acid was added. The mixture was extracted with ethyl acetate. The organic layer was dried over anhydrous magnesium sulfate, and the solvent was evaporated. The residue was recrystallized from ethyl acetate to give the title compound (12.3 g), melting point: 165–166° C.

Starting Material Synthesis Example 2

1-Phenyl-5-methylpyrazole-4-carboxylic acid

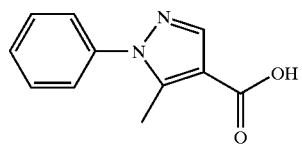

By the reaction and treatment in the same manner as in Starting Material Synthesis Example 1, except that phenylhydrazine was used instead of 4-fluorophenylhydrazine, the title compound was obtained, melting point: 118° C.

Starting Material Synthesis Example 3

1-(4-Methylphenyl)-5-methylpyrazole-4-carboxylic acid

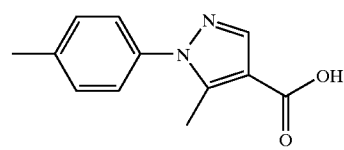

By the reaction and treatment in the same manner as in Starting Material Synthesis Example 1, except that 4-methylphenylhydrazine was used instead of 4-fluorophenylhydrazine, the title compound was obtained, melting point: 203° C.

Starting Material Synthesis Example 4

1-(2,4-Difluorophenyl)-5-methylpyrazole-4-carboxylic acid

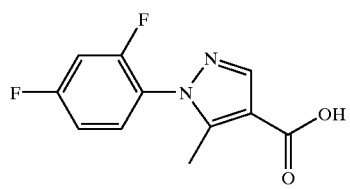

By the reaction and treatment in the same manner as in Starting Material Synthesis Example 1, except that 2,4-difluorophenylhydrazine was used instead of 4-fluorophenylhydrazine, the title compound was obtained, melting point: 183–184° C.

Starting Material Synthesis Example 5

1-(2-Chloro-5-trifluoromethylphenyl)-5-methylpyrazole-4-carboxylic acid

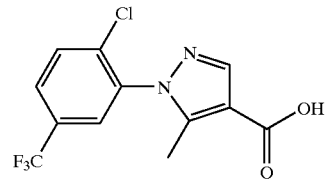

By the reaction and treatment in the same manner as in Starting Material Synthesis Example 1, except that 2-chloro-5-trifluoromethylphenylhydrazine was used instead of 4-fluorophenylhydrazine, the title compound was obtained, melting point: 124–125° C.

Starting Material Synthesis Example 6

1-(4-Methoxyphenyl)-5-methylpyrazole-4-carboxylic acid

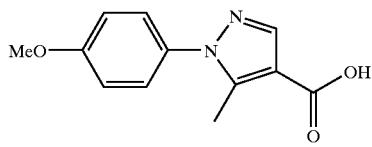

By the reaction and treatment in the same manner as in Starting Material Synthesis Example 1, except that 4-methoxyphenylhydrazine was used instead of 4-fluorophenylhydrazine, the title compound was obtained, melting point: 213–214° C.

Starting Material Synthesis Example 7

1-(3-Trifluoromethylphenyl)-5-methylpyrazole-4-carboxylic acid

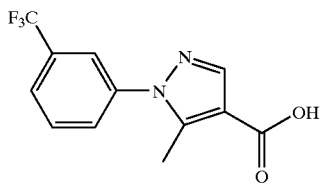

By the reaction and treatment in the same manner as in Starting Material Synthesis Example 1, except that 3-trifluoromethylphenylhydrazine was used instead of 4-fluorophenylhydrazine, the title compound was obtained, melting point: 153–154° C.

Starting Material Synthesis Example 8

1-(4-Chlorophenyl)-5-methylpyrazole-4-carboxylic acid

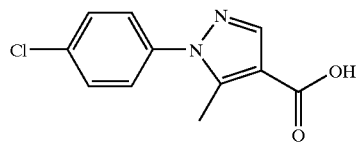

By the reaction and treatment in the same manner as in Starting Material Synthesis Example 1, except that 4-chlorophenylhydrazine was used instead of 4-fluorophenylhydrazine, the title compound was obtained, melting point: 199–200° C.

Starting Material Synthesis Example 9

1,5-Dimethylpyrazole-4-carboxylic acid

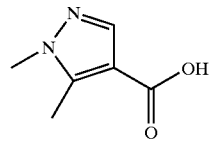

By the reaction and treatment in the same manner as in Starting Material Synthesis Example 1, except that methylhydrazine was used instead of 4-fluorophenylhydrazine, the title compound was obtained, melting point: 230° C. (decomposition).

Starting Material Synthesis Example 10

5-Methylpyrazole-4-carboxylic acid

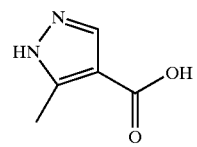

By the reaction and treatment in the same manner as in Starting Material Synthesis Example 1, except that hydrazine was used instead of 4-fluorophenylhydrazine, the title compound was obtained, melting point: 223° C.

Starting Material Synthesis Example 11

1-Cyclohexyl-5-methylpyrazole-4-carboxylic acid

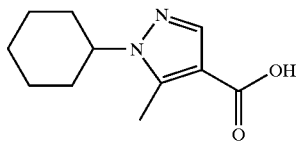

By the reaction and treatment in the same manner as in Starting Material Synthesis Example 1, except that cyclohexylhydrazine was used instead of 4-fluorophenylhydrazine, the title compound was obtained, melting point: 153–154° C.

Starting Material Synthesis Example 12

1-tert-Butyl-5-methylpyrazole-4-carboxylic acid

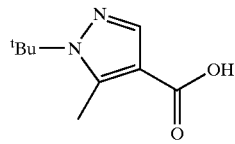

By the reaction and treatment in the same manner as in Starting Material Synthesis Example 1, except that tert-butylhydrazine was used instead of 4-fluorophenylhydrazine, the title compound was obtained, melting point: 213–214° C.

Starting Material Synthesis Example 13

1-(2-Hydroxyethyl)-5-methylpyrazole-4-carboxylic acid

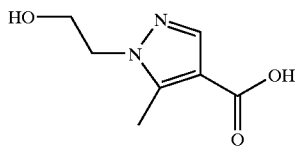

By the reaction and treatment in the same manner as in Starting Material Synthesis Example 1, except that 2-hydroxyethylhydrazine was used instead of 4-fluorophenylhydrazine, the title compound was obtained, melting point: 203° C.

Starting Material Synthesis Example 14

1-(2,2,2-Trifluoroethyl)-5-methylpyrazole-4-carboxylic acid

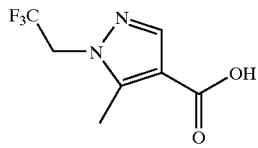

By the reaction and treatment in the same manner as in Starting Material Synthesis Example 1, except that (2,2,2-trifluoroethyl)hydrazine was used instead of 4-fluorophenylhydrazine, the title compound was obtained, melting point: 188–190° C.

Starting Material Synthesis Example 15

1-(4-Fluorophenyl)-3-methylpyrazole-4-carboxylic acid (1) Ethyl 5-amino-1-(4-fluorophenyl)-3-methylpyrazole-4-carboxylate

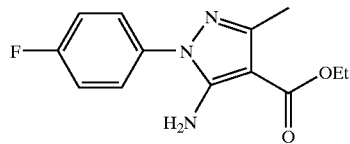

4-Fluorophenylhydrazine (25 g) and ethyl 2-cyano-3-ethoxy-3-methylacrylate (32 g) were stirred in ethanol (130 ml) at a refluxing temperature for 3 h. The solvent was evaporated and diisopropyl ether was added to the residue to allow crystallization. The crystals were recrystallized from a mixed solvent of ethyl acetate-n-hexane to give the title compound (10.7 g), melting point: 129–131° C.

(2) Ethyl 1-(4-fluorophenyl)-3-methylpyrazole-4-carboxylate

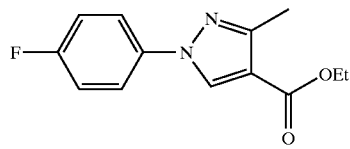

To a tetrahydrofuran solution (50 ml) containing ethyl 5-amino]1-(4-fluorophenyl)-3-methylpyrazole-4-carboxylate (10.5 g) was added isoamyl nitrite (14 g) and the mixture was stirred at a refluxing temperature for 2 h. The mixture was treated with aqueous potassium carbonate solution and extracted with ethyl acetate. The organic layer was dried over anhydrous magnesium sulfate and the solvent was evaporated under reduced pressure. n-Hexane was added to the obtained residue to allow crystallization. The crystals were recrystallized from a mixed solvent of ethyl acetate-n-hexane to give the title compound (7.8 g), melting point: 103–104° C.

(3) 1-(4-Fluorophenyl)-3-methylpyrazole-4-carboxylic acid

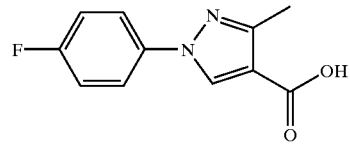

To a mixed solvent of ethanol (40 ml) and water (40 ml) were added ethyl 1-(4-fluorophenyl)-3-methylpyrazole-4-carboxylate (8.5 g) and sodium hydroxide (1.66 g), and the mixture was stirred at a refluxing temperature for 2 h. After the reaction, ethanol was evaporated and to the residue was added dilute hydrochloric acid. The obtained solid was recrystallized from aqueous methanol solution to give the title compound, melting point: 194–195° C Starting Material Synthesis Example 16

1-Phenyl-3-methylpyrazole-4-carboxylic acid

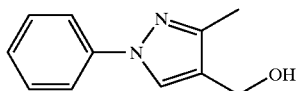

By the reaction and treatment in the same manner as in Starting Material Synthesis Example 15, except that phenylhydrazine was used instead of 4-fluorophenylhydrazine, the title compound was obtained, melting point: 194–195° C.

Starting Material Synthesis Example 17

1-(2,4-Difluorophenyl)-3-methylpyrazole-4-carboxylic acid

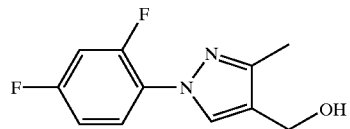

By the reaction and treatment in the same manner as in Starting Material Synthesis Example 15, except that 2,4-difluorophenylhydrazine was used instead of 4-fluorophenylhydrazine, the title compound was obtained, melting point: 245–247° C.

Starting Material Synthesis Example 18

1-(4-Methoxyphenyl)-3-methylpyrazole-4-carboxylic acid

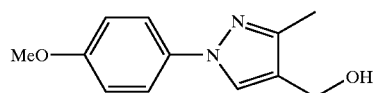

By the reaction and treatment in the same manner as in Starting Material Synthesis Example 15, except that 4-methoxyphenylhydrazine was used instead of 4-fluorophenylhydrazine, the title compound was obtained, melting point: 176–178° C.

Starting Material Synthesis Example 19

1-(2-Chloro-5-trifluoromethylphenyl)-3-methylpyrazole-4-carboxylic acid

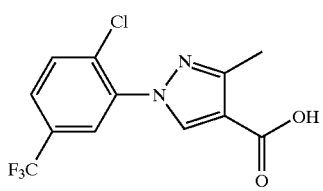

By the reaction and treatment in the same manner as in Starting Material Synthesis Example 15, except that 2-chloro-5-trifluoromethylphenylhydrazine was used instead of 4-fluorophenylhydrazine, the title compound was obtained, melting point: 206–208° C.

Starting Material Synthesis Example 20

1-(3-Trifluoromethylphenyl)-3-methylpyrazole-4-carboxylic acid

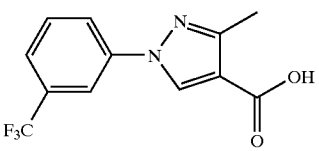

By the reaction and treatment in the same manner as in Starting Material Synthesis Example 15, except that 3-trifluoromethylphenylhydrazine was used instead of 4-fluorophenylhydrazine, the title compound was obtained, melting point: 166–168° C.

Starting Material Synthesis Example 21

1,3-Dimethylpyrazole-4-carboxylic acid

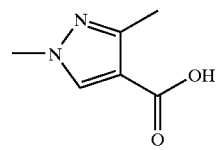

By the reaction and treatment in the same manner as in Starting Material Synthesis Example 15, except that methylhydrazine was used instead of 4-fluorophenylhydrazine, the title compound was obtained, melting point: 191–192° C.

Starting Material Synthesis Example 22

1-(4-Fluorophenyl)pyrazole-4-carboxylic acid (1) Ethyl 5-amino-1-(4-fluorophenyl)pyrazole-4-carboxylate

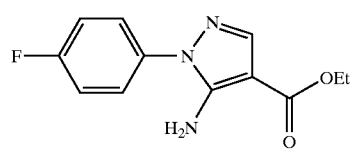

4-Fluorophenylhydrazine (20 g) and ethyl 2-cyano-3-ethoxyacrylate (26.7 g) were added to ethanol (200 ml), and the mixture was stirred at a refluxing temperature for 1 h. After cooling, the precipitated crystals were recrystallized from aqueous ethanol solution to give the title compound (38.9 g), melting point: 154–155° C.

(2) Ethyl 1-(4-fluorophenyl)pyrazole-4-carboxylate

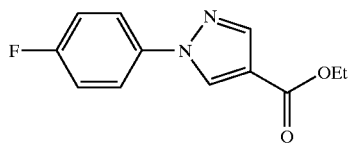

Ethyl 5-amino-1-(4-fluorophenyl)pyrazole-4-carboxylate (15 g) was dissolved in tetrahydrofuran (150 ml) and isoamyl nitrite (21.2 g) was added. The mixture was stirred at a refluxing temperature for 2 h. After cooling, the precipitated crystals were recrystallized from a mixed solvent of ethyl acetate-n-hexane to give the title compound (10.6 g).
$^1$H-NMR(270 MHz, CDCl$_3$) δ(ppm):1.37(3H, dd, J=6.6, 7.3 Hz), 4.33(2H, dd, J=6.6, 7.3 Hz),7.14–7.19(2H, m), 7.63–7.70(2H, m), 8.01(1H, s), 8.34(1H, (3) 1-(4-Fluorophenyl)pyrazole-4-carboxylic acid

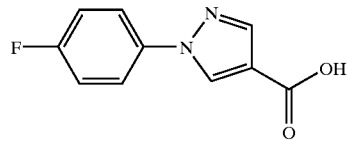

Ethyl 1-(4-fluorophenyl)pyrazole-4-carboxylate (10.6 g) was dissolved in a mixed solvent of ethanol (80 ml) and water (80 ml), and sodium hydroxide (2.2 g) was added. The mixture was stirred at a refluxing temperature for 30 min. After evaporation of ethanol, dilute hydrochloric acid was added to the residue. The obtained solid was recrystallized from aqueous methanol solution to give the title compound (8.9 g), melting point: 244–247° C.

Starting Material Synthesis Example 23

1-(2,2,2-Trifluoroethyl)pyrazole-4-carboxylic acid

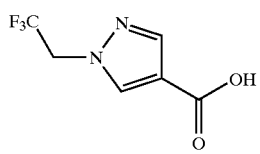

By the reaction and treatment in the same manner as in Starting Material Synthesis Example 22, except that 2,2,2 -trifluoroethylhydrazine was used instead of 4-fluorophenylhydrazine, the title compound was obtained, melting point: 160–162° C.

Starting Material Synthesis Example 24

Pyrazole-4-carboxylic acid

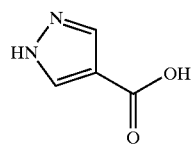

By the reaction and treatment in the same manner as in Starting Material Synthesis Example 22, except that hydrazine was used instead of 4-fluorophenylhydrazine, the title compound was obtained, melting point: 227–228° C.

Starting Material Synthesis Example 25

5-Chloro-1-(4-fluorophenyl)pyrazole-4-carboxylic acid

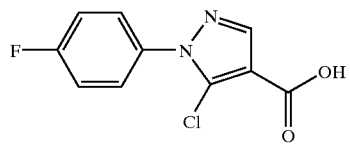

Ethyl 5-amino-1-(4-fluorophenyl)pyrazole-4-carboxylate (5.4 g) was dissolved in 12N hydrochloric acid, and aqueous solution (10 ml) containing sodium nitrite (4.5 g) was added dropwise thereto under ice-cooling, which was followed by stirring for 2 h. An aqueous solution (10 ml) containing copper(I) chloride (10.7 g) was added and the mixture was stirred for 30 min. The mixture was warmed to room temperature and stirred further for 2 h. Solid was filtered off with Celite and ethyl acetate was added to the filtrate to separate the organic layer. The organic layer was washed with saturated brine and dried over anhydrous magnesium sulfate, after which the solvent was evaporated under reduced pressure. n-Hexane was added to the obtained residue to allow crystallization. The crystals were recrystallized from a mixed solvent of ethyl acetate-n-hexane to give ethyl 5-chloro-1-(4-fluorophenyl)pyrazole-4-carboxylate (3.5 g), melting point: 70–72° C.

Ethyl 5-chloro-1-(4-fluorophenyl) pyrazole-4-carboxylate (3.5 g) was dissolved in a mixed solvent of ethanol (30 ml) and water (30 ml). Sodium hydroxide (0.62 g) was added and the mixture was stirred at a refluxing temperature for 30 min. Ethanol was evaporated and dilute hydrochloric acid was added. The obtained solid was recrystallized from an aqueous methanol solution to give the title compound (2.9 g), melting point: 230–231° C.

Starting Material Synthesis Example 26

Ethyl 1-(4-fluorophenyl)-5-hydroxypyrazole-4-carboxylate

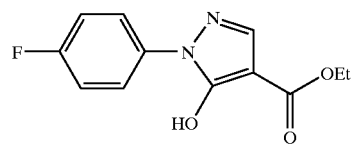

To ethanol (30 ml) were added 4-fluorophenylhydrazine (7.75 g) and ethyl ethoxymethylenemalonate (2.5 g), and the mixture was refluxed for 3 h. The solvent was evaporated under reduced pressure and diisopropyl ether was added to the residue to allow crystallization. The crystals were recrystallized from a mixed solvent of ethyl acetate-diisopropyl ether to give the title compound (2.5 g), melting point: 127–128° C.

Starting Material Synthesis Example 27

1-(4-Fluorophenyl)-3,5-dimethylpyrazole-4-carboxylic acid

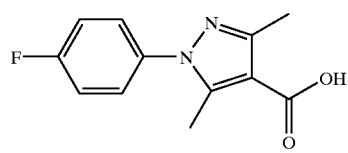

4-Fluorophenylhydrazine (7.75 g) and ethyl diacetoacetate (10.6 g) were added to ethanol (30 ml) and the mixture was refluxed for 3 h. The solvent was evaporated under reduced pressure and diisopropyl ether was added to the residue to allow crystallization. The crystals were recrystallized from a mixed solvent of ethyl acetate-diisopropyl ether to give ethyl 1-(4-fluorophenyl)-3,5-dimethylpyrazole-4-carboxylate (15.5 g), melting point: 59–60° C.

Then, ethyl 1-(4-fluorophenyl)-3,5-dimethylpyrazole-4-carboxylate (15.5 g) was dissolved in a mixed solvent of ethanol (30 ml) and water (30 ml). Sodium hydroxide (2.75 g) was added and the mixture was stirred at a refluxing temperature for 30 min. After evaporation of ethanol, dilute hydrochloric acid was added to the residue. The obtained solid was recrystallized from aqueous methanol solution to give the title compound (11.5 g), melting point: 219–220° C.

Starting Material Synthesis Example 28

Ethyl 1-(4-fluorophenyl)-3-methylpyrazole-5-carboxylate and ethyl 1-(4-fluorophenyl)-5-methylpyrazole-3-carboxylate

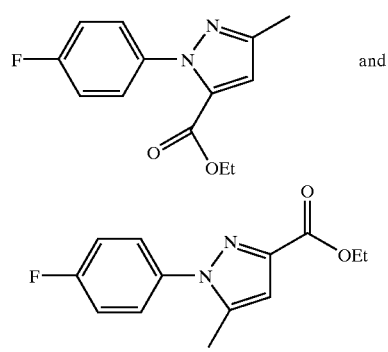

To ethanol (30 ml) were added 4-fluorophenylhydrazine (5 g) and ethyl 2,4-dioxovalerate (10.6 g) and the mixture was refluxed for 3 h. The solvent was evaporated under reduced pressure and the obtained residue was purified by silica gel column chromatography (mobile phase: chloroform) to give ethyl 1-(4-fluorophenyl)-3-methylpyrazole-5-carboxylate (2 g) and ethyl 1-(4-fluorophenyl)-5-methylpyrazole-3-carboxylate (3 g).

Ethyl 1-(4-fluorophenyl)-3-methylpyrazole-5-carboxylate:

$^1$H-NMR(270 MHz, CDCl$_3$) δ(ppm):1.37(3H,t, J=7.3 Hz), 2.34(3H, s), 4.22(2H, q, J=7.3 Hz), 6.80(1H, s), 7.08–7.14(2H, m), 7.35–7.40(2H, m)

Ethyl 1-(4-fluorophenyl)-5-methylpyrazole-3-carboxylate:

$^1$H-NMR(270 MHz, CDCl$_3$) δ(ppm):1.39(3H, dd, J=6.6, 7.3 Hz), 2.30(3H, s), 4.41(2H, dd, J=6.6, 7.3 Hz), 6.73(1H, s), 7.13–7.19(2H, m), 7.41–7.46(2H, m)

Starting Material Synthesis Example 29

1-(4-Fluorophenyl)-3-methylpyrazole-5-carboxylic acid

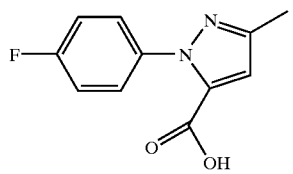

Ethyl 1-(4-fluorophenyl)-3-methylpyrazole-5-carboxylate (2 g) was dissolved in a mixed solvent of ethanol (10 ml)

and water (10 ml) and sodium hydroxide (0.4 g) was added. The mixture was stirred at a refluxing temperature for 30 min. Ethanol was evaporated and to the residue was added dilute hydrochloric acid. The obtained solid was recrystallized from aqueous methanol solution to give the title compound (1.4 g), melting point: 188° C.

Starting Material Synthesis Example 30

1-(4-Fluorophenyl)-5-methylpyrazole-3-carboxylic acid

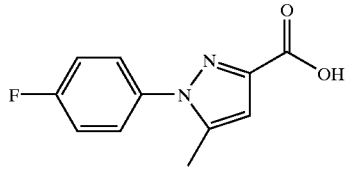

Ethyl 1-(4-fluorophenyl)-5-methylpyrazole-3-carboxylate (3 g) was dissolved in a mixed solvent of ethanol (15 ml) and water (15 ml) and sodium hydroxide (0.6 g) was added. The mixture was stirred at a refluxing temperature for 30 min. Ethanol was evaporated and to the residue was added dilute hydrochloric acid. The obtained solid was recrystallized from aqueous methanol solution to give the title compound (2.1 g), melting point: 177° C.

Starting Material Synthesis Example 31

Methyl 1-methyl-3-phenylpyrazole-5-carboxylate and methyl 1-methyl-5-phenylpyrazole-3-carboxylate

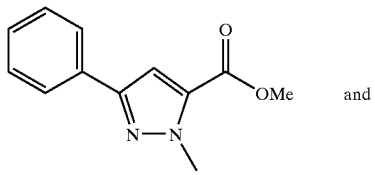 and

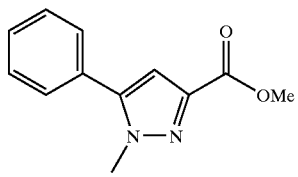

Methyl 4-phenyl-2,4-dioxobutanoate (10 g) obtained by acetophenone and dimethyl oxalate as starting materials and methylhydrazine were reacted in ethanol (60 ml) at a refluxing temperature for 1 h. The solvent was evaporated under reduced pressure, and the obtained residue was purified by silica gel column chromatography (mobile phase:dichloromethane) to give methyl 1-methyl-3-phenylpyrazole-5-carboxylate (3.0 g) and methyl 1-methyl-5-phenylpyrazole-3-carboxylate (3.6 g).

Methyl 1-methyl-3-phenylpyrazole-5-carboxylate:

melting point: 54–56° C.

Methyl 1-methyl-5-phenylpyrazole-3-carboxylate:

$^1$H-NMR(270 MHz, CDCl$_3$) δ(ppm):3.93(3H, s), 3.94 (3H, s), 6.84(1H, s), 7.33–7.48(5H, m)

Starting Material Synthesis Example 32

1-Methyl-3-phenylpyrazole-5-carboxylic acid

Methyl 1-methyl-3-phenylpyrazole-5-carboxylate (3 g) was dissolved in a mixed solvent of ethanol (20 ml) and water (20 ml) and sodium hydroxide (0.7 g) was added. The mixture was stirred at a refluxing temperature for 30 min. Ethanol was evaporated and to the residue was added dilute hydrochloric acid. The obtained solid was recrystallized from aqueous methanol solution to give the title compound (0.8 g), melting point: 189° C.

Starting Material Compound 33

1-Methyl-5-phenylpyrazole-3-carboxylic acid

Methyl 1-methyl-5-phenylpyrazole-3-carboxylate (3.6 g) was dissolved in a mixed solvent of ethanol (20 ml) and water (20 ml) and sodium hydroxide (0.8 g) was added. The mixture was stirred at a refluxing temperature for 30 min. Ethanol was evaporated and to the residue was added dilute hydrochloric acid. The obtained solid was recrystallized from aqueous methanol solution to give the title compound (2.2 g), melting point: 149–150° C.

Starting Material Synthesis Example 34

1-(4-Fluorophenyl)pyrrole-2-carboxylic acid and 1-(4-fluorophenyl)pyrrole-3-carboxylic acid

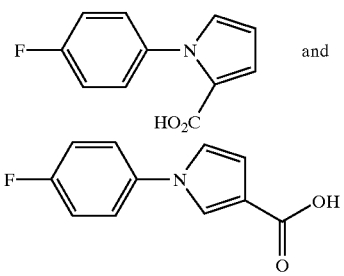

(1) 4-Fluoroaniline (100 g) and 2,5-dimethoxytetrahydrofuran (124.9 g) were added to acetic acid (500 ml) and the mixture was stirred at a refluxing temperature for 1 h. After cooling to room temperature, the reaction mixture was added to water (2.5 Liters) and the mixture was stirred further for 30 min. The precipitated crystals were recrystallized from a mixed solvent of methanol-acetone (ratio=2:1) to give 1-(4-fluorophenyl)pyrrole (156 g), melting point: 57–58° C.

(2) Phosphorus oxychloride (96.5 g) was added dropwise under ice-cooling to dimethylformamide (600 ml) containing 1-(4-fluorophenyl)pyrrole (101 g) over 1 h, and the mixture was stirred for 2 h and at room temperature for one day. The reaction mixture was added to 3 Liters of aqueous solution containing potassium carbonate (130 g) and extracted with ethyl acetate. The organic layer was washed with saturated brine, dried over anhydrous magnesium sulfate and the solvent was evaporated under reduced pressure. Diisopropyl ether was added to the residue to allow crystallization. The crystals were recrystallized from a mixed solvent of toluene-diisopropyl ether (ratio=1:10) to give 1-(4-fluorophenyl)-2-formylpyrrole (43 g), melting point: 82–83° C.

(3) Potassium permanganate (30.1 g) and sodium hydroxide (15.3 g) were added to a solution of dimethylformamide (380 ml) and pyridine (300 ml), and 1-(4-fluorophenyl)-2-formylpyrrole (30 g) was further added thereto under ice-cooling with stirring. The mixture was warmed to room temperature and stirred further for 3 h. The reaction mixture was filtrated and the filtrate was neutralized with hydrochloric acid. The precipitated crystals were recrystallized from hydrous ethanol to give 1-(4-fluorophenyl)pyrrole-2-carboxylic acid (20 g), melting point 195–196° C.

(4) Trifluoromethanesulfonic acid (127 ml) was added dropwise to a dichloroethane solution (680 ml) containing 1-(4-fluorophenyl)-2-formylpyrrole (68 g) at room temperature, and the mixture was stirred at a refluxing temperature for 5 h. After cooling to room temperature, the reaction mixture was poured into aqueous potassium carbonate solution and extracted with chloroform. The organic layer was washed with saturated brine and dried over anhydrous magnesium sulfate, after which the solvent was evaporated under reduced pressure. The obtained residue was purified by column chromatography (mobile phase:methylene chloride) to give 1-(4-fluorophenyl)-3-formylpyrrole (13 g).

(5) Potassium permanganate (13 g) and sodium hydroxide (6.6 g) were added to a solution of dimethylformamide (150 ml) and pyridine (130 ml), and 1-(4-fluorophenyl)-3-formylpyrrole (30 g) was added thereto under ice-cooling with stirring. The mixture was warmed to room temperature and stirred further for 3 h. The reaction mixture was filtrated and the filtrate was neutralized with hydrochloric acid. The precipitated crystals were recrystallized from hydrous ethanol to give 1-(4-fluorophenyl)pyrrole-3-carboxylic acid (9.2 g), melting point 204–205° C.

Starting Material Synthesis Example 35

2-Chloro-5-nitrobenzonitrile

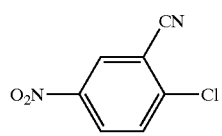

2-Chloro-5-nitrobenzoic acid (500 g) was added to a mixed solvent of dimethylformamide (500 ml) and toluene (1.5 Liters). Thionyl chloride (217 ml) was added thereto at room temperature with stirring and the mixture was stirred at a refluxing temperature for 3 h. The reaction mixture was then ice-cooled and added dropwise to 28% aqueous amonia (750 ml). The mixture was stirred further for 1 h. The precipitated crystals were collected by filtration, and the crystals were recrystallized from hydrous ethanol to give 2-chloro-5-nitrobenzamide (346 g), melting point: 177–179° C.

Further, 2-chloro-5-nitrobenzamide (100 g) was added to dimethylformamide (240 ml) and pyridine (100 ml). To the mixture was dropwise added benzenesulfonyl chloride at room temperature with stirring, and the mixture was stirred at 145° C. for 3 h. The reaction mixture was ice-cooled, and water (240 ml) was added thereto. The precipitated crystals were recrystallized from hydrous ethanol to give 2-chloro-5-nitrobenzonitrile (81.3 g), melting point: 108–110° C.

Starting Material Synthesis Example 36

5-Amino-2-neopentyloxybenzonitrile

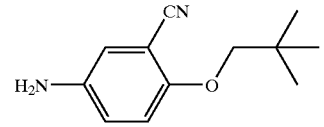

To dimethylformamide solution (364 ml) containing 2-chloro-5-nitrobenzonitrile (91 g) and neopentyl alcohol (52 g) was added sodium hydride (60% content, 27.8 g) under ice-cooling and the mixture was stirred for 1 h. The reaction mixture was poured into water and extracted with toluene. The organic layer was washed with saturated brine and dried over anhydrous magnesium sulfate, after which the solvent was evaporated under reduced pressure. Diisopropyl ether was added to the residue to allow crystallization. The crystals were recrystallized from a mixed solvent of ethyl acetate-n-hexane to give 5-nitro-2-neopentyloxybenzonitrile (105 g), melting point: 90–91° C.

Subsequently, Ammonium chloride (10 g) and iron powder (75 g) were added to a mixed solvent of water (286 ml) and ethanol (753 ml), and the mixture was heated to 65° C. Then, 5-nitro-2-neopentyloxybenzonitrile (80.5 g) was added in parts over 20 min and the mixture was stirred at a refluxing temperature for 30 min. After ice-cooling, the reaction mixture was filtrated and the solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (70 g), melting point: 55–56° C.

Starting Material Synthesis Example 37

3-Bromo-4-neopentyloxyaniline

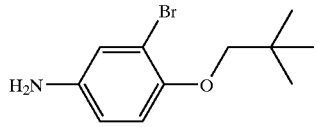

To dimethylformamide solution (78 ml) containing 4-chloronitrobenzene (15.7 g) and neopentyl alcohol (10.6 g) was added by portions sodium hydride (60% content, 4.8 g) under ice-cooling. The mixture was stirred under ice-cooling for 1 h. The mixture was warmed to room temperature and stirred further for 1 h. The reaction mixture was poured into water and extracted with toluene. The organic layer was washed with saturated brine and dried over anhydrous magnesium sulfate, after which the solvent was evaporated under reduced pressure. The obtained oily substance was distilled under reduced pressure to give 4-neopentyloxynitrobenzene (69 g), boiling point: 120–125° C./0.1 mmHg.

Subsequently, a catalytic amount of potassium iodide was added to 4-neopentyloxynitrobenzene (69 g), and bromine (66 g) was added dropwise at 60° C. The mixture was stirred for 5 h. The reaction mixture was poured into water and extracted with toluene. The organic layer was washed with aqueous sodium sulfite solution, dried over anhydrous magnesium sulfate, after which the solvent was evaporated under reduced pressure. The residue was recrystallized from n-hexane to give 3-bromo-4-neopentyloxynitrobenzene (80 g), melting point: 86–88° C.

Furthermore, ammonium chloride (10 g) and iron powder (75 g) were added to a mixed solvent of water (286 ml) and ethanol (753 ml), and the mixture was heated to 65° C. 3-Bromo-4-neopentyloxynitrobenzene (80 g) was added in parts over 20 min and the mixture was stirred at a refluxing temperature for 30 min. The reaction mixture was ice-cooled and filtrated. The solvent was evaporated under reduced pressure. To the residue was added sodium hydroxide and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (70 g), melting point: 45° C.

Starting Material Synthesis Example 38

Ethyl N-(3-cyano-4-neopentyloxyphenyl)glycine

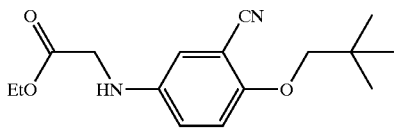

To a tetrahydrofuran solution (90 ml) containing 5-amino-2-neopentyloxybenzonitrile (30 g) and triethylamine (17.7 g) was added tert-butoxycarboxylic anhydride (35.2 g) under ice-cooling. The mixture was warmed to room temperature and stirred further for 4 h. The reaction mixture was poured into aqueous potassium carbonate solution and extracted with chloroform. The organic layer was washed with saturated brine and dried over anhydrous sodium sulfate, after which the solvent was evaporated under reduced pressure. n-Hexane was added to the residue to allow crystallization. The crystals were recrystallized from a mixed solvent of ethyl acetate-n-hexane to give N-(3-cyano-4-neopentyloxyphenyl)-tert-butoxycarboxamide (24.5 g), melting point: 169–170° C.

To dimethylformamide solution (240 ml) containing N-(3-cyano-4-neopentyloxyphenyl)-tert-butoxycarboxamide (24.5 g) was added sodium hydride (60% content, 1.15 g) under ice-cooling and the mixture was stirred for 30 min. The mixture was warmed to room temperature and stirred further for 1 h. The reaction mixture was ice-cooled and ethyl bromoacetate (24.5 g) was added, which was followed by stirring for 1 h. The reaction mixture was poured into water and extracted with ethyl acetate. The organic layer was washed with 0.1N hydrochloric acid and saturated brine, and dried over anhydrous magnesium sulfate, after which the solvent was evaporated under reduced pressure. The residue was purified by silica gel column chromatography (mobile phase: chloroform) to give ethyl N-tert-butoxycarbonyl-N-(3-cyano-4-neopentyloxyphenyl)glycine (36.5 g) as an oily substance. The obtained ethyl N-tert-butoxycarbonyl-N-(3-cyano-4-neopentyloxyphenyl)glycine (8.2 g) was added to trifluoroacetic acid (24 ml) at room temperature and the mixture was stirred for 1 h. The reaction mixture was poured into an aqueous potassium carbonate solution and extracted with ethyl acetate. The organic layer was washed with saturated brine and dried over anhydrous sodium sulfate, after which the solvent was evaporated. The residue was purified by silica gel column chromatography (mobile phase: chloroform) to give the title compound (5.9 g), melting point: 78° C.

Starting Material Synthesis Example 39

Ethyl 4-(3-cyano-4-neopentyloxyphenyl)aminobutyrate

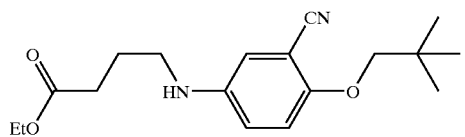

To dimethylformamide solution (50 ml) containing N-(3-cyano-4-neopentyloxyphenyl)-tert-butoxycarboxamide (5 g) was added sodium hydride (60% content, 0.79 g), and the mixture was stirred for 30 min under ice-cooling. The mixture was warmed to room temperature and stirred further for 1 h. The reaction mixture was ice-cooled and ethyl bromobutyrate (4.17 g) was added. The mixture was stirred for 1 h. The reaction mixture was poured into water and extracted with ethyl acetate. The organic layer was washed with 0.1N hydrochloric acid and saturated brine and dried over anhydrous magnesium sulfate, after which the solvent was evaporated under reduced pressure. The residue was purified by silica gel column chromatography (mobile phase: chloroform) to give ethyl 4-[N-tert-butoxycarbonyl-N-(3-cyano-4-neopentyloxyphenyl)]butyrate (7.2 g) as an oily substance. The obtained ethyl 4-[N-tert-butoxycarbonyl-N-(3-cyano-4-neopentyloxyphenyl)]butyrate (7.2 g) was added to trifluoroacetic acid (24 ml) at room temperature and the mixture was stirred for 1 h. The reaction mixture was poured into aqueous potassium carbonate solution and extracted with ethyl acetate. The organic layer was washed with saturated brine and dried over anhydrous sodium sulfate, after which the solvent was evaporated. The residue was purified by silica gel column chromatography (mobile phase: chloroform) to give the title compound (5.7 g), melting point: 88° C.

Starting Material Synthesis Example 40

5-Amino-2-piperidinobenzonitrile

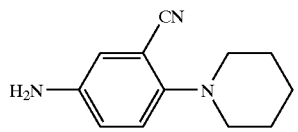

2-Chloro-5-nitrobenzonitrile (20 g) and piperidine (9.34 g) were added to ethanol (100 ml) and the mixture was stirred at a refluxing temperature for 1 h. The solvent was evaporated under reduced pressure and diisopropyl ether was added to the residue to allow crystallization. The crystals were recrystallized from hydrous ethanol to give 5-nitro-2-piperidinobenzonitrile (17 g), melting point 75° C.

Ammonium chloride (1.6 g) and iron powder (8.4 g) were added to a mixed solvent of water (40 ml) and ethanol (120 ml), and the mixture was heated to 65° C. Then, 5-nitro-2-piperidinobenzonitrile (10 g) was added in parts over 20 min and the mixture was stirred at a refluxing temperature for 30 min. The reaction mixture was ice-cooled and filtrated. The solvent was evaporated under reduced pressure. To the residue was added aqueous sodium hydroxide solution, and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (8.3 g), melting point: 148–149° C.

Starting Material Synthesis Example 41

5-Amino-2-(4-hydroxypiperidin-1-yl)benzonitrile

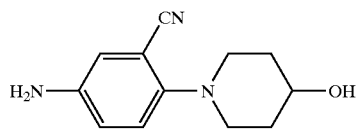

2-chloro-5-nitrobenzonitrile (36 g) and 4-hydroxypiperidine (50 g) were added to ethanol (300 ml), and the mixture was stirred at a refluxing temperature for 1 h. The solvent was evaporated under reduced pressure. Diisopropyl ether was added to the residue to allow crystallization. The crystals were recrystallized from hydrous ethanol to give 5-nitro-2-(4-hydroxypiperidin-1-yl)benzonitrile (37.4 g), melting point: 114–115° C.

Ammonium chloride (1.2 g) and iron powder (6.3 g) were added to a mixed solvent of water (16 ml) and ethanol (48 ml), and the mixture was heated to 65° C. Then, 5-nitro-2-(4-hydroxypiperidino)benzonitrile (10 g) was added in parts over 20 min and the mixture was stirred at a refluxing temperature for 30 min. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (4.5 g), melting point: 144–145° C.

Starting Material Synthesis Example 42

5-Amino-2-[4-(2-hydroxyethyl)piperazin-1-yl]benzonitrile

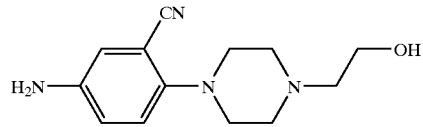

2-Chloro-5-nitrobenzonitrile (15 g) and piperazinoethanol (16 g) were added to ethanol (100 ml) and the mixture was stirred at a refluxing temperature for 1 h. The solvent was evaporated under reduced pressure. To the residue was added aqueous sodium hydroxide solution and the mixture was extracted with chloroform. The organic layer was washed with saturated brine and dried over anhydrous sodium sulfate, after which the solvent was evaporated under reduced pressure. To the residue diisopropyl ether was added to allow crystallization. The crystals were recrystallized from hydrous ethanol to give 5-nitro-2-(2-hydroxyethylpiperazin-1-yl)benzonitrile (18.7 g), melting point 100–102° C.

Ammonium chloride (1.5 g) and iron powder (13.8 g) were added to a mixed solvent of water (51 ml) and ethanol (170 ml), and the mixture was heated to 65° C. Then, 5-nitro-2-(2-hydroxyethylpiperazin-1-yl)benzonitrile (17 g) was added in parts over 20 min and the mixture was stirred at a refluxing temperature for 30 min. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (13 g), melting point: 137–138° C.

Starting Material Synthesis Example 43

5-Amino-2-morpholinobenzonitrile

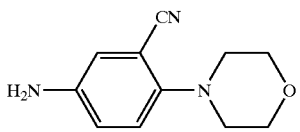

2-Chloro-5-nitrobenzonitrile (16.7 g) and morpholine (16 g) were added to ethanol (300 ml) and the mixture was stirred at a refluxing temperature for 1 h. The solvent was evaporated under reduced pressure. Diisopropyl ether was added to the residue to allow crystallization. The crystals were recrystallized from hydrous ethanol to give 5-nitro-2-morpholinobenzonitrile (19.7 g), melting point: 138–140° C.

Ammonium chloride (2 g) and iron powder (18.9 g) were added to a mixed solvent of water (65 ml) and ethanol (197 ml), and the mixture was heated to 65° C. Then, 5-nitro-2-morpholinobenzonitrile (19.7 g) was added in parts over 20 min and the mixture was stirred at a refluxing temperature for 30 min. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (12.9 g), melting point: 147–148° C.

Starting Material Synthesis Example 44

5-Amino-2-diethylaminobenzonitrile

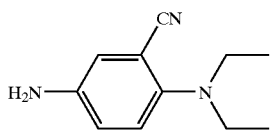

2-Chloro-5-nitrobenzonitrile (15 g) and diethylamine (15 g) were added to ethanol (100 ml) and the mixture was stirred at a refluxing temperature for 1 h. The solvent was evaporated under reduced pressure. Diisopropyl ether was added to the residue to allow crystallization. The crystals were recrystallized from hydrous ethanol to give 5-nitro-2-diethylaminobenzonitrile (15.6 g), melting point: 98° C.

Ammonium chloride (1.5 g) and iron powder (15.9 g) were added to a mixed solvent of water (50 ml) and ethanol (150 ml), and the mixture was heated to 65° C. Then, 5-nitro-2-diethylaminobenzonitrile (15.6 g) was added in parts over 20 min and the mixture was stirred at a refluxing temperature for 30 min. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (12.1 g), melting point: 63–66° C.

Starting Material Synthesis Example 45

5-Amino-2-(4-methylpiperazin-1-yl)benzonitrile

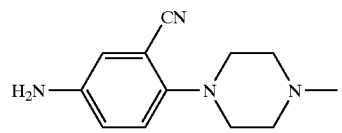

2-Chloro-5-nitrobenzonitrile (15 g) and methylpiperazine (9.8 g) were added to ethanol (100 ml) and the mixture was stirred at a refluxing temperature for 1 h. The solvent was evaporated under reduced pressure. Diisopropyl ether was added to the residue to allow crystallization. The crystals were recrystallized from hydrous ethanol to give 5-nitro-2-diethylaminobenzonitrile (12.7 g), melting point: 83–85° C.

Ammonium chloride (1.3 g) and iron powder (11.6 g) were added to a mixed solvent of water (43 ml) and ethanol (130 ml), and the mixture was heated to 65° C. Then, 5-nitro-2-diethylaminobenzonitrile (12.7 g) was added in parts over 20 min and the mixture was stirred at a refluxing temperature for 30 min. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (8.1 g), melting point: 45–46° C.

Starting Material Synthesis Example 46

Ethyl 1-(4-amino-2-cyanophenyl)piperidin-4-ylcarboxylate

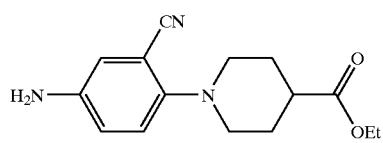

2-Chloro-5-nitrobenzonitrile (10 g), ethyl isonipecotate (60 g) and silver nitrate (11.1 g) were stirred at 120° C. for 3 h. The reaction mixture was cooled to room temperature and the solid was filtered off. To the filtrate was added dilute hydrochloric acid and the mixture was extracted with ethyl acetate. The organic layer was washed with dilute hydrochloric acid and saturated brine, and dried over anhydrous magnesium sulfate. The solvent was evaporated under reduced pressure. Diisopropyl ether was added to the residue to allow crystallization. The crystals were recrystallized from hydrous diisopropyl ether to give ethyl 1-(4-nitro-2-cyanophenyl)piperidin-4-ylcarboxylate (17.1 g).

$^1$H-NMR(270 MHz, CDCl$_3$) δ(ppm):1.28(3H, dd, J=6.6, 7.3 Hz), 1.94–2.15(4H, m), 2.55–2.62(1H, m), 3.21(2H, ddd, J=2.6, 4.3, 10.6 Hz), 3.88(2H, ddd, J=2.6, 4.3, 10.6 Hz), 4.15(2H, dd, J=6.6, 7.3 Hz), 6.98(1H, d, J=10.2 Hz), 8.25 (1H, dd, J=2.6, 10.2 Hz), 8.41(1H, d, J=2.6 Hz)

Ammonium chloride (2.1 g) and iron powder (11.1 g) were added to a mixed solvent of water (110 ml) and ethanol (30 ml), and the mixture was heated to 65° C. Then, ethyl 1-(4-nitro-2-cyanophenyl)piperidin-4-ylcarboxylate (17.1 g) was added in parts over 20 min and the mixture was stirred at a refluxing temperature for 30 min. The reaction mixture was ice-cooled and filtrated. The solvent was evaporated under reduced pressure. To the residue was added aqueous sodium hydroxide solution, and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (12 g), melting point: 98° C.

Starting Material Synthesis Example 47

5-Amino-2-[4-(tert-butoxycarbonyl)piperazin-1-yl]benzonitrile

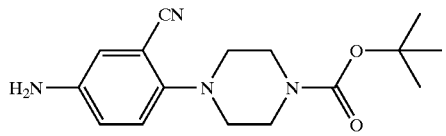

2-Chloro-5-nitrobenzonitrile (31.4 g) and piperazine (44.5 g) were added to acetonitrile (250 ml), and the mixture was stirred at room temperature for 1 h. The reaction mixture was added to water and extracted with chloroform. The organic layer was washed with saturated brine and dried over anhydrous sodium sulfate, after which the solvent was evaporated under reduced pressure. The residue was recrystallized from diisopropyl ether to give 5-nitro-2-piperazinebenzonitrile (48.8 g). tert-Butoxycarboxylic anhydride (91.5 g) was added under ice-cooling to tetrahydrofuran (150 ml) containing 5-nitro-2-piperazinebenzonitrile (48.8 g) and triethylamine (25 g). The mixture was stirred for 30 min and at room temperature for 1 h. The precipitated crystals were collected by filtration to give 5-nitro-2-(4-tert-butoxycarbonylpiperazin-1-yl)benzonitrile (62.1 g), melting point:141–142° C.

Ammonium chloride (7.0 g) and iron powder (36.6 g) were added to a mixed solvent of water (180 ml) and ethanol (540 ml), and the mixture was heated to 65° C. Then, 5-nitro-2-(4-tert-butoxycarbonylpiperazin-1-yl)benzonitrile (62.1 g) was added in parts over 40 min and the mixture was stirred at a refluxing temperature for 1 h. The reaction mixture was ice-cooled and filtrated. The solvent was evaporated under reduced pressure. To the residue was added aqueous sodium hydroxide solution, and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (50.7 g), melting point: 145° C.

Starting Material Synthesis Example 48

5-Amino-2-[4-(tertbutoxycarbonyl)homopiperazin-1-yl]benzonitrile

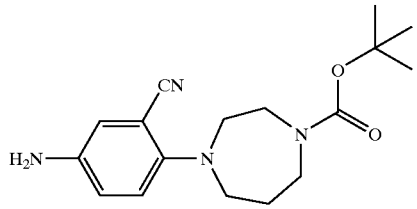

2-Chloro-5-nitrobenzonitrile (30.3 g) and homopiperazine (50 g) were added to acetonitrile (250 ml) and the mixture was stirred under ice-cooling for 1 h. The reaction mixture was added to water and extracted with chloroform. The organic layer was washed with saturated brine and dried over anhydrous sodium sulfate, after which the solvent was evaporated under reduced pressure. The residue was recrystallized from diisopropyl ether to give 5-nitro-2-homopiperazinebenzonitrile (32.4 g), melting point: 101° C.

tert-Butoxycarboxylic anhydride (70 g) was added under ice-cooling to tetrahydrofuran (150 ml) containing 5-nitro-2-homopiperazinebenzonitrile (32.4 g) and triethylamine (21 g). The mixture was stirred for 30 min and at room temperature for 1 h. The precipitated crystals were collected by filtration to give 5-nitro-2-(4-tert-butoxycarbonylhomopiperazin-1-yl)benzonitrile (56 g), melting point: 98° C.

Ammonium chloride (5.9 g) and iron powder (32 g) were added to a mixed solvent of water (160 ml) and ethanol (470 ml), and the mixture was heated to 65° C. Then, 5-nitro-2-(4-tert-butoxycarbonylhomopiperazin-1-yl)benzonitrile (56 g) was added in parts over 30 min and the mixture was stirred at a refluxing temperature for 1 h. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (32 g), melting point: 38° C.

Starting Material Synthesis Example 49:Ethyl cis-4-(4-amino-2-cyanophenyl)-2,6-dimethylpiperazin-1-ylacetate

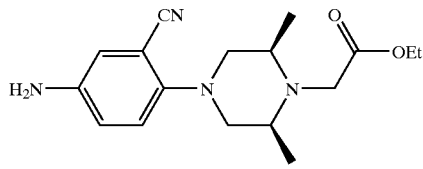

2-Chloro-5-nitrobenzonitrile (13.3 g) and cis-2,6-dimethylpiperazine (25 g) were added to acetonitrile (25 ml) andthe mixture was stirred at room temperature for 1 h. The reaction mixture was added to water and extracted with chloroform. The organic layer was washed with saturated brine and dried over anhydrous sodium sulfate. The solvent was evaporated under reduced pressure. The residue was recrystallized from diisopropyl ether to give cis-2-(3,5-dimethylpiperazin-1-yl)-5-nitrobenzonitrile (14.3 g), melting point: 109–110° C.

Then, cis-2-(3,5-dimethylpiperazin-1-yl)-5-nitrobenzonitrile (14.3 g), potassium carbonate (4.9 g) and ethyl bromoacetate (6 g) were added to dimethylformamide (35 ml), and the mixture was stirred at 60° C. for 1 h. The reaction mixture was added to water and extracted with ethyl acetate. The organic layer was washed with saturated brine and dried over anhydrous sodium sulfate, after which the solvent was evaporated under reduced pressure. The residue was purified by silica gel column chromatography (mobile phase: chloroform) to give ethyl cis-4-(4-nitro-2-cyanophenyl)-2,6-dimethylpiperazin-1-ylacetate (10.8 g) as an oily substance.

$^1$H-NMR(270 MHz, CDCl$_3$) δ(ppm):1.17(3H, s), 1.19 (3H, s), 1.27(3H, t, J=7.3 Hz), 2.88(1H, d, J=3.3 Hz) 2.96(1H, d, J=3.3 Hz), 3.23(2H, ddd, J=2.6, 3.3, 4.0 Hz), 3.61(2H, s), 3.83(2H, dd, J=2.6, 4.0 Hz), 4.17(2H, q, J=7.3 Hz), 6.95 (1H, d, J=9.2 Hz), 8.21(1H, dd, J=2.5, 9.2 Hz), 8.39(1H, d, J=2.5 Hz)

Ammonium chloride (1.2 g) and iron powder (6.1 g) were added to a mixed solvent of water (90 ml) and ethanol (270 ml), and the mixture was heated to 65° C. Then, ethanol solution (20 ml) containing ethyl cis-4-(4-nitro-2-cyanophenyl)-2,6-dimethylpiperazin-1-ylacetate (10.8 g) was dropwise added in parts over 20 min and the mixture was stirred at a refluxing temperature for 1 h. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. n-Hexane was added to the residue to allow crystallization. The crystals were recrystallized from a mixed solvent of diisopropyl ether-n-hexane to give the title compound (9.5 g), melting point: 45° C.

Starting Material Synthesis Example 50

5-Amino-2-isobutoxybenzonitrile

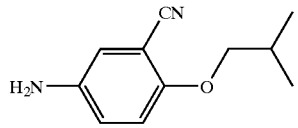

4-Nitrophenol (177 g), potassium carbonate (177 g) and isobutyl bromide (190 g) were added to dimethylformamide (500 ml) and the mixture was stirred at 90° C. for 4 h. The reaction mixture was poured into water, and extracted with ethyl acetate. The organic layer was washed with saturated brine and dried over anhydrous magnesium sulfate, after which the solvent was evaporated under reduced pressure. The obtained oily substance was distilled under reduced pressure to give 4-isobutoxynitrobenzene (203 g), boiling point: 125° C./0.15 mmHg Subsequently, a catalytic amount of potassium iodide was added to 4-isobutoxynitrobenzene (203 g) and the mixture was heated to 60° C. Bromine (183 g) was added dropwise over 3 h. The mixture was stirred further for 1 h. The reaction mixture was poured into water and extracted with toluene. The organic layer was washed with aqueous sodium sulfite solution and dried over anhydrous magnesium sulfate, after which the solvent was evaporated under reduced pressure. The obtained oily substance was distilled under reduced pressure to give 2-isobutoxy-5-nitrobromobenzene (248 g), boiling point: 135–140° C./0.25 mmHg.

2-Isobutoxy-5-nitrobromobenzene (193 g) and copper cyanide (72 g) were reacted in dimethylformamide (419 ml) at 140° C. for 4 h. The reaction mixture was cooled to room temperature and the solid was filtered off. To the filtrate was added water, and the mixture was extracted with toluene. The organic layer was washed with saturated brine and dried over anhydrous magnesium sulfate, after which the solvent was evaporated under reduced pressure. The residue was recrystallized from diisopropyl ether to give 2-isobutyl-5-nitrobenzonitrile (20 g), melting point: 73° C.

Ammonium chloride (5.6 g) and iron powder (21 g) were added to a mixed solvent of water (80 ml) and ethanol (240 ml), and the mixture was heated to 65° C. Then, 2-isobutyl-5-nitrobenzonitrile (20 g) was added in parts over 20 min and the mixture was stirred at a refluxing temperature for 30 min. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (17 g), melting point: 88–93° C.

Starting Material Synthesis Example 51

5-Amino-2-isobutylbenzonitrile

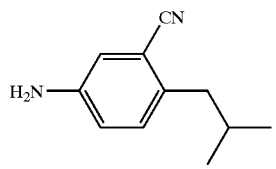

4'-isobutylacetophenone (215 g) was added to 49% sulfuric acid (1 Liter) was and potassium bromate (268 g) was added under ice-cooling over 1.5 h. The mixture was warmed to room temperature and stirred further for 1 h, which was followed by extraction with toluene. The organic layer was washed with water and dried over anhydrous magnesium sulfate, after which the solvent was evaporated under reduced pressure. The remaining oily substance was distilled under highly reduced pressure to give 3'-bromo-4'-isobutylacetophenone (182 g), boiling point: 130–140° C./0.15 mmHg 3'-Bromo-4'-isobutylacetophenone (182 g) and copper cyanide (95.7 g) were stirred in dimethylformamide (520 ml) at 140° C. for 7 h. The reaction mixture was cooled to room temperature and the solid was filtered off. To the filtrate was added water and the mixture was extracted with toluene. The organic layer was washed with saturated brine and dried over anhydrous magnesium sulfate, after which the solvent was evaporated under reduced pressure. The residue was recrystallized from n-hexane to give 3'-cyano-4'-isobutylacetophenone (70 g), melting point: 71–72° C.

Subsequently, 10% aqueous sodium hypochlorite solution (370 ml) containing sodium hydroxide (8 g) and methanol (5 ml) was heated to 60° C. 3'-Cyano-4'-isobutylacetophenone (20 g) was added thereto by portions and the mixture was stirred for 1 h. The reaction mixture was cooled to room temperature and dilute hydrochloric acid was added, which was followed by extraction with chloroform. The organic layer was washed with saturated brine and dried over anhydrous magnesium sulfate, after which the solvent was evaporated under reduced pressure. n-Hexane was added to the residue to allow crystallization. The crystals were recrystallized from a mixed solvent of ethyl acetate-n-hexane to give 3-cyano-4-isobutylbenzoic acid (8.5 g), melting point: 118° C.

To tert-butyl alcohol containing 3-cyano-4-isobutylbenzoic acid (8.5 g) and triethylamine (4.2 g) was added diphenylphosphoryl azide (11.5 g) at room temperature and the mixture was stirred at a refluxing temperature for 1 h. The solvent was evaporated under reduced pressure. To the residue was added aqueous potassium carbonate solution and the mixture was extracted with ethyl acetate. The organic layer was washed with saturated brine and dried over anhydrous sodium sulfate, after which the solvent was evaporated under reduced pressure. To the residue were added 6N hydrochloric acid (10 ml) and methanol (100 ml) and the mixture was stirred at a refluxing temperature for 1 h. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. n-Hexane was added to the residue to allow crystallization. The crystals were recrystallized from a mixed solvent of diisopropyl ether-n-hexane to give the title compound (6.0 g), melting point: 68° C.

Starting Material Synthesis Example 52

5-Amino-2-hexyloxybenzonitrile

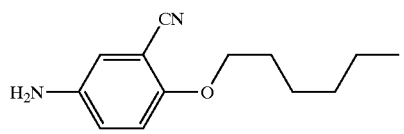

To dimethylformamide solution (91 ml) containing 2-chloro-5-nitrobenzonitrile (18.2 g) and n-hexanol (11.2 g) was added sodium hydride (60% content, 4.8 g) under ice-cooling and the mixture was stirred for 1 h. The reaction mixture was added to water and extracted with toluene. The organic layer was washed with saturated brine and dried over anhydrous magnesium sulfate, after which the solvent was evaporated under reduced pressure. The residue was purified by silica gel column chromatography (mobile phase: chloroform) to give 2-n-hexyloxy-5-nitrobenzonitrile (16.2 g). Then, ammonium chloride (0.2 g) and iron powder (1.6 g) were added to a mixed solvent of water (6.3 ml) and ethanol (17 ml), and the mixture was heated to 65° C. Then, the obtained ethanol solution (4 ml) containing 5-nitro-2-n-hexyloxybenzonitrile (16.2 g) was added dropwise thereto, and the mixture was stirred at a refluxing temperature for 30 min. The reaction mixture was ice-cooled and filtrated and the solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. The residue was purified by silica gel column chromatography (mobile phase: chloroform) to give the title compound (6.0 g).

$^1$H-NMR(270 MHz, CDCl$_3$) δ(ppm):0.87–0.93(3H, m), 1.30–1.37(4H, m), 1.43–1.51(2H, m), 1.78(2H, dt, J=6.6, 7.3 Hz), 4.03(2H, t, J=7.3 Hz), 6.90(1H, d, J=9.2 Hz), 7.66(1H, dd, J=2.6, 9.2 Hz), 7.76(1H, d, J=2.6 Hz)

Starting Material Synthesis Example 53

5-Amino-2-(2-(2-dimethylamino)ethoxy)benzonitrile

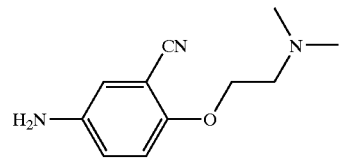

To dimethylformamide solution (30 ml) containing 2-chloro-5-nitrobenzonitrile (20 g) and 2-dimethylaminoethanol (10.7 g) was added sodium hydride (60% content, 4.9 g) under ice-cooling, and the mixture was stirred for 1 hr. The reaction mixture was added to water and extracted with toluene. The organic layer was washed with saturated brine and dried over anhydrous sodium sulfate, after which the solvent was evaporated under reduced pressure. The residue was purified by silica gel column chromatography (mobile phase: chloroform) to give 2-(2-(2-dimethylamino)ethoxy)-5-nitrobenzonitrile (34.8 g). Then, ammonium chloride (9.3 g) and iron powder (35 g) were added to a mixed solvent of water (130 ml) and ethanol (400 ml), and the mixture was heated to 65° C. Then, ethanol solution (20 ml) containing 2-(2-(2-dimethylamino)ethoxy)-5-nitrobenzonitrile (34.8 g) was added dropwise over 20 min and the mixture was stirred at a refluxing temperature for 30 min. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (20.1 g), melting point: 192–193° C.

Starting Material Synthesis Example 54

5-Amino-2-pheoxybenzonitrile

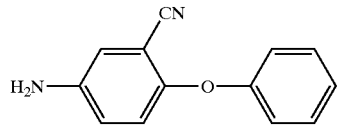

To a dimethylformamide solution (30 ml) containing 2-chloro-5-nitrobenzonitrile (10 g) and phenol (5.7 g) was added sodium hydride (60% content, 2.63 g) under ice-cooling, and the mixture was stirred for 1 h. The reaction mixture was added to water and extracted with toluene. The organic layer was washed saturated brine and dried over anhydrous sodium sulfate, after which the solvent was evaporated under reduced pressure. The residue was recrystallized from diisopropyl ether to give 5-nitro-2-phenoxybenzonitrile (10.8 g), melting point: 126° C.

Subsequently, ammonium chloride (2.9 g) and iron powder (8.8 g) were added to mixed solvent of water (130 ml) and ethanol (120 ml), and the mixture was heated to 65° C. Then, ethanol solution (20 ml) containing 5-nitro-2-phenoxybenzonitrile (10.8 g) was added dropwise over 20 min and the mixture was stirred at a refluxing temperature for 30 min. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (3 g), melting point: 89° C.

Starting Material Synthesis Example 55

5-Amino-2-cyclohexyloxybenzonitrile

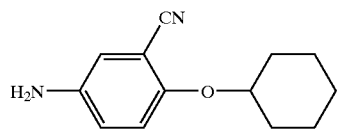

To dimethylformamide solution (35 ml) containing 2-chloro-5-nitrobenzonitrile (14.1 g) and cyclohexanol (8.5 g) was added sodium hydride (60% content, 3.7 g) under ice-cooling, and the mixture was stirred for 1 h. The reaction mixture was added to water and extracted with toluene. The organic layer was washed with saturated brine and dried over anhydrous sodium sulfate, after which the solvent was evaporated under reduced pressure. The residue was recrystallized from diisopropyl ether to give 2-cyclohexyloxy-5-nitrobenzonitrile (11.6 g), melting point: 97–98° C.

Subsequently, ammonium chloride (1.8 g) and iron powder (9.2 g) were added to a mixed solvent of water (32 ml) and ethanol (130 ml), and the mixture was heated to 65° C.

Then, ethanol solution (4 ml) containing 2-cyclohexyloxy-5-nitrobenzonitrile (11.6 g) was added dropwise over 20 min and the mixture was stirred at a refluxing temperature for 30 min. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. n-Hexane was added to the residue to allow crystallization. The crystals were recrystallized from a mixed solvent of diisopropyl ether-n-hexane to give the title compound (9.5 g), melting point: 59° C.

Starting Material Synthesis Example 56

5-Amino-2-[bis(2-hydroxyethyl)amino]benzonitrile

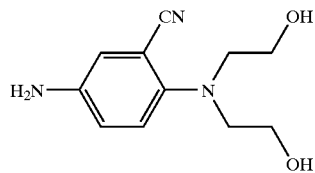

2-Chloro-5-nitrobenzonitrile (25.5 g) and silver nitrate (28.5 g) were added to diethanolamine (102 g) and the mixture was stirred at 100° C. for 1 h. The reaction mixture was cooled to room temperature and the solid was filtered off. To the filtrate was added water and the mixture was extracted with ethyl acetate. The organic layer was washed with saturated brine and dried over anhydrous sodium sulfate, after which the solvent was evaporated under reduced pressure. Diisopropyl ether was added to the residue to allow crystallization. The crystals were recrystallized from hydrous methanol to give 2-bis(2-hydroxyethyl)amino-5-nitrobenzonitrile (21.2 g).

$^1$H-NMR(270 MHz, CDCl$_3$) δ(ppm):3.69(4H, q, J=5.3 Hz), 3.84 (4H, q, J=5.3 Hz), 4.95 (2H, t, J=5.3 Hz), 7.15 (1H, d, J=9.4 Hz), 8.12 (1H, dd, J=2.6, 9.4 Hz), 8.36 (1H, d, J=2.6 Hz)

Subsequently, ammonium chloride (0.9 g) and iron powder (4.5 g) were added to a mixed solvent of water (10 ml) and ethanol (30 ml), and the mixture was heated to 65° C. Then, 2-bis(2-hydroxyethyl)amino-5-nitrobenzonitrile (11 g) was added in parts over 20 min and the mixture was stirred at a refluxing temperature for 30 min. The reaction mixture was ice-cooled and filtrated. The solvent was evaporated under reduced pressure. To the residue was added aqueous sodium hydroxide ice solution and the mixture was extracted with toluene. The organic layer was washed with saturated brine and dried over anhydrous sodium sulfate, after which the solvent was evaporated under reduced pressure. n-Hexane was added to the residue to allow crystallization. The crystals were recrystallized from a mixed solvent of diisopropyl ether-n-hexane to give the title compound (8 g), melting point: 38° C.

Starting Material Synthesis Example 57

5-Amino-2-(2,2,2,-trifluoroethoxy)benzonitrile

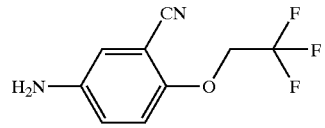

To a dimethylformamide solution (30 ml) containing 2-chloro-5-nitrobenzonitrile (10 g) and 2,2,2-trifluoroethanol (6 g) was added sodium hydride (60% content, 2.65 g) under ice-cooling, and the mixture was stirred for 1 h. The reaction mixture was added to water and extracted with toluene. The organic layer was washed with saturated brine and dried over anhydrous magnesium sulfate, after which the solvent was evaporated under reduced pressure. Diisopropyl ether was added to the residue to allow crystallization. The crystals were recrystallized from a mixed solvent of toluene-diisopropyl ether to give 5-nitro-2-(2,2,2-trifluoroethoxy)benzonitrile (9.4 g), melting point: 94° C.

Subsequently, ammonium chloride (0.5 g) and iron powder (2.5 g) were added to a mixed solvent of water (40 ml) and ethanol (120 ml), and the mixture was heated to 65° C. Then, 5-nitro-2-(2,2,2-trifluoroethoxy)benzonitrile (80.5 g) was added in parts over 20 min and the mixture was stirred at a refluxing temperature for 30 min. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (70 g), melting point: 98–100° C.

Starting Material Synthesis Example 58

5-Amino-2-(4-tert-butyldimethylsilyloxypiperidino)benzonitrile

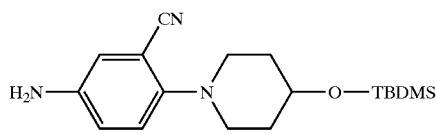

5-Amino-2-(4-hydroxypiperidino)benzonitrile (4.0 g), tert-butyldiethylsilyl chloride (3.0 g) and imidazole (1.6 g) were stirred in dimethylformamide (20 ml) at room temperature for 1 h. The reaction mixture was treated with aqueous sodium hydrogen carbonate solution and extracted with ethyl acetate. The organic layer was washed with saturated brine and dried over anhydrous magnesium sulfate, after which the solvent was evaporated under reduced pressure. The residue was recrystallized from n-hexane to give the title compound (4.2 g), melting point: 88–90° C.

Starting Material Synthesis Example 59

2-[N-(3-Cyano-4-neopentyloxyphenyl) amino]ethyl acetate

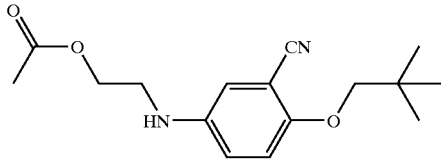

To a dimethylformamide solution (50 ml) containing N-(3-cyano-4-neopentyloxyphenyl)-tert-butoxycarboxamide (5 g) was added sodium hydride (60% content, 0.8 g) under ice-cooling, and the mixture was stirred for 30 min under ice-cooling. The mixture was warmed to room temperature and stirred further for 1 h. Thereafter, the mixture was ice-cooled again and 2-bromoethyl acetate (2.6 g) was added, and the mixture was stirred for 1 h. The reaction mixture was poured into water and extracted with ethyl acetate. The extract was washed with 0.1 N hydrochloric acid and saturated brine, and washed with anhydrous magnesium sulfate, after which the solvent was evaporated under reduced pressure. The residue was purified by silica gel column chromatography (mobile phase:methylene chloride) to give 2-[N-tert-butoxycarbonyl-N-(3-cyano-4-neopentyloxyphenyl)]aminoethyl acetate (3.5 g) as an oily substance. This oily substance was added to trifluoroacetic acid (7 ml) at room temperature and the mixture was stirred for 1 h. The reaction mixture was poured into aqueous potassium carbonate solution and extracted with ethyl acetate. The organic layer was washed with saturated brine and dried over anhydrous sodium sulfate. The solvent was evaporated and the obtained residue was purified by silica gel column chromatography (mobile phase: chloroform) to give the title compound (2.1 g) as an oily substance.

$^1$H-NMR(270 MHz, CDCl$_3$) δ(ppm):1.09(9H, s), 2.00 (3H, s), 3.69(2H, s), 3.81(2H, t, J=5.2 Hz), 4.20(2H, t, J=5.2 Hz), 6.99(1H, d, J=9.2 Hz), 7.35– 7.42(2H, m)

Starting Material Synthesis Example 60

5-Amino-2-(4-piperidinopiperidin-1-yl)benzonitrile

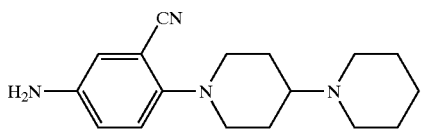

2-Chloro-5-nitrobenzonitrile (3.9 g) and piperidinopiperidine (7.2 g) were added to ethanol (40 ml), and the mixture was stirred at 78° C. for 3 h. The solvent was evaporated under reduced pressure. The residue was treated with aqueous sodium hydrogencarbonate and extracted with ethyl acetate. The organic layer was washed with saturated brine and dried over anhydrous magnesium sulfate, after which the solvent was evaporated under reduced pressure. Diisopropyl ether was added to the residue to allow crystallization. The crystals were recrystallized from ethanol to give 5-nitro-2-(4-piperidinopiperidin-1-yl)benzonitrile (6.2 g), melting point: 134–135° C.

Subsequently, ammonium chloride (0.7 g) and iron powder (3.8 g) were added to a mixed solvent of water (30 ml) and ethanol (120 ml), and the mixture was heated to 65° C. Then, 5-nitro-2-(4-piperidinopiperidin-1-yl)benzonitrile (6.2 g) was added in parts over 20 min and the mixture was stirred at a refluxing temperature for 30 min. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-h exane to give the title compound (4.8 g), melting point: 110–112° C.

Starting Material Synthesis Example 61

1-(4-Amino-2-cyanophenyl)-4-piperidinyl benzoate

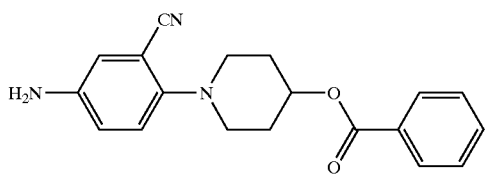

5-Nitro-2-(4-hydroxypiperidin-1-yl)benzonitrile (20 g) was dissolved in pyridine (100 ml). To the solution was added dropwise toluene solution (50 ml) containing benzoyl chloride (12.8 g) under ice-cooling, and the mixture was stirred at room temperature for 3 h. The reaction mixture was poured into water. The obtained crystals were recrystallized from a mixed solvent of ethyl acetate-n-hexane to give 1-(2-cyano-4-nitrophenyl)-4-piperidinyl benzoate (32.3 g), melting point: 143–145° C.

Subsequently, ammonium chloride (3.4 g) and iron powder (18 g) were added to a mixed solvent of water (80 ml) and ethanol (240 ml), and the mixture was heated to 65° C. Thereafter, 1-(2-cyano-4-nitrophenyl)-4-piperidinyl benzoate (32.3 g) was added in parts over 20 min and the mixture was stirred at a refluxing temperature for 30 min. The reaction mixture was ice-cooled and filtrated. The solvent was evaporated under reduced pressure. To the residue was added aqueous sodium hydroxide solution and the mixture was extracted with toluene. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (25.3 g), melting point: 154–155° C.

Starting Material Synthesis Example 62

1-(4-Bromophenyl)-5-methylpyrazole-4-carboxylic acid

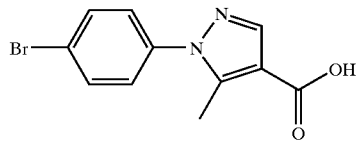

By the reaction and treatment in the same manner as in Starting Material Synthesis Example 1, except that 4-bromophenylhydrazine was used instead of 4-fluorophenylhydrazine, the title compound was obtained, melting point: 213° C.

Starting Material Synthesis Example 63

1-(4-Iodophenyl)-5-methylpyrazole-4-carboxylic acid

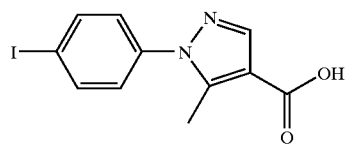

By the reaction and treatment in the same manner as in Starting Material Synthesis Example 1, except that 4-iodophenylhydrazine was used instead of 4-fluorophenylhydrazine, the title compound was obtained, melting point: 225° C.

Starting Material Synthesis Example 64

1-(4-Chlorophenyl)-3-methylpyrazole-4-carboxylic acid

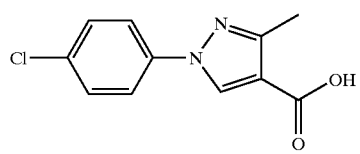

By the reaction and treatment in the same manner as in Starting Material Synthesis Example 15, except that 4-chlorophenylhydrazine was used instead of 4-fluorophenylhydrazine, the title compound was obtained, melting point: 217° C.

Starting Material Synthesis Example 65

1-(4-Bromophenyl)-3-methylpyrazole-4-carboxylic acid

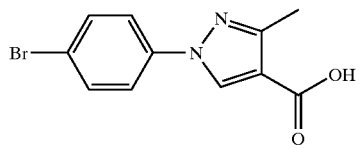

By the reaction and treatment in the same manner as in Starting Material Synthesis Example 15, except that 4-bromophenylhydrazine was used instead of 4-fluorophenylhydrazine, the title compound was obtained, melting point: 226° C.

Starting Material Synthesis Example 66

1-(4-Chlorophenyl)pyrrole-3-carboxylic acid

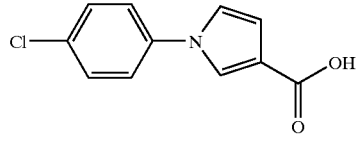

By the reaction and treatment in the same manner as in Starting Material Synthesis Example 34, except that 4-chloroaniline was used instead of 4-fluoroaniline, the title compound was obtained, melting point: 222–224° C.

Starting Material Synthesis Example 67

1-(3-Chlorophenyl)-5-methylpyrazole-4-carboxylic acid

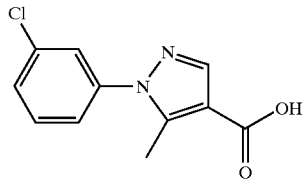

By the reaction and treatment in the same manner as in Starting Material Synthesis Example 1, except that 3-chlorophenylhydrazine was used instead of 4-fluorophenylhydrazine, the title compound was obtained, melting point: 145° C.

Starting Material Synthesis Example 68

1-(3,4-Dichlorophenyl)-5-methylpyrazole-4-carboxylic acid

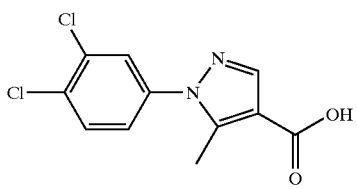

By the reaction and treatment in the same manner as in Starting Material Synthesis Example 1, except that 3,4-dichlorophenylhydrazine was used instead of 4-fluorophenylhydrazine, the title compound was obtained, melting point: 188° C.

Starting Material Synthesis Example 69

1-(3,4-Difluorophenyl)-5-methylpyrazole-4-carboxylic acid

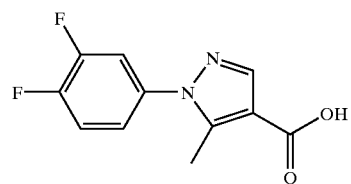

By the reaction and treatment in the same manner as in Starting Material Synthesis Example 1, except that 3,4-difluorophenylhydrazine was used instead of 4-fluorophenylhydrazine, the title compound was obtained, melting point: 148° C.

Starting Material Synthesis Example 70

1-(3-Chloro-4-fluorophenyl)-5-methylpyrazole-4-carboxylic acid

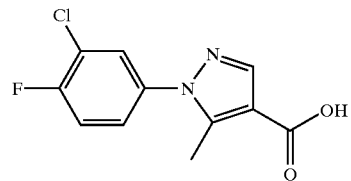

By the reaction and treatment in the same manner as in Starting Material Synthesis Example 1, except that 3-chloro-4-fluorophenylhydrazine was used instead of 4-fluorophenylhydrazine, the title compound was obtained, melting point: 187° C.

Starting Material Synthesis Example 71

1-(4-Trifluoromethylphenyl)-5-methylpyrazole-4-carboxylic acid

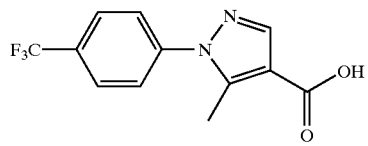

By the reaction and treatment in the same manner as in Starting Material Synthesis Example 1, except that 4-trifluoromethylphenylhydrazine was used instead of 4-fluorophenylhydrazine, the title compound was obtained, melting point: 181° C.

Starting Material Synthesis Example 72

5-Amino-2-(4-morpholinopiperidin-1-yl)benzonitrile

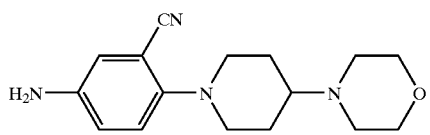

By the reaction and treatment in the same manner as in Starting Material Synthesis Example 40 using 4-morpholinopiperidine synthesized according to Tetrahedron, vol. 38, No. 3, p. 413 (1982) instead of piperidine, the title compound was obtained, melting point: 84–86° C.

Starting Material Synthesis Example 73

5-Amino-2-[4-(4-methylpiperazin-1-yl)piperidin-1-yl]benzonitrile

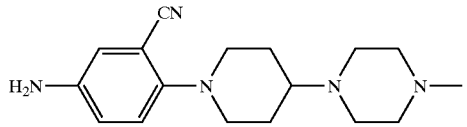

By the reaction and treatment in the same manner as in Starting Material Synthesis Example 40 using 4-(4-methylpiperazin-1-yl)piperidine synthesized according to Tetrahedron, vol. 38, No. 3, p. 413 (1982) instead of piperidine, the title compound was obtained, melting point: 174° C.

Starting Material Synthesis Example 74

5-Amino-2-{4-[bis(2-hydroxyethyl)amino]piperidin-1-yl}benzonitrile

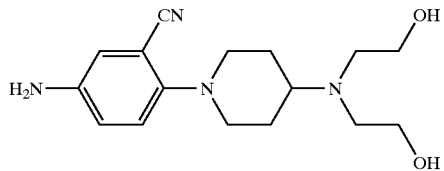

By the reaction and treatment in the same manner as in Starting Material Synthesis Example 40 using 4-[bis(2-hydroxyethyl)amino]piperidine synthesized according to Tetrahedron, vol. 38, No. 3, p. 413 (1982) instead of piperidine, the title compound was obtained, melting point: 45–47° C.

Starting Material Synthesis Example 75

5-Amino-2-[4-(dimethylamino)piperidin-1-yl]benzonitrile

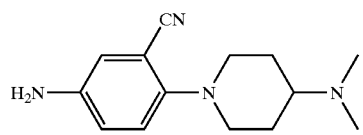

By the reaction and treatment in the same manner as in Starting Material Synthesis Example 40, except that 4-dimethylaminopiperidine was used instead of piperidine, the title compound was obtained.

1H-NMR (400 MHz, CDCl$_3$) δ(ppm): 1.75 (2H, dd, J=3.3, 11.9 Hz), 1.90 (2H, d, J=12.5 Hz), 2.21–2.43 (1H, m), 2.31 (6H, s), 2.64–2.77 (2H, d, J=11.9 Hz), 3.62 (2H, d, J=7.9 Hz), 6.81–6.95 (3H, m).

Starting Material Synthesis Example 76

5-Amino-2-pyrrolidinobenzonitrile

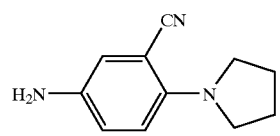

By the reaction and treatment in the same manner as in Starting Material Synthesis Example 40, except that pyrrolidine was used instead of piperidine, the title compound was obtained, melting point: 113° C.

Starting Material Synthesis Example 77

5-amino-2-homopiperidinobenzonitrile

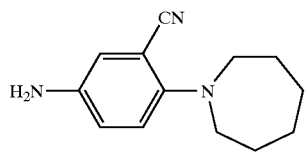

By the reaction and treatment in the same manner as in Starting Material Synthesis Example 40, except that homopiperidine was used instead of piperidine, the title compound was obtained.

$^1$H-NMR (400M Hz, CDCl$_3$) δ(ppm): 1.55–1.70 (4H, m), 1.75–1.90 (4H, m), 3.20 (2H, brs), 3.39 (4H, t, J=5.9 Hz), 6.7–6.9(3H, m)

Starting Material Synthesis Example 78

1-(2-chlorophenyl)-5-methylpyrazole-4-carboxylic acid

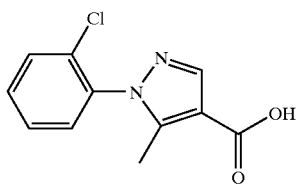

By the reaction and treatment in the same manner as in Starting Material Synthesis Example 1, except that 2-chlorophenylhydrazine was used instead of 4-fluorophenylhydrazine, the title compound was obtained, melting point: 114° C.

Starting Material Synthesis Example 79

5-Amino-2-{4-[2-(2-hydroxyethoxy)ethyl]piperazin-1-yl}benzonitrile

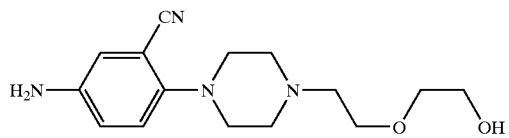

By the reaction and treatment in the same manner as in Starting Material Synthesis Example 40, except that 4-[2-(2-hydroxyethoxy) ethyl]piperazine was used instead of piperidine, the title compound was obtained.

$^1$H-NMR (270 MHz, CDCl$_3$)δ(ppm):2.66 (2H, d, J=5.3 Hz), 2.74 (2H, d, J=4.6 Hz), 3.09 (4H, dd, J=4.6, 5.3 Hz), 3.62–3.71 (8H, m), 4.2–4.8 (2H, br), 6.80–6.92 (3H, m)

Starting Material Synthesis Example 80

5-Amino-2-(1,4-dioxa-8-azaspiro [4,5]deca-8-yl)benzonitrile

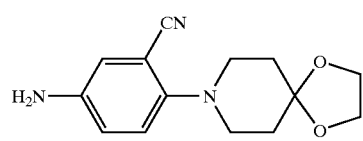

By the reaction and treatment in the same manner as in Starting Material Synthesis Example 40, except that 1,4-dioxa-8-azaspiro[4,5]decane was used instead of piperidine, the title compound was obtained, melting point: 98° C.

Starting Material Synthesis Example 81

5-Amino-2-(1-benzylpiperidin-4-yloxy)benzonitrile

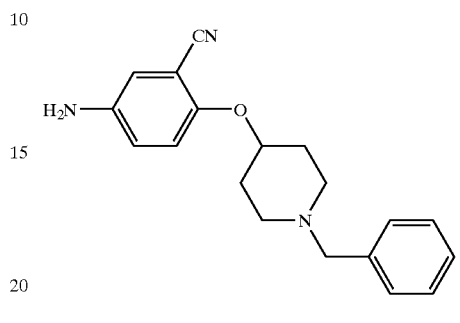

By the reaction and treatment in the same manner as in Starting Material Synthesis Example 36, except that 1-benzyl-4-hydroxypiperidine was used instead of neopentyl alcohol, the title compound was obtained as an oil.

$^1$H-NMR (400 MHz, CDCl$_3$) δ(ppm):1.80–1.98 (5H, m), 2.33 (2H, m), 2.70–2.85 (2H, m), 3.52 (2H, s), 3.59 (2H, brs), 4.29 (1H, m), 6.81–6.83(7H, m)

Starting Material Synthesis Example 82

5-Amino-2-(4-phenylpiperidin-1-yl)benzonitrile

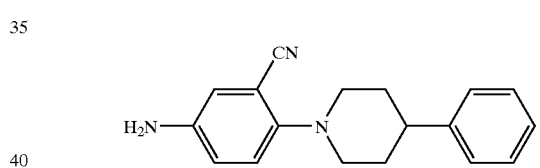

By the reaction and treatment in the same manner as in Starting Material Synthesis Example 40, except that 4-phenylpiperidine was used instead of piperidine, the title compound was obtained, melting point: 158–162° C.

Starting Material Synthesis Example 83

5-Amino-2-[4-(4-chlorophenyl)piperazin-1-yl]benzonitrile

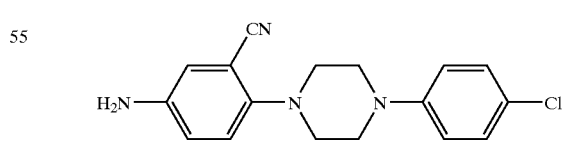

By the reaction and treatment in the same manner as in Starting Material Synthesis Example 40, except that 4-(4-chlorophenyl)piperazine was used instead of piperidine, the title compound was obtained as an oil.

$^1$H-NMR (400 MHz, DMSO) δ(ppm):3.05 (4H, brs), 3.28 (4H, brs), 5.25 (2H, brs), 6.84 (2H, m), 7.01 (1H, brs), 7.01 (2H, d, J=7.8 Hz), 7.25 (2H, d, J=7.8 Hz)

Starting Material Synthesis Example 84

5-Amino-2-(4-thiomorpholinopiperidin-1-yl)benzonitrile

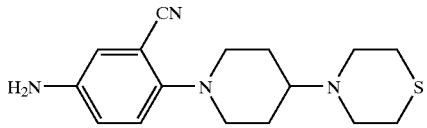

Reductive amination was conducted according to J. Org. Chem., vol. 55, p. 2552 (1990) using 5-nitro-2-(4-oxopiperidin-1-yl) benzonitrile and thiomorpholine. Then, the nitro group was reduced in the same manner as in Starting Material Synthesis Example 40 to give the title compound, melting point: 138° C.

Starting Material Synthesis Example 85

5-Amino-2-[4-[N-tert-butoxycarbonyl-N-(2-hydroxyethyl) amino] piperidin-1-yl]benzonitrile

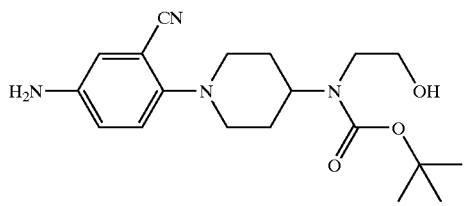

(1) 5-Nitro-2-(4-oxopiperidin-1-yl) benzonitrile

2-Chloro-5-nitrobenzonitrile (15 g), 4-piperidone monohydrate hydrochloride (13.9 g) and triethylamine (25 ml) were added to acetonitrile (100 ml), and the mixture was stirred at a refluxing temperature for 1.5 h. 0.5 N Aqueous hydrochloric acid solution (200 ml) was added to the reaction mixture to allow crystallization to give the title compound (16.1 g), melting point: 109° C.

(2) 2-[4-(2-Hydroxyethylamino)piperidin-1-yl]-5-nitrobenzonitrile

5-Nitro-2-(4-oxopiperidin-1-yl)benzonitrile (5.0 g), 2-hydroxyethylamine (1.5 g) and sodium cyanoborohydride (1.3 g) were added to a mixed solvent of methanol (100 ml) and tetrahydrofuran (50 ml) and the mixture was stirred at room temperature for 1 h. An aqueous hydrochloric acid solution was added to keep the reaction mixture acidic. The solvent was evaporated under reduced pressure. Aqueous sodium hydroxide solution was added to the residue and the mixture was extracted with ethyl acetate. The organic layer was washed with saturated brine and dried over anhydrous sodium sulfate, after which the solvent was evaporated under reduced pressure. Diisopropyl ether was added to the residue to allow precipitation, whereby the title compound (3.6 g) was obtained, melting point: 115° C.

(3) 2-[4-[N-tert-Butoxycarbonyl-N-(2-hydroxyethylamino)]piperidin-1-yl]-5-nitrobenzonitrile By the reaction and treatment in the same manner as in Starting Material Synthesis Example 48 using 2-[4-(2-hydroxyethylamino)piperidin-1-yl]-5-nitrobenzonitrile instead of 5-nitro-2-homopiperazinebenzonitrile, the title compound was obtained, melting point: 88° C.

(4) 5-Amino-2-[4-[N-tert-butoxycarbonyl-N-(2-hydroxyethyl)amino]piperidin-1-yl]benzonitrile Reduction was conducted according to Starting Material Synthesis Example 40 using 2-[4-[N-tert-butoxycarbonyl-N-(2-hydroxyethylamino)]piperidin-1-yl]-5-nitrobenzonitrile to give the title compound.
$^1$H-NMR (400 MHz, DMSO-d$_6$) δ(ppm):1.41 (9H, s), 1.5–1.7 (2H, m), 1.7–2.0 (2H, m), 2.6–2.8 (2H, m), 3.0–3.5 (7H, m), 4.68 (1H, brs), 5.19 (2H, s), 6.7–6.9 (2H, m), 6.96 (1H, d, J=9.8 Hz)

Starting Material Synthesis Example 86

5-Amino-2-[4-(3,4,5,6-tetrahydro-2H-pyran-4-yl)piperazin-1-yl]benzonitrile

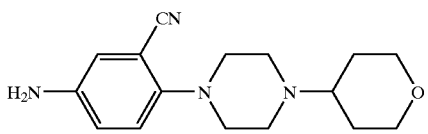

According to Tetrahedron vol. 38(3), p. 413 (1982), reductive amidation was conducted using 5-nitro-2-piperazinebenzonitrile synthesized in Starting Material Synthesis Example 47 and 2,3,5,6-tetrahydropyran-4-one, and reduction reaction was conducted in the same manner as in Starting Material Synthesis Example 40 to give the title compound, melting point: 162° C.
$^1$H-NMR (400 MHz, DMSO-dl) δ(ppm):1.39–1.43 (2H, m), 1.71 (2H, d, J=11.7 Hz), 2.38–2.50 (1H, m), 2.52–2.63 (4H, brs), 2.86–2.97 (4H, brs), 3.28 (2H, dd, J 11.2, 11.7 Hz), 3.88 (2H, d, J=9.7 Hz), 5.19 (2H, brs), 6.81 (2H, brs), 6.92–6.94 (1H, m)

Starting Material Synthesis Example 87

5-Amino-2-[4-(3,4,5,6-tetrahydro-2H-thiopyran-4-yl)piperazin-1-yl]benzonitrile

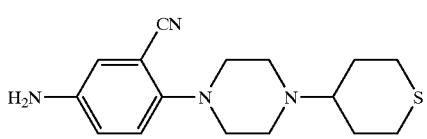

According to Tetrahedron vol. 38(3), p. 413 (1982), reductive amidation was conducted using 5-nitro-2-piperazinebenzonitrile synthesized in Starting Material Synthesis Example 47 and 2,3,5,6-tetrahydrothiopyran-4-one, and reduction reaction was conducted in the same manner as in Starting Material Synthesis Example 40 to give the title compound, melting point: 109° C.
$^1$H-NMR (400 MHz, DMSO-d$_6$) δ(ppm):1.60–1.76 (2H, m), 2.14 (2H, d, J=10.7 Hz), 2.34–2.40 (1H, m), 2.64–2.73 (2H, m) 2.73–2.75 (4H, m), 0.03 (4H, m), 3.61 (2H, brs), 6.79–6.88 (3H, m)

Starting Material Synthesis Example 88

1-(4-Chlorophenyl)-5-ethylpyrazole-4-carboxylic chloride

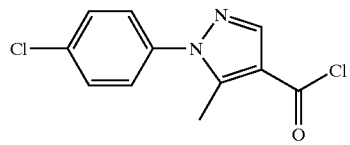

A suspension of 1-(4-chlorophenyl)-5-methylpyrazole-4-carboxylic acid (50 g) synthesized in Starting Material Synthesis Example 8, thionyl chloride (17 ml), toluene (200 ml) and dimethylformamide (0.1 ml) was refluxed under heating for 3 h. After the reaction, the solvent was evaporated to give the title compound (54 g), melting point: 105–107° C.

Starting Material Synthesis Example 89

5-Amino-2-[4-(N-2-hydroxyethyl-N-methylamino)piperidin-1-yl]benzonitrile

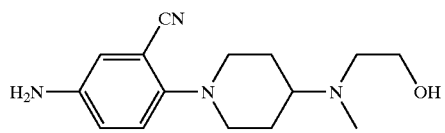

According to Tetrahedron, vol. 38, No. 3, p. 413 (1982) and using 5-nitro-2-(4-oxopiperidino) benzonitrile and N-methylethanolamine, 2-[4-(N-2-hydroxyethyl-N-methylamino) piperidin-1-yl]-5-nitrobenzonitrile was synthesized, which was subjected to reduction according to Starting Material Synthesis Example 40 to give the title compound.

$^1$H-NMR (400 MHz, DMSO-$d_6$) δ(ppm): 1.5–1.55 (2H, m), 1.7–1.85 (2H, m), 2.22 (3H, s), 2.35–2.5 (13H, m), 2.55–2.65 (2H, m), 3.15–3.25 (2H, m), 3.35–3.5 (4H, m), 4.30 (1H, brs), 5.16 (2H, brs), 6.7–6.9 (2H, m), 6.93 (1H, d, J=9.3 Hz)

Starting Material Synthesis Example 90

1-(4-Trifluoromethylphenyl)-5-methylpyrazole-4-carboxylic acid

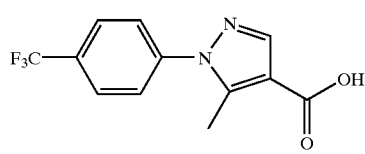

By the reaction and treatment in the same manner as in Starting Material Synthesis Example 1 using 4-trifluorom ethylphenylhydrazine (12.8 g) and ethyl 2-ethoxymethyleneacetoacetate (12.3 g), the title compound (12.3 g) was obtained, melting point: 181° C.

Starting Material Synthesis Example 91

5-Amino-2-[4-(4-tert-butoxycarbonylpiperazin-1-yl)piperidin-1-yl]benzonitrile

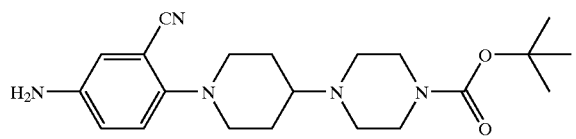

By the reaction and treatment in the same manner as in Starting Material Synthesis Example 84, except that 1-tert-butoxycarbonylpiperazine was used instead of thiomorpholine, the title compound was obtained, melting point: 172° C.

Starting Material Synthesis Example 92

1-Benzyl-3-methylpyrazole-4-carboxylic acid and 1-benzyl-5-methylpyrazole-4-carboxylic acid

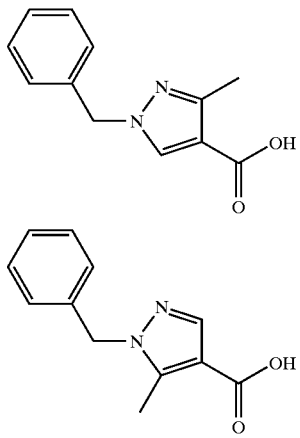

By the reaction and treatment in the same manner as in Starting Material Synthesis Example 1 using benzylhydrazine dihydrochloride (8.0 g) and ethyl 2-ethoxymethyleneacetoacetate (7.6 g), the residue was recrystallized from ethyl acetate to give 1-benzyl-3-methylpyrazole-4-carboxylic acid (2.45 g).

$^1$H-NMR (400 MHz, DMSO-$d_6$) δ(ppm):2.29 (3H, s), 5.26 (2H, s), 7.2–7.4 (5H, m), 8.26 (1H, s), 12.15 (1H, brs)

The mother liquor thereof was concentrated and recrystallized twice from a mixed solvent of ethyl acetate-diisopropyl ether to give 1-benzyl-5-methylpyrazole-4-carboxylic acid (0.8 g).

$^1$H-NMR (400 MHz, DMSO-$d_6$) δ(ppm):2.45 (3H, s), 5.36 (2H, s), 7.13 (2H, d, J=7.3 Hz), 7.2–7.4 (3H, m), 7.78 (1H, s), 12.23 (1H, brs)

Starting Material Synthesis Example 93

3-Methyl-1-phenethylpyrazole-4-carboxylic acid and 5-methyl-1-phenethylpyrazole-4-carboxylic acid

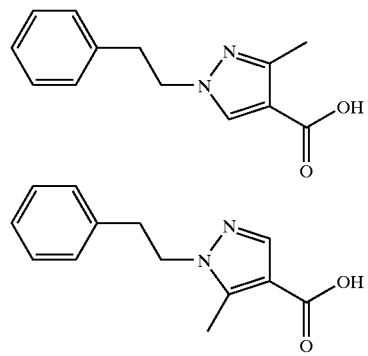

By the reaction and treatment in the same manner as in Starting Material Synthesis Example 1 using phenelzine (15 g) and ethyl 2-ethoxymethyleneacetoacetate (12 g), the residue was recrystallized from a mixed solvent of ethyl acetate-diisopropyl ether to give 3-methyl-1-phenethylpyrazole-4-carboxylic acid (5.5 g).

$^1$H-NMR (400 MHz, DMSO-d$_6$) δ(ppm):2.31 (3H, s), 3.08 (2H, d, J=6.8 Hz), 4.27 (2H, d, J c 6.8 Hz), 7.15–7.3 (5H, m), 7.99 (1H, s), 12.07 (1H, brs)

The mother liquor thereof was concentrated and hexane was added. The insoluble matter was filtrated and 5-methyl-1-phenethylpyrazole-4-carboxylic acid (0.9 g) was obtained as crystals from the filtrate.

$^1$H-NMR (400 MHz, DMSO-d$_6$) δ(pp):2.15 (3H, s), 3.04 (2H, d, J=6.8 Hz), 4.27 (2H, d, J=6.8 Hz), 7.08 (2H, d, J=7.3 Hz), 7.15–7.3 (3H, m), 7.75 (1H, s), 12.13 (1H, brs)

Starting Material Synthesis Example 94

5-Amino-2-[4-[N-tert-butoxycarbonyl-N-(2-methoxyethyl)amino]piperidin-1-yl]benzonitrile

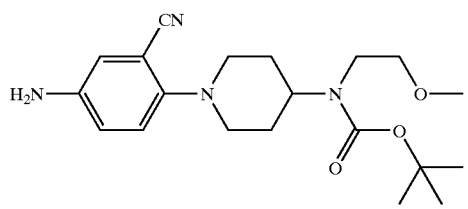

By the reaction and treatment in the same manner as in Starting Material Synthesis Example 85(2), (3) and (4) using 5-nitro-2-(4-oxopiperidino)benzonitrile and 2-methoxyethylamine, the title compound as obtained.

$^1$H-NMR (400 MHz, DMSO-d$_6$) δ(ppm):1.41 (9H, s), 1.55–1.75 (2H, m), 1.75–2.0 (2H, m), 2.6–2.75 (2H, m), 3.15–3.45 (7H, m), 3.26 (3H, s), 5.19 (2H, s), 6.75–6.85 (2H, m), 6.92 (1H, d, J=9.2 Hz)

Starting Material Synthesis Example 95

5-Amino-2-[4-[N-(2-methoxyethyl)-N-methylamino]piperidin-1-yl]benzonitrile

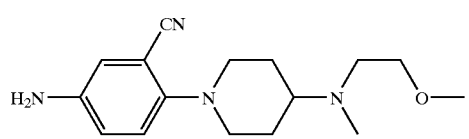

By the reaction and treatment in the same manner as in Starting Material Synthesis Example 84, except that 2-methoxyethylmethylamine was used instead of thiomorpholine, the title compound was obtained, melting point: 88° C.

Starting Material Synthesis Example 96

5-Amino-2-[4-bis(2-methoxyethyl)aminopiperidin-1-yl]enzonitrile

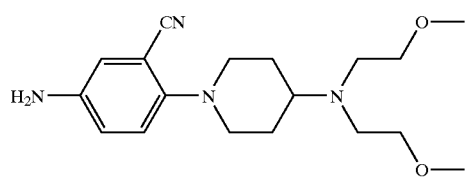

By the reaction and treatment in the same manner as in Starting Material Synthesis Example 84, except that bis(2-methoxyethyl)amine was used instead of thiomorpholine, the title compound was obtained.

$^1$H-NMR (400 MHz, DMSO-d$_6$) δ(ppm):1.45–1.6 (2H, m), 1.7–1.8 (2H, m), 2.5–2.65 (3H, m), 2.65 (4H, t, J=6.3 Hz), 3.15–3.25 (2H, m), 3.24 (6H, s), 3.33 (4H, t, J=6.3 Hz), 5.17 (2H, s), 6.75–6.8 (2H, m), 6.93 (1H, d, J=9.7 Hz)

Starting Material Synthesis Example 97

5-Methyl-1-(2-pyridyl)pyrazole-4-carboxylic acid

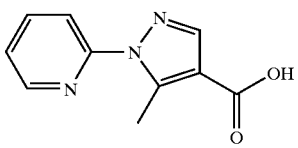

By the reaction and treatment in the same manner as in Starting Material Synthesis Example 1 using 2-pyridylhydrazine (8.0 g) and ethyl 2-ethoxymethyleneacetoacetate (13.7 g), the title compound (9.4 g) was obtained, melting point: 165° C.

Starting Material Synthesis Example 98

5-Amino-2-[4-(4-hydroxypiperidino)piperidin-1-yl]benzonitrile

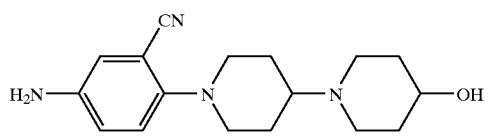

According to Tetrahedron vol. 38(3), p. 413 (1982), reductive amidation was conducted using 5-nitro-2-(4-oxopiperidin-1-yl)benzonitrile and 4-hydroxypiperazine, and reduction reaction was conducted in the same manner as in Starting Material Synthesis Example 40 to give the title compound, melting point: 175° C.

Starting Material Synthesis Example 99

5-Amino-2-[4-(4-morpholinomethylpiperidino)]benzonitrile

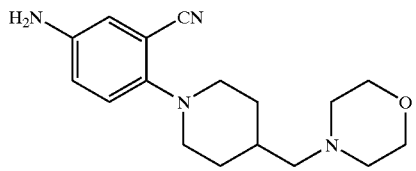

By the reaction and treatment in the same manner as in Starting Material Synthesis Example 40 using 2-chloro-5-nitrobenzonitrile and 4-morpholinomethylpiperidine, the title compound was obtained.
1H-NMR (400 MHz, DMSO-$d_6$) δ(ppm):1.15–1.3 (2H, m), 1.55–1.65 (1H, m), 1.75–1.85 (2H, m), 2.17 (2H, d, J=7.3 Hz), 2.25–2.4 (4H, m), 2.55–2.65 (2H, m), 3.1–3.2 (2H, m), 3.57 (4H, t, J=4.4 Hz), 5.16 (2H, s), 6.75–6.85 (2H, m), 6.93 (1H, d, J=9.3 Hz)

Starting Material Synthesis Example 100

1-(4-Nitrophenyl)-5-methylpyrazole-4-carboxylic acid

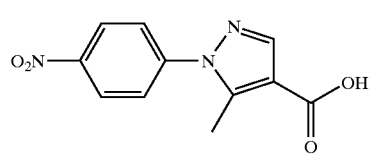

By the reaction and treatment in the same manner as in Starting Material Synthesis Example 1 using 4-nitrophenylhydrazine and ethyl 2-ethoxymethyleneacetoacetate, the title compound was obtained, melting point: 202° C.

Starting Material Synthesis Example 101

3-Bromo-4-(4-morpholinopiperidin-1-yl)aniline

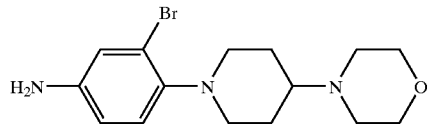

By the reaction and treatment in the same manner as in Starting Material Synthesis Example 40 using 3-bromo-4-chloronitrobenzene and 4-morpholinopiperidine, the title compound was obtained, melting point: 215–217° C.

Starting Material Synthesis Example 102

2-Amino-5-(4-morpholinopiperidin-1-yl)benzonitrile

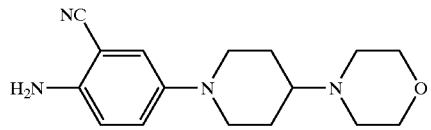

By the reaction and treatment in the same manner as in Starting Material Synthesis Example 40 using 5-chloro-2-nitrobenzonitrile and 4-morpholinopiperidine, the title compound was obtained, melting point: 178–180° C.

Starting Material Synthesis Example 103

N-(4-Chloro-3-nitrophenyl)-1-(4-chlorophenyl)-5-methylpyrazole-4-carboxamide

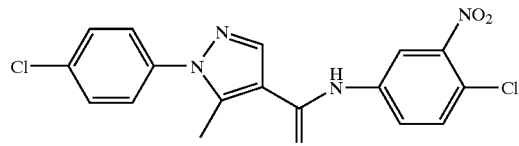

1-(4-Chlorophenyl)-5-methylpyrazole-4-carboxylic chloride (1.7 g) was added to a pyridine solution of 4-chloro-3-nitroaniline (1 g) and the mixture was stirred at room temperature for 2 h. After the reaction, water was added and the precipitated solid was collected by filtration to give the title compound (2.1 g), melting point:221–225° C.

Starting Material Synthesis Example 104

N-(4-Chloro-3-nitrophenyl)-5-methyl-1-(4-trifluoromethylphenyl)pyrazole-4-carboxamide

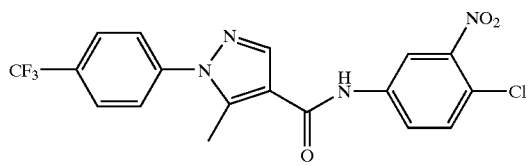

1-(4-Trifluoromethylphenyl)-5-methylpyrazole-4-carboxylic acid obtained in Starting Material Synthesis Example 90 was converted to acid chloride according to Starting Material Synthesis Example 88. The acid chloride was reacted and treated in the same manner as in Starting Material Synthesis Example 103 to give the title compound, melting point: 206–208° C.

Starting Material Synthesis Example 105

3-Methyl-4-(4-morpholinopiperidin-1-yl)aniline

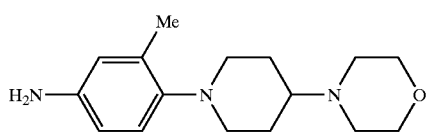

By the reaction and treatment in the same manner as in Starting Material Synthesis Example 40 using 4-chloro-3-methylnitrobenzene and 4-morpholinopiperidine, the title compound was obtained, melting point: 199–200° C.

Starting Material Synthesis Example 106

3-Chloro-4-(4-morpholinopiperidin-1-yl)aniline

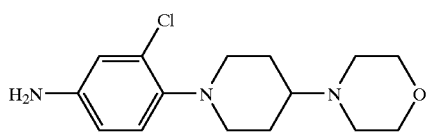

By the reaction and treatment in the same manner as in Starting Material Synthesis Example 40 using 3,4-dichloronitrobenzene and 4-morpholinopiperidine, the title compound was obtained, melting point: 220–223° C.

Starting Material Synthesis Example 107

4-(4-Morpholinopiperidin-1-yl)-3-trifluoromethylaniline

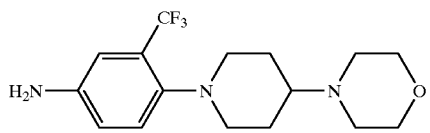

By the reaction and treatment in the same manner as in Starting Material Synthesis Example 40 using 4-chloro-3-trifluoromethylnitrobenzene and 4-morpholinopiperidine, the title compound was obtained, melting point: 118–120° C.

Starting Material Synthesis Example 108

5-Amino-2-(4-methoxymethoxypiperidin-1-yl)benzonitrile

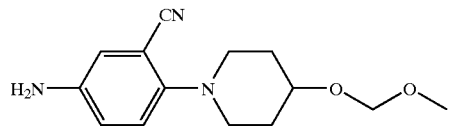

By the reaction and treatment in the same manner as in Starting Material Synthesis Example 59 using N-(tert-butoxycarbonyl)-4-hydroxypiperidine, sodium hydride and methoxymethylchloride, N-(tert-butoxycarbonyl)-4-methoxymethoxypiperidine was obtained. This was treated with trifluoroacetic acid-chloroform to give 4-methoxymethoxypiperidine, which was subjected to the reaction and treatment in the same manner as in Starting Material Synthesis Example 40 using 4-fold equivalents of triethylamine to give the title compound.

$^1$H-NMR (400 MHz, DMSO-$d_6$) δ(ppm):1.6–1.7 (2H, m), 1.9–2.0 (2H, m), 2.7–2.8 (2H, m), 3.0–3.1 (2H, m), 3.27 (3H, s), 3.6–3.7 (1H, m), 4.65 (2H, s), 5.18 (2H, s, NH2), 6.7–6.8 (2H, m), 6.96 (1H, d, J=9.3 Hz).

Starting Material Synthesis Example 109

5-Amino-2-[4-(2-methoxyethoxy)piperidin-1-yl]benzonitrile

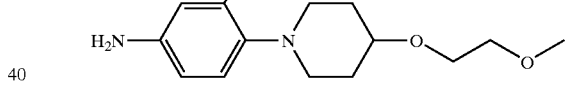

By the reaction and treatment in the same manner as in Starting Material Synthesis Example 108 using N-(tert-butoxycarbonyl)-4-hydroxypiperidine, the title compound was obtained.

1H-NMR (400 MHz, DMSO-$d_6$) δ(ppm):1.5–1.65 (2H, m), 1.9–2.0 (2H, m), 2.65–2.75 (2H, m), 3.0–3.1 (2H, m), 3.26 (3H, s), 3.4–3.5 (3H, m), 3.5–3.6 (2H, m), 5.18 (2H, s, NH2), 6.75–6.85 (2H, m), 6.95 (1H, d, J=9.3 Hz).

Starting Material Synthesis Example 110

3,5-Dichloro-4-(4-morpholinopiperidin-1-yl)aniline

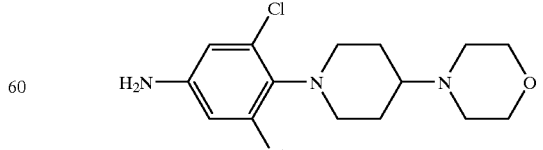

By the reaction and treatment in the same manner as in Starting Material Synthesis Example 40 using 3,4,5-trichloronitrobenzene and 4-morpholinopiperidine, the title compound was obtained, melting point: 144–146° C.

Starting Material Synthesis Example 111

5-Amino-2-{4-(2-hydroxyethyl)piperidin-1-yl}benzonitrile

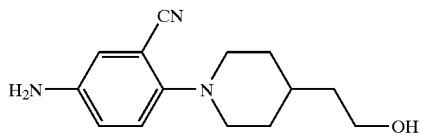

By the reaction and treatment in the same manner as in Starting Material Synthesis Example 40, except that 4-piperidineethanol was used instead of piperidine, the title compound was obtained, melting point: 60–63° C.

Starting Material Synthesis Example 112

5-Amino-2-[4-(2-methoxyethyl)piperazin-1-yl]benzonitrile

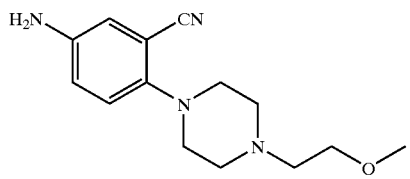

By the reaction and treatment in the same manner as in Starting Material Synthesis Example 40, except that 1-(2-methoxyethyl)piperazine was used instead of piperidine, the title compound was obtained.

$^1$H-NMR (400 MHz, DMSO-d$_6$) δ(ppm):2.45–2.6 (6H, m), 2.85–2.95 (4H, m), 3.24 (3H, s), 3.45 (2H, t, J=5.9 Hz), 5.20 (2H, s), 6.75–6.85 (2H, m), 6.95 (1H, d, J=9.3 Hz).

Starting Material Synthesis Example 113

5-Amino-2-[4-(4-methoxypiperidin-1-yl)piperidin-1-yl]benzonitrile

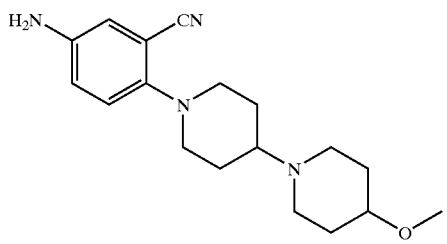

By the reaction and treatment in the same manner as in Starting Material Synthesis Example 84, except that 4-methoxypiperidine was used instead of thiomorpholine, the title compound was obtained, melting point: 125–130° C.

Starting Material Synthesis Example 114

5-Amino-2-(3-morpholinopropoxy)benzonitrile

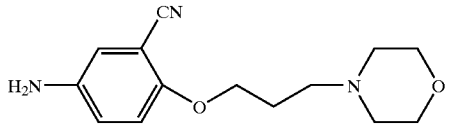

By the reaction and treatment in the same manner as in Starting Material Synthesis Example 36, using 1-(3-hydroxypropyl)morpholine and 2-chloro-5-nitrobenzonitrile, the title compound was obtained.

$^1$H-NMR (400 MHz, DMSO-d$_6$) δ (ppm):1.8–1.9 (2H, m), 2.3–2.5 (6H, m), 3.5–3.6 (4H, m), 3.95–4.05 (2H, m), 5.06 (2H, s), 6.78 (1H, d, J=2.9 Hz), 6.84 (1H, dd, J=8.8, 2.9 Hz), 6.96 (1H, d, J=8.8 Hz)

Starting Material Synthesis Example 115

5-Amino-2-(2-morpholinoethoxy)benzonitrile

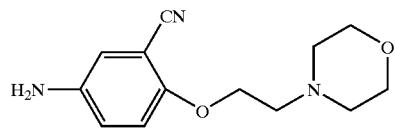

By the reaction and treatment in the same manner as in Starting Material Synthesis Example 36 using 1-(2-hydroxyethyl)morpholine and 2-chloro-5-nitrobenzonitrile, the title compound was obtained.

$^1$H-NMR (400 MHz, DMSO) δ(ppm):2.4–2.5 (4H, m), 2.6–2.7 (2H, m), 3.5–3.6 (4H, m), 4.08 (2H, d, J=5.9 Hz), 5.08 (2H, s), 6.78 (1H, d, J=2.5 Hz), 6.84 (1H, dd, J=8.8, 2.5 Hz), 6.98 (1H, d, J=8.8 Hz).

Starting Material Synthesis Example 116

5-Amino-2-(4-morpholinopiperidin-1-ylmethyl)benzonitrile

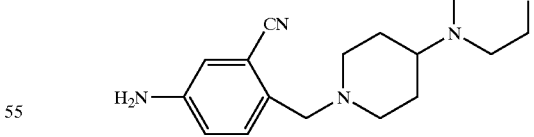

A suspension of carbon tetrachloride (400 ml) containing 2-methyl-5-nitrobenzonitrile (24 g), N-bromosuccinicimide (26.4 g) and 2,2'-azobis(isobutyronitrile) (0.8 g) was stirred at a refluxing temperature for 4 h. The reaction mixture was added into saturated aqueous sodium thiosulfate solution under room temperature, washed with water and saturated brine and dried over anhydrous magnesium sulfate, after which the solvent was evaporated under reduced pressure. Acetonitrile (50 ml) solution of the obtained 2-bromomethyl-5-nitrobenzonitrile (5 g), 4-morpholinopiperidine (5.3 g) and diisopropylethylamine (8.0 g) was stirred at a refluxing temperature for 1 h. 4N Hydrochloric acid was added under ice-cooling to adjust the solution to pH 2 and the solution was washed with chloroform. The solution was adjusted to pH 10 with a 30% aqueous potassium carbonate solution and extracted with chloroform. The organic layer was washed with water and saturated brine and dried over anhydrous magnesium sulfate, after which the solvent was evaporated under reduced pressure. The residue was purified by silica gel column chromatography (mobile phase:chloroform-methanol) to give 2-(4-morpholinopiperidin-1-ylmethyl)-5-nitrobenzonitrile (1.7 g). Using this compound, reduction was conducted acording to Starting Material Synthesis Example 40 to give the title compound, melting point: 162–165° C.

Starting Material Synthesis Example 117

5-Amino-2-(3-hydroxypropylthio)benzonitrile

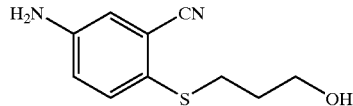

By the reaction and treatment in the same manner as in Starting Material Synthesis Example 40, except that 3-mercapto-1-propanol was used instead of piperidine, the title compound was obtained.

$^1$H-NMR (400 MHz, DMSO-d$_6$) δ(ppm):1.5–1.7 (2H, m), 2.84 (2H, t, J=6.8 Hz), 3.45 (2H, q apparent, J=5.3 Hz), 4.50 (1H, t, J=5.3 Hz), 5.77 (2H, s), 7.60 (1H, dd, J=8.8, 2.4 Hz), 6.89 (1H, d, J=2.4 Hz), 7.32 (1H, d, J=8.8 Hz).

EXAMPLE 1

N-(3-Cyano-4-neopentyloxyphenyl)-1,5-dimethyl pyrazole-4-carboxamide

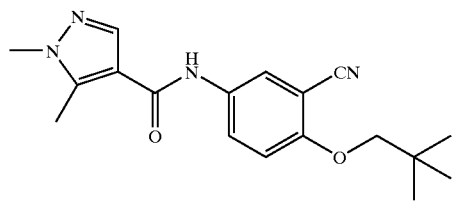

1,5-Dimethylpyrazole-4-carboxylic acid (10 g), 1-hydroxybenzotriazole (11.6 g) and 1-ethyl-3-(3'dimethylaminopropyl)carbodiimide (16.3 g) were added to dimethylformamide (200 ml) and the mixture was stirred at room temperature for 1.5 h. The reaction mixture was treated with aqueous potassium carbonate solution. The organic layer was extracted with ethyl acetate, washed with saturated brine and dried over anhydrous magnesium sulfate, after which the solvent was evaporated under reduced pressure. Diisopropyl ether was added to the residue to allow crystallization. The crystals were recrystallized from ethyl acetate to give 1-benzotriazole 1,5-dimethylpyrazole-4-carboxylate (11.8 g), melting point 167–168° C.

1-Benzotriazole 1,5-dimethylpyrazole-4-carboxylate (3 g) and 5-amino-2-neopentyloxybenzonitrile (2.4 g) were added to ethanol (30 ml) and the mixture was stirred at 78° C. for 3 h. After evaporation of the solvent, the residue was purified by silica gel column chromatography (mobile phase:chloroform:methanol=50:1) to give the title compound (2.56 g), melting point: 187–188° C.

EXAMPLE 2

N-(3-Cyano-4-isobutoxyphenyl)-1,5-dimethylpyrazole-44-carboxamide

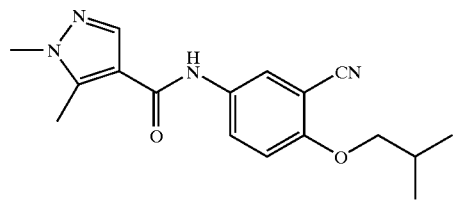

1-Hydroxybenzotriazole 1,5-dimethylpyrazole-4-carboxylate (2 g) and 5-amino-2-isobutoxybenzonitrile (1.9 g) were added to ethanol (25 ml) and the mixture was stirred at 78° C. for 3 h. After evaporation of the solvent, the residue was purified by silica gel column chromatography (mobile phase:chloroform:methanol=50:1) to give the title compound (0.8 g), melting point: 160–162° C.

EXAMPLE 3

N-(3-Cyano-4-piperidinophenyl)-1,5-dimethylpyrazole-44-carboxamide

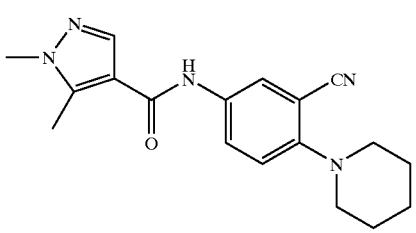

1-Hydroxybenzotriazole 1,5-dimethylpyrazole-4-carboxylate (1.2 g) and 5-amino-2-piperidinobenzonitrile (0.9 g) were added to ethanol (20 ml) and the mixture was stirred at 78° C. for 3 h. After evaporation of the solvent, aqueous potassium carbonate solution was added to the residue and the mixture was extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous ethanol to give the title compound (0.7 g), melting point: 217–218° C.

EXAMPLE 4

N-{3-Cyano-4-[4-(2-hydroxyethyl)piperazin-1-yl]phenyl}-1,5-dimethylpyrazole-4-carboxamide

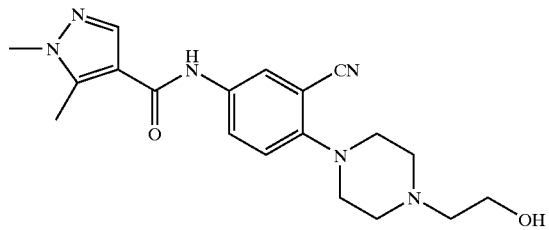

1-Benzotriazole 1,5-dimethylpyrazole-4-carboxylate (3 g) and 5-amino-2-[4-(2-hydroxyethyl)piperazin-1-yl]benzonitrile (2.9 g) were added to ethanol (25 ml) and the mixture was stirred at 78° C. for 3 h. After evaporation of the solvent, aqueous potassium carbonate solution was added to the residue and the mixture was extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous ethanol to give the title compound (0.65 g), melting point: 228–230° C.

EXAMPLE 5

N-[3-Cyano-(4-hydroxypiperidin-1-yl)phenyl]-1,5-dimethylpyrazole-4-carboxamide

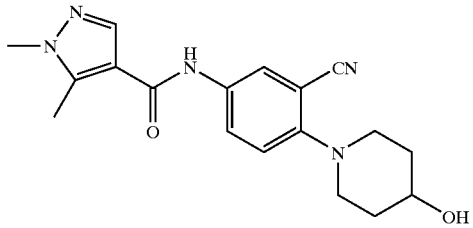

1-Benzotriazole 1,5-dimethylpyrazole-4-carboxylate (3 g) and 5-amino-2-(4-hydroxypiperidin-1-yl)benzonitrile(2.5 g) were added to ethanol (35 ml) and the mixture was stirred at 78° C. for 3 h. After evaporation of the solvent, aqueous potassium carbonate solution was added to the residue and the mixture was extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous ethanol to give the title compound (0.9 g), melting point: 261–262° C.

EXAMPLE 6

4-(1-[2-Cyano-4-(1,5-dimethyl-4-pyrazolecarboxamide) phenyl]piperidine-4-yloxy)-4-oxobutyric acid

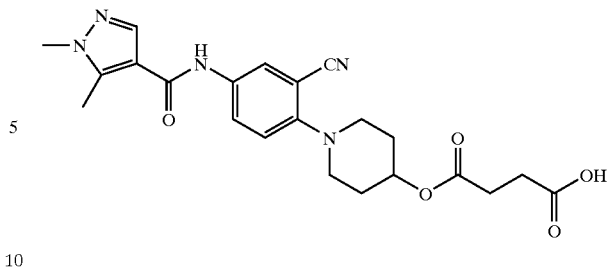

N-[3-Cyano-(4-hydroxypiperidin-1-yl)phenyl]-1,5-dimethylpyrazole-4-carboxamide (0.7 g), succinic anhydride (0.2 g) and a catalytic amount of p-toluenesulfonic acid monohydrate were added to nitrobenzene (5 ml), and the mixture was reacted at 120° C. for 3 h. After cooling to roan temperature, diisopropyl ether was added and the precipitated crystals were recrystallized from hydrous dimethylformamide to give the title compound (0.5 g), melting point: 211–212° C.

EXAMPLE 7

N-(3-Cyano-4-n-hexyloxyphenyl)-1,5-dimethylpyrazole-4-carboxamide

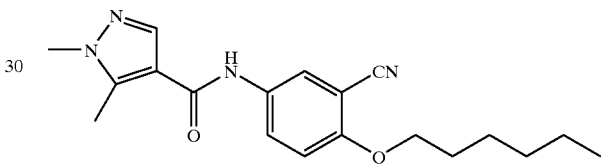

1-Benzotriazole 1,5-dimethylpyrazole-4-carboxylate (1 g) and 5-amino-2-n-hexyloxybenzonitrile (0.8 g) were added to ethanol (10 ml) and the mixture was stirred at 78° C. for 3 h. After evaporation of the solvent, aqueous potassium carbonate solution was added to the residue and the mixture was extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous ethanol to give the title compound (0.7 g), melting point: 150–151° C.

EXAMPLE 8

N-(3-Cyano-4-neopentyloxyphenyl)-1,3-dimethylpyrazole-4-carboxamide

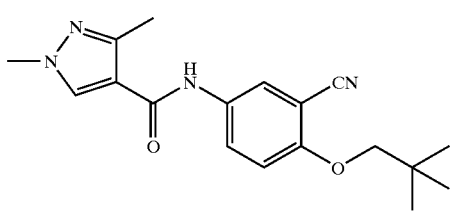

1,3-Dimethylpyrazole-4-carboxylic acid (0.6 g), 5-amino-2-neopentyloxybenzonitrile (0.9 g), triethylamine (1.0 g) and diethyl cyanophosphate (1.0 g) were added to dimethylformamide (10 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous methanol to give the title compound (0.5 g), melting point: 193–194° C.

EXAMPLE 9

N-(3-Cyano-4-neopentyloxyphenyl)-1-(4-fluorophenyl)-3-methylpyrazole-4-carboxamide

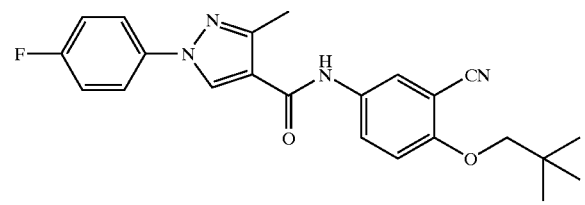

1-(4-Fluorophenyl)-3-methylpyrazole-4-carboxylic acid (1.2 g), 5-amino-2-neopentyloxybenzonitrile (1.3 g), triethylamine (1.7 g) and diethyl cyanophosphate (1.3 g) were added to dimethylformamide (10 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from a mixed solvent of ethyl acetate-n-hexane to give the title compound (0.4 g), melting point: 181–182° C.

EXAMPLE 10

N-(3-Cyano-4-neopentyloxyphenyl)-1-(4-fluorophenyl)-5-methylpyrazole-4-carboxamide ½ hydrate

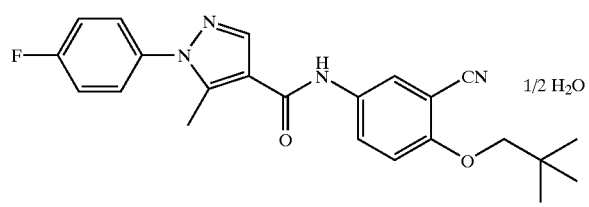

1-(4-Fluorophenyl)-5-methylpyrazole-4-carboxylic acid (2.1 g), 5-amino-2-neopentyloxybenzonitrile (1.3 g), triethylamine (1.7 g) and diethyl cyanophosphate (1.3 g) were added to dimethylformamide (10 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous ethanol to give the title compound (0.2 g), melting point: 126–127° C.

EXAMPLE 11

N-(3-Cyano-4-isobutoxyphenyl)-1-(4-fluorophenyl)-3-methylpyrazole-4-carboxamide

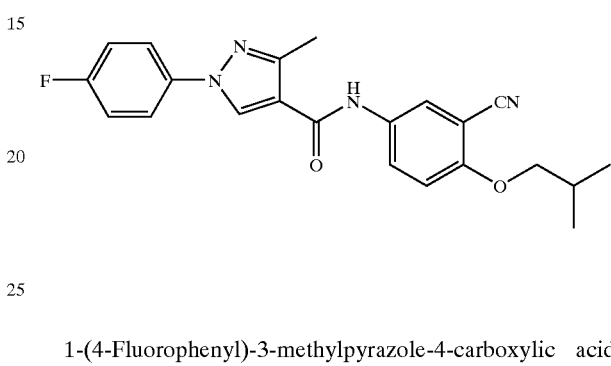

1-(4-Fluorophenyl)-3-methylpyrazole-4-carboxylic acid (0.6 g), 5-amino-2-isobutoxybenzonitrile (0.5 g), triethylamine (0.8 g) and diethyl cyanophosphate (0.7 g) were added to dimethylformamide (8 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous ethanol to give the title compound (0.2 g), melting point: 179–180° C.

EXAMPLE 12

N-(3-Cyano-4-neopentyloxyphenyl)-1-(4-fluorophenyl)-3,5-dimethylpyrazole-4-carboxamide

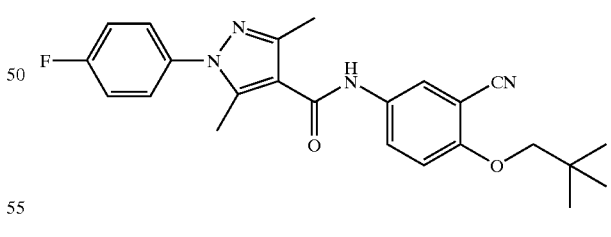

1-(4-Fluorophenyl)-3,5-dimethylpyrazole-4-carboxylic acid (2 g), 5-amino-2-neopentyloxybenzonitrile (1.7 g), triethylamine (1.7 g) and diethyl cyanophosphate (1.4 g) were added to dimethylformamide (20 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous methanol to give the title compound (0.6 g), melting point: 174–175° C.

EXAMPLE 13

N-(3-Cyano-4-neopentyloxyphenyl)-1-(4-fluorophenyl)pyrazole-4-carboxamide

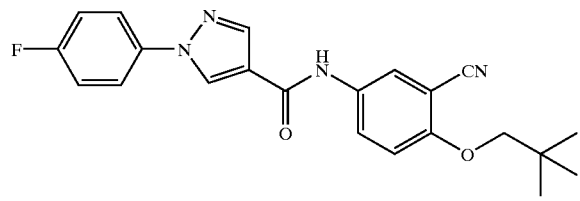

1-(4-Fluorophenyl)pyrazole-4-carboxylic acid (2 g), 5-amino-2-neopentyloxybenzonitrile (2.2 g), triethylamine (2 g) and diethyl cyanophosphate (1.6 g) were added to dimethylformamide (20 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous methanol to give the title compound (1.2 g), melting point: 196–197° C.

EXAMPLE 14

N-(3-Cyano-4-neopentyloxyphenyl)-1(3-trifluoromethylphenyl)-5-methylpyrazole-4-carboxamide

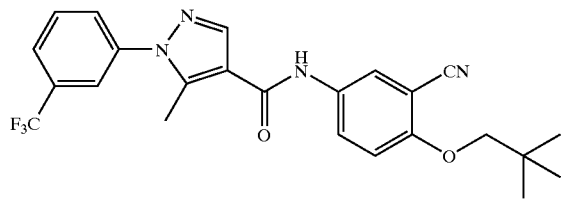

1-(3-Trifluoromethylphenyl)-5-methylpyrazole-4-carboxylic acid (2 g), 5-amino-2-neopentyloxybenzonitrile (1.8 g), triethylamine (1.6 g) and diethyl cyanophosphate (1.4 g) were added to dimethylformamide (20 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous ethanol to give the title compound (1.4 g), melting point: 116–118° C.

EXAMPLE 15

N-(3-Cyano-4-neopentyloxyphenyl)-1-(4-fluorophenyl)pyrrole-3-carboxamide

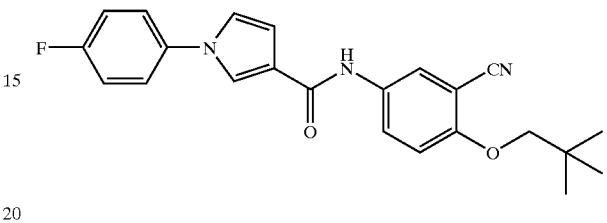

1-(4-Fluorophenyl)pyrrole-3-carboxylic acid (2 g), 5-amino-2-neopentyloxybenzonitrile (1.8 g), triethylamine (1.7 g) and diethyl cyanophosphate (1.6 g) were added to dimethylformamide (20 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous methanol to give the title compound (0.7 g), melting point: 167–169° C.

EXAMPLE 16

N-(3-Cyano-4-isobutoxyphenyl)-1-(4-fluorophenyl)-5-methylpyrazole-4-carboxamide

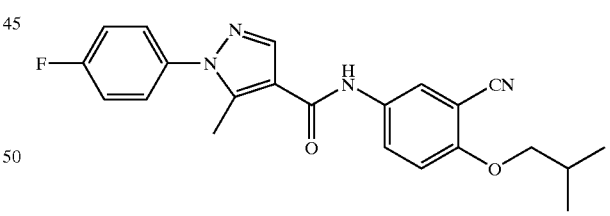

1-(4-Fluorophenyl)-5-methylpyrazole-4-carboxylic acid (2 g), 5-amino-2-isobutoxybenzonitrile (1.7 g), triethylamine (2.7 g) and diethyl cyanophosphate (2.2 g) were added to dimethylformamide (20 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. Diisopropyl ether was added to the residue to allow crystallization. The crystals were recrystallized from a mixed solvent of ethyl acetate-n-hexane to give the title compound (1.2 g), melting point: 177–178° C.

EXAMPLE 17

N-(3-Cyano-4-isobutoxyphenyl)-1-(4-fluorophenyl)-5-hydroxypyrazole-4-carboxamide

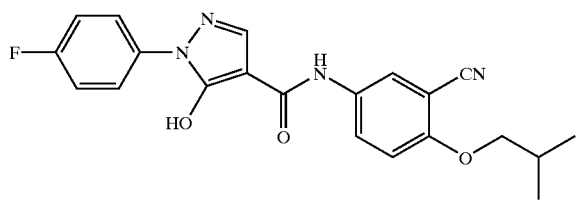

Ethyl 1-(4-fluorophenyl)-5-hydroxypyrazole-4-carboxylate (1 g) and 5-amino-2-isobutoxybenzonitrile (0.8 g) were added to pyridine (10 ml) and the mixture was stirred at 120° C. for 4 h. After evaporation of the solvent under reduced pressure, hydrochloric acid was added to the residue and the mixture was extracted with chloroform. The organic layer was washed with saturated brine and dried over anhydrous magnesium sulfate, after which the solvent was evaporated under reduced pressure. Diisopropyl ether was added to the residue to allow crystallization. The crystals were recrystallized from a mixed solvent of ethanol-diisopropyl ether to give the title compound (0.2 g), melting point: 207–208° C.

EXAMPLE 18

N-(3-Cyano-4-neopentyloxyphenyl)-1-(4-fluorophenyl)-N,3-dimethylpyrazole-4-carboxamide ½ hydrate

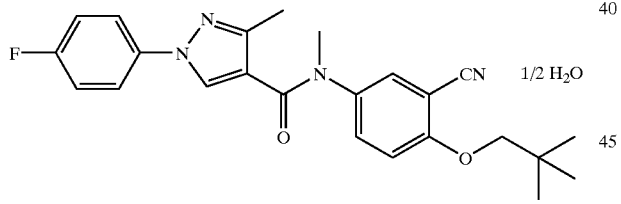

To dimethylformamide (5 ml) solution containing N-(3-cyano-4-neopentyloxyphenyl)-1-(4-fluorophenyl)-3-methylpyrazole-4-carboxamide (1.5 g) was added sodium hydride (60% content, 0.2 g) under ice-cooling and the mixture was stirred for 1 h. A solution of dimethylformamide (1 ml) containing methyl iodide (0.6 g) was added and the mixture was stirred under ice-cooling for 1 h. The mixture was allowed to warm to room temperature and stirred for 1 h. The reaction mixture was added into water and extracted with ethyl acetate. The organic layer was washed with saturated brine and dried over anhydrous magnesium sulfate, after which the solvent was evaporated under reduced pressure. The residue was purified by silica gel column chromatography (mobile phase: ethyl acetate:n-hexane=5:1) to give the title compound (0.5 g), melting point: 65–69° C.

EXAMPLE 19

N-(3-Cyano-4-neopentyloxyphenyl)-N-[1-(4-fluorophenyl)-3-methylpyrazol-4-ylcarbonyl]glycine

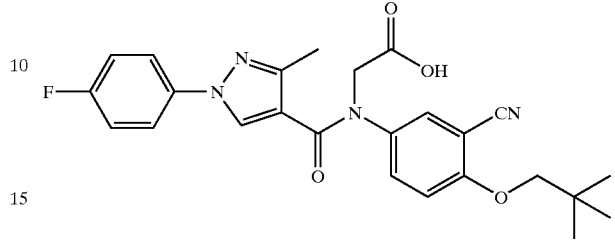

Dichloroethane solution (45 ml) containing 1-(4-fluorophenyl)-3-methylpyrazole-4-carboxylic acid (8.1 g) and thionyl chloride (5.3 g) was stirred at 83° C. for 30 min to give acid chloride. This was added to pyridine solution (80 ml) containing ethyl N-(3-cyano-4-neopentyloxyphenyl) glycine (5.3 g) under ice-cooling and the mixture was stirred for 1 h. The reaction mixture was added into water and extracted with ethyl acetate. The organic layer was washed with saturated brine, after which the solvent was evaporated under reduced pressure. Sodium hydroxide (1.8 g), water (40 ml) and ethanol (40 ml) were added to the residue and the mixture was stirred at a refluxing temperature for 1 h. The solvent was evaporated under reduced pressure. Dilute hydrochloric acid was added, and the mixture was extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from a mixed solvent of toluene-n-hexane to give the title compound (4.7 g), melting point: 156.7° C.

EXAMPLE 20

N-(3-Cyano-4-neopentyloxyphenyl)-1-phenyl-3-methylpyrazole-4-carboxamide

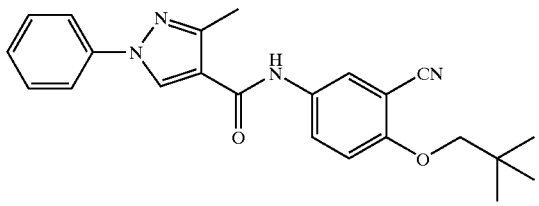

1-Phenyl-3-methylpyrazole-4-carboxylic acid (2.2 g), 5-amino-2-neopentyloxybenzonitrile (2.2 g), triethylamine (3.3 g) and diethyl cyanophosphate (2.7 g) were added to dimethylformamide (20 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous methanol to give the title compound (2.4 g), melting point: 155–156° C.

EXAMPLE 21

N-(3-Cyano-4-neopentyloxyphenyl)-1-methyl-3-phenylpyrazole-5-carboxamide

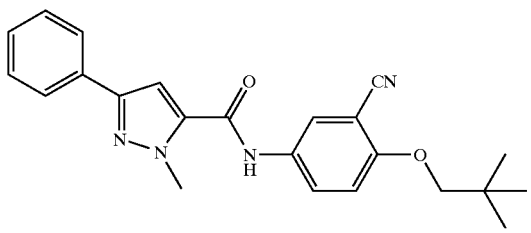

1-Methyl-3-phenylpyrazole-5-carboxylic acid (0.8 g), 5-amino-2-neopentyloxybenzonitrile (0.8 g), triethylamine (1.2 g) and diethyl cyanophosphate (1.0 g) were added to dimethylformamide (10 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous methanol to give the title compound (0.3 g), melting point: 223–224° C.

EXAMPLE 22

N-(3-Cyano-4-neopentyloxyphenyl)-1-methyl-5-phenylpyrazole-3-carboxamide

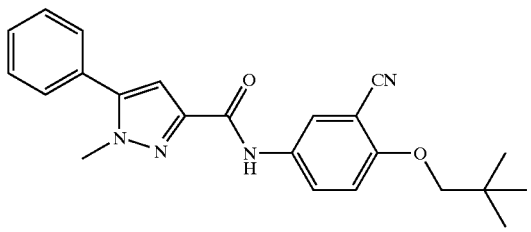

1-Methyl-5-phenylpyrazole-3-carboxylic acid (2.1 g), 5-amino-2-neopentyloxybenzonitrile (2.2 g), triethylamine (3.4 g) and diethyl cyanophosphate (2.7 g) were added to dimethylformamide (25 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous dimethylformamide to give the title compound (3.1 g), melting point: 156–157° C.

EXAMPLE 23

N-(3-Bromo-4-neopentyloxyphenyl)-1-(4-fluorophenyl)-3-methylpyrazole-4-carboxamide

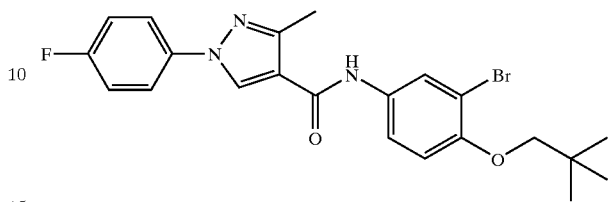

1-(4-Fluorophenyl)-3-methylpyrazole-4-carboxylic acid (1.7 g), 3-bromo-4-neopentyloxyaniline (2 g), triethylamine (2.3 g) and diethyl cyanophosphate (1.9 g) were added to dimethylformamide (20 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous dimethylformamide to give the title compound (1.4 g), melting point: 193–194° C.

EXAMPLE 24

N-(3-Cyano-4-n-hexyloxyphenyl)-1-(4-fluorophenyl)-3-methylpyrazole-4-carboxamide

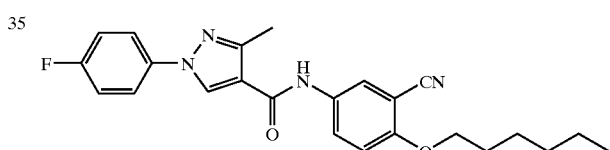

1-(4-Fluorophenyl)-3-methylpyrazole-4-carboxylic acid (1.0 g), 5-amino-2-n-hexyloxybenzonitrile (1.0 g), triethylamine (1.4 g) and diethyl cyanophosphate (1.2 g) were added to dimethylformamide (20 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from ethyl acetate to give the title compound (0.5 g), melting point: 160–161° C.

EXAMPLE 25

5-Chloro-N-(3-cyano-4-neopentyloxyphenyl)-1-(4-fluorophenyl)pyrazole-4-carboxamide

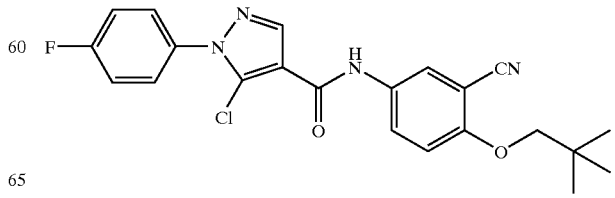

5-Chloro-1-(4-fluorophenyl)-3-pyrazole-4-carboxylic acid (1.0 g), 5-amino-2-neopentyloxybenzonitrile (0.9 g), triethylamine (1.3 g) and diethyl cyanophosphate (1.0 g) were added to dimethylformamide (10 ml) and the mixture was stirred at roan temperature for 1 h. The reaction mixture was added into water and extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from hydrous methanol to give the title compound (0.6 g), melting point: 149–150° C.

EXAMPLE 26

N-(3-Cyano-4-neopentyloxyphenyl)-1-(2,2,2-trifluoroethyl)pyrazole-4-carboxamide

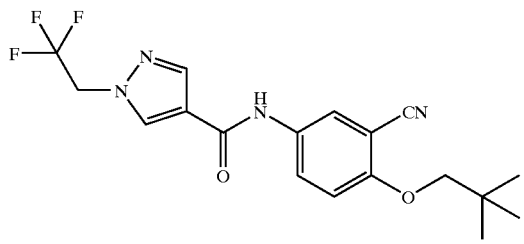

1-(2,2,2-Trifluoroethyl)pyrazole-4-carboxylic acid (2.2 g), 5-amino-2-neopentyloxybenzonitrile (2.5 g), 1-hydroxybenzotriazole (1.8 g) and 1-ethyl-3-(3'-dimethylaminopropyl)carbodiimide (2.6 g) were added to dimethylformamide (20 ml) and the mixture was stirred at room temperature for 1.5 h. The reaction mixture was treated with aqueous potassium carbonate solution and extracted with ethyl acetate. The organic layer was washed with saturated brine and dried over anhydrous magnesium sulfate, after which the solvent was evaporated under reduced pressure. Diisopropyl ether was added to the residue to allow crystallization. The crystals were recrystallized from ethyl acetate to give the title compound (1.8 g), melting point 159–160° C.

EXAMPLE 27

N-(3-Cyano-4-neopentyloxyphenyl)-1-(4-fluorophenyl)-5-methylpyrazole-3-carboxamide

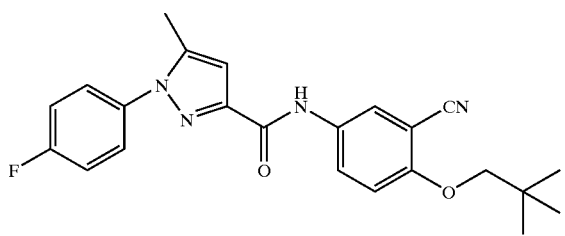

1-(4-Fluorophenyl)-5-methylpyrazole-3-carboxylic acid (2.1 g), 5-amino-2-neopentyloxybenzonitrile (2.0 g), triethylamine (2.9 g) and diethyl cyanophosphate (2.3 g) were added to dimethylformamide (25 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. Methanol was added to the residue to allow crystallization. The crystals were recrystallized from hydrous methanol to give the title compound (1.9 g), melting point: 146–147° C.

EXAMPLE 28

N-(3-Cyano-4-neopentyloxyphenyl)-1-(4-fluorophenyl)-3-methylpyrazole-5-carboxamide

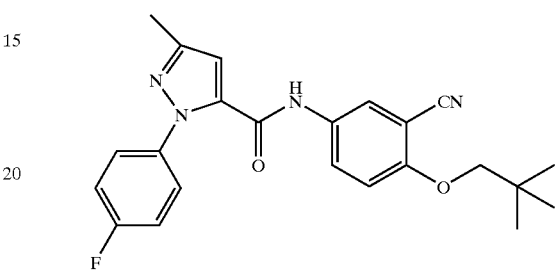

1-(4-Fluorophenyl)-3-methylpyrazole-5-carboxylic acid (1.4 g), 5-amino-2-neopentyloxybenzonitrile (1.3 g), triethylamine (1.9 g) and diethyl cyanophosphate (1.6 g) were added to dimethylformamide (20 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. Methanol was added to the residue to allow crystallization. The crystals were recrystallized from hydrous methanol to give the title compound (0.3 g), melting point: 165° C.

EXAMPLE 29

N-(3-Cyano-4-isobutylphenyl)-1-(4-fluorophenyl)-3-methylpyrazole-4-carboxamide

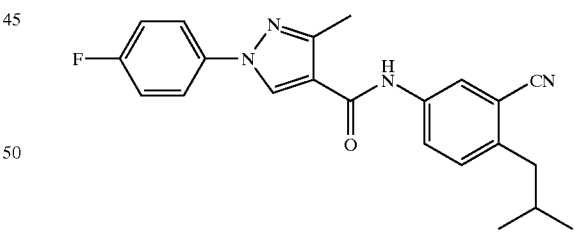

1-(4-Fluorophenyl)-3-methylpyrazole-4-carboxylic acid (1.5 g), 5-amino-2-isobutylbenzonitrile (1.2 g), triethylamine (2.0 g) and diethyl cyanophosphate (1.2 g) were added to dimethylformamide (15 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. A mixed solvent of ethyl acetate-n-hexane was added to the residue to allow crystallization. The crystals were recrystallized from hydrous dimethylformamide to give the title compound (0.9 g), melting point: 178–179° C.

EXAMPLE 30

1-tert-Butyl-N-(3-cyano-4-neopentyloxyphenyl)-5-methylpyrazole-4-carboxamide

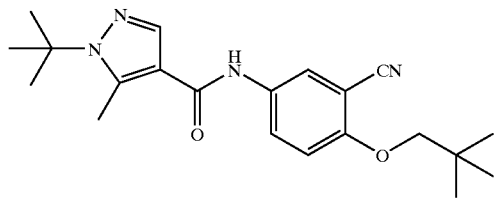

1-tert-Butyl-5-methylpyrazole-4-carboxylic acid (2 g), 5-amino-2-neopentyloxybenzonitrile (2.2 g), triethylamine (3.3 g) and diethyl cyanophosphate (2.7 g) were added to dimethylformamide (20 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. Methanol was added to the residue to allow crystallization. The crystals were recrystallized from hydrous dimethylformamide to give the title compound (2.2 g), melting point: 143–144° C.

EXAMPLE 31

N-{3-Cyano-4-(2-(dimethylamino)ethoxy)phenyl}-1-(4-fluorophenyl)-5-methylpyrazole-4-carboxamide hydrochloride ¼ hydrate

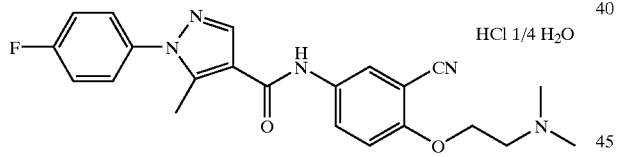

1-(4-Fluorophenyl)-5-dimethylpyrazole-4-carboxylic acid (35 g), 1-hydroxybenzotriazole (25.5 g) and 1-ethyl-3-(3'-dimethylaminopropyl) carbodiimide (36 g) were added to dimethylformamide (360 ml) and the mixture was stirred at roan temperature for 1.5 h. The reaction mixture was treated with aqueous potassium carbonate solution and extracted with ethyl acetate. The organic layer was washed with saturated brine and dried over anhydrous magnesium sulfate, after which the solvent was evaporated under reduced pressure. Diisopropyl ether was added to the residue to allow crystallization. The crystals were recrystallized from ethyl acetate to give 1-benzotriazole 1-(4-fluorophenyl)-5-dimethylpyrazole-4-carboxylate (62 g), melting point 166–168° C.

1-Benzotriazole 1-(4-fluorophenyl)-5-dimethylpyrazole-4-carboxylate (3 g) and 5-amino-2-(2-(dimethylamino)ethoxy)benzonitrile (2.3 g) were added to ethanol (30 ml) and the mixture was stirred at 78° C. for 3 h. The solvent was evaporated and the residue was purified by silica gel column chromatography (mobile phase:chloroform:methanol=50:1). To the obtained oily substance was added 10% hydrogen chloride-isopropanol solution to allow crystallization and the crystals were recrystallized from a mixed solvent of methanol-ethyl acetate to give the title compound (0.4 g), melting point: 258° C.

EXAMPLE 32

N-(3-Cyano-4-neopentyloxyphenyl)-1-cyclohexyl-5-methylpyrazole-4-carboxamide 1 hydrate

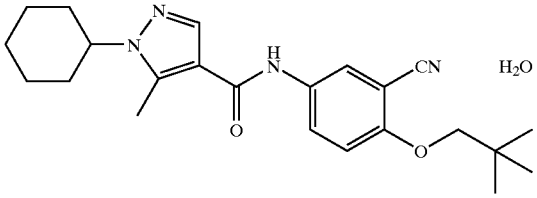

1-Cyclohexyl-5-methylpyrazole-4-carboxylic acid (1.2 g), 5-amino-2-neopentyloxybenzonitrile (1.1 g), triethylamine (1.7 g) and diethyl cyanophosphate (1.4 g) were added to dimethylformamide (15 ml) and the mixture was stirred at room temperature for 1 h. The reaction mixture was added into water and extracted with ethyl acetate. The organic layer was washed with saturated brine and dried over anhydrous magnesium sulfate, after which the solvent was evaporated under reduced pressure. Methanol was added to the residue to allow crystallization. The crystals were recrystallized from hydrous dimethylformamide to give the title compound (1.2 g), melting point: 126–128° C.

EXAMPLE 33

N-[3-Cyano-4-phenoxyphenyl]-1-(4-fluorophenyl)-5-methylpyrazole-4-carboxamide

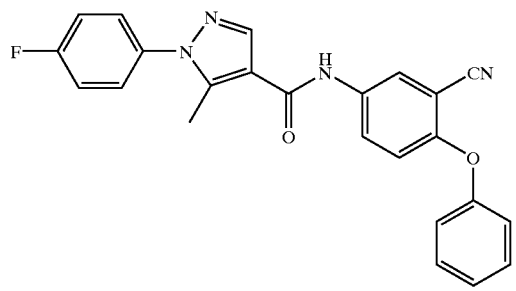

1-Benzotriazole 1-(4-fluorophenyl)-5-methylpyrazole-4-carboxylate (1.6 g) and 5-amino-2-phenoxybenzonitrile (1 g) were added to ethanol (12 ml) and the mixture was stirred at 78° C. for 3 h. The solvent was evaporated and the residue was purified by silica gel column chromatography (mobile phase:chloroform:methanol=50:1) and recrystallized from ethyl acetate to give the title compound (0.7 g), melting point: 182–183° C.

EXAMPLE 34

N-[3-Cyano-4-(2,2,2-trifluoroethoxy)phenyl-1-(4-fluorophenyl)pyrrole-3-carboxamide

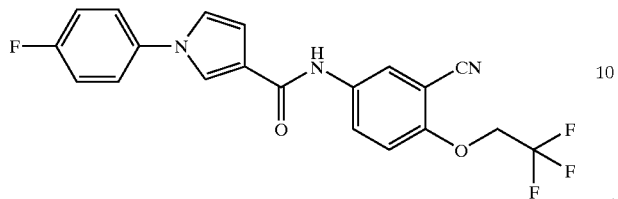

Dichloroethane solution (10 ml) containing 1-(4-fluorophenyl)pyrrole-3-carboxylic acid (1 g) and thionyl chloride (0.7 g) was stirred at 83° C. for 30 min to give acid chloride. This was added to pyridine solution (10 ml) containing 5-amino-2-(2,2,2-trifluoroethoxy) benzonitrile (1.1 g) under ice-cooling and the mixture was stirred for 1 h. The reaction mixture was added into water and extracted with ethyl acetate. The organic layer was washed with saturated brine and the solvent was evaporated under reduced pressure. Diisopropyl ether was added to the residue to allow crystallization. The crystals were recrystallized from a mixed solvent of toluene-acetonitrile to give the title compound (0.4 g), melting point: 227–228° C.

EXAMPLE 35

N-(3-Cyano-4-neopentyloxyphenyl)-N-[1-(4-fluorophenyl)pyrrole-3-ylcarbonyl]glycine

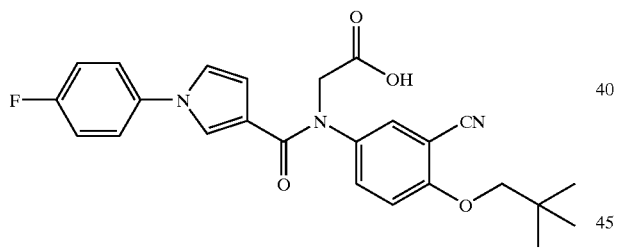

To dimethylformamide solution (24 ml) containing N-(3-cyano-4-neopentyloxyphenyl)-1-(4-fluorophenyl)pyrrole-3-carboxamide (2.2 g) was added sodium hydride (60% content, 0.3 g) under ice-cooling and the mixture was stirred for 1 h. Dimethylformamide solution (1 ml) containing ethyl bromoacetate (1.2 g) was added and the mixture was stirred for 1 h under ice-cooling, and after being warmed to room temperature, stirred for another 1 h. The reaction mixture was added into water and extracted with ethyl acetate. The organic layer was washed with saturated brine and dried over anhydrous magnesium sulfate, after which the solvent was evaporated under reduced pressure. The residue was purified by silica gel column chromatography (mobile phase: ethyl acetate:n-hexane=5:1) to give ethyl N-(3-cyano-4-neopentyloxyphenyl)-N-[1-(4-fluorophenyl)pyrrole-3-ylcarbonyl]glycine ethyl as an oily sybstance. This was added to ethanol (10 ml) and 10% aqueous sodium hydroxide solution (10 ml) was added. The mixture was stirred for 30 min at a refluxing temperature. The solvent was evaporated under reduced pressure and dilute hydrochloric acid was added. The resulting crystals were recrystallized from hydrous dimethylformamide to give the title compound (0.8 g), melting point: 248–249° C.

EXAMPLE 36

N-(3-Cyano-4-cyclohexyloxyphenyl)-1-(4-fluorophenyl)pyrrole-3-carboxamide

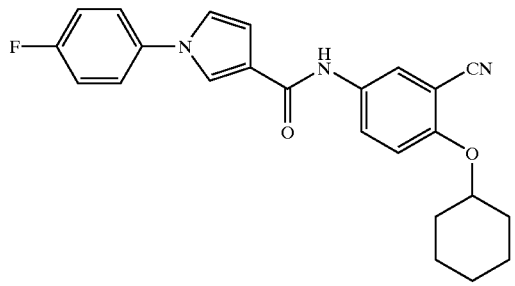

1-(4-Fluorophenyl)pyrrole-3-carboxylic acid (1.5 g) and thionyl chloride (1.0 g) were reacted in dichloroethane (10 ml) at 110° C. for 30 min to give acid chloride. The solvent was evaporated under reduced pressure. To the residue were added 5-amino-2-cyclohexyloxybenzonitrile (1.6 g) and pyridine (10 ml) and the mixture was stirred at room temperature for 1 h. The reaction mixture was treated with dilute hydrochloric acid and extracted with ethyl acetate. The organic layer was washed with sodium hydrogen carbonate and saturated brine, and dried over anhydrous magnesium sulfate, after which the solvent was evaporated under reduced pressure. Hydrous methanol was added to the residue to allow crystallization. The crystals were further recrystallized from hydrous methanol to give the title compound (1.9 g), melting point: 111–113° C.

EXAMPLE 37

N-(3-Cyano-4-piperidinophenyl)-1-(4-fluorophenyl)-5-methylpyrazole-4-carboxamide

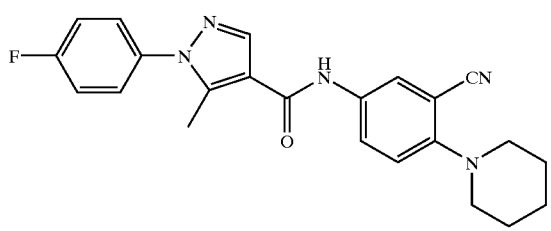

1-Benzotriazole 1-(4-fluorophenyl)-5-methylpyrazole-4-carboxylate (2 g) and 5-amino-2-piperidinobenzonitrile (1.1 g) were reacted at 78° C. for 3 h in ethanol (20 ml). After evaporation of the solvent, aqueous potassium carbonate solution was added to the residue and the mixture was extracted with ethyl acetate. The organic layer was washed with dilute hydrochloric acid and saturated brine, and dried over anhydrous sodium sulfate, after which the solvent was evaporated. A mixed solvent of ethyl acetate-n-hexane was added to the residue to allow crystallization. The crystals were recrystallized from ethyl acetate to give the title compound (1.2 g), melting point: 196–197° C.

EXAMPLE 38

N-(3-Cyano-4-neopentyloxyphenyl)-N-[1-(4-fluorophenyl)-5-methylpyrazol-4-ylcarbonyl]glycine

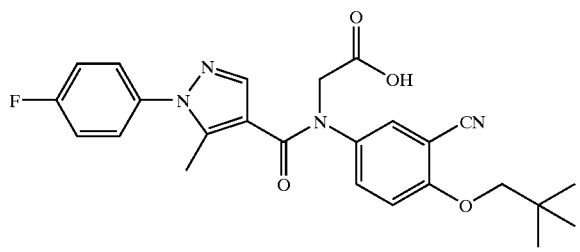

N-(3-Cyano-4-neopentyloxyphenyl)-1-(4-fluorophenyl)-5-methylpyrazole-4-carboxamide (1.8 g) and sodium hydride (60% content, 0.2 g) were reacted for 1 h in dimethylformamide (24 ml) under ice-cooling. Dimethylformamide solution (1 ml) containing ethyl bromoacetate (0.8 g) was added and the mixture was stirred for 1 h under ice-cooling and, after allowed to warm to room temperature, stirred for another 1 h. The reaction mixture was added into water and extracted with ethyl acetate. The organic layer was washed with saturated brine and dried over anhydrous magnesium sulfate, after which the solvent was evaporated under reduced pressure. The residue was purified by silica gel column chromatography (mobile phase:ethyl acetate:n-hexane=5:1) to give ethyl N-(3-cyano-4-neopentyloxyphenyl)-N-[1-(4-fluorophenyl)-5-methylpyrazol-4-ylcarbonyl] glycine as an oily substance. This was added to ethanol (10 ml) and 10% aqueous sodium hydroxide solution (10 ml) was added. The mixture was stirred at a refluxing temperature for 30 min. The solvent was evaporated under reduced pressure. To the residue was added dilute hydrochloric acid and the mixture was extracted with ethyl acetate, washed with saturated brine and dried over anhydrous magnesium sulfate, after which the solvent was evaporated under reduced pressure. A mixed solvent of toluene-n-hexane was added to the residue to allow crystallization. The crystals were recrystallized from a mixed solvent of toluene-n-hexane to give the title compound (0.7 g), melting point: 105–110° C.

EXAMPLE 39

N-(3-Cyano-4-neopentyloxyphenyl)-1-(4-fluorophenyl)-5-methoxypyrazole-4-carboxamide

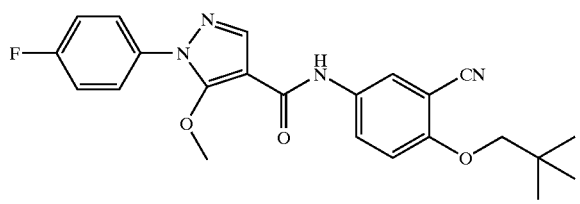

To a methanol solution (20 ml) containing metallic sodium (0.065 g) were added 5-chloro-N-(3-cyano-4-neopentyloxyphenyl)-1-(4-fluorophenyl)pyrazole-4-carboxamide (1 g) and a catalytic amount of potassium iodide, and the mixture was stirred at 65° C. for 5 h. The solvent was evaporated. Water was added to the residue to allow crystallization. The crystals were recrystallized from hydrous methanol to give the title compound (0.3 g), melting point: 120–123° C.

EXAMPLE 40

N-(3-Cyano-4-morpholinophenyl)-1-(4-fluorophenyl)-5-methylpyrazole-4-carboxamide

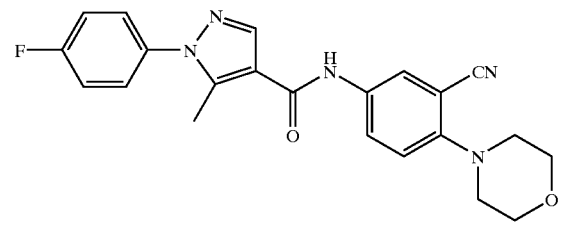

Dichloroethane solution (20 ml) containing 1-(4-fluorophenyl)-5-methylpyrazole-4-carboxylic acid (2.2 g) and thionyl chloride (1.5 g) was stirred at 83° C. for 30 min to give acid chloride. To this was added pyridine solution (10 ml) containing 5-amino-2-morpholinobenzonitrile (2.0 g) under ice-cooling and the mixture was stirred for 1 h. The reaction mixture was added into water and extracted with ethyl acetate. The organic layer was washed with saturated brine, and the solvent was evaporated under reduced pressure. Diisopropyl ether was added to the residue to allow crystallization. The crystals were recrystallized from hydrous ethanol to give the title compound (2.1 g), melting point: 201–202° C.

EXAMPLE 41

N-(3-Cyano-4-diethylaminophenyl)-1-(4-fluorophenyl)-5-methylpyrazole-4-carboxamide

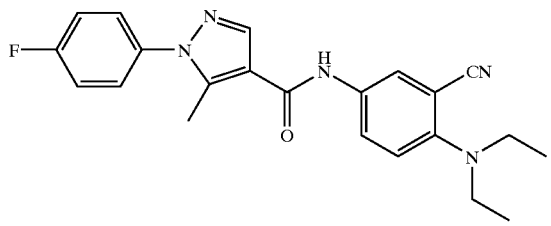

Dichloroethane solution (20 ml) containing 1-(4-fluorophenyl)-5-methylpyrazole-4-carboxylic acid (2.2 g) and thionyl chloride (1.5 g) was stirred at 83° C. for 30 min to give acid chloride. To this was added pyridine solution (10 ml) containing 5-amino-2-diethylaminobenzonitrile (1.9 g) under ice-cooling and the mixture was stirred for 1 h. The reaction mixture was added into water and extracted with ethyl acetate. The organic layer was washed with saturated brine, and the solvent was evaporated under reduced pressure. Diisopropyl ether was added to the residue to allow crystallization. The crystals were recrystallized from hydrous methanol to give the title compound (2.1 g), melting point: 135–136° C.

EXAMPLE 42

N-[3-Cyano-4-(4-methylpiperazin-1-yl)phenyl]-1-(4-fluorophenyl)-5-methylpyrazole-4-carboxamide

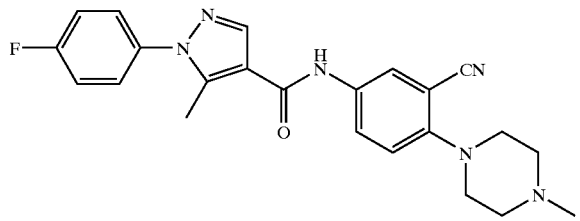

Dichloroethane solution (20 ml) containing 1-(4-fluorophenyl)-5-methylpyrazole-4-carboxylic acid (2.2 g) and thionyl chloride (1.5 g) was stirred at 83° C. for 30 min to give acid chloride. To this was added pyridine solution (10 ml) containing 5-amino-2-(4-methylpiperazin-1-yl)benzonitrile (1.9 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Diisopropyl ether was added to the residue to allow crystallization. The crystals were recrystallized from ethanol to give the title compound (1.6 g), melting point: 205–207° C.

EXAMPLE 43

N-(3-Cyano-4-piperidinophenyl)-1-(4-fluorophenyl)pyrrole-2-carboxamide

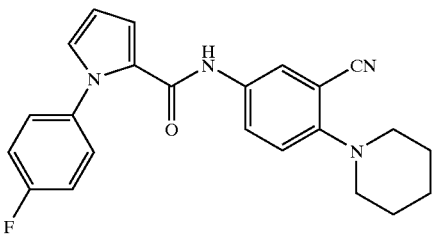

Dichloroethane solution (20 ml) containing 1-(4-fluorophenyl)pyrrole-2-carboxylic acid (2 g) and thionyl chloride (1.4 g) was stirred at 83° C. for 30 min to give acid chloride. To this was added pyridine solution (20 ml) containing 5-amino-2-piperidinobenzonitrile (2.0 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Diisopropyl ether was added to the residue to allow crystallization. The crystals were recrystallized from a mixed solvent of ethyl acetate-toluene to give the title compound (0.7 g), melting point: 158–159° C.

EXAMPLE 44

N-(3-Cyano-4-neopentyloxyphenyl)-5-methylpyrazole-44-carboxamide

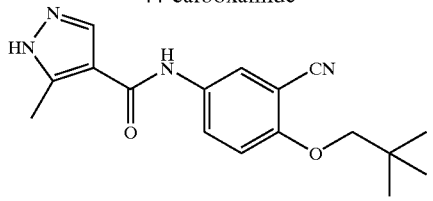

5-Methylpyrazole-4-carboxylic acid (2 g), 5-amino-2-neopentyloxybenzonitrile (3.2 g), 1-hydroxybenzotriazole (2.5 g) and 1-ethyl-3-(3'-dimethylaminopropyl)carbodiimide (3.6 g) were added to dimethylformamide (110 ml) and the mixture was stirred at room temperature for 5 h. The reaction mixture was treated with aqueous potassium carbonate solution and extracted with ethyl acetate. The organic layer was washed with saturated brine and dried over anhydrous magnesium sulfate, after which the solvent was evaporated under reduced pressure. The residue was purified by silica gel column chromatography (mobile phase:chloroform:methanol=100:1), and the obtained oily substance was recrystallized from a mixed solvent of toluene-n-hexane to give the title compound (0.8 g), melting point: 133–134° C.

EXAMPLE 45

N-[3-Cyano-4-(4-hydroxypiperidin-1-yl)phenyl]-1-(4-fluorophenyl)-5-methylpyrazole-4-carboxamide

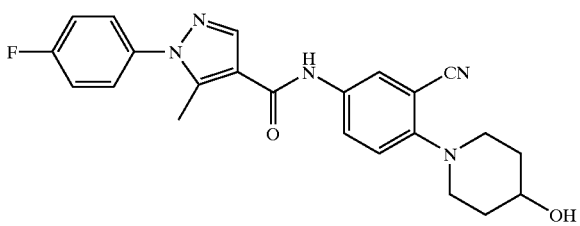

1-Benzotriazole 1-(4-fluorophenyl)-5-methylpyrazole-4-carboxylate (2 g) and 5-amino-2-(4-hydroxypiperidino) benzonitrile (1.0 g) were reacted in ethanol (20 ml) at 78° C. for 3 h. After the evaporation of the solvent, aqueous potassium carbonate solution was added to the residue and the mixture was extracted with ethyl acetate. The organic layer was washed with dilute hydrochloric acid and saturated brine, and dried over anhydrous sodium sulfate, after which the solvent was evaporated. Diisopropanol was added to the residue to allow crystallization. The crystals were recrystallized from a mixed solvent of ethyl acetate-toluene to give the title compound (0.7 g), melting point: 215–216° C.

EXAMPLE 46

N-(3-Cyano-4-neopentyloxyphenyl)-1-(2-hydroxyethyl)-5-methylpyrazole-4-carboxamide

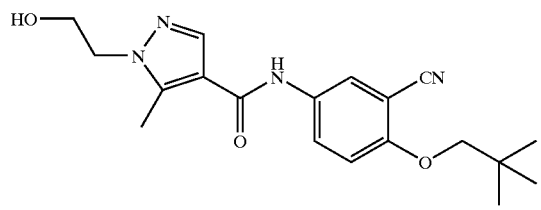

1-(2-Hydroxyethyl)-5-methylpyrazole-4-carboxylic acid (1.7 g), 5-amino-2-neopentyloxybenzonitrile (2.1 g), 1-hydroxybenzotriazole (1.6 g) and 1-ethyl-3-(3'-dimethylaminopropyl)carbodiimide (2.3 g) were added to dimethylformamide (20 ml) and the mixture was stirred at room temperature for 5 h. The reaction mixture was treated with aqueous potassium carbonate solution and extracted with ethyl acetate. The organic layer was washed with saturated brine, and dried over anhydrous magnesium sulfate, after which the solvent was evaporated under reduced pressure. The residue was purified by silica gel column chromatography (mobile phase:chloroform:methanol=100:1). Diisopropyl ether was added to the obtained oily substance to allow crystallization. The crystals were recrystallized from a mixed solvent of ethyl acetate-diisopropyl ether to give the title compound (1.1 g), melting point: 98–100° C.

EXAMPLE 47

Ethyl N-(3-Cyano-4-piperidinophenyl)-N-[1-(4-fluorophenyl)pyrrol-2-ylcarbonyl]glycine

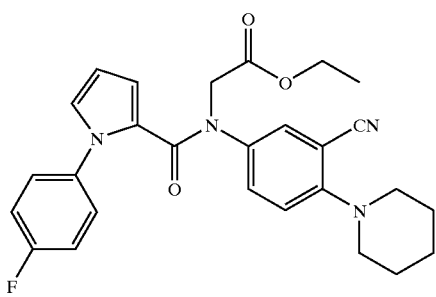

N-(3-Cyano-4-piperidinophenyl)-1-(4-fluorophenyl)pyrrol-2-ylcarboxamide (1.1 g) and sodium hydride (60% content, 0.2 g) were reacted in dimethylformamide (24 ml) under ice-cooling for 1 h. Dimethylformamide solution (1 ml) containing ethyl bromoacetate (0.8 g) was added and the mixture was stirred under ice-cooling for 1 h and, after allowed to warm to room temperature, stirred for another 1 h. The reaction mixture was added into water and extracted with ethyl acetate. The organic layer was washed with saturated brine and dried over anhydrous magnesium sulfate, after which the solvent was evaporated under reduced pressure. A mixed solvent of toluene-diisopropyl ether was added to the residue to allow crystallization. The crystals were recrystallized from a mixed solvent of ethyl acetate-n-hexane to give the title compound (1.3 g), melting point: 138–139° C.

EXAMPLE 48

N-(3-Cyano-4-piperidinophenyl)-N-[1-(4-fluorophenyl)pyrrol-2-ylcarbonyl]glycine 1 hydrate

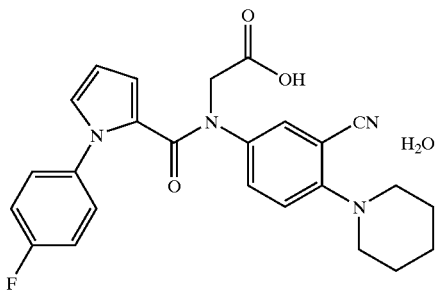

Ethyl N-(3-cyano-4-piperidinophenyl)-N-[1-(4-fluorophenyl)pyrrol-2-ylcarbonyl]glycine (1.0 g) was added to ethanol (10 ml), and 10% aqueous sodium hydroxide solution (10 ml) was added. The mixture was stirred at a refluxing temperature for 30 min. The solvent was evaporated under reduced pressure. Dilute hydrochloric acid was added to the residue and the mixture was extracted with ethyl acetate. The organic layer was washed with saturated brine and dried over anhydrous magnesium sulfate, after which the solvent was evaporated under reduced pressure. A mixed solvent of toluene-diisopropyl ether was added to the residue to allow crystallization. The crystals were recrystallized from hydrous methanol to give the title compound (0.5 g), melting point: 117–120° C.

EXAMPLE 49

N-(3-Cyano-4-piperidinophenyl)-1-(4-fluorophenyl) pyrrole-3-carboxamide

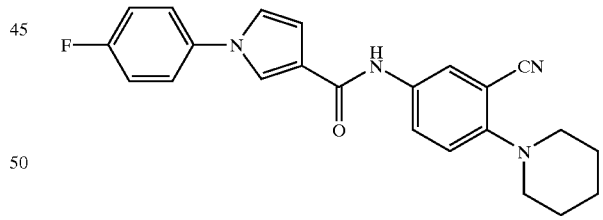

Dichloroethane solution (20 ml) containing 1-(4-fluorophenyl)pyrrole-3-carboxylic acid (2 g) and thionyl chloride (1.4 g) was stirred at 83° C. for 30 min to give acid chloride. To this was added pyridine solution (20 ml) containing 5-amino-2-piperidinobenzonitrile (2.0 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Diisopropyl ether was added to the residue to allow crystallization. The crystals were recrystallized from a mixed solvent of ethyl acetate-n-hexane to give the title compound (0.7 g), melting point: 195–196° C.

EXAMPLE 50

N-[3-Cyano-4-neopentyloxyphenyl]-1-(4-fluorophenyl)pyrrole-2-carboxamide

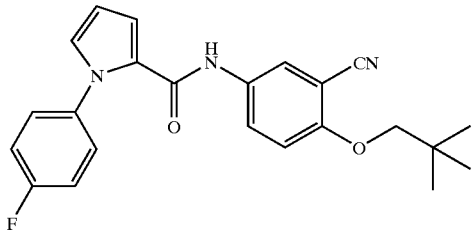

Dichloroethane solution (50 ml) containing 1-(4-fluorophenyl)pyrrole-2-carboxylic acid (5 g) and thionyl chloride (3.5 g) was stirred at 83° C. for 1 h to give acid chloride. To this was added pyridine solution (50 ml) containing 5-amino-2-neopentyloxybenzonitrile (5 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Diisopropyl ether was added to the residue to allow crystallization. The crystals were recrystallized from a mixed solvent of toluene-ethyl acetate to give the title compound (7.9 g), melting point: 181–182° C.

EXAMPLE 51

Ethyl 4-[N-(3-cyano-4-neopentyloxyphenyl)carbamoyl]-3-methylpyrazol-1-ylacetate

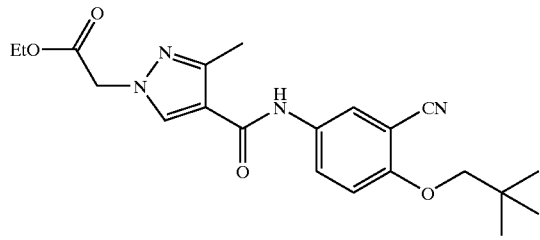

N-(3-Cyano-4-neopentyloxyphenyl)-5-methylpyrazole-4-carboxamide (2.4 g), potassium carbonate (1.1 g), potassium iodide (1.4 g) and ethyl bromoacetate (1.4 g) were added to a mixed solvent of dimethylformamide (24 ml) and toluene (24 ml) and the mixture was stirred at 60° C. for 4 h. The reaction mixture was added into water, washed with dilute hydrochloric acid and saturated brine, and dried over anhydrous magnesium sulfate, after which the solvent was evaporated under reduced pressure. The residue was purified by silica gel column chromatography (mobile phase: chloroform). Methylene chloride was added to the obtained oily substance to allow crystallization. The crystals were recrystallized from a mixed solvent of methylene chloride-n-hexane to give the title compound (0.7 g), melting point: 240° C.

EXAMPLE 52

4-[N-(3-Cyano-4-neopentyloxyphenyl)carbamoyl]-3-methylpyrazol-1-ylacetic acid

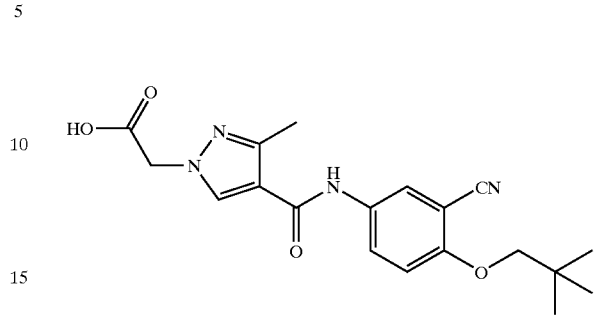

Ethyl 4-[N-(3-cyano-4-neopentyloxyphenyl)carbamoyl]-3-methylpyrazol-1-ylacetate (0.7 g) was added to ethanol (5 ml) and 10% aqueous sodium hydroxide solution (5 ml) was added. The mixture was stirred at a refluxing temperature for 30 min. The solvent was evaporated under reduced pressure. To the residue was added dilute hydrochloric acid and the mixture was extracted with ethyl acetate. The organic layer was washed with saturated brine and dried over anhydrous magnesium sulfate, after which the solvent was evaporated under reduced pressure. Diisopropyl ether was added to the residue to allow crystallization. The crystals were recrystallized from a mixed solvent of ethyl acetate-diisopropyl ether to give the title compound (0.2 g), melting point: 234–245° C.

EXAMPLE 53

N-(3-Cyano-4-neopentyloxyphenyl)-N-[1-(4-fluorophenyl)pyrrol-2-ylcarbonyl]glycine ½ hydrate

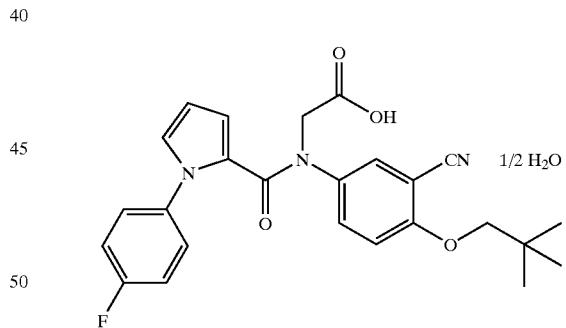

N-[3-Cyano-4-neopentyloxyphenyl]-1-(4-fluorophenyl)pyrrole-2-carboxamide (4.0 g) and sodium hydride (60% content, 0.6 g) were reacted in dimethylformamide (40 ml) under ice-cooling for 1 h. Dimethylformamide solution (3 ml) containing ethyl bromoacetate (3.4g) was added and the mixture was stirred under ice-cooling for 1 h, and after allowed to warm to room temperature, stirred for another 1 h. The reaction mixture was added into water and extracted with ethyl acetate. The organic layer was washed with saturated brine and dried over anhydrous magnesium sulfate, after which the solvent was evaporated under reduced pressure. To the residue were added ethanol (40 ml) and then 10% aqueous sodium hydroxide solution (50 ml). The mixture was stirred at a refluxing temperature for 30 min.

The solvent was evaporated under reduced pressure. Dilute hydrochloric acid was added to the residue and the mixture was extracted with ethyl acetate. The organic layer was washed with saturated brine and dried over anhydrous magnesium sulfate, after which the solvent was evaporated under reduced pressure. A mixed solvent of chloroform-n-hexane was added to the residue to allow crystallization. The crystals were recrystallized from hydrous ethanol to give the title compound (3.0 g), melting point: 140–143° C.

EXAMPLE 54

N-[3-Cyano-4-(4-hydroxypiperidin-1-yl)phenyl)-1-(4-fluorophenyl)-3-methylpyrazole-4-carboxamide

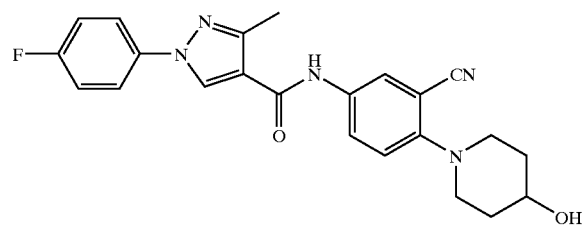

1-(4-Fluorophenyl)-3-methylpyrazole-4-carboxylic acid (1.0 g), 5-amino-2-(4-hydroxypiperidin-1-yl)benzonitrile (1.0 g), 1-hydroxybenzotriazole (0.7 g) and 1-ethyl-3-(3'dimethylaminopropyl)carbodiimide (1.0 g) were added to dimethylformamide (20 ml) and the mixture was stirred at room temperature for 5 h. The reaction mixture was treated with aqueous potassium carbonate solution and extracted with ethyl acetate. The organic layer was washed with saturated brine and dried over anhydrous magnesium sulfate, after which the solvent was evaporated under reduced pressure. The residue was purified by silica gel column chromatography (mobile phase:chloroform:methanol=100:1). Diisopropyl ether was added to the obtained oily substance to allow crystallization. The crystals were recrystallized from a mixed solvent of ethyl acetate-diisopropyl ether to give the title compound (0.7 g), melting point: 224–225° C.

EXAMPLE 55

N-(3-Cyano-4-(4-tert-butyldimethylsilyloxypiperidin-1-yl)phenyl)-1-(4-fluorophenyl)-5-methylpyrazole-4-carboxamide

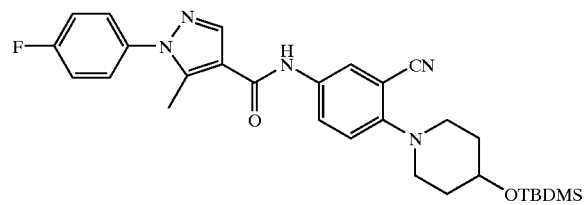

Dichloroethane solution (20 ml) containing 1-(4-fluorophenyl)-5-methylpyrazole-4-carboxylic acid (2.4 g) and thionyl chloride (1.6 g) was stirred at 83° C. for 30 min to give acid chloride. To this were added 5-amino-2-(4-tert-butyldimethylsilyloxypiperidin-1-yl)benzonitrile (3.6 g) and pyridine (40 ml), and the mixture was stirred at room temperature for 1 h. The reaction mixture was treated with aqueous sodium hydroxide solution and extracted with ethyl acetate. The organic layer was washed with saturated brine, and the solvent was evaporated under reduced pressure. Diisopropyl ether was added to the residue to allow crystallization. The crystals were recrystallized from ethyl acetate to give the title compound (5.1 g), melting point: 195–197° C.

EXAMPLE 56

N-(3-Cyano-4-(4-hydroxypiperidin-1-yl)phenyl)-1-(4-fluorophenyl)-N,5-dimethylpyrazole-4-carboxamide

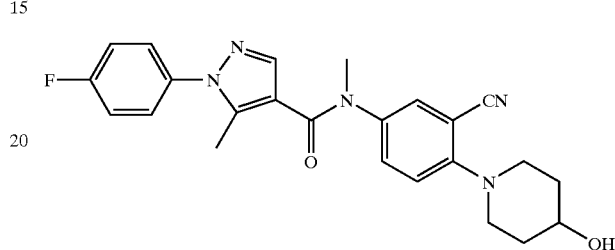

N-[3-Cyano-4-(4-tert-butyldimethylsilyloxypiperidin-1-yl)phenyl]-1-(4-fluorophenyl)-5-methylpyrazole-4-carboxamide (1.5 g) and sodium hydride (60% content, 0.2 g) were reacted in dimethylformamide (10 ml) under ice-cooling for 1 h. Dimethylformamide solution (1 ml) containing methyl iodide (0.6 g) was added and the mixture was stirred under ice-cooling for 1 h and, after allowed to warm to room temperature, stirred for another 1 h. The reaction mixture was added into water and extracted with ethyl acetate. The organic layer was washed with dilute hydrochloric acid and saturated brine, and dried over anhydrous magnesium sulfate, after which the solvent was evaporated under reduced pressure. Tetrabutylammonium fluoride (1.4 g), tetrahydrofuran (10 ml) and acetonitrile (10 ml) were added to the residue, and the mixture was stirred at 80° C. for 2 h. The reaction mixture was added into water and extracted with ethyl acetate. The organic layer was washed with saturated brine and dried over anhydrous magnesium sulfate, after which the solvent was evaporated under reduced pressure. A mixed solvent of ethyl acetate-n-hexane was added to the residue to allow crystallization. The crystals were recrystallized from a mixed solvent of ethyl acetate-ethanol to give the title compound (0.8 g), melting point: 211–212° C.

EXAMPLE 57

N-[3-Cyano-4-(4-hydroxypiperidin-1-yl)phenyl]-N-[1-(4-fluorophenyl)-5-methylpyrazol-4-ylcarbonyl]glycine ½ isopropanol

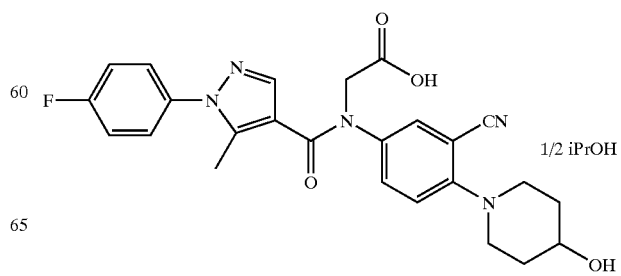

N-(3-Cyano-4-(4-tert-butyldimethylsilyloxypiperidin-1-yl) phenyl)-1-(4-fluorophenyl)-5-methylpyrazole-4-carboxamide (3.3 g) and sodium hydride (60% content, 0.3 g) were reacted in dimethylformamide (30 ml) under ice-cooling for 1 h. Dimethylformamide solution (10 ml) containing ethyl bromoacetate (1.4 g) was added and the mixture was stirred under ice-cooling for 1 h and, after allowed to warm to roan temperature, stirred for another 1 h. The reaction mixture was added into water and extracted with ethyl acetate. The organic layer was washed with saturated brine and dried over anhydrous magnesium sulfate, after which the solvent was evaporated under reduced pressure. Tetrabutylammonium fluoride (3.0 g), tetrahydrofuran (20 ml) and acetonitrile (20 ml) were added to the residue and the mixture was stirred at 80° C. for 1 h. The solvent was evaporated under reduced pressure. To the residue was added dilute hydrochloric acid and the mixture was extracted with ethyl acetate. The organic layer was washed with saturated brine and dried over anhydrous magnesium sulfate, after which the solvent was evaporated under reduced pressure. A mixed solvent of toluene-ethyl acetate was added to the residue to allow crystallization. The crystals were recrystallized from hydrous isopropanol to give the title compound (0.3 g), melting point: 155–158° C.

EXAMPLE 58

Ethyl N-(3-Cyano-4-neopentyloxyphenyl)-N-[1-(4-fluorophenyl)pyrazol-4-ylcarbonyl]glycine

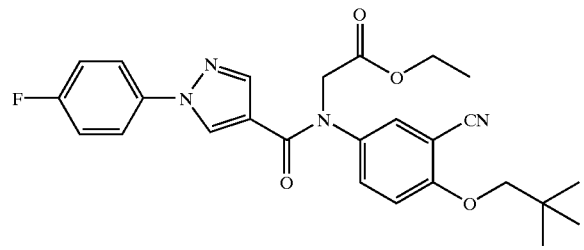

Dichloroethane solution (15 ml) containing 1-(4-fluorophenyl)pyrazole-4-carboxylic acid (1.2 g) and thionyl chloride (0.7 g) was stirred at 83° C. for 1 h to give acid chloride. To this was added pyridine solution (15 ml) containing ethyl N-(3-cyano-4-neopentyloxyphenyl)glycine (1.5 g) under ice-cooling and the mixture was stirred for 1 h. The reaction mixture was added into water and extracted with ethyl acetate. The organic layer was washed with saturated brine, and the solvent was evaporated under reduced pressure. A mixed solvent of toluene-n-hexane was added to the residue to allow crystallization. The crystals were recrystallized from hydrous ethanol to give the title compound (1.7 g), melting point: 153–155° C.

EXAMPLE 59

N-(3-Cyano-4-neopentyloxyphenyl)-N-[1-(4-fluorophenyl) pyrazol-4-ylcarbonyl]glycine

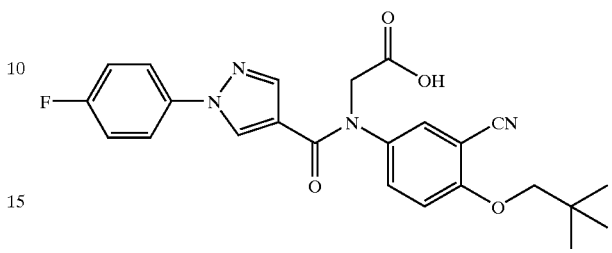

Ethyl N-(3-cyano-4-neopentyloxyphenyl)-N-[1(4-fluorophenyl)pyrazol-4-ylcarbonyl]glycine (1.5 g) was added to ethanol (15 ml). 10% aqueous sodium hydroxide solution (10 ml) was added and the mixture was stirred at a refluxing temperature for 30 min. The solvent was evaporated under reducer pressure. To the residue was added dilute hydrochloric acid and the mixture was extracted with ethyl acetate. The organic layer was washed with saturated brine and dried over anhydrous magnesium sulfate, after which the solvent was evaporated under reduced pressure. A mixed solvent of chloroform-n-hexane was added to the residue to allow crystallization. The crystals were recrystallized from hydrous acetic acid to give the title compound (0.9 g), melting point: 274–275° C./decomposition

EXAMPLE 60

N-{3-Cyano-4-[4-(2-hydroxyethyl)piperazin-1-yl]phenyl}-1-(4-fluorophenyl)-5-methylpyrazole-4-carboxamide

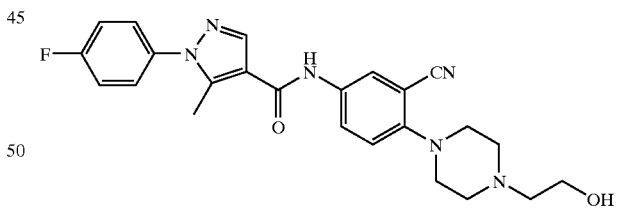

1-Benzotriazole 1-(4-fluorophenyl)-5-methylpyrazole-4-carboxylate (30 g) and 5-amino-2-[4-(2-hydroxyethyl)piperazin-1-yl]benzonitrile (21.9 g) were reacted in ethanol (100 ml) at 78° C. for 3 h. After the evaporation of the solvent, aqueous potassium carbonate solution was added to the residue and the mixture was extracted with ethyl acetate. The organic layer was washed with saturated brine and dried over anhydrous magnesium sulfate, after which the solvent was evaporated. Ethyl acetate was added to the residue to allow crystallization. The crystals were recrystallized from ethyl acetate to give the title compound (25 g), melting point: 179–180° C.

EXAMPLE 61

4-(1-{2-Cyano-4-[1-(4-fluorophenyl)-5-methylpyrazole-4-carboxamide]phenyl}piperidin-4-yloxy)-4-oxobutyric acid

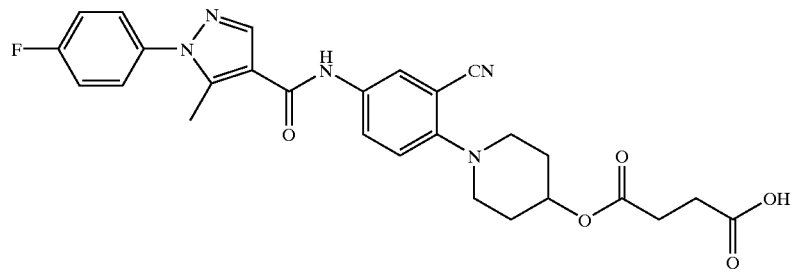

N-[3-Cyano-4-(4-hydroxypiperidino)phenyl]-1-(4-fluorophenyl)-5-methylpyrazole-4-carboxamide (1.9 g), succinic anhydride (0.5 g) and a catalytic amount of p-toluenesulfonic acid 1 hydrate were added to nitrobenzene (40 ml) and the mixture was stirred at 110° C. for 6 h. The reaction mixture was ice-cooled, diisopropyl ether was added thereto. The precipitated crystals was collected by filtration and recrystallized from hydrous ethanol to give the title compound (1.2 g), melting point: 219–220° C.

EXAMPLE 62

Ethyl N-[3-cyano-4-neopentyloxyphenyl]-N-[1-(3-trifluoromethylphenyl)-3-methylpyrazol-4-ylcarbonyl]glycine

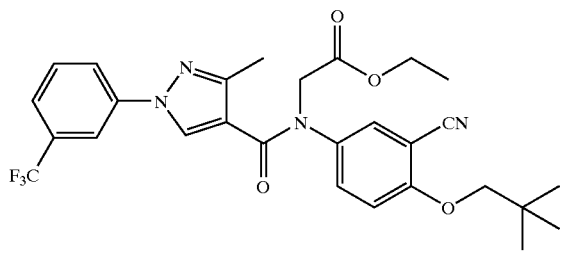

Dichloroethane solution (20 ml) containing 1-(3-trifluoromethylphenyl)-3-methylpyrazole-4-carboxylic acid (1.6 g) and thionyl chloride (0.8 g) was stirred at 83° C. for 1 h to give acid chloride. Pyridine solution (15 ml) containing ethyl N-(3-cyano-4-neopentyloxyphenyl)glycine (1.4 g) was added thereto under ice-cooling and the mixture was stirred for 1 h. The reaction mixture was added into water and extracted with ethyl acetate. The organic layer was washed with saturated brine, and the solvent was evaporated under reduced pressure. The residue was recrystallized from ethanol to give the title compound (1.7 g), melting point: 156–158° C.

EXAMPLE 63

N-(3-Cyano-4-neopentyloxyphenyl)-N-[1-(3-trifluoromethylphenyl)-3-methylpyrazol-4-ylcarbonyl]glycine

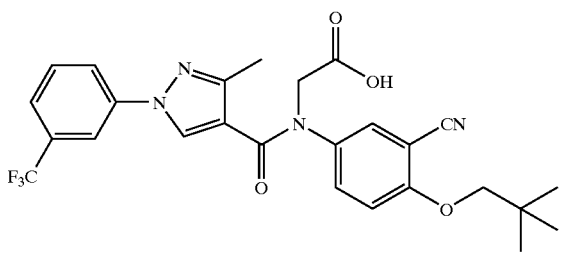

Ethyl N-(3-cyano-4-neopentyloxyphenyl)-N-[1-(3-trifluoromethylphenyl)-3-methylpyrazol-4-ylcarbonyl]glycine (1.5 g) was added to ethanol (15 ml). 10% Aqueous sodium hydroxide solution (10 ml) was added and the mixture was stirred at a refluxing temperature for 30 min. The solvent was evaporated under reduced pressure. Dilute hydrochloric acid was added to the residue and the mixture was extracted with ethyl acetate. The organic layer was washed with saturated brine and dried over anhydrous magnesium sulfate, after which the solvent was evaporated under reduced pressure. A mixed solvent of chloroform-n-hexane was added to the residue to allow crystallization. The crystals were recrystallized from hydrous acetic acid to give the title compound (0.9 g), melting point: 110–112° C.

EXAMPLE 64

N-{3-Cyano-4-[4-(2-hydroxyethyl)piperazin-1-yl]phenyl}-1-(2,4-difluorophenyl)-5-methylpyrazole-4-carboxamide ¼ isopropanol

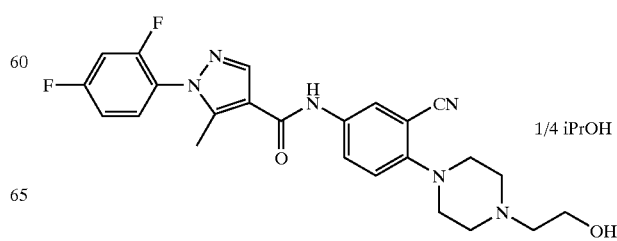

1/4 iPrOH

Dichloroethane solution (20 ml) containing 1-(2,4-difluorophenyl)-5-methylpyrazole-4-carboxylic acid (2.3 g) and thionyl chloride (1.4 g) was stirred at 83° C. for 30 min to give acid chloride. To this was added pyridine solution (20 ml) containing 5-amino-2-[4-(2-hydroxyethyl)piperazin-1-yl]benzonitrile (2.8 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Ethyl acetate was added to the residue to allow crystallization. The crystals were recrystallized from a mixed solvent of ethyl acetate-isopropanol to give the title compound (3.1 g), melting point: 149–151° C.

EXAMPLE 65

Ethyl N-(3-Cyano-4-neopentyloxyphenyl)-N-[1-(4-methoxyphenyl)-3-methylpyrazol-4-ylcarbonyl]glycine

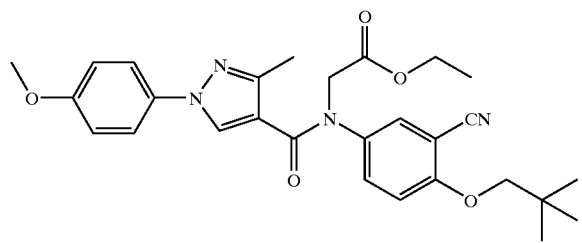

Dichloroethane solution (20 ml) containing 1-(4-methoxyphenyl)-3-methylpyrazole-4-carboxylic acid (1.4 g) and thionyl chloride (0.8 g) was stirred at 83° C. for 1 h to give acid chloride. To this was added pyridine solution (15 ml) containing ethyl N-(3-cyano-4-neopentyloxyphenyl)glycine (1.4 g) under ice-cooling and the mixture was stirred for 1 h. The reaction mixture was added into water and extracted with ethyl acetate. The organic layer was washed with saturated brine, and the solvent was evaporated under reduced pressure. The residue was recrystallized form ethanol to give the title compound (1.8 g), melting point: 113–114° C.

EXAMPLE 66

N-(3-Cyano-4-neopentyloxyphenyl)-N-[1-(4-methoxyphenyl)-3-methylpyrazol-4-ylcarbonyl]glycine

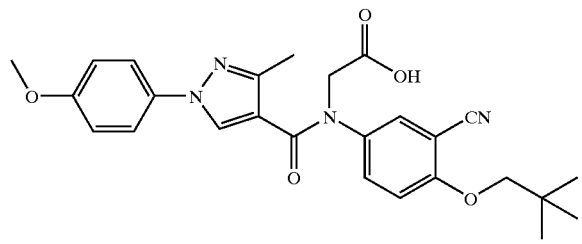

Ethyl N-(3-cyano-4-neopentyloxyphenyl)-N-[1-(4-methoxyphenyl)-3-methylpyrazol-4-ylcarbonyl]glycine (1.8 g) was added to ethanol (20 ml). 10% aqueous sodium hydroxide solution (20 ml) was added and the mixture was stirred at a refluxing temperature for 30 min. The solvent was evaporated under reduced pressure. Dilute hydrochloric acid was added to the residue and the mixture was extracted with ethyl acetate. The organic layer was washed with saturated brine and dried over anhydrous magnesium sulfate, after which the solvent was evaporated under reduced pressure. A mixed solvent of chloroform-n-hexane was added to the residue to allow crystallization. The crystals were recrystallized from hydrous acetic acid to give the title compound (1.6 g), melting point: 98–101° C.

EXAMPLE 67

Ethyl N-[1-(2-chloro-5-trifluoromethylphenyl)-3-methylpyrazol-4-ylcarbonyl]-N-[3-cyano-4-neopentyloxyphenyl]glycine

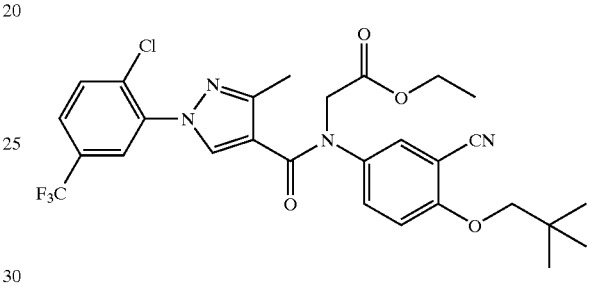

Dichloroethane solution (15 ml) containing 1-(2-chloro-5-trifluoromethylphenyl)-3-methylpyrazole-4-carboxylic acid (1.8 g) and thionyl chloride (0.8 g) was stirred at 83° C. for 1 h to give acid chloride. To this was added pyridine solution (15 ml) containing ethyl N-(3-cyano-4-neopentyloxyphenyl)glycine (1.4 g) under ice-cooling and the mixture was stirred for 1 h. The reaction mixture was added into water and extracted with ethyl acetate. The organic layer was washed with saturated brine, and the solvent was evaporated under reduced pressure. Diisopropyl ether was added to the residue to allow crystallization. The crystals were recrystallized from ethanol to give the title compound (1.8 g), melting point: 134–135° C.

EXAMPLE 68

N-[1-(2-chloro-5-trifluoromethylphenyl)-3-methylpyrazol-4-ylcarbonyl]-N-(3-cyano-4-neopentyloxyphenyl)glycine

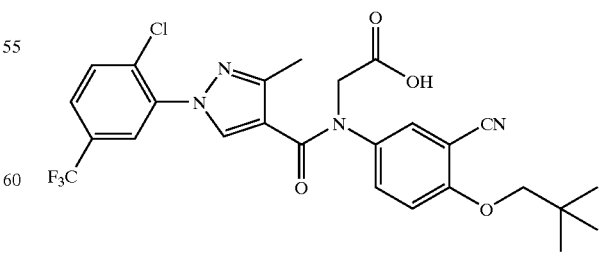

Ethyl N-[1-(2-Chloro-5-trifluoromethylphenyl)-3-methylpyrazol-4-ylcarbonyl]-N-(3-cyano-4-neopentyloxyphenyl)glycine (1.8 g) was added to ethanol (15 ml). 10% aqueous sodium hydroxide solution (15 ml) was added and the mixture was stirred at a refluxing temperature for 30 min. The solvent was evaporated under reduced pressure, and dilute hydrochloric acid was added. The mixture was extracted with ethyl acetate. The organic layer was washed with saturated brine and dried over anhydrous magnesium sulfate, after which the solvent was evaporated under reduced pressure. A mixed solvent of chloroform-n-hexane was added to the residue to allow crystallization. The crystals were recrystallized from a mixed solvent of diisopropyl ether-n-hexane to give the title compound (1.2 g), melting point: 189–190° C.

EXAMPLE 69

2-{N-(3-Cyano-4-neopentyloxyphenyl)-N-[1-(4-fluorophenyl)-3-methylpyrazol-4-ylcarbonyl]amino}ethylacetate

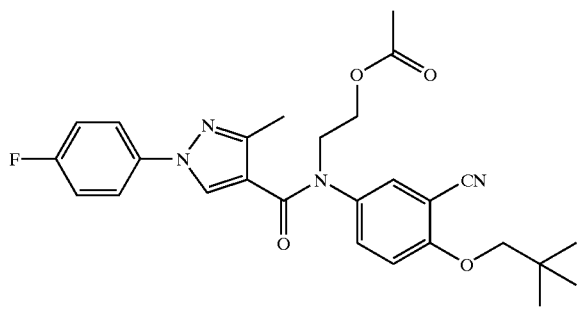

Dichloroethane solution (20 ml) containing 1-(4-fluorophenyl)-3-methylpyrazole-4-carboxylic acid (1.8 g) and thionyl chloride (1.2 g) was stirred at 83° C. for 1 h to give acid chloride. To this was added pyridine solution (20 ml) containing 2-[N-(3-cyano-4-neopentyloxyphenyl)amino]ethylacetate (2.4 g) under ice-cooling and the mixture was stirred for 1 h. The reaction mixture was added into water and extracted with ethyl acetate. The organic layer was washed with saturated brine, and the solvent was evaporated under reduced pressure. Diisopropyl ether was added to the residue to allow crystallization. The crystals were recrystallized from hydrous ethanol to give the title compound (1.7 g), melting point: 112–113° C.

EXAMPLE 70

4-[N-(3-cyano-4-neopentyloxyphenyl)-N-[1-(4-fluorophenyl)-3-methylpyrazol-4-ylcarbonyl]amino]butyric acid

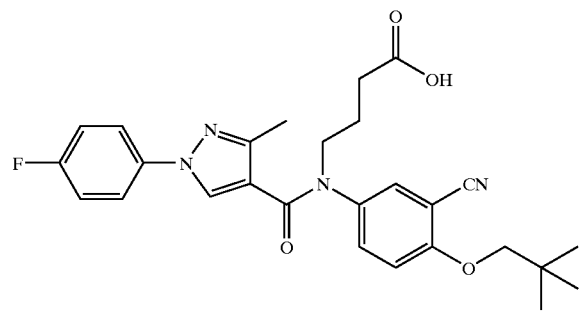

Dichloroethane solution (20 ml) containing 1-(4-fluorophenyl)-3-methylpyrazole-4-carboxylic acid (2.0 g) and thionyl chloride (1.3 g) was stirred at 83° C. for 1 h to give acid chloride. To this was added pyridine solution (20 ml) containing ethyl 4-[N-(3-cyano-4-neopentyloxyphenyl)amino]butyrate (2.6 g) under ice-cooling and the mixture was stirred for 1 h. The reaction mixture was added into water and extracted with ethyl acetate. The organic layer was washed with saturated brine, and the solvent was evaporated under reduced pressure. To the residue were added 10% aqueous sodium hydroxide solution (30 ml) and ethanol (30 ml) and the mixture was stirred at 78° C. for 1 h. The reaction mixture was cooled to room temperature, after which the mixture was treated with dilute hydrochloric acid and extracted with ethyl acetate. The organic layer was washed with saturated brine and dried over anhydrous magnesium sulfate, after which the solvent was evaporated under reduced pressure. Toluene was added to the residue to allow crystallization. The crystals were recrystallized from a mixed solvent of ethyl acetate-toluene to give the title compound (2.2 g), melting point: 178–180° C.

EXAMPLE 71

N-[3-Cyano-4-(4-tert-butyldimethylsilyloxypiperidin-1-yl)phenyl]-1-(4-fluorophenyl)-3-methylpyrazole-4-carboxamide

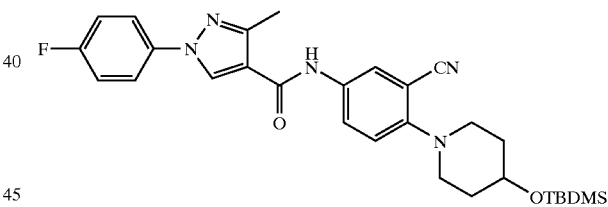

Dichloroethane solution (30 ml) containing 1-(4-fluorophenyl)-3-methylpyrazole-4-carboxylic acid (3.0 g) and thionyl chloride (1.9 g) was stirred at 83° C. for 30 min to give acid chloride. To this were added 5-amino-2-(4-tert-butyldimethylsilyloxypiperidin-1-yl)benzonitrile (4.5 g) and pyridine (30 ml) and the mixture was stirred at room temperature for 1 h. The reaction mixture was treated with aqueous sodium hydroxide solution and extracted with ethyl acetate. The organic layer was washed with saturated brine, and the solvent was evaporated under reduced pressure. Diisopropyl ether was added to the residue to allow crystallization. The crystals were recrystallized from a mixed solvent of ethyl acetate-n-hexane to give the title compound (5.5 g), melting point: 190–191° C.

EXAMPLE 72

N-[3-Cyano-4-(4-hydroxypiperidin-1-yl)phenyl]-N-[1-(4-fluorophenyl)-3-methylpyrazol-4-ylcarbonyl]glycine ½ hydrate

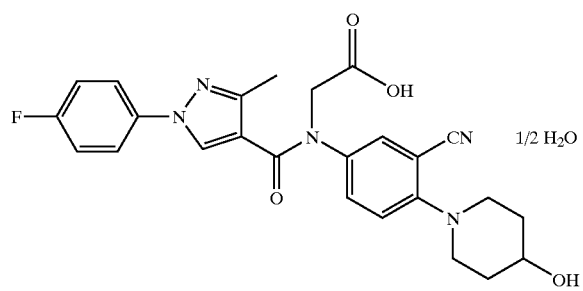

N-(3-Cyano-4-(4-tert-butyldimethylsilyloxypiperidin-1-yl)phenyl)-1-(4-fluorophenyl)-3-methylpyrazole-4-carboxamide (2.1 g) and sodium hydride (60% content, 0.2 g) were reacted in dimethylformamide (30 ml) under ice-cooling for 1 h. Dimethylformamide solution (10 ml) containing ethyl bromoacetate (1.0 g) was added and the mixture was stirred under ice-cooling for 1 h and, after allowed to warm to room temperature, stirred for another 1 h. The reaction mixture was added into water and extracted with ethyl acetate. The organic layer was washed with saturated brine and dried over anhydrous magnesium sulfate, after which the solvent was evaporated under reduced pressure. To the residue were added tetrabutylammonium fluoride (2.0 g), tetrahydrofuran (20 ml) and acetonitrile (20 ml) and the mixture was stirred at 80° C. for 1 h. The solvent was evaporated under reduced pressure. To the residue was added dilute hydrochloric acid, and the mixture was extracted with ethyl acetate. The organic layer was washed with saturated brine and dried over anhydrous magnesium sulfate, after which the solvent was evaporated under reduced pressure. A mixed solvent of toluene-ethyl acetate was added to the residue to allow crystallization. The crystals were recrystallized from hydrous isopropanol to give the title compound (0.2 g), melting point: 124–125° C.

EXAMPLE 73

N-{3-Cyano-4-[bis(2-hydroxyethyl)amino]phenyl}-1-(4-fluorophenyl)-5-methylpyrazole-4-carboxamide

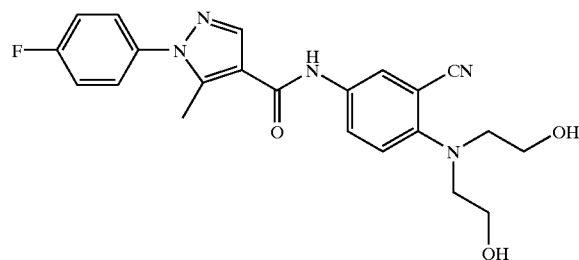

1-(4-Fluorophenyl)-5-methylpyrazole-4-carboxylic acid (2.0 g), 5-amino-2-[bis(2-hydroxyethyl)amino]benzonitrile (2.0 g), 1-hydroxybenzotriazole (1.5 g) and 1-ethyl-3-(3'-dimethylaminopropyl)carbodiimide (2.0 g) were added to dimethylformamide (25 ml) and the mixture was stirred at room temperature for 5 h. The reaction mixture was treated with aqueous potassium carbonate solution and extracted with ethyl acetate. The organic layer was washed with saturated brine and dried over anhydrous magnesium sulfate, after which the solvent was evaporated under reduced pressure. The residue was purified by silica gel column chromatography (mobile phase:chloroform:methanol=100:1) to give an oily substance. Diisopropyl ether was added to the oily substance to allow crystallization. The crystals were recrystallized from a mixed solvent of ethyl acetate-diisopropyl ether to give the title compound (0.9 g), melting point: 158–159° C.

EXAMPLE 74

Ethyl N-[3-Cyano-4-neopentyloxyphenyl]-N-[1-(2,4-difluorophenyl)-3-methylpyrazol-4-ylcarbonyl]glycine

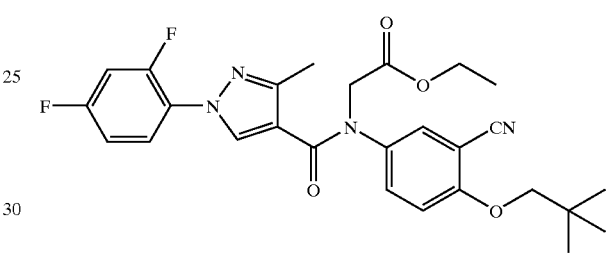

Dichloroethane solution (15 ml) containing 1-(2,4-difluorophenyl)-3-methylpyrazole-4-carboxylic acid (1.0 g) and thionyl chloride (0.6 g) was stirred at 83° C. for 1 h to give acid chloride. To this was added pyridine solution (15 ml) containing ethyl N-(3-cyano-4-neopentyloxyphenyl)glycine (1.4 g) under ice-cooling and the mixture was stirred for 1 h. The reaction mixture was added into water and extracted with ethyl acetate. The organic layer was washed with saturated brine, and the solvent was evaporated under reduced pressure. Diisopropyl ether was added to the residue to allow crystallization. The crystals were recrystallized from ethanol to give the title compound (0.9 g), melting point: 110° C.

EXAMPLE 75

N-[3-Cyano-4-neopentyloxyphenyl]-N-[(1-(2,4-difluorophenyl)-3-methylpyrazol-4-ylcarbonyl]glycine

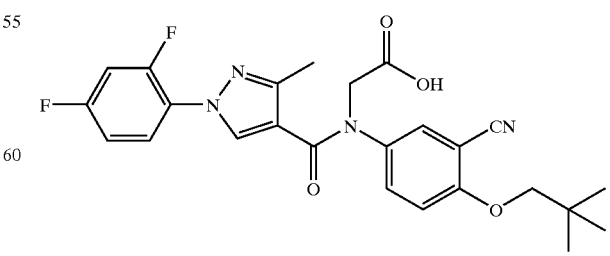

Ethyl N-[3-cyano-4-neopentyloxyphenyl]-N-[1-(2,4-difluorophenyl)-3-methylpyrazol-4-ylcarbonyl]glycine (0.9 g)

was added to ethanol (15 ml). 10% aqueous sodium hydroxide solution (15 ml) was added and the mixture was stirred at a refluxing temperature for 30 min. The solvent was evaporated under reduced pressure. To the residue was added dilute hydrochloric acid and the mixture was extracted with ethyl acetate. The organic layer was washed with saturated brine and dried over anhydrous magnesium sulfate, after which the solvent was evaporated under reduced pressure. A mixed solvent of chloroform-n-hexane was added to the residue to allow crystallization. The crystals were recrystallized from toluene to give the title compound (0.6 g), melting point: 157–158° C.

EXAMPLE 76

N-{3-Cyano-4-[4-(2-hydroxyethyl)piperazin-1-yl]phenyl}-1-(2,4-difluorophenyl)-5-methylpyrazole-4-carboxamide

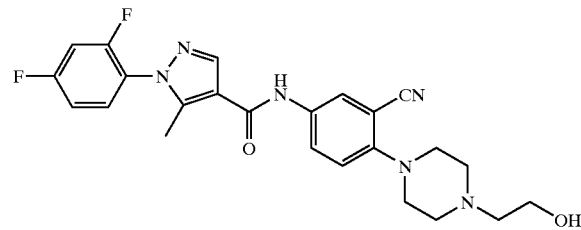

1-(2,4-Difluorophenyl)-5-methylpyrazole-4-carboxylic acid (2.4 g), 5-amino-2-[4-(2-hydroxyethyl)piperazin-1-yl]benzonitrile (2.4 g), 1-hydroxybenzotriazole (1.6 g) and 1-ethyl-3-(3'-dimethylaminopropyl)carbodiimide (2.3 g) were added to dimethylformamide (25 ml) and the mixture was stirred at room temperature for 5 h. The reaction mixture was treated with aqueous potassium carbonate solution and extracted with ethyl acetate. The organic layer was washed with saturated brine and dried over anhydrous magnesium sulfate, after which the solvent was evaporated under reduced pressure. The residue was purified by silica gel column chromatography (mobile phase:chloroform:methanol=100:1). Diisopropyl ether was added to the obtained oily substance to allow crystallization. The crystals were recrystallized from isopropyl alcohol to give the title compound (2.4 g), melting point: 193–194° C.

EXAMPLE 77

Ethyl 1-{2-cyano-4-[1-(4-fluorophenyl)-5-methyl-4-pyrazolecarboxamide]phenyl}piperidine-4-carboxylate

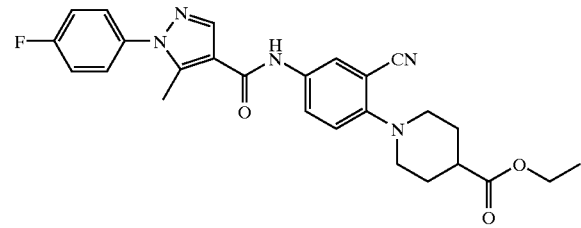

Dichloroethane solution (30 ml) containing 1-(4-fluorophenyl)-5-methylpyrazole-4-carboxylic acid (3.3 g) and thionyl chloride (2.1 g) was stirred at 83° C. for 1 h to give acid chloride. To this was added pyridine solution (30 ml) containing ethyl 1-(4-amino-2-cyanophenyl)piperidin-4-yl-carboxylate (4.1 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. A mixed solvent of toluene-diisopropyl ether was added to the residue to allow crystallization. The crystals were recrystallized from a mixed solvent of ethyl acetate-diisopropyl ether to give the title compound (4.8 g), melting point: 186–188° C.

EXAMPLE 78

1-{2-Cyano-4-[1-(4-fluorophenyl)-5-methyl-4-pyrazolecarboxamide]phenyl}piperidine-4-carboxylic acid

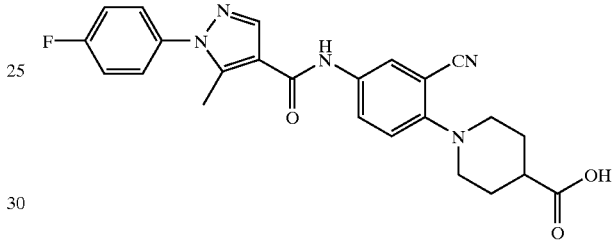

Ethyl 1-{2-cyano-4-[1-(4-fluorophenyl)-5-methyl-4-pyrazolecarboxamide]phenyl}piperidine-4-carboxylate (2.5 g) was added to ethanol (20 ml). 10% aqueous sodium hydroxide solution (20 ml) was added and the mixture was stirred at a refluxing temperature for 30 min. The solvent was evaporated under reduced pressure. To the residue was added dilute hydrochloric acid and the mixture was extracted with ethyl acetate. The organic layer was washed with saturated brine and dried over anhydrous magnesium sulfate, after which the solvent was evaporated under reduced pressure. A mixed solvent of chloroform-n-hexane was added to the residue to allow crystallization. The crystals were recrystallized from hydrous dimethylformamide to give the title compound (1.4 g), melting point: 260–261° C./decomposition.

EXAMPLE 79

N-{3-Cyano-4-[4-(2-hydroxyethyl)piperazin-1-yl]phenyl}-1-(4-fluorophenyl)pyrrole-3-carboxamide

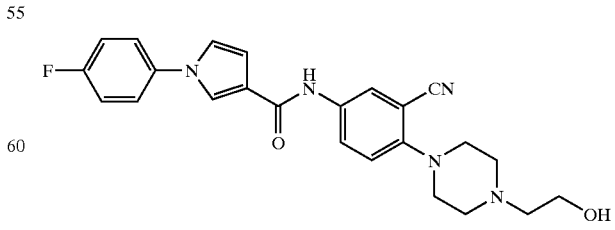

Dichloroethane solution (30 ml) containing 1-(4-fluorophenyl)pyrrole-3-carboxylic acid (1 g) and thionyl chloride (0.7 g) was stirred at 83° C. for 1 h to give acid chloride.

The solvent was evaporated under reduced pressure. To the residue was added pyridine solution (10 ml) containing 5-amino-2-[4-(2-hydroxyethyl)piperazin-1-yl]benzonitrile (1.4 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Ethyl acetate was added to the residue to allow crystallization. The crystals were recrystallized from a mixed solvent of ethyl acetate-diisopropyl ether to give the title compound (0.6 g), melting point: 138–140° C.

EXAMPLE 80

N-[3-Cyano-4-(4-piperidinopiperidin-1-yl)phenyl]-1-(4-fluorophenyl)-5-methylpyrazole-4-carboxamide

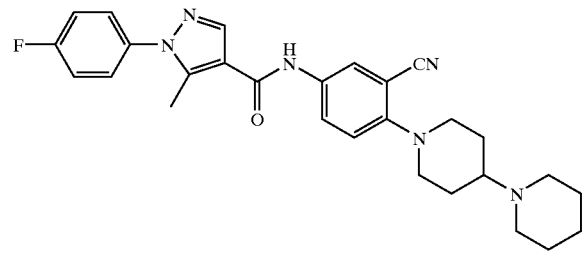

1-Benzotriazole 1-(4-fluorophenyl)-5-methylpyrazole-4-carboxylate (1.6 g) and 5-amino-2-(4-piperidinopiperidin-1-yl)benzonitrile (1.4 g) were reacted in ethanol (15 ml) at 78° C. for 3 h. The solvent was evaporated. To the residue was added aqueous potassium carbonate solution and the mixture was extracted with ethyl acetate. The organic layer was washed with dilute hydrochloric acid and saturated brine, and dried over anhydrous magnesium sulfate, after which the solvent was evaporated. Diisopropanol was added to the residue to allow crystallization. The crystals were recrystallized from hydrous ethanol to give the title compound (0.3 g), melting point: 237–238° C.

EXAMPLE 81

N-{3-Cyano-4-[4-(2-hydroxyethyl)piperazin-1-yl]phenyl}-1-(4-fluorophenyl)-3-methylpyrazole-4-carboxamide 1 hydrate

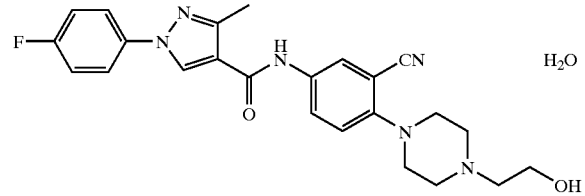

Dichloroethane solution (30 ml) containing 1-(4-fluorophenyl)-3-methylpyrazole-4-carboxylic acid (3 g) and thionyl chloride (1.9 g) was stirred at 83° C. for 1 h to give acid chloride. The solvent was evaporated under reduced pressure. To the residue was added pyridine solution (40 ml) containing 5-amino-2-[4-(2-hydroxyethyl)piperazin-1-yl] benzonitrile (5 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Ethyl acetate was added to the residue to allow crystallization. The crystals were recrystallized from hydrous ethanol to give the title compound (2.6 g), melting point: 120–121° C.

EXAMPLE 82

N-{3-Cyano-4-[4-(2-hydroxyethyl)piperazin-1-yl]phenyl}-1-(4-fluorophenyl)-3,5-dimethylpyrazole-4-carboxamide

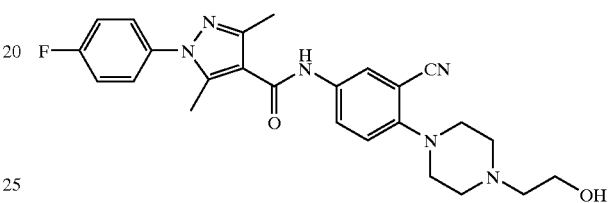

Dichloroethane solution (25 ml) containing 1-(4-fluorophenyl)-3,5-dimethylpyrazole-4-carboxylic acid (2.3 g) and thionyl chloride (1.4 g) was stirred at 83° C. for 1 h to give acid chloride. The solvent was evaporated under reduced pressure. To the residue was added pyridine solution (40 ml) containing 5-amino-2-[4-(2-hydroxyethyl)piperazin-1-yl]benzonitrile (2.9 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Ethyl acetate was added to the residue to allow crystallization. The crystals were recrystallized from hydrous dimethylformamide to give the title compound (2.4 g), melting point: 203–204° C.

EXAMPLE 83

N-{3-Cyano-4-[4-(2-hydroxyethyl)piperazin-1-yl]phenyl}-1-(4-fluorophenyl)pyrazole-4-carboxamide

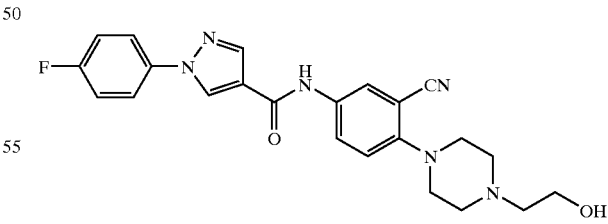

Dichloroethane solution (25 ml) containing 1-(4-fluorophenyl)pyrazole-4-carboxylic acid (2.2 g) and thionyl chloride (1.6 g) was stirred at 83° C. for 1 h to give acid chloride. The solvent was evaporated under reduced pressure. To the residue was added pyridine solution (25 ml) containing 5-amino-2-[4-(2-hydroxyethyl)piperazin-1-yl] benzonitrile (3.2 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Ethyl acetate was added to the residue to allow crystallization. The crystals were recrystallized from hydrous ethanol to give the title compound (2.1 g), melting point: 205–206° C.

EXAMPLE 84

N-{3-Cyano-4-[4-(2-hydroxyethyl)piperazin-1-yl]
phenyl}-1-(4-fluorophenyl)pyrrole-2-carboxamide

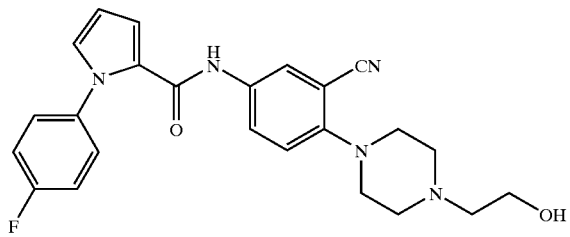

1-(4-Fluorophenyl)pyrrole-2-carboxylic acid (2 g), 5-amino-2-[4-(2-hydroxyethyl)piperazin-1-yl]benzonitrile (2.4 g), 1-hydroxybenzotriazole (1.8 g) and 1-ethyl-3-(3'-dimethylaminopropyl)carbodiimide (2.2 g) were added to dimethylformamide (25 ml) and the mixture was stirred at room temperature for 5 h. The reaction mixture was treated with aqueous potassium carbonate solution and extracted with ethyl acetate. The organic layer was washed with saturated brine and dried over anhydrous magnesium sulfate, after which the solvent was evaporated under reduced pressure. The residue was purified by silica gel column chromatography (mobile phase:chloroform:methanol=100:1) to give an oily substance. The obtained oily substance was recrystallized from a mixed solvent of toluene-n-hexane to give the title compound (1.5 g), melting point: 170–171° C.

EXAMPLE 85 tert-Butyl 4-{2-cyano-4-[1-(4-fluorophenyl)-5-methyl-4-pyrazolecarboxamide]phenyl}piperazin-1-ylcarboxylate

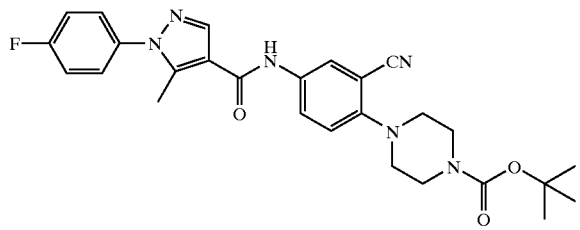

Dichloroethane solution (40 ml) containing 1-(4-fluorophenyl)-5-methylpyrazole-4-carboxylic acid (3.9 g) and thionyl chloride (2.5 g) was stirred at 83° C. for 1 h to give acid chloride. The solvent was evaporated under reduced pressure. To the residue was added pyridine solution (40 ml) containing 5-amino-2-[4-(tert-butoxycarbonyl)piperazin-1-yl]benzonitrile (5.4 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Diisopropyl ether was added to the residue to allow crystallization. The crystals were recrystallized from a mixed solvent of ethyl acetate-n-hexane to give the title compound (5.5 g), melting point: 223–224° C.

EXAMPLE 86

N-[3-Cyano-4-(piperazin-1-yl) phenyl]-1-(4-fluorophenyl)-5-methylpyrazole-4-carboxamide

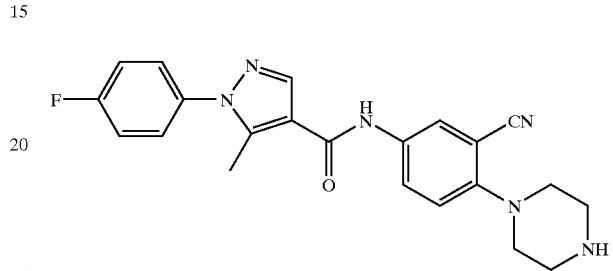

tert-Butyl 4-{2-cyano-4-[1-(4-fluorophenyl)-5-methyl-4-pyrazolecarboxamide]phenyl}piperazin-1-ylcarboxylate (5.0 g) was added to trifluoroacetic acid (30 ml) under ice-cooling and the mixture was stirred for 1 h. The reaction mixture was treated with aqueous sodium hydroxide solution and extracted with chloroform. The organic layer was washed with saturated brine and dried over anhydrous sodium sulfate, after which the solvent was evaporated under reduced pressure. Diisopropyl ether was added to the residue to allow crystallization. The crystals were recrystallized from hydrous ethanol to give the title compound (3.6 g), melting point: 218–219° C.

EXAMPLE 87

N-{3-Cyano-4-[4-(3-hydroxypropyl)piperazin-1-yl]
phenyl}-1-(4-fluorophenyl)-5-methylpyrazole-4-carboxamide hydrochloride

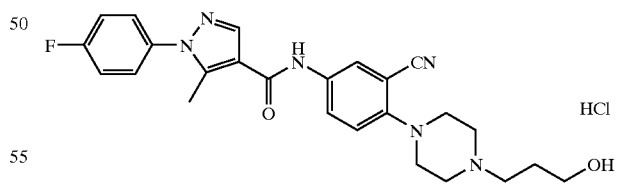

N-[3-Cyano-4-(piperazin-1-yl) phenyl]-1-(4-fluorophenyl)-5-methylpyrazole-4-carboxamide (2 g), potassium carbonate (0.8 g) and 3-bromopropanol (0.8 g) were added into dimethylformamide (20 ml) and the mixture was stirred at 60° C. for 3 h. The reaction mixture was added into water and extracted with ethyl acetate. The organic layer was washed with saturated brine and dried over anhydrous sodium sulfate, after which the solvent was evaporated under reduced pressure. The residue was purified by silica gel column chromatography (mobile phase: chloroform:methanol=50:1). To the resulting oily substance was added hydrogen chloride-isopropyl alcohol solution to give a hydrochloride, which was recrystallized from hydrous ethanol to give the title compound (0.5 g), melting point: 280° C. or higher.

EXAMPLE 88

Ethyl 4-(4-{2-cyano-4-[1-(4-fluorophenyl)-5-methyl-4-pyrazolecarboxamide]phenyl}piperazin-1-yl)butyrate

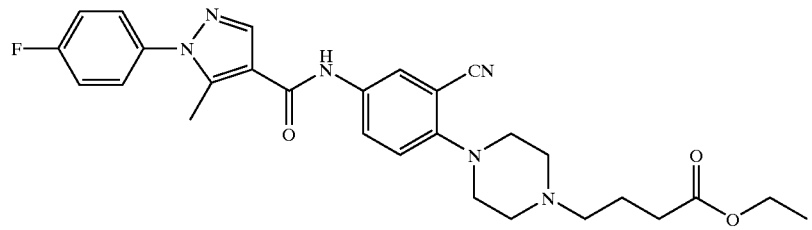

N-[3-Cyano-4-(piperazin-1-yl)phenyl]-1-(4-fluorophenyl)-5-methylpyrazole-4-carboxamide (4 g), potassium carbonate (1.6 g) and ethyl 4-bromobutyrate (2.3 g) were added into dimethylformamide (20 ml) and the mixture was stirred at 60° C. for 3 h. The reaction mixture was added into water and extracted with ethyl acetate. The organic layer was washed with saturated brine and dried over anhydrous sodium sulfate, after which the solvent was evaporated under reduced pressure. Diisopropyl ether was added to the residue to allow crystallization. The crystals were recrystallized from a mixed solvent of ethyl acetate-n-hexane to give the title compound (3.8 g), melting point: 149–150° C.

EXAMPLE 89

N-{3-Cyano-4-[4-(2-hydroxyethyl)piperazin-1-yl]phenyl}-5-methyl-1-phenylpyrazole-4-carboxamide

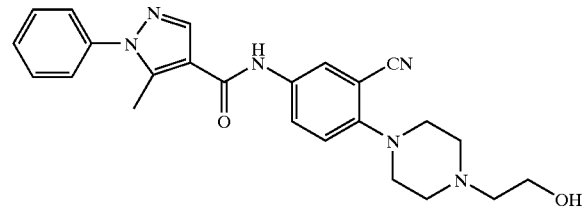

Dichloroethane solution (15 ml) containing 5-methyl-1-phenylpyrazole-4-carboxylic acid (1.3 g) and thionyl chloride (0.9 g) was stirred at 83° C. for 1 h to give acid chloride. The solvent was evaporated under reduced pressure. To the residue was added pyridine solution (15 ml) containing 5-amino-2-[4-(2-hydroxyethyl)piperazin-1 -yl]benzonitrile (1.9 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Ethyl acetate was added to the residue to allow crystallization. The crystals were recrystallized from hydrous ethanol to give the title compound (0.9 g), melting point: 214–215° C.

EXAMPLE 90

1-(2-Chloro-5-trifluoromethylphenyl)-N-{3-cyano-4-[4-(2-hydroxyethyl)piperazin-1-yl]phenyl}-5-methylpyrazole-4-carboxamide

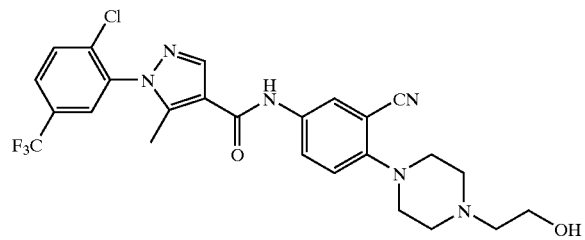

Dichloroethane solution (15 ml) containing 1-(2-chloro-5-trifluoromethylphenyl)-5-methylpyrazole-4-carboxylic acid (2 g) and thionyl chloride (0.9 g) was stirred at 83° C. for 1 h to give acid chloride. The solvent was evaporated under reduced pressure. To the residue was added pyridine solution (15 ml) containing 5-amino-2-[4-(2-hydroxyethyl)piperazin-1-yl]benzonitrile (1.9 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Ethyl acetate was added to the residue to allow crystallization. The crystals were recrystallized from a mixed solvent of ethyl acetate-diisopropyl ether to give the title compound (1.5 g), melting point: 208–209° C.

EXAMPLE 91

Ethyl cis-4-{2-cyano-4-[1-(4-fluorophenyl)-5-methylpyrazole-4-carboxamide]phenyl}-2,6-dimethylpiperazin-1-ylacetate

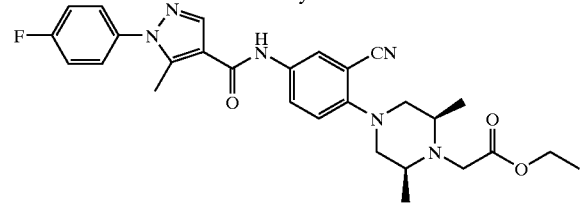

Dichloroethane solution (15 ml) containing 1-(4-fluorophenyl)-5-methylpyrazole-4-carboxylic acid (2.2 g) and thionyl chloride (1.4 g) was stirred at 83° C. for 1 h to give acid chloride. The solvent was evaporated under reduced pressure. To the residue was added pyridine solution (20 ml) containing ethyl cis-4-(4-amino-2-cyanophenyl)-2,6-dimethylpiperazin-1-ylacetate (3.2 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. The residue was purified by silica gel column chromatography (mobile phase:chloroform:methanol=50:1). A solution of hydrogen chloride-isopropyl alcohol was added to the obtained oily substance to allow crystallization. The crystals were recrystallized from hydrous methanol to give the title compound (4.5 g), melting point: 231–233° C.

EXAMPLE 92 cis-4-{2-Cyano-4-[1-(4-fluorophenyl)-5-methylpyrazole-4-carboxamide]phenyl}-2,6-dimethylpiperazin-1-ylacetic acid 1 hydrate

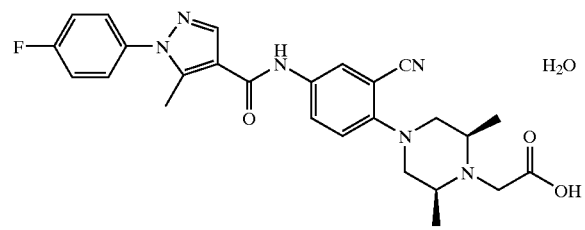

Ethyl cis-4-{2-cyano-4-[1-(4-fluorophenyl)-5-methylpyrazole-4-carboxamide]phenyl}-2,6-dimethylpiperazin-1-ylacetate (3.5 g) and 10% aqueous sodium hydroxide solution (40 ml) were added to ethanol (40 ml) and the mixture was stirred at 78° C. for 1 h. The solvent was evaporated under reduced pressure. Dilute hydrochloric acid was added and the precipitated crystals were recrystallized from hydrous ethanol to give the title compound (1.2 g), melting point 239–240° C.

EXAMPLE 93

1-(4-Chlorophenyl)-N-{3-cyano-4-[4-(2-hydroxyethyl)piperazin-1-yl]phenyl}-5-methylpyrazole-4-carboxamide

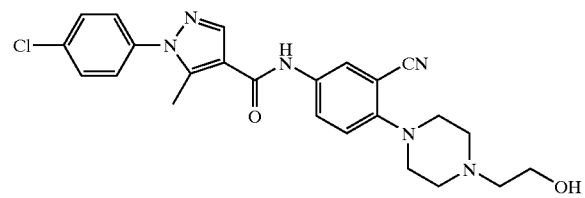

Dichloroethane solution (20 ml) containing 1-(4-Chlorophenyl)-5-methylpyrazole-4-carboxylic acid (2 g) and thionyl chloride (1.2 g) was stirred at 83° C. for 1 h to give acid chloride. The solvent was evaporated under reduced pressure. To the residue was added pyridine solution (20 ml) containing 5-amino-2-[4-(2-hydroxyethyl)piperazin-1-yl]benzonitrile (2.5 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Ethyl acetate was added to the residue to allow crystallization. The crystals were recrystallized from hydrous dimethylformamide to give the title compound (2.8 g), melting point: 220–221° C.

EXAMPLE 94

N-{3-Cyano-4-[4-(2-hydroxyethyl)piperazin-1-yl]phenyl}-1-(4-methylphenyl)-5-methylpyrazole-4-carboxamide

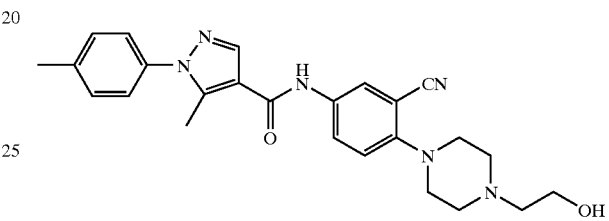

Dichloroethane solution (20 ml) containing 1-(4-methylphenyl)-5-methylpyrazole-4-carboxylic acid (2 g) and thionyl chloride (1.4 g) was stirred at 83° C. for 1 h to give acid chloride. The solvent was evaporated under reduced pressure. To the residue was added pyridine solution (20 ml) containing 5-amino-2-[4-(2-hydroxyethyl)piperazin-1-yl]benzonitrile (2.9 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. The residue was recrystallized from ethyl acetate to give the title compound (1.2 g), melting point: 183–184° C.

EXAMPLE 95

N-{3-Cyano-4-[4-(2-hydroxyethyl)piperazin-1-yl]phenyl}-1-(4-methoxyphenyl)-5-methylpyrazole-4-carboxamide

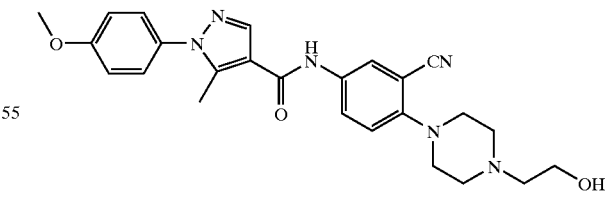

Dichloroethane solution (20 ml) containing 1-(4-methoxyphenyl)-5-methylpyrazole-4-carboxylic acid (2 g) and thionyl chloride (1.2 g) was stirred at 83° C. for 1 h to give acid chloride. The solvent was evaporated under reduced pressure. To the residue was added pyridine solution (20 ml) containing 5-amino-2-[4-(2-hydroxyethyl) piperazin-1-yl]benzonitrile (2.5 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Ethyl acetate was added to the residue to allow crystallization. The crystals were recrystallized from hydrous dimethylformamide to give the title compound (2.8 g), melting point: 210–211° C.

EXAMPLE 96

4-(4-{2-cyano-4-[1-(4-fluorophenyl)-5-methyl-4-pyrazolecarboxamide]phenyl}piperazin-1-yl) butyric acid 1 hydrochloride ½ hydrate

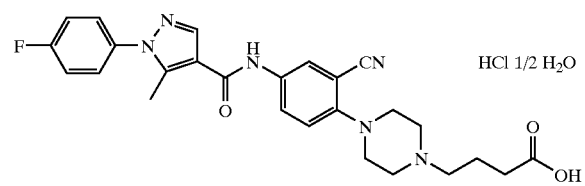

Ethyl 4-(4-{2-cyano-4-[1-(4-fluorophenyl)-5-methyl-4-pyrazolecarboxamide]phenyl}piperazin-1-yl)butyrate (2.0 g) and sodium hydroxide (0.2 g) were added to a mixed solvent of ethanol (20 ml) and water (20 ml), and the mixture was stirred at a refluxing temperature for 1 h. The solvent was evaporated under reduced pressure. Dilute hydrochloric acid was added to the residue and the resulting crystals were recrystallized from hydrous dimethylformamide to give the title compound (1.30 g), melting point: 233° C.

EXAMPLE 97

1-(4-Bromophenyl)-N-{3-cyano-4-[4-(2-hydroxyethyl)piperazin-1-yl]phenyl}-5-methylpyrazole-4-carboxamide 1 hydrate

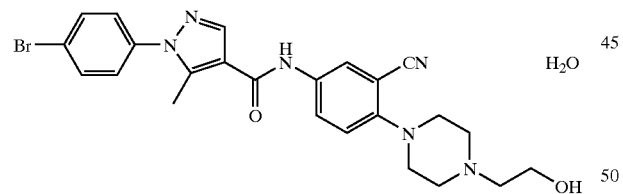

Dichloroethane solution (20 ml) containing 1-(4-bromophenyl)-5-methylpyrazole-4-carboxylic acid (1.5 g) and thionyl chloride (0.76 g) was stirred at 83° C. for 1 h to give acid chloride. The solvent was evaporated under reduced pressure. To the residue was added pyridine solution (20 ml) containing 5-amino-2-[4-(2-hydroxyethyl)piperazin-1-yl] benzonitrile (1.57 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Ethyl acetate was added to the residue to allow crystallization. The crystals were recrystallized from hydrous dimethylformamide to give the title compound (2.07 g), melting point: 232° C.

EXAMPLE 98

N-{3-Cyano-4-[4-(2-hydroxyethyl)piperazin-1-yl] phenyl}-1-(4-iodophenyl)-5-methylpyrazole-4-carboxamide 1 hydrate

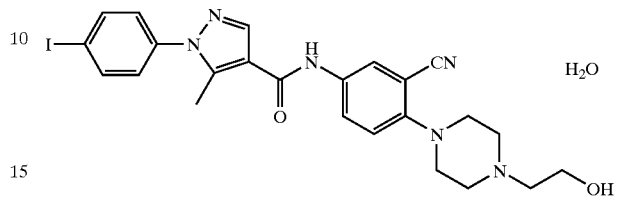

Dichloroethane solution (20 ml) containing 1-(4-iodophenyl)-5-methylpyrazole-4-carboxylic acid (2 g) and thionyl chloride (0.8 g) was stirred at 83° C. for 1 h to give acid chloride. The solvent was evaporated under reduced pressure. To the residue was added pyridine solution (20 ml) containing 5-amino-2-[4-(2-hydroxyethyl)piperazin-1-yl] benzonitrile (1.8 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Ethyl acetate was added to the residue to allow crystallization. The crystals were recrystallized from hydrous dimethylformamide to give the title compound (2.5 g), melting point: 240° C.

EXAMPLE 99

N-{3-Cyano-4-[4-(5-methylisoxazol-4-ylcarbonyl) piperazin-1-yl]phenyl}-1-(4-fluorophenyl)-5-methylpyrazole-4-carboxamide

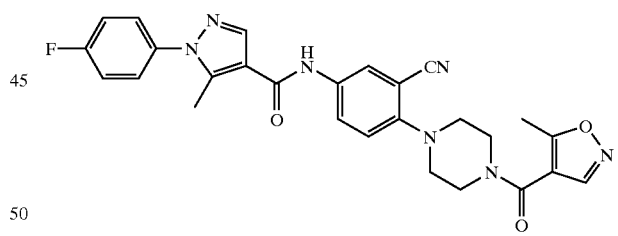

5-Methylisoxazole-4-carbonyl chloride (1.4 g) synthesized according to the method described in J. Chem. Soc. Perkin Trans. I, pp. 1875–1879 (1988) was added to a pyridine solution (20 ml) containing N-[3-cyano-4-(piperazin-1-yl)phenyl]-1-(4-fluorophenyl)-5-methylpyrazole-4-carboxamide (4 g) under ice-cooling, and the mixture was stirred for 1 h. The reaction mixture was poured into water and extracted with ethyl acetate. The organic layer was washed with dilute hydrochloric acid and saturated brine and dried over anhydrous magnesium sulfate, after which the solvent was evaporated under pressure. Diisopropyl ether was added to the obtained residue to allow crystallization. The crystals were recrystallized from hydrous dimethylformamide to give the title compound (2.9 g), melting point: 208° C.

EXAMPLE 100

N-{3-Cyano-4-[4-(2-cyano-3-hydroxycrotonoyl) piperazin-1-yl]phenyl}-1-(4-fluorophenyl)-5-methylpyrazole-4-carboxamide

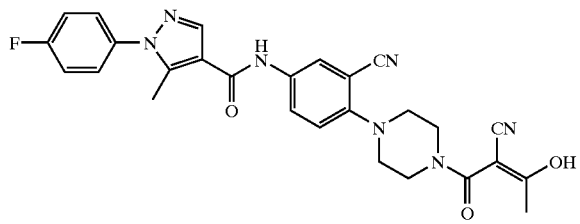

A mixed solvent of ethanol (10 ml) and water (10 ml) containing N-{3-cyano-4-[4-(5-methylisoxazol-4-ylcarbonyl) piperazin-1-yl]phenyl}-1-(4-fluorophenyl)-5-methylpyrazole-4-carboxamide (0.95 g) and sodium hydroxide (0.1 g) was stirred at a refluxing temperature for 2 h. The solvent was evaporated under reduced pressure. Dilute hydrochloric acid was added to the residue to allow crystallization. The crystals were recrystallized from hydrous dimethylformamide to give the title compound (0.45 g), melting point: 210° C.

EXAMPLE 101

N-[3-cyano-4-(1-homopiperazinyl) phenyl]-1-(4-fluorophenyl)-5-methylpyrazole-4-carboxamide

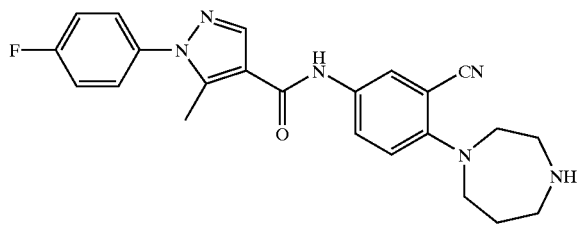

Dichloroethane solution (40 ml) containing 1-(4-fluorophenyl)-5-methylpyrazole-4-carboxylic acid (3.0 g) and thionyl chloride (2.0 g) was stirred at 83° C. for 1 h to give acid chloride. The solvent was evaporated under reduced pressure. To the residue was added pyridine solution (30 ml) containing 5-amino-2-[4-(tert-butoxycarbonyl)homopiperazin-1-yl]benzonitrile (4.8 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. To the residue was added trifluoroacetic acid (25 ml) under ice-cooling, and the mixture was stirred for 1 h. The reaction mixture was treated with aqueous sodium hydroxide solution and extracted with chloroform. The organic layer was washed with saturated brine and dried over anhydrous sodium sulfate, after which the solvent was evaporated under reduced pressure. Diisopropyl ether was added to the residue to allow crystallization. The crystals were recrystallized from hydrous ethanol to give the title compound (1.6 g), melting point: 158° C.

EXAMPLE 102

N-{3-Cyano-4-[4-(2-hydroxyethyl)homopiperazin-1-yl]phenyl}-1-(4-fluorophenyl)-5-methylpyrazole-4-carboxamide ½ hydrate

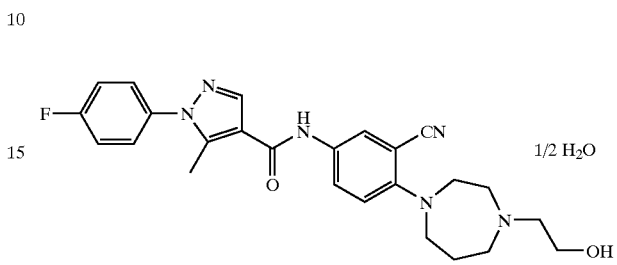

N-[3-Cyano-4-(homopiperazin-1-yl)phenyl]-1-(4-fluorophenyl)-5-methylpyrazole-4-carboxamide (1.5 g), potassium carbonate (0.6 g) and 2-bromoethyl acetate (0.7 g) were added to dimethylformamide (20 ml) and the mixture was stirred at 60° C. for 1 h. The reaction mixture was added into water and extracted with ethyl acetate. The organic layer was washed with saturated brine, and the solvent was evaporated under reduced pressure. To the residue were added 2N aqueous sodium hydroxide solution (10 ml) and ethanol (20 ml) and the mixture was stirred at a refluxing temperature for 1 h. The solvent was evaporated under reduced pressure and dilute hydrochloric acid was added. The obtained crystals were recrystallized from hydrous ethanol to give the title compound (1.1 g), melting point: 124° C.

EXAMPLE 103

N-{4-[4-(2-Dimethylaminoethyl)piperazin-1-yl]-3-cyanophenyl}-1-(4-fluorophenyl)-5-methylpyrazole-4-carboxamide ¾ hydrate

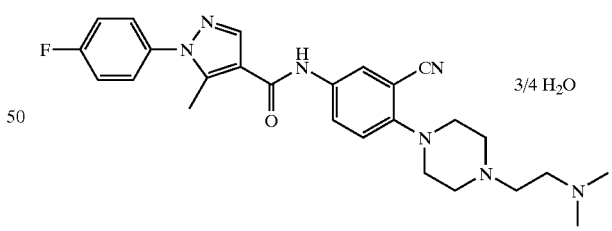

N-[3-Cyano-4-(piperazin-1-yl)phenyl]-1-(4-fluorophenyl)-5-methylpyrazole-4-carboxamide (2 g), 2-dimethylaminoethyl chloride hydrochloride (0.85 g) and potassium carbonate (0.8 g) were added to dimethylformamide (20 ml) and the mixture was stirred at 60° C. for 3 h. The reaction mixture was added into water and extracted with ethyl acetate. The organic layer was washed with saturated brine, and the solvent was evaporated under reduced pressure. Ethanol was added to the residue to allow crystallization. The crystals were recrystallized from hydrous ethanol to give the title compound (0.3 g), melting point: 185° C.

153

EXAMPLE 104

1-(4-Chlorophenyl)-N-(3-cyano-4-piperidinophenyl)-5-methylpyrazole-4-carboxamide

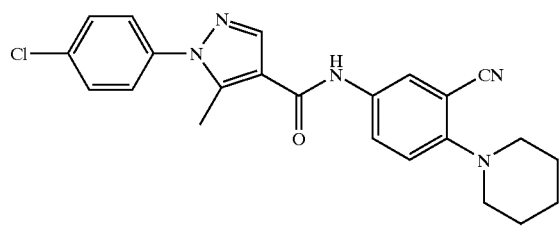

Dichloroethane solution (20 ml) containing 1-(4-chlorophenyl)-5-methylpyrazole-4-carboxylic acid (1.5 g) and thionyl chloride (0.9 g) was stirred at 83° C. for 1 h to give acid chloride. The solvent was evaporated under reduced pressure. To the residue was added pyridine solution (20 ml) containing 5-amino-2-piperidinobenzonitrile (1.4 g), and the mixture was stirred at room temperature for 1 h. The reaction mixture was added into water, and the obtained crystals were recrystallized from hydrous dimethylformamide to give the title compound (2.0 g), melting point: 192° C.

EXAMPLE 105 tert-Butyl 4-{4-[1-(4-chlorophenyl)-5-methyl-4-pyrazolecarboxamide]-2-cyanophenyl}piperazin-1-ylcarboxyate

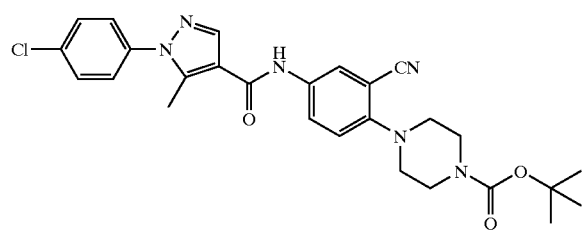

Dichloroethane solution (40 ml) containing 1-(4-chlorophenyl)-5-methylpyrazole-4-carboxylic acid (3.9 g) and thionyl chloride (2.4 g) was stirred at 83° C. for 1 h to give acid chloride. The solvent was evaporated under reduced pressure. To the residue was added pyridine solution (40 ml) containing 5-amino-2-[4-(tert-butoxycarbonyl)piperazin-1-yl]benzonitrile (5.1 g) under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. Diisopropyl ether was added to the residue to allow crys

154 tallization. The crystals were recrystallized from a mixed solvent of ethyl acetate-n-hexane to give the title compound (5.5 g), melting point: 251–252° C.

EXAMPLE 106

1-(4-Chlorophenyl)-N-[3-cyano-4-(piperazin-1-yl)phenyl]-5-methylpyrazole-4-carboxamide

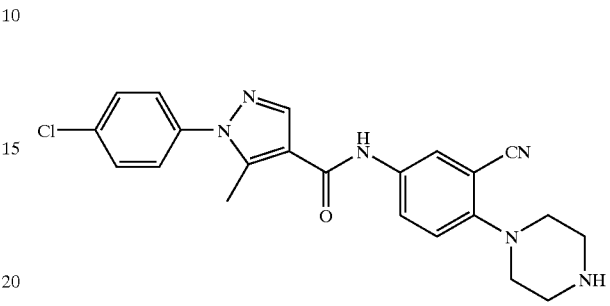

tert-Butyl 4-{4-[1-(4-chlorophenyl)-5-methyl-4-pyrazolecarboxamide]-2-cyanophenyl piperazin-1-ylcarboxylate (9.92 g) was added to trifluoroacetic acid (50 ml) under ice-cooling and the mixture was stirred for 1 h. The reaction mixture was treated with aqueous sodium hydroxide solution and extracted with chloroform. The organic layer was washed with saturated brine and dried over anhydrous sodium sulfate, after which the solvent was evaporated under reduced pressure. Diisopropyl ether was added to the residue to allow crystallization. The crystals were recrystallized from hydrous ethanol to give the title compound (4.7 g), melting point: 184° C.

EXAMPLE 107

1-(4-Chlorophenyl)-N-{3-cyano-4-[4-(3-hydroxypropyl)piperazin-1-yl]phenyl}-5-methylpyrazole-4-carboxamide 1 hydrate

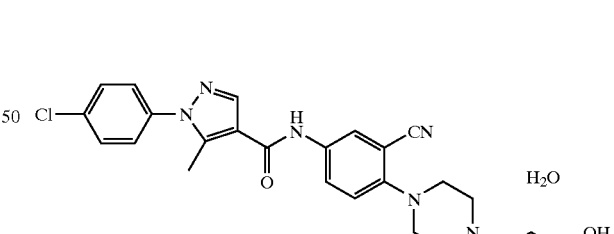

1-(4-Chlorophenyl)-N-[3-cyano-4-(piperazin-1-yl)phenyl]-5-methylpyrazole-4-carboxamide (4.0 g), 3-bromopropanol (1.6 g) and potassium carbonate (1.6 g) were added to dimethylformamide (25 ml) and the mixture was stirred at 60° C. for 3 h. The reaction mixture was added into water, and the obtained crystals were recrystallized from hydrous dimethylformamide to give the title compound (2.5 g), melting point: 213° C.

EXAMPLE 108

1-{4-[1-(4-Chlorophenyl)-5-methylpyrazole-4-carboxamide]-2-cyanophenyl}-4-piperidinylbenzoate

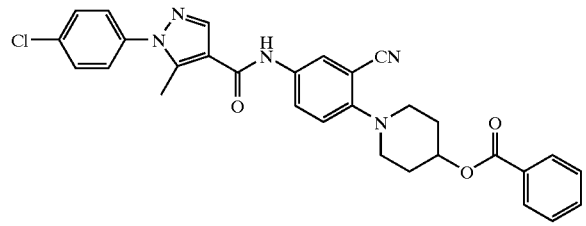

Dichloroethane solution (40 ml) containing 1-(4-chlorophenyl)-5-methylpyrazole-4-carboxylic acid (4 g) and thionyl chloride (2.4 g) was stirred at 83° C. for 1 h to give acid chloride. The solvent was evaporated under reduced pressure. To the residue was added pyridine solution (40 ml) containing 1-(4-amino-2-cyanophenyl)-4-piperidinylbenzoate (5.4 g) under ice-cooling and the mixture was stirred for 1 h. The reaction mixture was added into water, and the obtained crystals were recrystallized from hydrous dimethylformamide to give the title compound (8.8 g), melting point: 227° C.

EXAMPLE 109

1-(4-Chlorophenyl)-N-[3-cyano-4-(4-hydroxypiperidin-1-yl)phenyl]-5-methylpyrazole-4-carboxamide ¾ hydrate

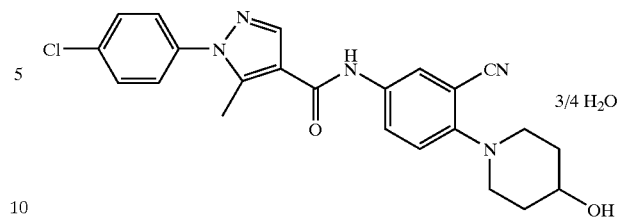

1-{4-[1-(4-Chlorophenyl)-5-methylpyrazole-4-carboxamide]-2-cyanophenyl}piperidin-4-ylbenzoate (8.2 g), 10% aqueous sodium hydroxide solution (90 ml) were added ethanol (90 ml) and the mixture was stirred at 78° C. for 1 h. The precipitated crystals were collected by filtration and recrystallized from hydrous dimethylformamide to give the title compound (4.7 g), melting point: 247° C.

EXAMPLE 110

4-(1-{4-[1-(4-Chlorophenyl)-5-methylpyrazole-4-carboxamide]-2-cyanophenyl}piperidin-4-yloxy)-4-oxobutyric acid

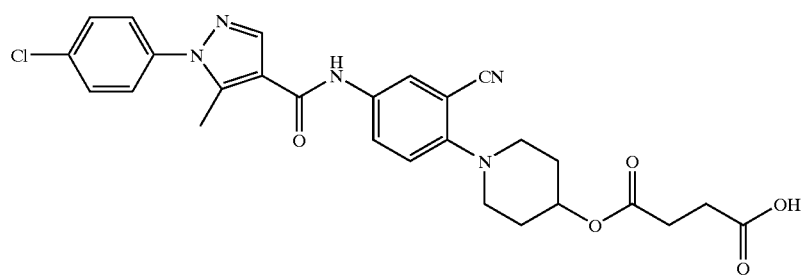

1-(4-chlorophenyl)-N-[3-cyano-4-(4-hydroxypiperidino)phenyl]-5-methylpyrazole-4-carboxamide (2.0 g), succinic anhydride (0.5 g) and a catalytic amount of p-toluenesulfonic acid 1 hydrate were added to nitrobenzene (40 ml) and the mixture was stirred at 110° C. for 6 h. The reaction mixture was ice-cooled, and diisopropyl ether was added thereto. The precipitated crystals were filtered and recrystallized from hydrous ethanol to give the title compound (1.2 g), melting point: 246–248° C.

EXAMPLE 111

N-[1-(4-Chlorophenyl)-3-methylpyrazol-4-ylcarbonyl]-N-(3-cyano-4-neopentyloxyphenyl)glycine

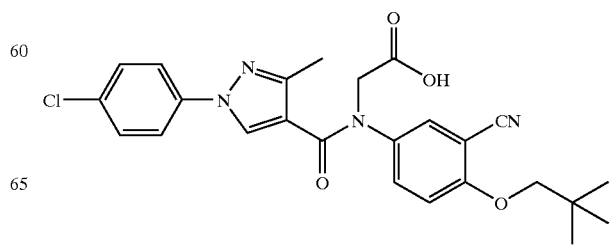

Dichloroethane solution (45 ml) containing 1-(4-chlorophenyl)-3-methylpyrazole-4-carboxylic acid (2.0 g) and thionyl chloride (1.2 g) was stirred at 83° C. for 30 min to give acid chloride. The acid chloride was added into pyridine solution (80 ml) containing ethyl N-(3-cyano-4-neopentyloxyphenyl)glycine (2.5 g) under ice-cooling, and the mixture was stirred for 1 h. The reaction mixture was added into water and extracted with ethyl acetate. The organic layer was washed with saturated brine, and the solvent was evaporated under reduced pressure. Sodium hydroxide (1.8 g), water (40 ml) and ethanol (40 ml) were added to the residue and the mixture was stirred at a refluxing temperature for further 1 h. The solvent was evaporated under reduced pressure, dilute hydrochloric acid was added, and the mixture was extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from a mixed solvent of toluene-n-hexane to give the title compound (1.7 g), melting point: 186–189° C.

EXAMPLE 112

N-[1-(4-Bromophenyl)-3-methylpyrazol-4-ylcarbonyl]-N-(3-cyano-4-neopentyloxyphenyl)glycine ¼ isopropyl ether

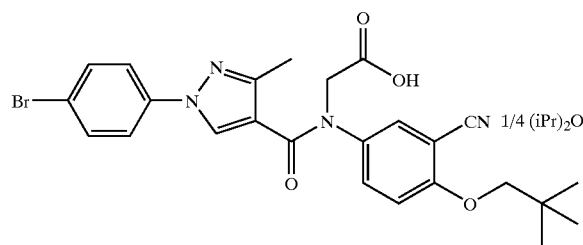

Dichloroethane solution (12 ml) containing 1-(4-bromophenyl)-3-methylpyrazole-4-carboxylic acid (1.2 g) and thionyl chloride (0.6 g) was stirred at 83° C. for 30 min to give acid chloride. The acid chloride was added pyridine solution (20 ml) containing ethyl N-(3-cyano-4-neopentyloxyphenyl)glycine (1.2 g) under ice-cooling and the mixture was stirred for 1 h. The reaction mixture was added into water and extracted with ethyl acetate. The organic layer was washed with saturated brine, and the solvent was evaporated under reduced pressure. Sodium hydroxide (0.3 g), water (10 ml) and ethanol (10 ml) were added to the residue and the mixture was stirred at a refluxing temperature for further 1 h. The solvent was evaporated under reduced pressure, dilute hydrochloric acid was added, and the mixture was extracted with ethyl acetate. The organic layer was washed with saturated brine and dried over anhydrous magnesium sulfate, after which the solvent was evaporated under reduced pressure. n-Hexane was added to the residue to allow crystallization. The crystals were recrystallized from a mixed solvent of toluene-isopropyl ether to give the title compound (0.7 g), melting point: 169–170° C.

EXAMPLE 113

1-(4-Chlorophenyl)-N-{3-cyano-4-[4-(2-hydroxyethyl)piperazin-1-yl]phenyl}pyrrole-3-carboxamide

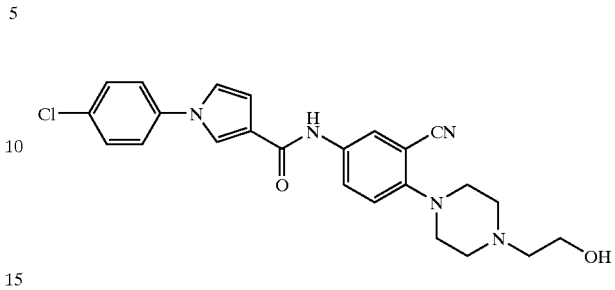

By the reaction and treatment in the same manner as in Example 64 using 1-(4-chlorophenyl)pyrrole-3-carboxylic acid (2 g) and 5-amino-2-[4-(2-hydroxyethyl)piperazin-1-yl]benzonitrile (2.67 g), the title compound (1.1 g) was obtained, melting point: 196° C.

EXAMPLE 114

1-(3-chlorophenyl)-N-{3-cyano-4-[4-(2-hydroxyethyl)piperazin-1-yl]phenyl}-5-methylpyrazole-4-carboxamide

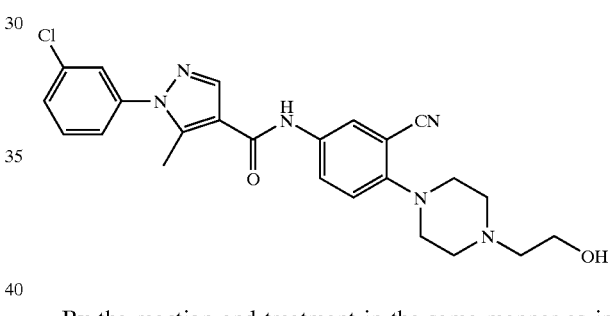

By the reaction and treatment in the same manner as in Example 64 using 1-(3-chlorophenyl)-5-methylpyrazole-4-carboxylic acid (2 g) and 5-amino-2-[4-(2-hydroxyethyl)piperazin-1-yl]benzonitrile (2.5 g), the title compound (0.5 g) was obtained, melting point: 176–177° C.

EXAMPLE 115

1-(3,4-Dichlorophenyl)-N-{3-cyano-4-[4-(2-hydroxyethyl) piperazin-1-yl]phenyl}-5-methylpyrazole-4-carboxamide

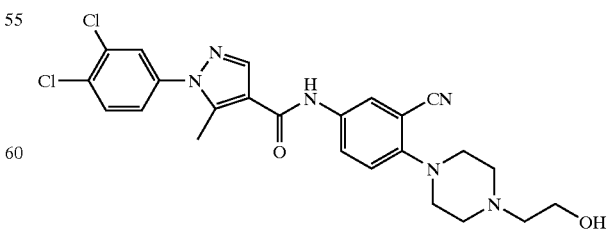

By the reaction and treatment in the same manner as in Example 64 using 1-(3,4-dichlorophenyl)-5-methylpyrazole-4-carboxylic acid (2 g) and 5-amino-2-[4-(2-hydroxyethyl)piperazin-1-yl]benzonitrile (2.67 g), the title compound (1.2 g) was obtained, melting point: 195–197° C.

EXAMPLE 116

1-(4-Chlorophenyl)-N-[3-cyano-4-(4-morpholinopiperidin-1-yl)phenyl]-5-methylpyrazole-4-carboxamide hydrochloride

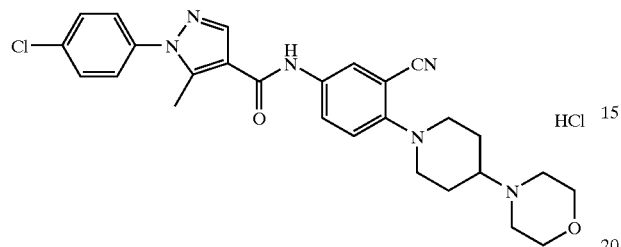

By the reaction and treatment in the same manner as in Example 64 using 1-(4-chlorophenyl)-5-methylpyrazole-4-carboxylic acid (2 g) and 5-amino-2-(4-morpholinopiperidin-1-yl)benzonitrile (2.2 g), 1-(4-chlorophenyl)-N-[3-cyano-4-(4-morpholinopiperidin-1-yl)phenyl]-5-methylpyrazole-4-carboxamide (1.3 g) was obtained, melting point: 249–250° C.

$^1$H-NMR (270 MHz, DMSO-d6) δ(ppm):1.57 (2H, dd, J=2.6, 11.9 Hz), 1.90 (2H, d, J=11.2 Hz), 2.25–2.28 (1H, m), 2.47–2.51(4H, m), 2.55 (3H, s), 2.75 (2H, t, 11.2 Hz), 3.45 (2H, d, 11.9 Hz), 3.58 (4H, dd, J=4.0, 4.6 Hz), 7.16 (1H, d, J=8.6 Hz), 7.5–7.7(4H, m), 7.84 (1H, dd, J=2.6, 8.6 Hz), 8.06(1H, d, J=2.6 Hz), 8.30 (1H, s), 9.97 (1H, br).

The above compound was treated with 1N hydrogen chloride-ethanol solution to give 1-(4-chlorophenyl)-N-[3-cyano-4-(4-morpholinopiperidin-1-yl)phenyl]-5-methylpyrazole-4-carboxamide hydrochloride was obtained, melting point: 286° C. (decomposition).

EXAMPLE 117

N-(1-(4-(1-(4-Chlorophenyl)-5-methyl-4-pyrazolecarboxamide)-2-cyanophenyl)piperidine-4-yl)morpholine N-oxide

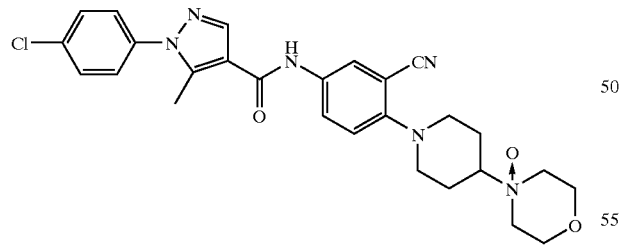

1-(4-Chlorophenyl)-N-[3-cyano-4-(4-morpholinopiperidin-1-yl)phenyl]-5-methylpyrazole-4-carboxamide (1 g) and m-chloroperbenzoic acid (0.4 g) were stirred in dichloromethane (10 ml) at room temperature for 8 h. To the reaction mixture was added sodium hydrogen carbonate solution. The organic layer was extracted with chloroform and dried over anhydrous magnesium sulfate. The solvent was evaporated and the residue was purified by silica gel column chromatography (chloroform:methanol=1:1) to give the title compound (0.3 g), melting point: 200–201° C.

EXAMPLE 118

1-(2-Chlorophenyl)-N-{3-cyano-4-[4-(2-hydroxyethyl)piperazin-1-yl]phenyl}-5-methylpyrazole-4-carboxamide hydrochloride

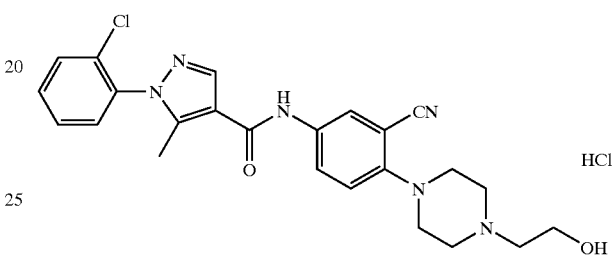

Dichloroethane solution (20 ml) containing 1-(2-chlorophenyl)-5-methylpyrazole-4-carboxylic acid (2 g) and thionyl chloride (1.4 g) was stirred at 83° C. for 30 min to give acid chloride. A pyridine solution (20 ml) containing 5-amino-2-[4-(2-hydroxyethyl) piperazin-1-yl]benzonitrile (2.5 g) was added thereto under ice-cooling and the mixture was stirred for 1 h. The reaction mixture was treated with aqueous sodium hydroxide solution and extracted with ethyl acetate. The organic layer was washed with saturated brine, and the solvent was evaporated under reduced pressure. 1N Hydrogen chloride-ethanol solution was added to the residue to allow crystallization. The crystals were recrystallized from hydrous ethanol to give the title compound (0.8 g), melting point: 280° C. or higher.

$^1$H-NMR(270 MHz, CDCl$_3$) δ(ppm):2.33(3H, s),3.21–3.32(6H, m), 3.55 (2H, d, J=10.9 Hz), 3.66 (2H, d, J=10.9 Hz), 3.84(2H, dd, J=4.4, 5.2 Hz),5.3–5.5 (1H, br), 7.28 (1H, d, J=11.2 Hz), 7.57–7.68 (3H, m), 7.74(1H, d, J=9.2 Hz), 7.99 (1H, dd, J=2.6, 9.2 Hz), 8.20 (1H, d, J=2.6 Hz), 8.46 (1H, s), 10.26 (1H, s), 10.65–10.83 (1H, br)

EXAMPLE 119

1-(4-Chlorophenyl)-N-(3-cyano-4-{4-[3-(3-pyridyl)propyl]piperazin-1-yl}phenyl)-5-methylpyrazole-4-carboxamide 1 hydrate

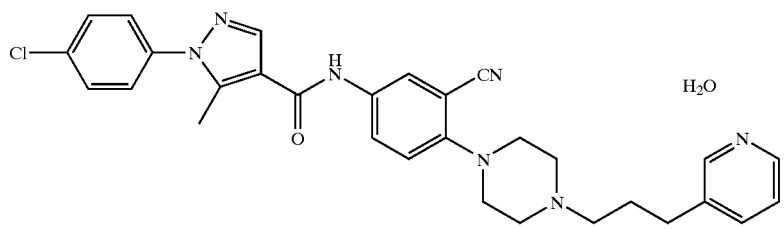

3-(3-Pyridyl)propanol (0.2 g) and thionyl chloride (0.2 g) were added into dichloroethane (5 ml) and the mixture was stirred at a refluxing temperature for 1 h. After the evaporation of the solvent, 1-(4-chlorophenyl)-N-[3-cyano-4-(piperazin-1-yl) phenyl]-5-methylpyrazole-4-carboxamide (0.6 g), potassium carbonate (0.1 g) and dimethylformamide (5 ml) were added and the mixture was stirred at 60° C. for 1 h. The reaction mixture was treated with water, and the organic layer was extracted with ethyl acetate. The extract was washed with saturated brine and dried over anhydrous sodium sulfate, after which the solvent was evaporated under reduced pressure. The residue was purified by silica gel column chromatography (chloroform:methanol=20:1) to give the title compound (0.1 g), melting point: 201–203° C.

EXAMPLE 120

1-(4-Chlorophenyl)-N-(3-cyano-4-{4-[2-(2-hydroxyethoxy) ethyl]piperazin-1-yl}phenyl)-5-methylpyrazole-4-carboxamide ¼ hydrate

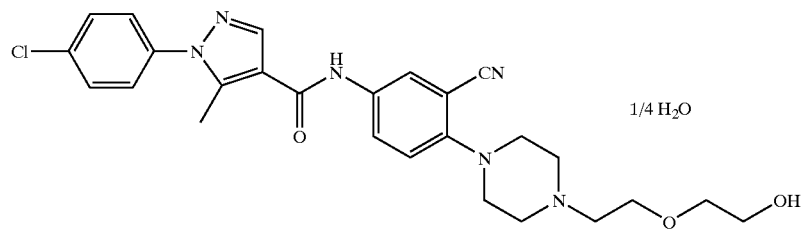

1/4 H₂O

By the reaction and treatment in the same manner as in Example 64 using 1-(4-chlorophenyl)-5-methylpyrazole-4-carboxylic acid (2 g) and 5-amino-2-{4-[2-(2-hydroxyethoxy)ethyl]piperazin-1-yl}benzonitrile (4.2 g), the title compound (2.8 g) was obtained, melting point: 196° C.

EXAMPLE 121

1-(4-Chlorophenyl)-N-[3-cyano-4-(1,4-dioxa-8-azaspiro[4,5]deca-8-yl)phenyl]-5-methylpyrazole-4-carboxamide

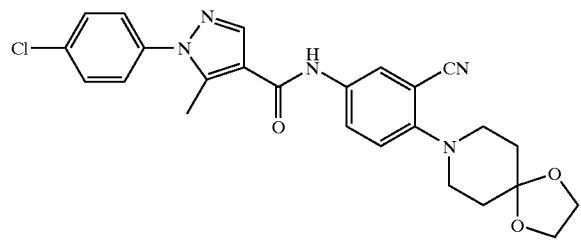

By the reaction and treatment in the same manner as in Example 64 using 1-(4-chlorophenyl)-5-methylpyrazole-4-carboxylic acid (4.2 g) and 5-amino-2-(1,4-dioxa-8-azaspiro[4,5]deca-8-yl) benzonitrile (4.6 g), the title compound (5.4 g) was obtained, melting point: 241° C.

EXAMPLE 122

1-(4-Chlorophenyl)-N-[3-cyano-4-(4-oxopiperidin-1-yl)phenyl]-5-methylpyrazole-4-carboxamide

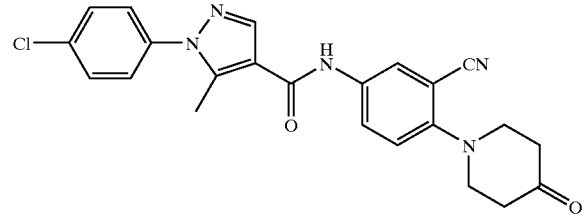

1-(4-Chlorophenyl)-N-[3-cyano-4-(1,4-dioxa-8-azaspiro[4,5]deca-8-yl)phenyl]-5-methylpyrazole-4-carboxamide (5.3 g) and 0.1N hydrochloric acid (6 ml) were added to tetrahydrofuran (60 ml) and the mixture was stirred at a refluxing temperature for 3 h. The organic layer was extracted with ethyl acetate and dried over anhydrous magnesium sulfate, after which the solvent was evaporated under reduced pressure. Diisopropyl ether was added to the residue to allow crystallization. The crystals were recrystallized from ethyl acetate-n-hexane to give the title compound (4.5 g), melting point: 238° C.

EXAMPLE 123

Ethyl 1-{4-[1-(4-chlorophenyl)-5-methyl-4-pyrazolecarboxamide]-2-cyanophenyl}piperidine-4-carboxylate

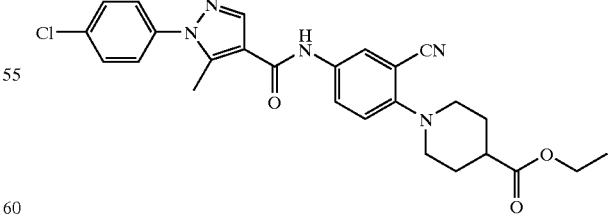

By the reaction and treatment in the same manner as in Example 77, except that 1-(4-chlorophenyl)-5-methylpyrazole-4-carboxylic acid was used instead of 1-(4-fluorophenyl)-5-methylpyrazole-4-carboxylic acid, the title compound was obtained, melting point: 193° C.

EXAMPLE 124

1-{4-[1-(4-Chlorophenyl)-5-methyl-4-pyrazolecarboxamide]-2-cyanophenyl}piperidine-4-carboxylic acid 1 hydrate

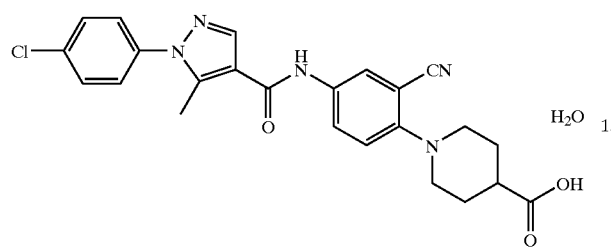

By the reaction and treatment in the same manner as in Example 78, except that ethyl 1-{4-[1-(4-chlorophenyl)-5-methyl-4-pyrazolecarboxamide]-2-cyanophenyl}piperidine-4-carboxylate was used instead of ethyl 1-{2-cyano-4-[1-(4-fluorophenyl)-5-methyl-4-pyrazolecarboxamide]phenyl}piperidine-4-carboxylate, the title compound was obtained, melting point: 260° C. or higher.

$^1$H-NMR(270 MHz, CDCl$_3$) δ(ppm):1.80 (2H, dd, J=3.2, 9.9 Hz),1.95 (2H, dd, J=3.2, 9.9 Hz), 2.40 (1H, ddd, J=3.2, 9.2, 11.2 Hz), 2.55 (3H, s), 2.83 (2H, dd, J=9.2, 11.2 Hz),3.2–3.5 (2H, br), 7.18 (1H, d, J=8.6 Hz), 7.61 (4H, m), 7.85 (1H, dd, J=2.6, 8.6 Hz), 8.08 (1H, d, J=2.6 Hz), 8.32 (1H, s), 10.01 (1H, s)

EXAMPLE 125

2-(4-{4-[1-(4-Chlorophenyl)-5-methyl-4-pyrazolecarboxamide]-2-cyanophenyl]piperazin-1-yl)ethyl acetate

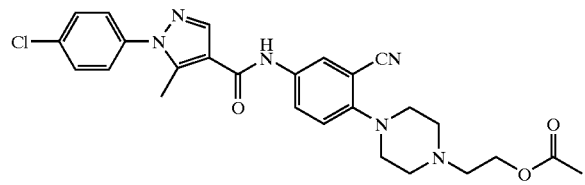

1-(4-Chlorophenyl)-N-(3-cyano-4-[4-(2-hydroxyethyl)piperazin-1-yl]phenyl-5-methylpyrazolecarboxamide (1 g) was dissolved in pyridine (10 ml). Acetyl chloride (0.17 g) was added under ice-cooling and the mixture was stirred for 1 h. The reaction mixture was treated with aqueous potassium carbonate solution. The organic layer was extracted with ethyl acetate. The extract was washed with saturated brine and dried over anhydrous sodium sulfate, after which the solvent was evaporated under reduced pressure. n-Hexane was added to the residue to allow crystallization. The crystals were recrystallized from a mixed solvent of ethyl acetate-n-hexane to give the title compound (0.6 g), melting point: 175° C.

EXAMPLE 126

1-(4-Chlorophenyl)-N-{3-cyano-4-[4-(N,N-dimethylamino)piperidin-1-yl]phenyl}-5-methylpyrazole-4-carboxamide

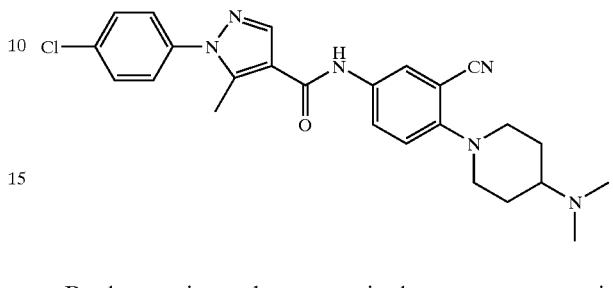

By the reaction and treatment in the same manner as in Example 64 using 1-(4-chlorophenyl)-5-methylpyrazole-4-carboxylic acid (3.3 g) and 5-amino-2-[4-(N,N-dimethylamino)piperidin-1-yl]benzonitrile (2.9 g), the title compound (1.7 g) was obtained, melting point: 210–213° C.

EXAMPLE 127

N-(4-{4-[N,N-Bis(2-hydroxyethyl)amino]piperidin-1-yl}-3-cyanophenyl)-1-(4-chlorophenyl)-5-methylpyrazole-4-carboxamide

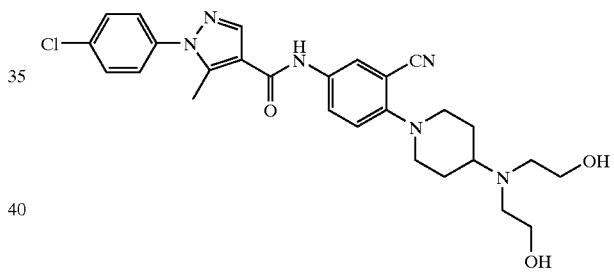

By the reaction and treatment in the same manner as in Example 64 using 1-(4-chlorophenyl)-5-methylpyrazole-4-carboxylic acid (1.0 g) and 5-amino-2-{4-[N,N-bis(2-hydroxyethyl)amino]piperidin-1-yl}benzonitrile (1.2 g), the title compound (0.2 g) was obtained, melting point: 230–233° C.

EXAMPLE 128

N-{3-Cyano-4-[4-(2-hydroxyethyl)piperazin-1-yl]phenyl}-1-(3,4-difluorophenyl)-5-methylpyrazole-4-carboxamide

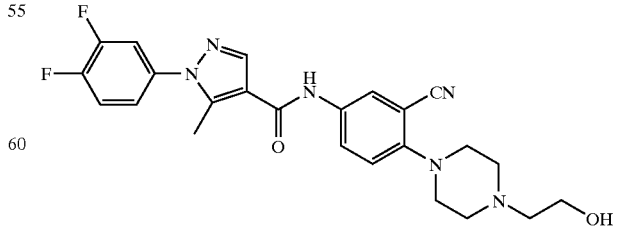

By the reaction and treatment in the same manner as in Example 64 using 1-(3,4-difluorophenyl)-5-methylpyrazole-4-carboxylic acid (3 g) and 5-amino-2-[4-(2-hydroxyethyl)piperazin-1-yl]benzonitrile (3.7 g), the title compound (1.9 g) was obtained, melting point: 164–165° C.

EXAMPLE 129

1-(4-Chlorophenyl)-N-{3-cyano-4-[4-(4-methylpiperazin-1-yl)piperidin-1-yl]phenyl}-5-methylpyrazole-4-carboxamide ¼ hydrate

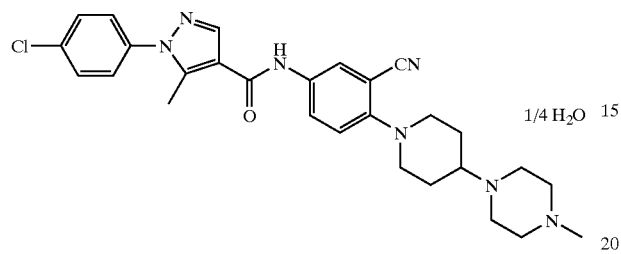

By the reaction and treatment in the same manner as in Example 64 using 1-(4-chlorophenyl)-5-methylpyrazole-4-carboxylic acid (1.7 g) and 5-amino-2-[4-(4-methylpiperazin-1-yl)piperidin-1-yl]benzonitrile (2.0 g), the title compound (0.6 g) was obtained, melting point: 240° C. (decomposition).

EXAMPLE 130

1-(3-Chloro-4-fluorophenyl)-N-{3-cyano-4-[4-(2-hydroxyethyl)piperazin-1-yl]phenyl}-5-methylpyrazole-4-carboxamide

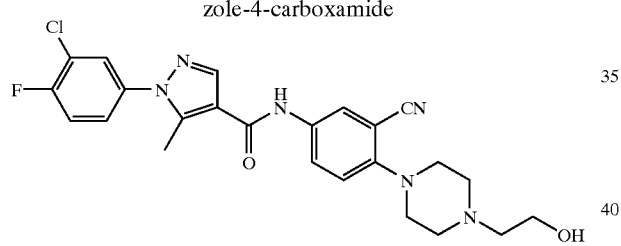

By the reaction and treatment in the same manner as in Example 64 using 1-(3-chloro-4-fluorophenyl)-5-methylpyrazole-4-carboxylic acid is (3.5 g) and 5-amino-2-[4-(2-hydroxyethyl)-piperazin-1-yl]benzonitrile (3.7 g), the title compound (1.0 g) was obtained, melting point: 191° C.

EXAMPLE 131

1-(3,4-Dichlorophenyl)-N-[3-cyano-4-(4-morpholinopiperidin-1-yl) phenyl]-5-methylpyrazole-4-carboxamide ½ hydrate

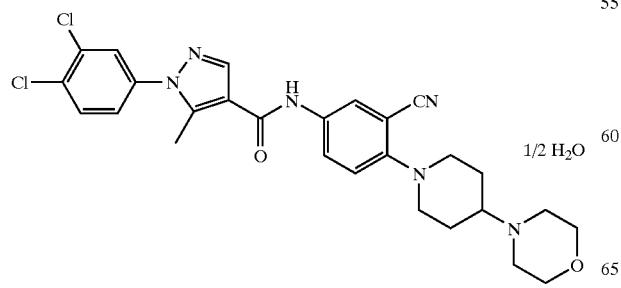

By the reaction and treatment in the same manner as in Example 64 using 1-(3,4-dichlorophenyl)-5-methylpyrazole-4-carboxylic acid (1.5 g) and 5-amino-2-(4-morpholinopiperidin-1-yl)benzonitrile (1.7 g), the title compound (1.2 g) was obtained, melting point: 242° C.

EXAMPLE 132

N-[3-Cyano-4-(4-morpholinopiperidin-1-yl)phenyl]-1-(3,4-difluorophenyl)-5-methylpyrazole-4-carboxamide ½ hydrate

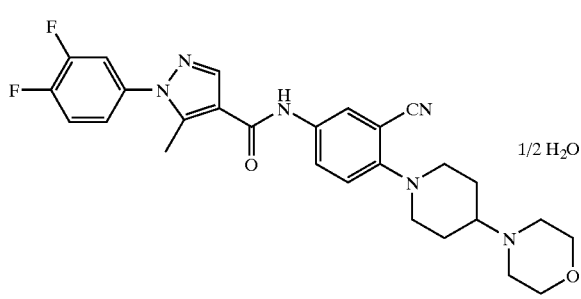

By the reaction and treatment in the same manner as in Example 64 using 1-(3,4-fluorophenyl)-5-methylpyrazole-4-carboxylic acid (1.5 g) and 5-amino-2-(4-morpholinopiperidin-1-yl) benzonitrile (2.0 g), the title compound (0.8 g) was obtained, melting point: 243° C.

EXAMPLE 133

1-(3-Chloro-4-fluorophenyl)-N-[3-cyano-4-(4-morpholinopiperidin-1-yl) phenyl]-5-methylpyrazole-4-carboxamide

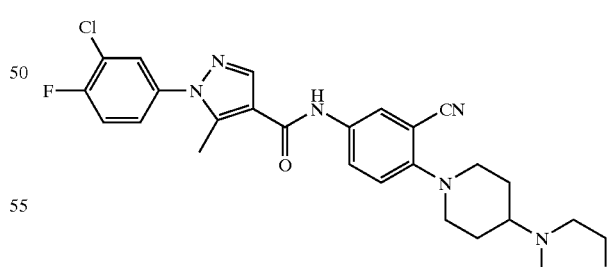

By the reaction and treatment in the same manner as in Example 64 using 1-(3-chloro-4-fluorophenyl)-5-methylpyrazole-4-carboxylic acid (1.5 g) and 5-amino-2-(4-morpholinopiperidin-1-yl) benzonitrile (1.9 g), the title compound (1.3 g) was obtained, melting point: 266° C.

EXAMPLE 134

1-(4-Bromophenyl)-N-[3-cyano-4-(4-morpholinopiperidin-1-yl)phenyl]-5-methylpyrazole-4-carboxamide

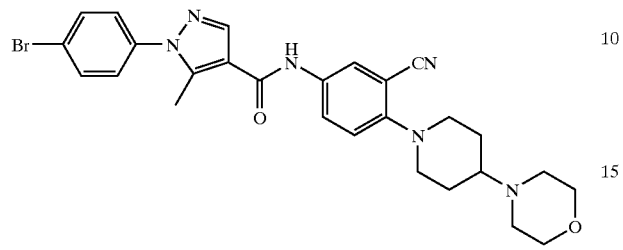

By the reaction and treatment in the same manner as in Example 64 using 1-(4-bromophenyl)-5-methylpyrazole-4-carboxylic acid (0.6 g) and 5-amino-2-(4-morpholinopiperidin-1-yl)benzonitrile (0.6 g), the title compound (0.5 g) was obtained, melting point: 250–252° C.

EXAMPLE 135

N-[3-Cyano-4-(4-morpholinopiperidin-1-yl)phenyl]-1-phenyl-5-methylpyrazole-4-carboxamide

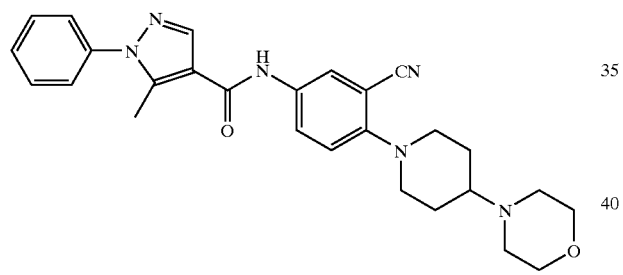

By the reaction and treatment in the same manner as in Example 64 using 1-phenyl-5-methylpyrazole-4-carboxylic acid (0.6 g) and 5-amino-2-(4-morpholinopiperidin-1-yl)benzonitrile (0.6 g), the title compound (0.2 g) was obtained, melting point: 223° C.

EXAMPLE 136

N-{3-Cyano-4-[4-(2-hydroxyethyl) piperazin-1-yl]phenyl)}-1-(4-trifluoromethylphenyl)-5-methylpyrazole-4-carboxamide 1 hydrate

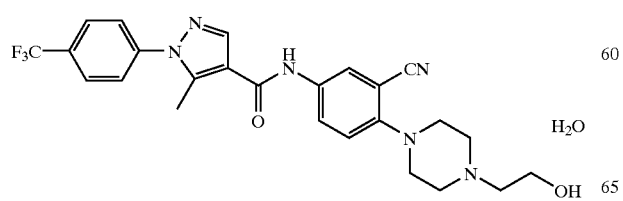

By the reaction and treatment in the same manner as in Example 64 using 1-(4-trifluoromethylphenyl)-5-methylpyrazole-4-carboxylic acid (1.0 g) and 5-amino-2-[4-(2-hydroxyethyl)piperazin-1-yl]benzonitrile (0.6 g), the title compound (0.4 g) was obtained, melting point: 218° C.

EXAMPLE 137

N-[3-Cyano-4-(4-morpholinopiperidin-1-yl)phenyl]-1-(4-trifluoromethylphenyl)-5-methylpyrazole-4-carboxamide ½ hydrate

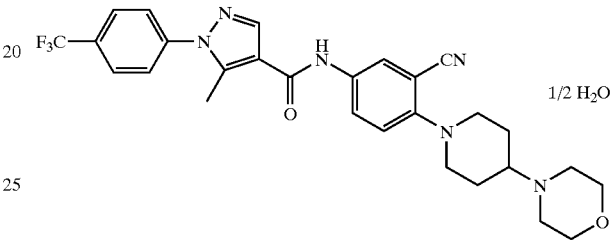

By the reaction and treatment in the same manner as in Example 64 using 1-(4-trifluoromethylphenyl)-5-methylpyrazole-4-carboxylic acid (0.7 g) and 5-amino-2-(4-morpholinopiperidin-1-yl)benzonitrile (0.6 g), the title compound (0.1 g) was obtained, melting point: 257° C. (decomposition).

EXAMPLE 138

N-[3-Cyano-4-(4-morpholinopiperidin-1-yl)phenyl]-1-(4-fluorophenyl)-5-methylpyrazole-4-carboxamide ½ hydrate

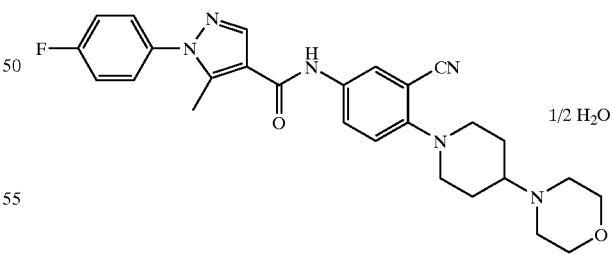

By the reaction and treatment in the same manner as in Example 64 using 1-(4-fluorophenyl)-5-methylpyrazole-4-carboxylic acid (0.8 g) and 5-amino-2-(4-morpholinopiperidin-1-yl)benzonitrile (0.6 g), the title compound (0.3 g) was obtained, melting point: 226° C.(decomposition).

EXAMPLE 139

N-(3-Cyano-4-pyrrolidinophenyl)-1-(4-fluorophenyl)-5-methylpyrazole-4-carboxamide

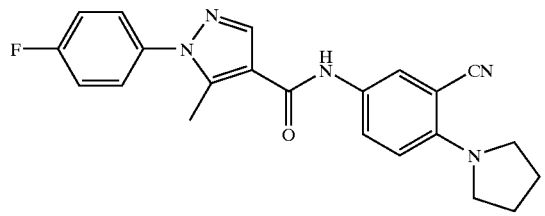

By the reaction and treatment in the same manner as in Example 64 using 1-(4-fluorophenyl)-5-methylpyrazole-4-carboxylic acid (1.2 g) and 5-amino-2-pyrrolidinobenzonitrile (0.8 g), the title compound (0.8 g) was obtained, melting point: 185° C.

EXAMPLE 140

1-(4-Chlorophenyl)-N-(3-cyano-4-pyrrolidinophenyl)-5-methylpyrazole-4-carboxamide

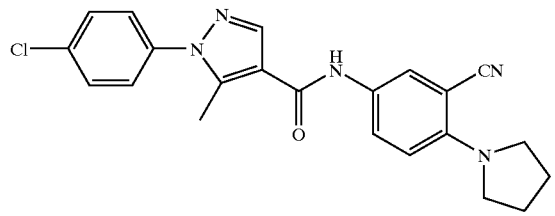

By the reaction and treatment in the same manner as in Example 64 using 1-(4-chlorophenyl)-5-methylpyrazole-4-carboxylic acid (1.3 g) and 5-amino-2-pyrrolidinobenzonitrile (0.8 g), the title compound (0.4 g) was obtained, melting point: 205° C.

EXAMPLE 141

N-(3-Cyano-4-homopiperidinophenyl)-1-(4-fluorophenyl)-5-methylpyrazole-4-carboxamide

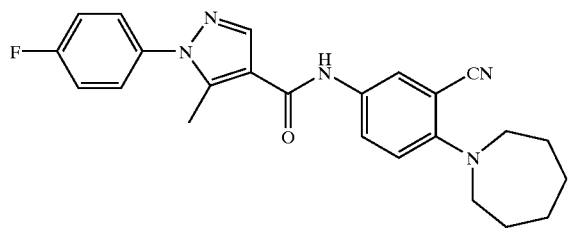

By the reaction and treatment in the same manner as in Example 64 using 1-(4-fluorophenyl)-5-methylpyrazole-4-carboxylic acid (1.1 g) and 5-amino-2-homopiperidinobenzonitrile (0.8 g), the title compound (0.6 g) was obtained, melting point: 138° C.

EXAMPLE 142

1-(4-chlorophenyl)-N-(3-cyano-4-homopiperidinophenyl)-5-methylpyrazole-4-carboxamide

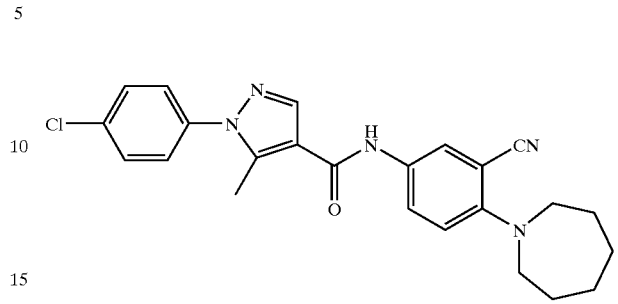

By the reaction and treatment in the same manner as in Example 64 using 1-(4-chlorophenyl)-5-methylpyrazole-4-carboxylic acid (1.1 g) and 5-amino-2-homopiperidinobenzonitrile (0.8 g), the title compound (0.5 g) was obtained, melting point: 131° C.

EXAMPLE 143

N-[3-Cyano-4-(4-morpholinopiperidin-1-yl)phenyl]-1-(4-fluorophenyl)pyrrole-3-carboxamide

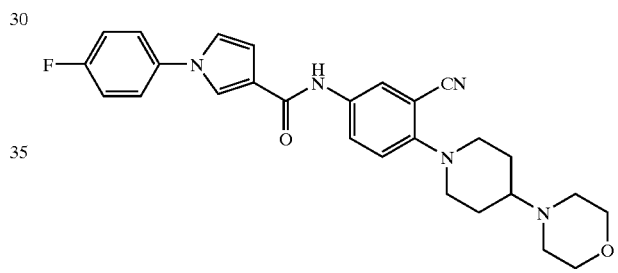

By the reaction and treatment in the same manner as in Example 64 using 1-(4-fluorophenyl)pyrrole-3-carboxylic acid (0.5 g) and 5-amino-2-(4-morpholinopiperidin-1-yl) benzonitrile (0.7 g), the title compound (0.4 g) was obtained, melting point: 182–183° C.

EXAMPLE 144

1-(3-Chlorophenyl)-N-[3-cyano-4-(4-morpholinopiperidin-1-yl)phenyl]-5-methylpyrazole-4-carboxamide

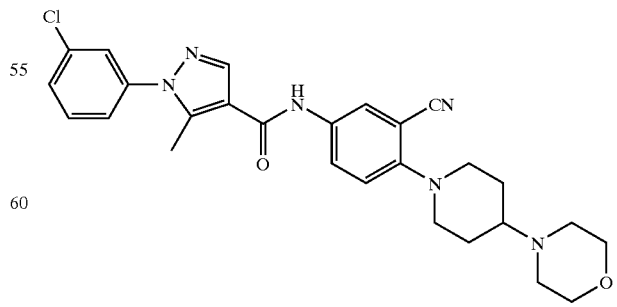

By the reaction and treatment in the same manner as in Example 64 using 1-(3-chlorophenyl)-5-methylpyrazole-4- carboxylic acid (2.0 g) and 5-amino-2-(4-morpholinopiperidin-1-yl)benzonitrile (2.4 g), the title compound (1.0 g) was obtained, melting point: 210° C.

EXAMPLE 145

N-[3-Cyano-4-(4-morpholinopiperidin-1-yl)phenyl]-1-(3-trifluoromethylphenyl)-5-methylpyrazole-4-carboxamide

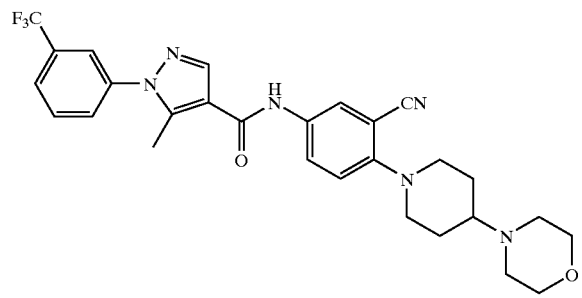

By the reaction and treatment in the same manner as in Example 64 using 1-(3-trifluoromethylphenyl)-5-methylpyrazole-4-carboxylic acid (2.0 g) and 5-amino-2-(4-morpholinopiperidin-1-yl)benzonitrile (2.4 g), the title compound (1.0 g) was obtained, melting point: 215–216° C.

$^1$H-NMR (400 MHz, DMSO-$d_6$) δ(ppm): 1.55–1.61 (2H, m), 1.91 (2H, d, J=11.2 Hz), 2.28–2.31 (1H, m), 2.48–2.60 (4H, m), 2.60 (3H, s), 2.77 (2H, t, J=11.2 Hz), 3.47 (2H, d, J=11.8 Hz), 3.50–3.59 (4H, m), 7.19 (1H, d, J=9.2 Hz), 7.80–7.95 (5H, m), 8.08 (1H, d, J=2.0 Hz), 8.35 (1H, s), 10.02 (1H, s).

EXAMPLE 146

1-(2-Chlorophenyl)-N-[3-cyano-4-(4-morpholinopiperidin-1-yl)phenyl]-5-methylpyrazole-4-carboxamide

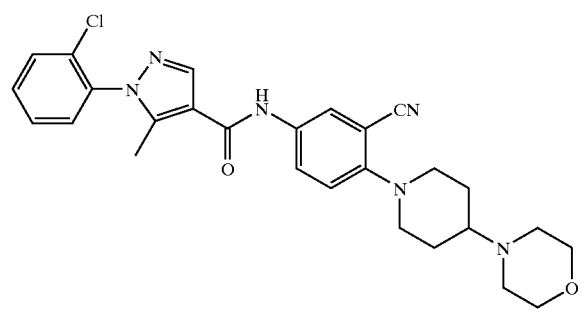

By the reaction and treatment in the same manner as in Example 64 using 1-(2-chlorophenyl)-5-methylpyrazole-4-carboxylic acid (1.0 g) and 5-amino-2-(4-morpholinopiperidin-1-yl)benzonitrile (1.2 g), the title compound (0.79 g) was obtained, melting point: 218° C.

$^1$H-NMR (400 MHz, DMSO-$d_6$) δ(ppm): 1.57 (2H, ddd, J=3.0, 11.2, 11.7 Hz), 1.90 (2H, d, J=11.7 Hz), 2.25–2.30 (1H, m), 2.33 (3H, s), 2.47–2.51 (4H, m), 2.77 (2H, t, J=11.7 Hz), 3.47 (2H, d, J=11.7 Hz), 3.58–3.60 (4H, m), 7.19 (1H, d, J=9.3 Hz), 7.53–7.66 (3H, m), 7.75 (1H, d, J=9.8 Hz), 7.85 (1H, dd, J=2.4, 9.3 Hz), 8.77 (1H, d, J=2.4 Hz), 8.32 (1H, s), 10.00 (1H, s).

EXAMPLE 147

N-[3-Cyano-4-(4-morpholinopiperidin-1-yl)phenyl]-1-(4-iodophenyl)-5-methylpyrazole-4-carboxamide

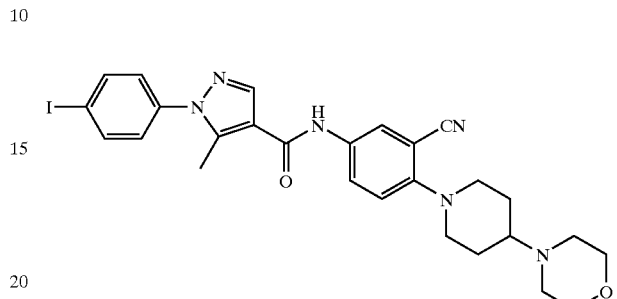

By the reaction and treatment in the same manner as in Example 64 using 1-(4-iodophenyl)-5-methylpyrazole-4-carboxylic acid (1.2 g) and 5-amino-2-(4-morpholinopiperidin-1-yl)benzonitrile (1 g), the title compound (1.0 g) was obtained, melting point: 280° C.

$^1$H-NMR (400 MHz, DMSO-$d_6$) δ(ppm): 1.57 (2H, dd, J=11.2, 11.7 Hz), 1.91 (2H, d, J=10.5 Hz), 2.26–2.34 (1H, m), 2.49–2.54 (4H, m), 2.55 (3H, s), 2.77 (2H, dd, J=10.5, 11.7 Hz), 3.47 (2H, d, J=11.7 Hz), 3.57–3.60 (4H, m), 9.19 (1H, d, J=9.3 Hz), 7.37 (2H, dd, J=2.0, 6.8 Hz), 7.86 (1H, dd, J=2.4, 9.3 Hz), 7.91 (2H, dd, J=2.0, 6.8 Hz), 8.06 (1H, d, J=2.0 Hz), 8.30 (1H, s), 9.98 (1H, s).

EXAMPLE 148

N-[3-Cyano-4-(4-morpholinopiperidin-1-yl)phenyl]-1-(4-methylphenyl)-5-methylpyrazole-4-carboxamide

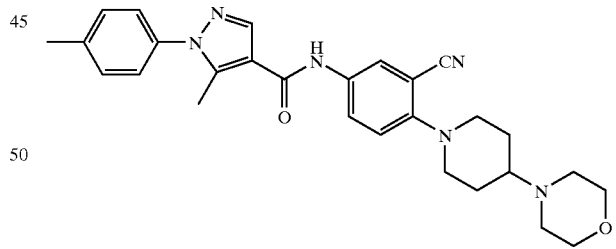

By the reaction and treatment in the same manner as in Example 64 using 1-(4-methylphenyl)-5-methylpyrazole-4-carboxylic acid (1.0 g) and 5-amino-2-(4-morpholinopiperidin-1-yl)benzonitrile (1.4 g), the title compound (0.94 g) was obtained, melting point: 243° C.

$^1$H-NMR (400 MHz, DMSO-$d_6$) δ(ppm): 1.53–1.60 (2H, m), 1.91 (2H, d, J=11.7 Hz), 2.27–2.31 (1H, m), 2.40 (3H, s), 2.50–2.52 (4H, m), 2.77 (2H, dd, J=10.2, 11.7 Hz), 3.33–3.37 (4H, m), 3.38 (3H, s), 3.46 (2H, d, J=11.7 Hz), 3.56–3.60 (4H, m), 7.19 (1H, d, J=11.2 Hz), 7.36 (2H, d, J=8.6 Hz), 7.41 (2H, d, J=8.6 Hz), 7.84 (1H, dd, J=2.7, 11.2 Hz), 8.06 (1H, d, J=2.7 Hz), 8.27 (1H, s), 9.96 (1H, s).

EXAMPLE 149

N-[3-Cyano-4-(4-morpholinopiperidin-1-yl)phenyl]-1-(4-methoxyphenyl)-5-methylpyrazole-4-carboxamide

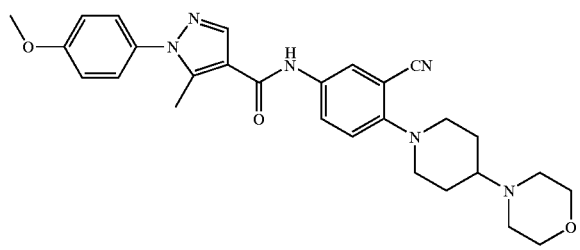

By the reaction and treatment in the same manner as in Example 64 using 1-(4-methoxyphenyl)-5-methylpyrazole-4-carboxylic acid (1.0 g) and 5-amino-2-(4-morpholinopiperidin-1-yl) benzonitrile (1.2 g), the title compound (1.3 g) was obtained, melting point: 238° C.

$^1$H-NMR (400 MHz, DMSO-d$_6$) δ (ppm): 1.52–1.62 (2H, m), 1.90 (2H, d, J=11.8 Hz), 2.25–2.32 (1H, m), 2.48–2.50 (4H, m), 2.49 (3H, s), 2.76 (2H, t, J=11.2 Hz), 3.46 (2H, d, J=11.8 Hz), 3.57–3.59 (4H, m), 3.83 (3H, s), 7.09 (2H, d, J=8.3 Hz), 7.17 (1H, d, J=8.8 Hz), 7.44 (2H, d, J=8.3 Hz), 7.84 (1H, dd, J=2.5, 8.8 Hz), 8.07 (1H, d, J=2.5 Hz), 8.25 (1H, s), 9.94 (1H, s).

EXAMPLE 150

1-(4-Chlorophenyl)-N-[3-cyano-4-(4-thiomorpholinopiperidin-1-yl) phenyl]-5-methylpyrazole-4-carboxamide

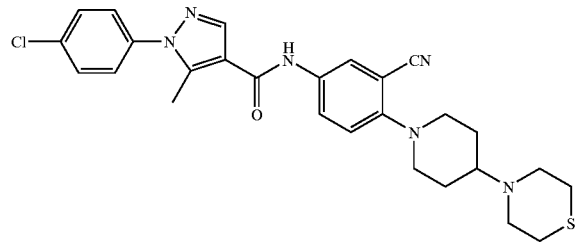

1-(4-chlorophenyl)-5-methylpyrazole-4-carboxylic chloride (0.67 g) and 5-amino-2-(4-thiomorpholinopiperidin-1-yl)benzonitrile (0.8 g) were added to pyridine (10 ml) and the reaction was conducted for 1 h at room temperature. To the reaction mixture was added aqueous potassium carbonate solution and the precipitated crystals were recrystallized from hydrous dimethylformamide to give the title compound (0.52 g), melting point: 256° C./decomposition.

EXAMPLE 151

1-(4-Chlorophenyl)-N-(3-cyano-4-[4-(N-(2-hydroxyethyl)amino)piperidin-1-yl]phenyl}-5-methylpyrazole-4-carboxamide

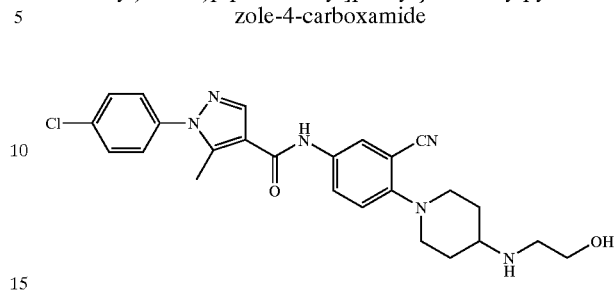

The reaction and treatment in the same manner as in Example 150 were conducted using 1-(4-chlorophenyl)-5-methylpyrazole-4-carboxylic chloride (1.19 g) and 5-amino-2-[4-(N-tert-butoxycarbonyl-N-(2-hydroxyethyl)amino)piperidin-1-yl]benzonitrile and the resulting mixture was further stirred in trifluoroacetic acid (10 ml) under ice-cooling for 1 h. The reaction mixture was treated with aqueous sodium hydroxide solution and extracted with ethyl acetate. The organic layer was washed with saturated brine and dried over anhydrous sodium sulfate. The solvent was evaporated under reduced pressure. The residue was recrystallized from ethanol to give the title compound (0.29 g), melting point: 181° C.

EXAMPLE 152

1-(4-Chlorophenyl)-N-{3-cyano-4-[4-(N-(2-hydroxyethyl)-N-methylamino)piperidin-1-yl]phenyl}-5-methylpyrazole-4-carboxamide

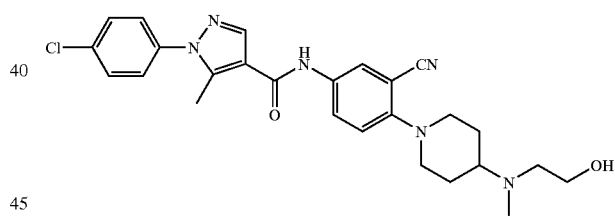

By the reaction and treatment in the same manner as in Example 150 using 1-(4-chlorophenyl)-5-methylpyrazole-4-carboxylic chloride (0.73 g) and 5-amino-2-[4-[N-(2-hydroxyethyl)-N-methylamino]piperidin-1-yl]benzonitrile (0.65 g), the title compound (0.2 g) was obtained, melting point: 186° C.

EXAMPLE 153

N-{3-Cyano-4-[4-(N-(2-hydroxyethyl)amino)piperidin-1-yl]phenyl}-1-(4-trifluoromethylphenyl)-5-methylpyrazole-4-carboxamide

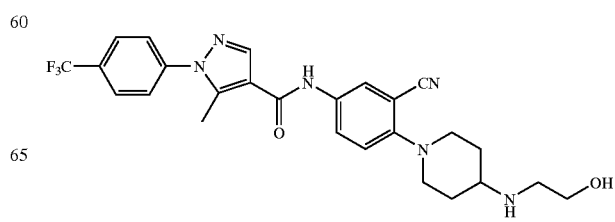

The reaction and treatment in the same manner as in Example 64 were conducted using 1-(4-trifluoromethylphenyl)-5-methylpyrazole-4-carboxylic acid (1.94 g) and 5-amino-2-[4-(N-tert-butoxycarbonyl-2-hydroxyethylamino)piperidin-1-yl]benzonitrile (2.59 g) and the resulting mixture was further stirred in trifluoroacetic acid (10 ml) under ice-cooling for 1 h. The reaction mixture was treated with aqueous sodium hydroxide solution and extracted with ethyl acetate. The organic layer was washed with saturated brine and dried over anhydrous sodium sulfate. The solvent was evaporated under reduced pressure. The residue was recrystallized from a mixed solvent of dimethylformamide-water to give the title compound (0.34 g), melting point: 202° C.

EXAMPLE 154

1-(4-Chlorophenyl)-N-[3-cyano-4-(4-piperidinopiperidin-1-yl)phenyl]-5-methylpyrazole-4-carboxamide

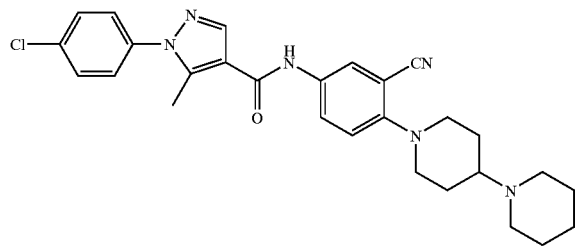

By the reaction and treatment in the same manner as in Example 150 using 1-(4-chlorophenyl)-5-methylpyrazole-4-carboxylic chloride (0.86 g) and 5-amino-2-(4-piperidinopiperidin-1-yl)benzonitrile (0.8 g), the title compound (0.78 g) was obtained, melting point: 252° C./decomposition. b3

EXAMPLE 155

N-[3-Carbamoyl-4-(4-morpholinopiperidin-1-yl)phenyl]-1-(4-chlorophenyl)-5-methylpyrazole-4-carboxamide 5/2 hydrate

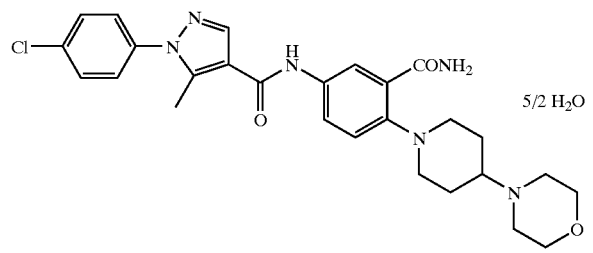

By the reaction and treatment in the same manner as in Example 64 using 1-(4-chlorophenyl)-5-methylpyrazole-4-carboxylic acid (2.0 g) and 5-amino-2-(4-morpholinopiperidin-1-yl)benzamide (2.5 g), the title compound (0.94 g) was obtained, melting point: 270° C.

1H-NMR (400 MHz, DMSO-$d_6$) δ(ppm): 1.53–1.59 (2H, m), 1.93 (2H, d, J=12.2 Hz), 2.21–2.29(1H, m), 2.45–2.57 (4H, m), 2.56 (3H, s), 2.70 (2H, d, J=11.3 Hz), 3.11 (2H, d, J=11.3 Hz), 3.55–3.62 (4H, m), 7.23 (1H, d, J=8.3 Hz), 7.24 (1H, brs), 7.58–7.64 (4H, m), 7.80–7.82 (1H, m), 8.09–8.14 (1H, m), 8.36 (1H, s), 8.96 (1H, s), 9.92(1H, s).

EXAMPLE 156

1-(4-Chlorophenyl)-N-[3-cyano-4-(4-piperazinopiperidin-1-yl)phenyl]-5-methylpyrazole-4-carboxamide ½ hydrate

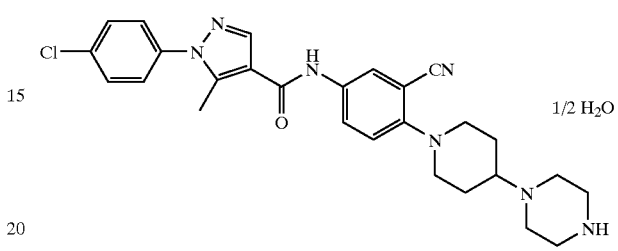

By the reaction and treatment in the same manner as in Example 151 using 1-(4-chlorophenyl)-5-methylpyrazole-4-carboxylic chloride (0.66 g) and 5-amino-2-[4-(4-tert-butoxycarbonylpiperazin-1-yl)piperidin-1-yl]benzonitrile (1.0 g), the title compound (0.54 g) was obtained, melting point: 226° C.

EXAMPLE 157

N-{4-[4-(4-Acetylpiperazin-1-yl)piperidin-1-yl]-3-cyanophenyl}-1-(4-chlorophenyl)-5-methylpyrazole-4-carboxamide ½ hydrate

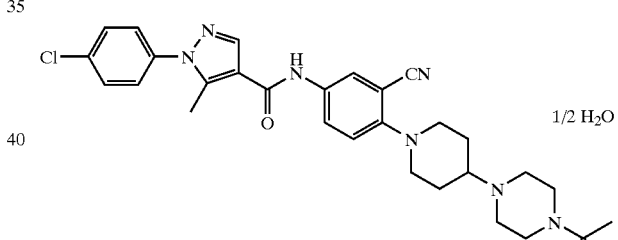

By the reaction and treatment in the same manner as in Example 125 using 1-(4-chlorophenyl)-N-[3-cyano-4-(4-piperazinopiperidin-1-yl)phenyl]-5-methylpyrazole-4-carboxamide (0.18 g), the title compound (0.16 g) was obtained, melting point: 247° C.

EXAMPLE 158

N-[3-Bromo-4-(4-morpholinopiperidin-1-yl)phenyl]-1-(4-chlorophenyl)-5-methylpyrazole-4-carboxamide ½ hydrate

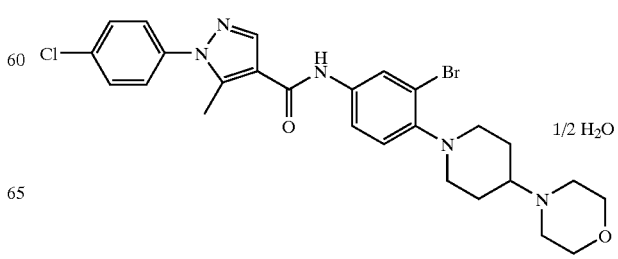

By the reaction and treatment in the same manner as in Example 150 using 1-(4-chlorophenyl)-5-methylpyrazole-4-carboxylic chloride (4.8 g) and 3-bromo-4-(4-morpholinopiperidin-1-yl)aniline (5 g), the title compound (4.5 g) was obtained, melting point: 205–210° C.

$^1$H-NMR (400 MHz, DMSO-d$_6$) δ(ppm): 1.5–1.7 (2H, m), 1.8–1.9 (2H, m), 2.2–2.3 (1H, m), 2.5–2.55 (4H, m), 2.55 (3H, s), 2.55–2.65 (2H, m), 3.2–3.4 (2H, m), 3.55–3.65 (4H, m), 7.15 (1H, d, J=8.8 Hz), 7.5–7.7 (5H, m), 8.06 (1H, d, J=2.5 Hz), 8.31 (1H, s), 9.88 (1H, s, NH)

EXAMPLE 159

N-[3-Bromo-4-(4-morpholinopiperidin-1-yl)phenyl]-5-methyl-1-(4-trifluoromethylphenyl)pyrazole-4-carboxamide ½ hydrate

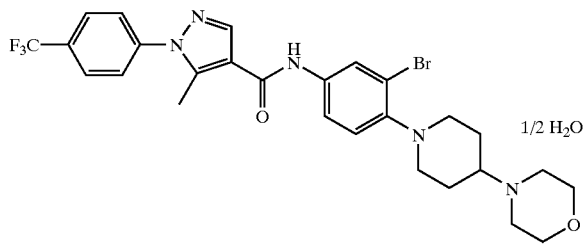

By the reaction and treatment in the same manner as in Example 150 using 5-methyl-1-(4-trifluoromethylphenyl)pyrazole-4-carboxylic chloride (1.7 g) and 3-bromo-4-(4-morpholinopiperidin-1-yl)aniline (2.0 g), the title compound (2.1 g) was obtained, melting point: 220–230° C.

$^1$H-NMR (400 MHz, DMSO-d$_6$) δ(ppm): 1.5–1.6 (2H, m), 1.8–1.9 (2H, m), 2.25–2.35 (1H, m), 2.45–2.55 (4H, m), 2.62 (3H, s), 2.55–2.65 (2H, m), 3.2–3.3 (2H, m), 3.55–3.65 (4H, m), 7.15 (1H, d, J=8.8 Hz), 7.67 (1H, dd, J=1.9, 8.8 Hz), 7.83 (2H, d, J=8.3 Hz), 7.95 (2H, d, J=8.3 Hz), 8.06 (1H, d, J=1.9 Hz), 8.36 (1H, s), 9.92 (1H, s).

EXAMPLE 160

1-(4-Chlorophenyl)-N-[2-cyano-4-(4-morpholinopiperidin-1-yl)phenyl]-5-methylpyrazole-4-carboxamide

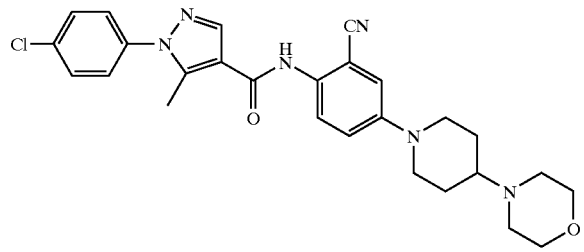

By the reaction and treatment in the same manner as in Example 150 using 1-(4-chlorophenyl)-5-methylpyrazole-4-carboxylic chloride (0.81 g) and 2-amino-5-(4-morpholinopiperidin-1-yl)benzonitrile (0.9 g), the title compound (0.29 g) was obtained, melting point: 212–213° C.

$^1$H-NMR (400 MHz, DMSO-d$_6$) δ(ppm): 1.4–1.5 (2H, m), 1.8–1.9 (2H, m), 2.3–2.4 (1H, m), 2.5–2.55 (4H, m), 2.54 (3H, s), 2.7–2.8 (2H, m), 3.5–3.6 (4H, m), 3.75–3.85 (2H, m), 7.3–7.35 (3H, m), 7.61 (2H, d, J=8.8 Hz), 7.64 (2H, d, J=8.8 Hz), 8.29 (1H, s), 9.98 (1H, s).

EXAMPLE 161

N-[2-Cyano-4-(4-morpholinopiperidin-1-yl)phenyl]-5-methyl-1-(4-trifluoromethylphenyl)pyrazole-4-carboxamide 1 hydrate

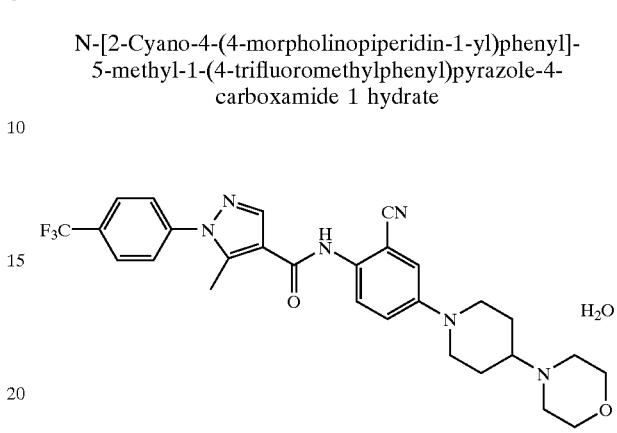

By the reaction and treatment in the same manner as in Example 150 using 5-methyl-1-(4-trifluoromethylphenyl)pyrazole-4-carboxylic chloride (0.9 g) and 2-amino-5-(4-morpholinopiperidin-1-yl)benzonitrile (0.9 g), the title compound (0.67 g) was obtained, melting point: 210–212° C.

$^1$H-NMR (400 MHz, DMSO-d$_6$) δ(ppm): 1.4–1.5 (2H, m), 1.8–1.9 (2H, m), 2.3–2.35 (1H, m), 2.4–2.55 (4H, m), 2.61 (3H, s), 2.7–2.8 (2H, m), 3.55–3.65 (4H, m), 3.8–3.85 (2H, m), 7.3–7.35 (3H, m), 7.84 (2H, d, J=8.3 Hz), 7.95 (2H, d, J=8.3 Hz), 8.34 (1H, s), 10.02 (1H, s).

EXAMPLE 162

1-(4-Chlorophenyl)-5-methyl-N-[4-(4-morpholinopiperidin-1-yl)-3-nitrophenyl]pyrazole-4-carboxamide

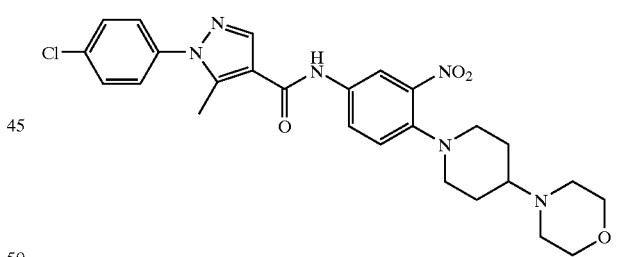

1-(4-Chlorophenyl)-N-(4-chloro-3-nitrophenyl)-5-methylpyrazole-4-carboxamide (1.6 g) and 4-morpholinopiperidine (2.4 g) were added to dimethyl sulfoxide (20 ml) and the mixture was stirred at a refluxing temperature for 1.5 h. After cooling to room temperature, water was added and the precipitated solid was collected by filtration and extracted with chloroform. The organic layer was washed with 30% potassium carbonate and saturated brine, and dried over anhydrous sodium sulfate. The solvent was evaporated under reduced pressure. The residue was purified by silica gel column chromatography (mobile phase:chloroform/methanol) and recrystallized from hydrous dimethylformamide to give the title compound (0.7 g), melting point: 195–200° C.

$^1$H-NMR (400 MHz, DMSO-d$_6$) δ(ppm): 1.45–1.55 (2H, m), 1.8–1.9 (2H, m), 2.25–2.35 (1H, m), 2.5–2.55 (4H, m), 2.56 (3H, s), 2.7–2.8 (2H, m), 3.15–3.2 (2H, m), 3.55–3.60 (4H, m), 7.35 (1H, d, J=9.3 Hz), 7.60 (2H, d, J=8.8 Hz), 7.64 (2H, d, J=8.8 Hz), 7.88 (1H, dd, J=1.9, 9.3 Hz), 8.30 (1H, d, J=1.9 Hz), 8.33 (1H, s), 10.09 (1H, s).

EXAMPLE 163

5-Methyl-N-[4-(4-morpholinopiperidin-1-yl)-3-nitrophenyl]-1-(4-trifluoromethylphenyl)pyrazole-4-carboxamide

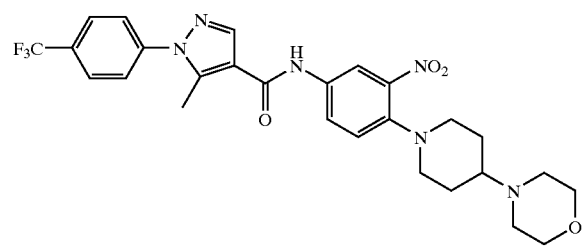

The reaction and treatment in the same manner as in Example 162 using N-(4-chloro-3-nitrophenyl)-5-methyl-1-(4-trifluoromethylphenyl)pyrazole-4-carboxamide (1.0 g) and 4-morpholinopiperidine (1.4 g), the title compound (0.12 g) was obtained, melting point: 225–230° C.

$^1$H-NMR (400 MHz, DMSO-d$_6$) δ(ppm): 1.5–1.6 (2H, m), 1.8–1.9 (2H, m), 2.25–2.35 (1H, m), 2.5–2.6 (4H, m), 2.63 (3H, s), 2.75–2.85 (2H, m), 3.15–3.25 (2H, m), 3.55–3.60 (4H, m), 7.36 (1H, d, J=8.8 Hz), 7.84 (2H, d, J=8.8 Hz), 7.88 (1H, dd, J=2.4, 8.8 Hz), 7.95 (2H, d, J=8.8 Hz), 8.30 (1H, d, J=2.4 Hz), 8.38 (1H, s), 10.12 (1H, s).

EXAMPLE 164

1-(4-Chlorophenyl)-5-methyl-N-[3-methyl-4-(4-morpholinopiperidin-1-yl)phenyl]pyrazole-4-carboxamide ½ hydrate

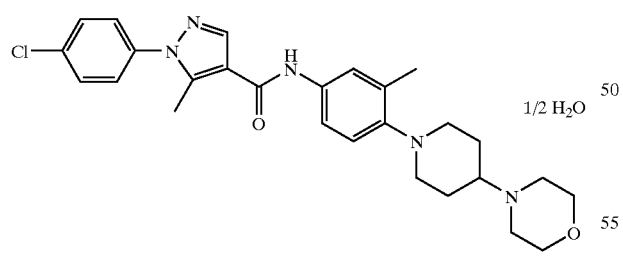

By the reaction and treatment in the same manner as in Example 150 using 1-(4-chlorophenyl)-5-methylpyrazole-4-carboxylic chloride (1.0 g) and 3-methyl-4-(4-morpholinopiperidin-1-yl)aniline (1.07 g), the title compound (1.0 g) was obtained, melting point: 235–245° C.

$^1$H-NMR (400 MHz, DMSO-d$_6$) δ(PPM): 1.5–1.6 (2H, m), 1.8–1.9 (2H, m), 2.24 (3H, s), 2.4–2.6 (7H, m), 2.55 (3H, s), 3.0–3.1 (2H, m), 3.5–3.6 (4H, m), 6.98 (1H, d, J=8.3 Hz), 7.4–7.5 (2H, m), 7.59 (2H, d, J=8.8 Hz), 7.63 (2H, d, J=8.8 Hz), 8.31 (1H, s), 9.68 (1H, s).

EXAMPLE 165

5-Methyl-N-[3-methyl-4-(4-morpholinopiperidin-1-yl)phenyl]-1-(4-trifluoromethylphenyl)pyrazole-4-carboxamide 1 hydrate

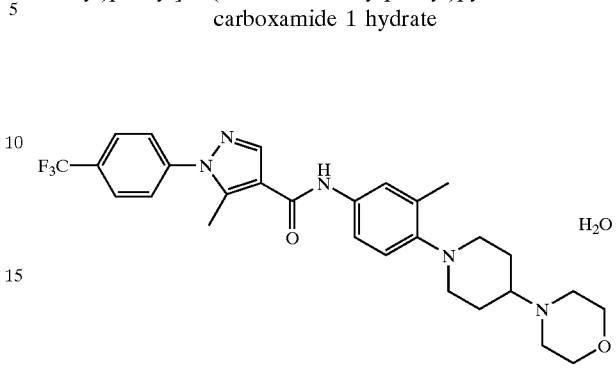

By the reaction and treatment the same manner as in Example 150 using 5-methyl-1-(4-trifluoromethylphenyl)pyrazole-4-carboxylic chloride (1.0 g) and 3-methyl-4-(4-morpholinopiperidin-1-yl)aniline (0.95 g), the title compound (1.1 g) was obtained, melting point: 252–255° C.

$^1$H-NMR (400 MHz, DMSO-d$_6$) δ(ppm): 1.5–1.6 (2H, m), 1.8–1.9 (2H, m), 2.2–2.3 (1H, m), 2.24 (3H, s), 2.45–2.55 (4H, m), 2.55–2.65 (2H, m), 2.62 (3H, s), 3.0–3.1 (2H, m), 3.5–3.6 (4H, m), 6.99 (1H, d, J=8.7 Hz), 7.4–7.5 (2H, m), 7.83 (2H, d, J=8.3 Hz), 7.95 (2H, d, J=8.3 Hz), 8.36 (1H, s), 9.73 (1H, s).

EXAMPLE 166

1-(4-Chlorophenyl)-N-[3-chloro-4-(4-morpholinopiperidin-1-yl) phenyl]-5-methylpyrazole-4-carboxamide

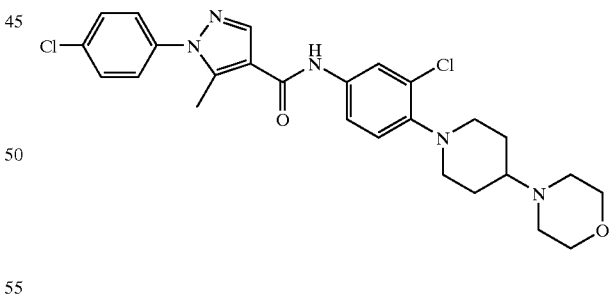

By the reaction and treatment in the same manner as in Example 150 using 1-(4-chlorophenyl)-5-methylpyrazole-4-carboxylic chloride (0.6 g) and 3-chloro-4-(4-morpholinopiperidin-1-yl)aniline (0.7 g), the title compound (0.51 g) was obtained, melting point: 238–240° C.

$^1$H-NMR (400 MHz, DMSO-d$_6$) δ(ppm): 1.5–1.6 (2H, m), 1.85–1.95 (2H, m), 2.2–2.3 (1H, m), 2.5–2.55 (4H, m), 2.55 (3H, s), 2.6–2.7 (2H, m), 3.2–3.4 (2H, m), 3.55–3.65 (4H, m), 7.14 (1H, d, J=8.7 Hz), 7.55–7.65 (5H, m), 7.88 (1H, s), 8.31 (1H, s), 9.89 (1H, s).

EXAMPLE 167

N-[3-Chloro-4-(4-morpholinopiperidin-1-yl)phenyl]-5-methyl-1-(4-trifluoromethylphenyl)pyrazole-4-carboxamide dimethylformamide

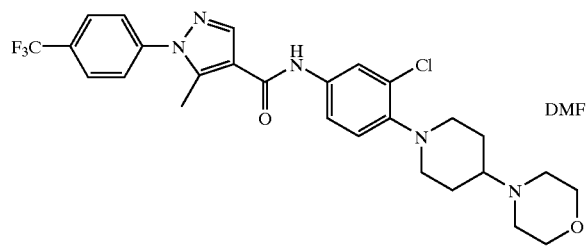

DMF

By the reaction and treatment in the same manner as in Example 150 using 5-methyl-1-(4-trifluoromethylphenyl)pyrazole-4-carboxylic chloride (0.6 g) and 3-chloro-4-(4-morpholinopiperidin-1-yl)aniline (0.61 g), the title compound (0.79 g) was obtained, melting point: 252–256° C.

$^1$H-NMR (400 MHz, DMSO-d$_6$) δ(ppm): 1.5–1.6 (2H, m), 1.8–1.9 (2H, m), 2.2–2.3 (1H, m), 2.5–2.65 (6H, m), 2.62 (3H, s), 3.3–3.4 (2H, m), 3.4–3.6 (4H, m), 7.15 (1H, d, J=8.8 Hz), 7.59 (1H, d, J=8.8 Hz), 7.8–7.95 (5H, m), 8.36 (1H, s), 9.93 (1H, s).

EXAMPLE 168

1-(4-Chlorophenyl)-N-[3-cyano-4-(4-phenylpiperidin-1-yl)phenyl]-5-methylpyrazole-4-carboxamide

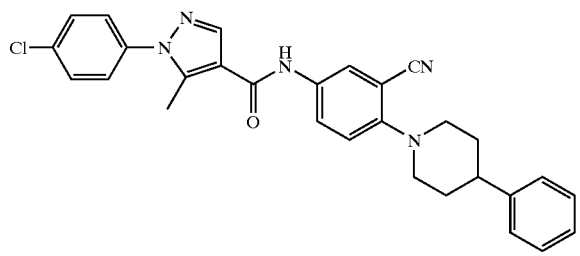

By the reaction and treatment in the same manner as in Example 150 using 1-(4-chlorophenyl)-5-methylpyrazole-4-carboxylic chloride (0.6 g) and 5-amino-2-(4-phenylpiperidin-1-yl)benzonitrile (0.65 g), the title compound (0.7 g) was obtained, melting point: 186–188° C.

$^1$H-NMR (400 MHz, DMSO-d$_6$) δ (ppm): 1.8–1.95 (4H, m), 2.56 (3H, s), 2.7–2.75 (1H, m), 2.85–2.95 (2H, m), 3.55–3.6 (2H, m), 7.25 (1H, d, J=9.3 Hz), 7.3–7.4 (5H, m), 7.61 (2H, d, J=8.8 Hz), 7.65 (2H, d, J=8.8 Hz), 7.88 (1H, dd, J=2.4, 9.3 Hz), 8.10 (1H, d, J=2.4 Hz), 8.52 (1H, s), 10.01 (1H, s).

EXAMPLE 169

N-[4-(1-Benzylpiperidin-4-yloxy)-3-cyanophenyl]-1-(4-chlorophenyl)-5-methylpyrazole-4-carboxamide

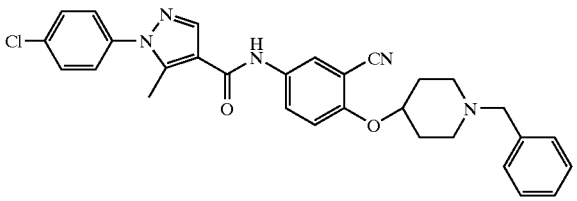

By the reaction and treatment in the same manner as in Example 64 using 1-(4-chlorophenyl)-5-methylpyrazole-4-carboxylic acid (1.0 g) and 5-amino-2-(1-benzylpiperidin-4-yloxy)benzonitrile (1.2 g), the title compound (0.6 g) was obtained, melting point: 194° C.

EXAMPLE 170

1-(4-Chlorophenyl)-N-{3-cyano-4-[4-(3,4,5,6-tetrahydro-2H-pyran-4-yl)piperazin-1-yl]phenyl}-5-methylpyrazole-4-carboxamide

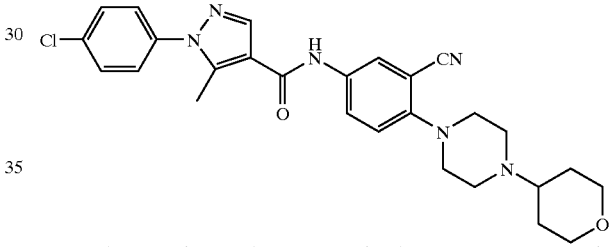

By the reaction and treatment in the same manner as in Example 64 using 1-(4-chlorophenyl)-5-methylpyrazole-4-carboxylic acid (1 g) and 5-amino-2-[4-(3,4,5,6-tetrahydro-2H-pyran-4-yl)piperazin-1-yl]benzonitrile (1.1 g), the title compound (0.9 g) was obtained, melting point: 276° C.

$^1$H-NMR (400 MHz, DMSO-d$_6$) δ(ppm): d: 1.44 (2H, ddd, J=4.0, 11.7, 12.2 Hz), 1.75 (2H, d, J=12.2 Hz), 2.41–2.49 (1H, m), 2.56 (3H, s), 2.66–2.69 (4H, m), 3.07–3.12 (4H, m), 3.27–3.36 (2H, m), 3.90 (2H, d, J=10.7 Hz), 7.19 (1H, d, J=8.8 Hz), 7.59–7.65 (4H, m), 7.86 (1H, dd, J=2.5, 8.8 Hz), 8.08 (1H, d, J=2.5 Hz), 8.31 (1H, s), 10.00 (1H, s).

EXAMPLE 171

1-(4-Chlorophenyl)-N-[3-ethynyl-4-(4-morpholinopiperidin-1-yl)phenyl]-5-methylpyrazole-4-carboxamide ½ hydrate

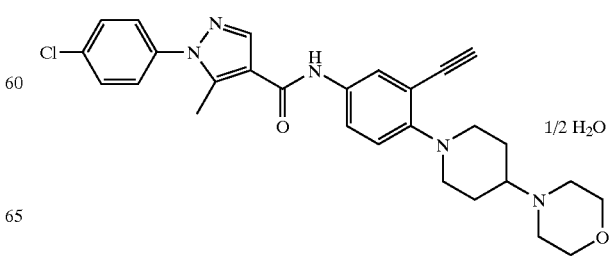

1/2 H$_2$O

A suspension of N-[3-bromo-4-(4-morpholinopiperidin-1-yl)phenyl]-1-(4-chlorophenyl)-5-methylpyrazole-4-carboxamide (1 g), bistriphenylphosphinepalladium dichloride (0.38 g), cuprous iodide (0.06 g), trimethylsilylacetylene (0.53 g) and piperidine (50 ml) was refluxed under heating for 15 h. The solvent was evaporated and the residue was purified by silica gel column chromatography (mobile phase: ethyl acetate/hexane). The resulting residue was dissolved in methanol (10 ml) and potassium carbonate (170 mg) was added. The mixture was stirred at room temperature for 1 h. After the reaction, potassium carbonate was filtered off. The filtrate was purified by silica gel column chromatography (mobile phase: chloroform/methanol) and recrystallized from a mixed solvent of chloroform-diisopropyl ether to give the title compound (27 mg), melting point: 203–205° C.

$^1$H-NMR (400 MHz, DMSO-d$_6$) δ(ppm): 1.5–1.6 (2H, m), 1.8–1.9 (2H, m), 2.2–2.3 (1H, m), 2.50–2.55 (4H, m), 2.55 (3H, s), 2.5–2.6 (2H, m), 3.5–3.6 (6H, m), 4.37 (1H, s), 6.98 (1H, d, J=8.8 Hz), 7.5–7.65 (5H, m), 7.81 (1H, d, J=2.5 Hz), 8.30 (1H, s), 9.78 (1H, s).

EXAMPLE 172

N-{3-Cyano-4-[4-(3,4,5,6-tetrahydro-2H-pyran-4-yl)piperazin-1-yl]phenyl}-5-methyl-1-(4-trifluoromethylphenyl)pyrazole 4-carboxamide

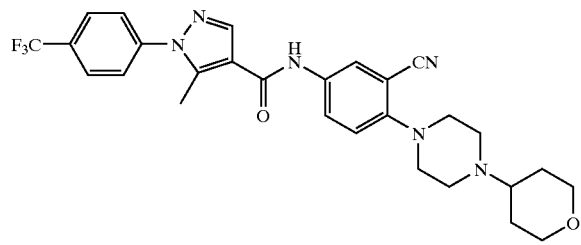

By the reaction and treatment in the same manner as in Example 64 using 5-methyl-1-(4-trifluoromethylphenyl)pyrazole-4-carboxylic acid (1.1 g) and 5-amino-2-[4-(3,4,5,6-tetrahydro-2H-pyran-4-yl)piperazin-1-yl]benzonitrile (1.1 g), the title compound (1.0 g) was obtained, melting point: 274° C.

$^1$H-NMR (400 MHz, DMSO-d$_6$) δ(ppm): 1.43 (2H, dq, J=3.6, 11.7 Hz), 1.74 (2H, d, J=11.7 Hz), 2.41–2.50 (1H, m), 2.62 (3H, s), 2.50–2.63 (4H, m), 3.09–3.15 (4H, m), 3.26–3.34 (2H, m), 3.90 (2H, d, J=11.7 Hz), 7.18 (1H, d, J=8.8 Hz), 7.83 (2H, d, J=8.3 Hz), 7.86 (1H, dd, J=2.4, 8.8 Hz), 7.95 (2H, d, J=8.3 Hz), 8.08 (1H, d, J=2.4 Hz), 8.35 (1H, s), 10.03 (1H, s).

EXAMPLE 173

1-(4-Chlorophenyl)-N-{4-[4-(4-chlorophenyl)piperazin-1-yl]-3-cyanophenyl}-5-methylpyrazole-4-carboxamide

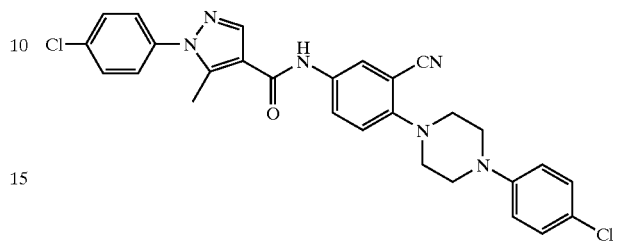

By the reaction and treatment in the same manner as in Example 64 using 1-(4-chlorophenyl)-5-methylpyrazole-4-carboxylic-acid (0.5 g) and 5-amino-2-[4-(4-chlorophenyl)piperazin-1-yl]benzonitrile (0.6 g), the title compound (0.5 g) was obtained, melting point: 265° C.

EXAMPLE 174

1-Benzyl-N-[3-cyano-4-(4-morpholinopiperidin-1-yl)phenyl]-3-methylpyrazole-4-carboxamide ⅓ hydrate

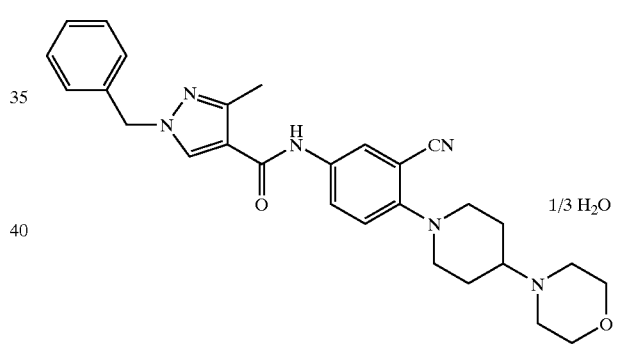

By the reaction and treatment in the same manner as in Example 64 using 1-benzyl-3-methylpyrazole-4-carboxylic acid (0.6 g) and 5-amino-2-(4-morpholinopiperidin-1-yl)benzonitrile (0.8 g), the title compound (0.63 g) was obtained, melting point: 193° C.

EXAMPLE 175

N-[3-Cyano-4-(4-morpholinopiperidin-1-yl) phenyl]-3-methyl-1-(2-phenylethyl) pyrazole-4-carboxamide

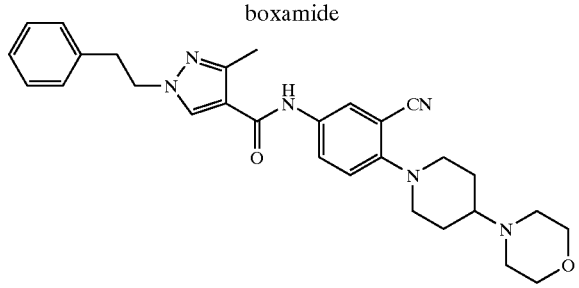

By the reaction and treatment in the same manner as in Example 64 using 3-methyl-1-(2-phenylethyl)pyrazole-4- carboxylic acid (0.64 g) and 5-amino-2-(4-morpholinopiperidin-1-yl)benzonitrile (0.8 g), the title compound (0.8 g) was obtained, melting point: 188° C.

EXAMPLE 176

1-(4-Chlorophenyl)-N-{3-cyano-4-[4-(2-methoxyethylamino)piperidin-1-yl]phenyl}-5-methylpyrazole-4-carboxamide

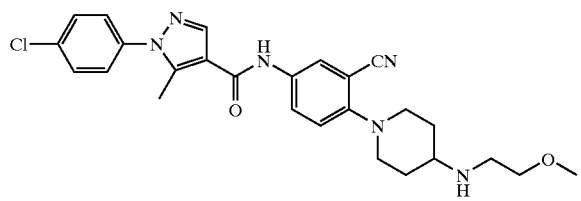

By the reaction and treatment in the same manner as in Example 151 using 1-(4-chlorophenyl)-5-methylpyrazole-4-carboxylic chloride (0.6 g) and 5-amino-2-[4-[N-tert-butoxycarbonyl-N-(2-methoxyethyl) amino]piperidin-1-yl]benzonitrile (0.9 g), the title compound (0.6 g) was obtained, melting point: 194° C.

EXAMPLE 177

1-(4-Chlorophenyl)-N-{(3-cyano-4-[4-[N-(2-methoxyethyl)-N-methylamino]piperidin-1-yl]phenyl}-5-methylpyrazole-4-carboxamide

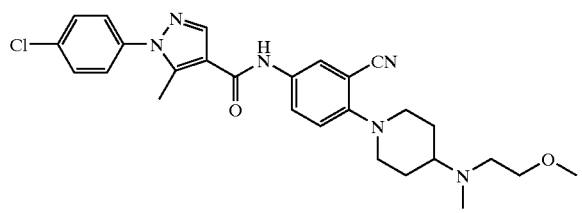

By the reaction and treatment in the same manner as in Example 150 using 1-(4-chlorophenyl)-5-methylpyrazole-4-carboxylic chloride (0.53 g) and 5-amino-2-[4-[N-(2-methoxyethyl)-N-methylamino]piperidin-1-yl]benzonitrile (0.6 g), the title compound (0.66 g) was obtained, melting point: 187° C.

EXAMPLE 178

1-(4-Chlorophenyl)-5-methyl-N-[4-(4-morpholinopiperidin-1-yl)-3-trifluoromethylphenyl]pyrazole-4-carboxamide

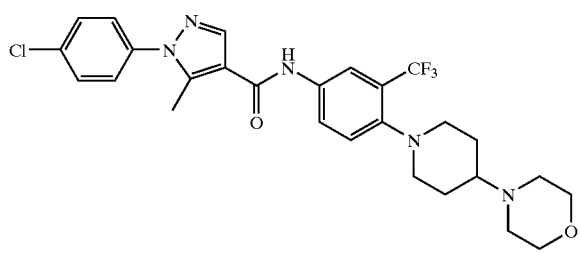

By the reaction and treatment in the same manner as in Example 150 using 1-(4-chlorophenyl)-5-methylpyrazole-4-carboxylic chloride (0.77 g) and 4-(4-morpholinopiperidin-1-yl)-3-trifluoromethylaniline (1 g), the title compound (1.1 g) was obtained, melting point: 193–194° C.

$^1$H-NMR (400 MHz, DMSO-d$_6$) δ(ppm): 1.5–1.6 (2H, m), 1.8–1.9 (2H, m), 2.2–2.3 (1H, m), 2.5–2.6 (4H, m), 2.56 (3H, s), 2.7–2.8 (2H, m), 2.9–3.0 (2H, m), 3.5–3.6 (4H, m), 7.51 (1H, d, J=8.8 Hz), 7.55–7.7 (4H, m), 7.98 (1H, dd, J=2.5, 8.8 Hz), 8.09 (1H, d, J=2.5 Hz), 8.34 (1H, s), 10.06 (1H, s).

EXAMPLE 179

N-{4-[4-[Bis(2-methoxyethyl)aminopiperidin-1-yl]-3-cyanophenyl}-1-(4-chlorophenyl)-5-methylpyrazole-4-carboxamide ¼ hydrate

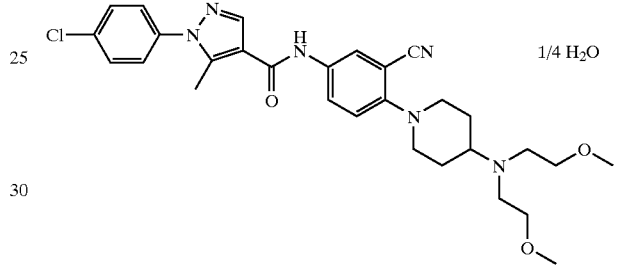

1/4 H$_2$O

By the reaction and treatment in the same manner as in Example 150 using 1-(4-chlorophenyl)-5-methylpyrazole-4-carboxylic chloride (0.83 g) and 5-amino-2-[4-bis(2-methoxyethyl)aminopiperidin-1-yl]benzonitrile (0.9 g), the title compound (0.52 g) was obtained, melting point: 152° C.

EXAMPLE 180

N-[3-Cyano-4-(4-morpholinopiperidin-1-yl)phenyl]-5-methyl-1-(2-pyridyl)pyrazole-4-carboxamide

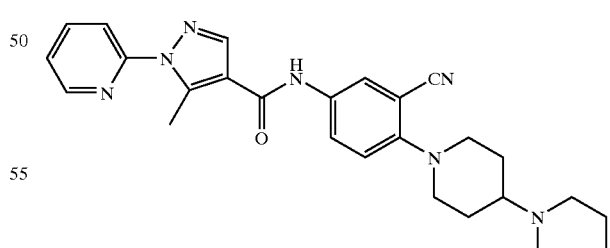

By the reaction and treatment in the same manner as in Example 64 using 5-methyl-1-(2-pyridyl)pyrazole-4-carboxylic acid (2.0 g) and 5-amino-2-(4-morpholinopiperidin-1-yl)benzonitrile (1.88 g), the title compound (1.52 g) was obtained, melting point: 251° C.

EXAMPLE 181

N-[3-Cyano-4-(4-morpholinopiperidin-1-yl)phenyl]-5-methyl-1-(2-phenylethyl)pyrazole-4-carboxamide

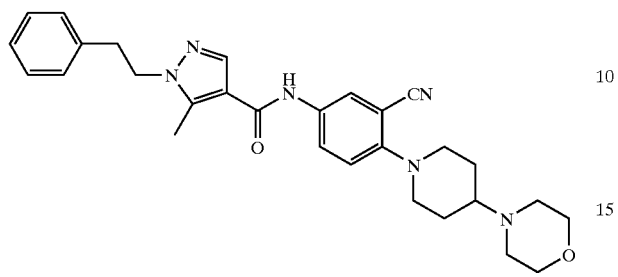

The reaction and treatment in the same manner as in Example 64 were conducted using 5-methyl-1-(2-phenylethyl)pyrazole-4-carboxylic acid (0.6 g) and 5-amino-2-(4-morpholinopiperidin-1-yl)benzonitrile (0.75 g) and the resulting product was recrystallized from ethyl acetate to give the title compound (0.4 g), melting point: 195° C.

EXAMPLE 182

1-Benzyl-N-[3-cyano-4-(4-morpholinopiperidin-1-yl)phenyl]-5-methylpyrazole-4-carboxamide ⅓ hydrate

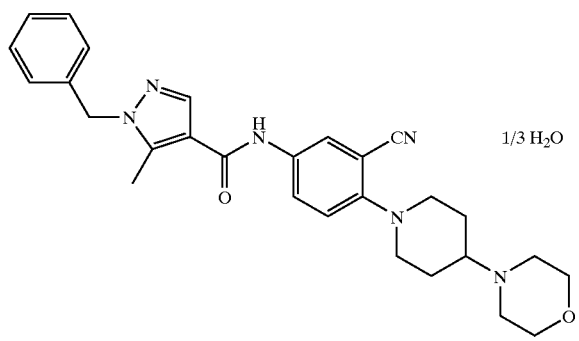

The reaction and treatment in the same manner as in Example 64 were conducted using 1-benzyl-5-methylpyrazole-4-carboxylic acid (0.7 g) and 5-amino-2-(4-morpholinopiperidin-1-yl)benzonitrile (0.93 g) and the resulting product was recrystallized from a mixed solvent of ethyl acetate-diisopropyl ether to give the title compound (0.36 g), melting point: 155° C.

EXAMPLE 183

1-(4-Chlorophenyl)-N-[3-cyano-4-(4-methoxymethoxypiperidin-1-yl)phenyl]-5-methylpyrazole-4-carboxamide

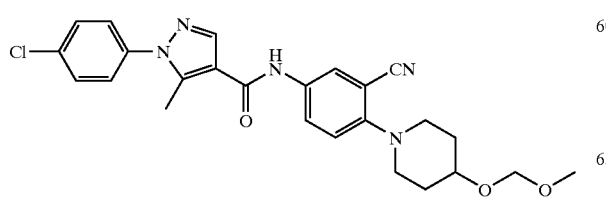

By the reaction and treatment in the same manner as in Example 150 using 1-(4-chlorophenyl)-5-methylpyrazole-4-carboxylic chloride (0.62 g) and 5-amino-2-(4-methoxymethoxypiperidin-1-yl) benzonitrile (0.63 g), the title compound (0.33 g) was obtained, melting point: 186–188° C.

$^1$H-NMR (400 MHz, DMSO-d$_6$) δ(ppm): 1.6–1.7 (2H, m), 1.9–2.0 (2H, m), 2.56 (3H, s), 2.9–3.0 (2H, m), 3.29 (3H, s), 3.3–3.4 (2H, m), 3.65–3.75 (1H, m), 4.67 (2H, s), 7.21 (1H, d, J=8.8 Hz), 7.60 (2H, d, J=8.8 Hz), 7.64 (2H, d, J=8.8 Hz), 7.85 (1H, d, J=8.8 Hz), 8.07 (1H, s), 8.31 (1H, s), 10.00 (1H, s).

EXAMPLE 184

1-(4-Chlorophenyl)-N-[3-cyano-4-[4-(2-methoxyethoxy) piperidin-1-yl]phenyl]-5-methylpyrazole-4-carboxamide

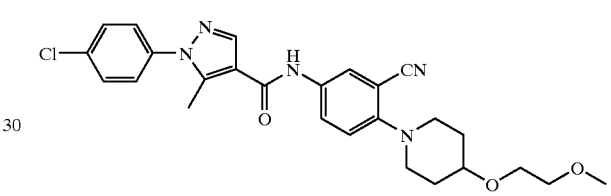

By the reaction and treatment in the same manner as in Example 150 using 1-(4-chlorophenyl)-5-methylpyrazole-4-carboxylic chloride (0.13 g) and 5-amino-2-[4-(2-methoxyethoxy)piperidin-1-yl]benzonitrile (0.14 g), the title compound (0.05 g) was obtained, melting point: 180–182° C.

$^1$H-NMR (400 MHz, DMSO-d$_6$) δ (ppm): 1.6–1.7 (2H, m), 1.9–2.0 (2H, m), 2.50 (3H, s), 2.85–2.95 (2H, m), 3.27 (3H, s), 3.2–3.3 (2H, m), 3.4–3.5 (3H, m), 3.5–3.6 (2H, m), 7.20 (1H, d, J=8.8 Hz), 7.60 (2H, d, J=9.3 Hz), 7.64 (2H, d, J=9.3 Hz), 7.85 (1H, dd, J=8.8, 2.5 Hz), 8.07 (1H, d, J=2.5 Hz), 8.31 (1H, s), 10.00 (1H, s).

EXAMPLE 185

1-(4-Chlorophenyl)-N-[3,5-dichloro-4-(4-morpholinopiperidin-1-yl)phenyl]-5-methylpyrazole-4-carboxamide ¼ hydrate

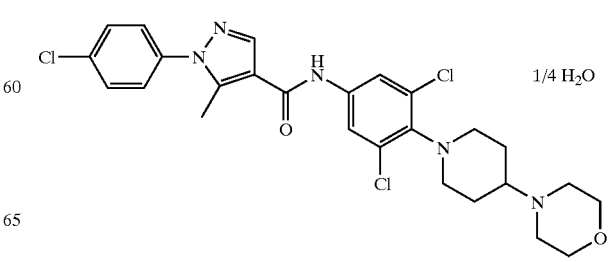

By the reaction and treatment in the same manner as in Example 150 using 1-(4-chlorophenyl)-5-methylpyrazole-4-carboxylic chloride (0.77 g) and 3,5-dichloro-4-(4-morpholinopiperidin-1-yl)aniline (1.0 g), the title compound (1.0 g) was obtained, melting point: 246–248° C.

$^1$H-NMR (400 MHz, DMSO-d$_6$) δ(ppm): 1.5–1.6 (2H, m), 1.8–1.85 (2H, m), 2.25–2.35 (1H, m), 2.5–2.55 (4H, m), 2.55 (3H, s), 2.95–3.00 (2H, m), 3.2–3.3 (2H, m), 3.55–3.65 (4H, m), 7.60 (2H, d, J=9.3 Hz), 7.64 (2H, d, J=9.3 Hz), 7.80 (1H, s), 7.88 (1H, s), 8.31 (1H, s), 10.02 (1H, s).

EXAMPLE 186

N-[3,5-Dichloro-4-(4-morpholinopiperidin-1-yl)phenyl]-5-methyl-1-(4-trifluoromethylphenyl)pyrazole-4-carboxamide ½ hydrate

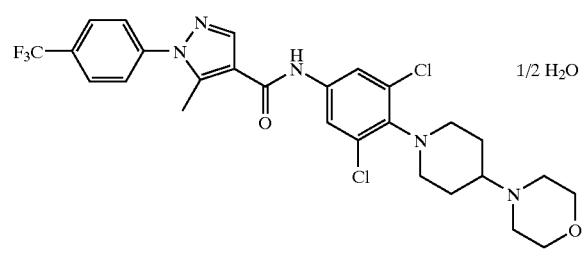

By the reaction and treatment in the same manner as in Example 150 using 5-methyl-1-(4-trifluoromethylphenyl)pyrazole-4-carboxylic chloride (0.87 g) and 3,5-dichloro-4-(4-morpholinopiperidin-1-yl)aniline (1.0 g), the title compound (1.2 g) was obtained, melting point: 252–254° C.

$^1$H-NMR (400 MHz, DMSO-{) δ(ppm): 1.5–1.6 (2H, m), 1.75–1.85 (2H, m), 2.25–2.35 (1H, m), 2.5–2.55 (4H, m), 2.61 (3H, s), 2.95–3.0 (2H, m), 3.2–3.3 (2H, m), 3.55–3.65 (4H, m), 7.8–8.00 (6H, m), 8.36 (1H, s), 10.07 (1H, s).

EXAMPLE 187

N-[3-Cyano-4-(4-hydroxypiperidin-1-yl)phenyl]-5-methyl-1-phenylpyrazole-4-carboxamide

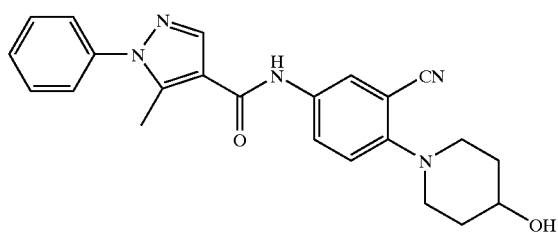

By the reaction and treatment in the same manner as in Example 64 using 5-methyl-1-phenylpyrazole-4-carboxylic acid (0.4 g) and 5-mino-2-(4-hydroxypiperidin-1-yl)benzonitrile (0.4 g), the title compound (0.3 g) was obtained, melting point: 182° C.

EXAMPLE 188

N-{3-Cyano-4-[4-(2-hydroxyethyl)piperidin-1-yl]phenyl}-1-(4-fluorophenyl)-5-methylpyrazole-4-carboxamide ¼ hydrate

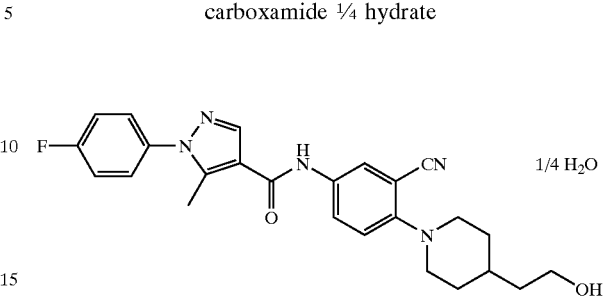

By the reaction and treatment in the same manner as in Example 64 using 1-(4-fluorophenyl)-5-methylpyrazole-4-carboxylic acid (1 g) and 5-amino-2-[4-(2-hydroxyethyl)piperidin-1-yl]benzonitrile (1.6 g), the title compound (0.2 g) was obtained, melting point: 186° C.

EXAMPLE 189

1-(4-Chlorophenyl)-N-{3-cyano-4-[4-(4-hydroxypiperidin-1-yl)piperidin-1-yl]phenyl}-5-methylpyrazole-4-carboxamide 1 hydrate

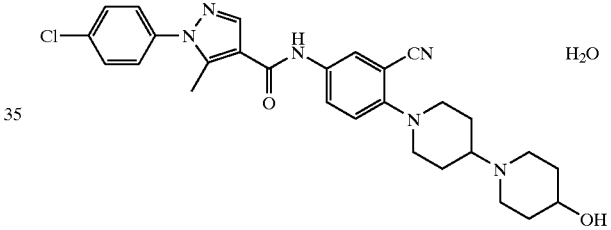

By the reaction and treatment in the same manner as in Example 150 using 1-(4-chlorophenyl)-5-methylpyrazole-4-carboxylic chloride (0.6 g) and 5-amino-2-[4-(4-hydroxypiperidin-1-yl) piperidin-1-yl]benzonitrile (0.6 g), the title compound (0.2 g) was obtained, melting point: 213° C.

EXAMPLE 190

1-(4-Chlorophenyl)-N-[3-cyano-(4-morpholinopiperidin-1-yl) phenyl]pyrrole-3-carboxamide ¼ hydrate

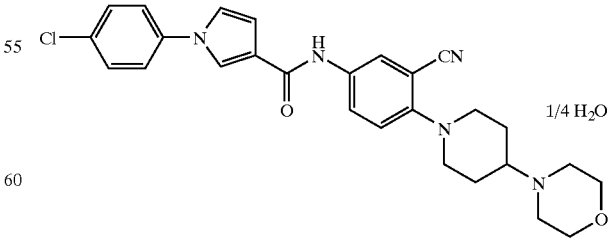

By the reaction and treatment in the same manner as in Example 64 using 1-(4-chlorophenyl)pyrrole-3-carboxylic acid (0.6 g) and 5-amino-2-(4-morpholinopiperidin-1-yl)benzonitrile (0.7 g), the title compound (0.49 g) was obtained, melting point: 220° C.

EXAMPLE 191

1-(4-Chlorophenyl)-N-[3-cyano-(4-morpholinomethylpiperidin-1-yl)phenyl]-5-methylpyrazole-4-carboxamide

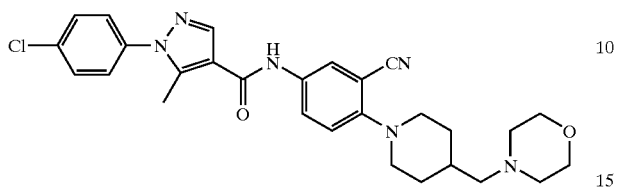

By the reaction and treatment in the same manner as in Example 150 using 1-(4-chlorophenyl)-5-methylpyrazole-4-carboxylic chloride (1.17 g) and 5-amino-2-[4-(4-morpholinomethylpiperidin-1-yl)phenyl]benzonitrile (1.25 g), the title compound (0.94 g) was obtained, melting point: 235° C.

EXAMPLE 192

N-[3-Cyano-(4-morpholinopiperidin-1-yl)phenyl]-5-methyl-1-(4-nitrophenyl)pyrazole-4-carboxamide

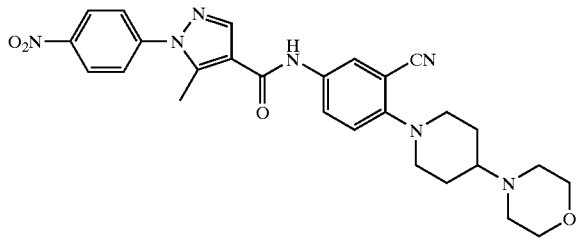

By the reaction and treatment in the same manner as in Example 150 using 5-methyl-1-(4-nitrophenyl)pyrazole-4-carboxylic acid (1.6 g) and 5-amino-2-(4-morpholinopiperidin-1-yl)benzonitrile (1.8 g), the title compound (0.8 g) was obtained, melting point: 265° C./decomposition.

EXAMPLE 193

N-{3-Cyano-4-[4-(3,4,5,6-tetrahydro-2H-pyran-4-yl)piperazin-1-yl]phenyl}-1-(4-fluorophenyl)-5-methylpyrazole-4-carboxamide

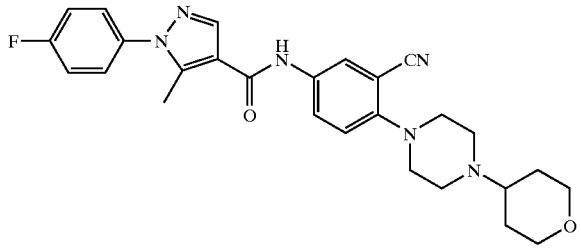

By the reaction and treatment in the same manner as in Example 64 using 1-(4-fluorophenyl)-5-methylpyrazole-4-carboxylic acid (0.6 g) and 5-amino-2-[4-(3,4,5,6-tetrahydro-2H-pyran-4-yl)piperazin-1-yl]benzonitrile (0.8 g), the title compound (0.6 g) was obtained, melting point: 240° C.

$^1$H-NMR (400 MHz, DMSO-d$_6$) δ(ppm): 1.43 (2H, dq, J=3.4, 11.7 Hz), 1.75 (2H, d, J=12.2 Hz), 2.40–2.50 (1H, m), 2.50 (3H, s), 2.67 (4H, m), 3.10 (4H, m), 3.31 (2H, d, J=13.6 Hz), 3.90 (2H, d, J=13.6 Hz), 7.19 (1H, d, J=8.8 Hz), 7.41 (2H, t, J=8.8 Hz), 7.60 (2H, dd, J=4.8, 8.8 Hz), 7.87 (1H, dd, J=2.4, 8.8 Hz), 8.09 (1H, d, J=2.4 Hz), 8.29 (1H, s), 10.00 (1H, s).

EXAMPLE 194

N-{3-Cyano-4-[4-(3,4,5,6-tetrahydro-2H-pyran-4-yl)piperazin-1-yl]phenyl}-1-(4-fluorophenyl)pyrrole-3-carboxamide ¼ hydrate

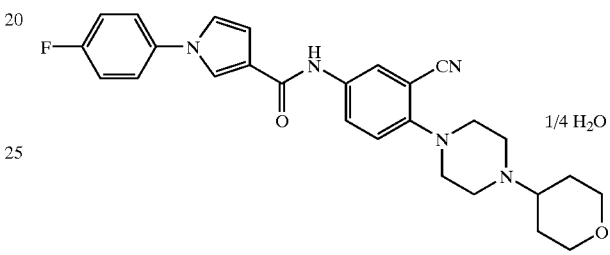

By the reaction and treatment in the same manner as in Example 64 using 1-(4-fluorophenyl)pyrrole-3-carboxylic acid (0.3 g) and 5-amino-2-[4-(3,4,5,6-tetrahydro-2H-pyran-4-yl)piperazin-1-yl]benzonitrile (0.5 g), the title compound (0.4 g) was obtained, melting point: 240° C.

$^1$H-NMR (400 MHz, DMSO-d$_6$) δ(ppm): 1.43 (2H, dq, J=4.0, 12.2 Hz), 1.74 (2H, d, J=12.2 Hz), 2.41–2.50 (1H, m), 2.67 (4H, m), 3.10 (4H, m), 3.27 (2H, d, J=11.2 Hz), 3.89 (2H, d, J=11.8 Hz), 6.85 (1H, d, J= 9.3 Hz), 7.19 (1H, d, J=9.3 Hz), 7.37 (2H, t, J=8.8 Hz), 7.43 (1H, s), 7.70 (2H, dd, J=4.4, 8.8 Hz), 7.89 (1H, dd, J=2.4, 9.3 Hz), 8.05(1H, s), 8.10 (1H, d, J=2.4 Hz), 9.82 (1H, s).

EXAMPLE 195

1-(4-Chlorophenyl)-N-{3-cyano-4-[4-(3,4,5,6-tetrahydro-2H-pyran-4-yl)piperazin-1-yl]phenyl}pyrrole-3-carboxamide ⅖ hydrate

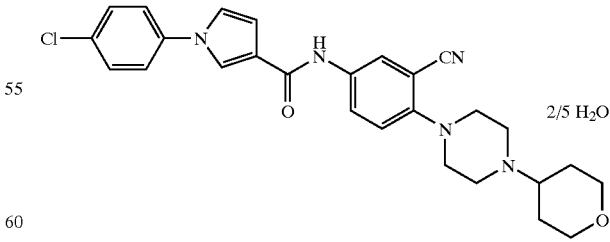

By the reaction and treatment in the same manner as in Example 64 using 1-(4-chlorophenyl)pyrrole-3-carboxylic acid (0.5 g) and 5-amino-2-[4-(3,4,5,6-tetrahydro-2H-pyran-4-yl)piperazin-1-yl]benzonitrile (0.7 g), the title compound (0.4 g) was obtained, melting point: 224° C.

¹H-NMR (400 MHz, DMSO-d₆) δ (ppm): 1.38–1.73 (2H, m), 1.74(2H, d, J=12.2 Hz), 2.41–2.50 (1H, m), 2.67 (4H, m), 3.10 (4H, m), 3.27 (2H, d, J=11.7 Hz), 3.89 (2H, d, J=11.7 Hz), 6.86 (1H, m), 7.19 (1H, d, J=9.3 Hz), 7.49 (1H, m), 7.67 (2H, d, J=9.2 Hz), 7.70 (2H, d, J=9.2 Hz), 7.88 (1H, dd, J=2.4, 9.3 Hz), 8.09 (1H, d, J=2.4 Hz), 8.11 (1H, s), 9.84 (1H, s).

EXAMPLE 196

1-(3,4-Dichlorophenyl)-N-{3-cyano-4-[4-(3,4,5,6-tetrahydro-2H-pyran-4-yl)piperazin-1-yl]phenyl}-5-methylpyrazole-4-carboxamide 1 hydrate

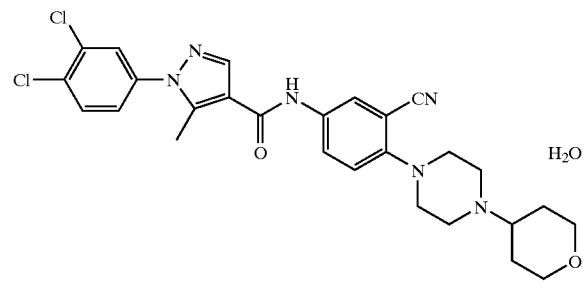

By the reaction and treatment in the same manner as in Example 64 using 1-(3,4-dichlorophenyl)-5-methylpyrazole-4-carboxylic acid (1.0 g) and 5-amino-2-[4-(3,4,5,6-tetrahydro-2H-pyran-4-yl)piperazin-1-yl]benzonitrile (1.1 g), the title compound (0.6 g) was obtained, melting point: 242° C.

¹H-NMR (400 MHz, DMSO-d₆) δ(ppm): 1.43 (2H, dq, J=3.5, 11.8 Hz), 1.73 (2H, d, J=11.8 Hz), 2.41–2.50 (1H, m), 2.51 (3H, s), 2.67 (4H, m), 3.10 (3H, m), 3.27 (2H, d, J=11.7 Hz), 3.91 (2H, d, J=10.2 Hz), 7.18 (1H, d, J=8.8 Hz), 7.60(1H, dd, J=2.5, 8.8 Hz), 7.85 (1H, dd, J=2.5, 8.8 Hz), 7.92 (1H, d, J=2.5 Hz), 8.08 (1H, d, J=2.5 Hz), 8.33 (1H, s), 10.01 (1H, s)

EXAMPLE 197

1-(4-Bromophenyl)-N-{3-cyano-4-[4-(3,4,5,6-tetrahydro-2H-pyran-4-yl)piperazin-1-yl]phenyl}-5-methylpyrazole-4-carboxamide

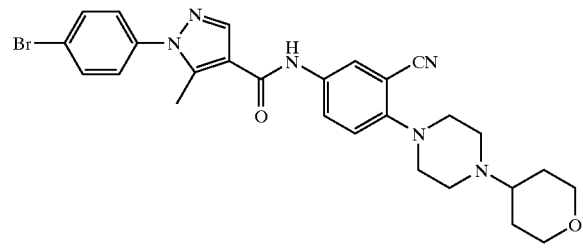

By the reaction and treatment in the same manner as in Example 64 using 1-(4-bromophenyl)-5-methylpyrazole-4-carboxylic acid (1.0 g) and 5-amino-2-[4-(3,4,5,6-tetrahydro-2H-pyran-4-yl) piperazin-1-yl]benzonitrile (1.0 g), the title compound (0.7 g) was obtained, melting point: 288° C.

¹H-NMR (400 MHz, DMSO-d₆) δ(ppm): 1.43 (2H, ddd, J=2.9, 11.5, 12.2 Hz), 1.75 (2H, d, J=12.2 Hz), 2.42–2.51 (1H, m), 2.56 (3H, s), 2.67 (4H, m), 3.10 (4H, m), 3.28 (2H, d, J=11.5 Hz), 3.90 (2H, d, J=7.8 Hz), 7.19 (1H, d, J=8.3 Hz), 7.53 (2H, 3, J=8.8 Hz), 7.77 (2H, 3, J=8.8 Hz), 7.86 (1H, dd, J=2.4, 8.3 Hz), 8.08 (1H, d, J=2.4 Hz), 8.31 (1H, s), 10.00 (1H, s).

EXAMPLE 198

N-{3-Cyano-4-[4-(3,4,5,6-tetrahydro-2H-pyran-4-yl)piperazin-1-yl]phenyl}-1-(3,4-difluorophenyl)-5-methylpyrazole-4-carboxamide ¼ hydrate

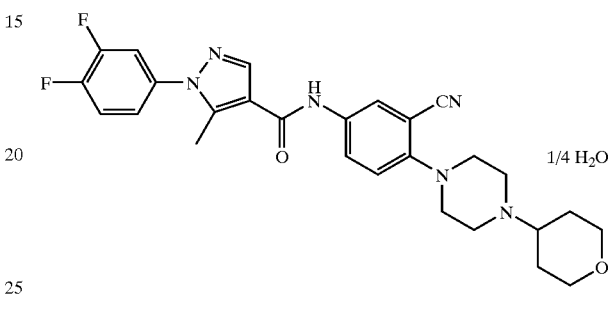

By the reaction and treatment in the same manner as in Example 64 using 1-(3,4-difluorophenyl)-5-methylpyrazole-4-carboxylic acid (0.7 g) and 5-amino-2-[4-(3,4,5,6-tetrahydro-2H-pyran-4-yl)piperazin-1-yl]benzonitrile (1.0 g), the title compound (0.8 g) was obtained, melting point: 235° C.

H-NMR (400 MHz, DMSO-d₆) δ(ppm): 1.42 (2H, ddd, J=4.9, 11.2, 11.7 Hz), 1.73 (2H, d, J=12.2 Hz), 2.41–2.50 (1H, m), 2.56 (3H, s), 2.66 (4H, m), 3.10 (4H, m), 3.27 (2H, d, J=11.7 Hz), 3.90 (2H, d, J=10.3 Hz), 7.17 (1H, d, J=8.8 Hz), 7.19 (1H, m), 7.63 (1H, m), 7.78 (1H, m), 7.86 (1H, d, J=8.8 Hz), 8.09 (1H, s), 8.31 (1H, s), 10.00 (1H, s).

EXAMPLE 199

N-{3-Cyano-4-[4-(3,4,5,6-tetrahydro-2H-pyran-4-yl)piperazin-1-yl]phenyl}-5-methyl-1-phenylpyrazole-4-carboxamide ⅔ hydrate

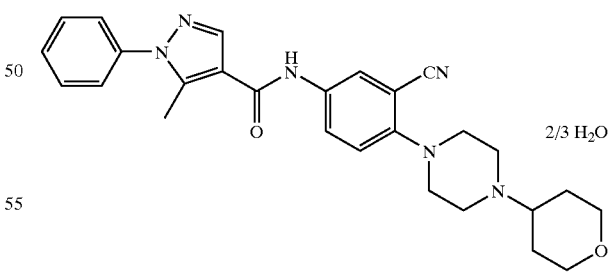

By the reaction and treatment in the same manner as in Example 64 using 5-methyl-1-phenylpyrazole-4-carboxylic acid (0.5 g) and 5-amino-2-[4-(3,4,5,6-tetrahydro-2H-pyran-4-yl)piperazin-1-yl]benzonitrile (0.7 g), the title compound (0.8 g) was obtained, melting point: 227° C.

¹H-NMR (400 MHz, DMSO-d₆) δ(ppm): 1.43 (2H, dq, J=3.5, 11.7 Hz), 1.75(2H, d, J=13.7 Hz), 2.45–2.50 (1H, m), 2.55 (3H, s), 2.67 (4H, m), 3.11 (4H, m), 3.29 (2H, d, J=11.7

Hz), 3.90 (2H, d, J=7.8 Hz), 7.19 (1H, d, J=8.8 Hz), 7.39–7.70 (5H, m), 7.85 (1H, dd, J=2.5, 8.8 Hz), 8.09 (1H, d, J=2.5 Hz), 8.29 (1H, s), 9.99 (1H, s).

EXAMPLE 200

1-(3-Chlorophenyl)-N-{3-cyano-4-[4-(3,4,5,6-tetrahydro-2H-pyran-4-yl)piperazin-1-yl]phenyl}-5-methylpyrazole-4-carboxamide

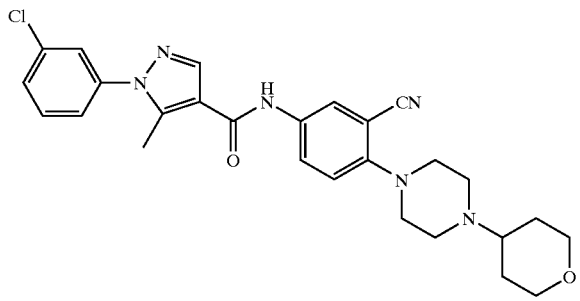

By the reaction and treatment in the same manner as in Example 64 using 1-(3-chlorophenyl)-5-methylpyrazole-4-carboxylic acid (0.8 g) and 5-amino-2-[4-(3,4,5,6-tetrahydro-2H-pyran-4-yl)piperazin-1-yl]benzonitrile (1.0 g), the title compound (0.7 g) was obtained, melting point: 230° C.
$^1$H-NMR (400 MHz, DMSO-$d_6$) δ(ppm): 1.43 (2H, ddd, J=3.9, 11.2, 11.7 Hz), 1.75 (2H, d, J=13.7 Hz), 2.42–2.45 (1H, m), 2.50 (3H, s), 2.67 (4H, m), 3.10 (4H, m), 3.28 (2H, d, J=11.7 Hz), 3.90 (2H, d, J=11.2 Hz), 7.19 (1H, d, J=9.2 Hz), 7.55–7.58 (3H, m), 7.59 (1H, s), 7.86 (1H, d, J=2.4, 9.2 Hz), 8.09 (1H, d, J=2.4 Hz), 8.32 (1H, s), 10.01 (1H, s).

EXAMPLE 201

N-{3-Cyano-4-[4-(3,4,5,6-tetrahydro-2H-pyran-4-yl)piperazin-1-yl]phenyl}-5-methyl-1-(4-methylphenyl)pyrazole-4-carboxamide

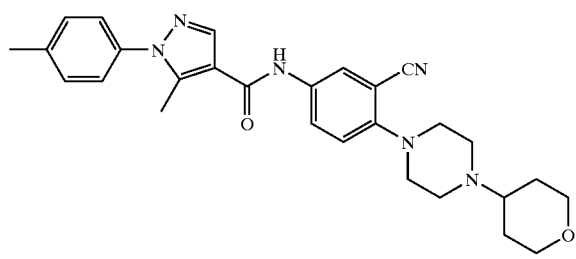

By the reaction and treatment in the same manner as in Example 64 using 1-(4-chlorophenyl)-5-methylpyrazole-4-carboxylic acid (0.7 g) and 5-amino-2-[4-(3,4,5,6-tetrahydro-2H-pyran-4-yl)piperazin-1-yl]benzonitrile (0.9 g), the title compound (0.7 g) was obtained, melting point: 258° C.
$^1$H-NMR (400 MHz, DMSO-$d_6$) δ(ppm): 1.43 (2H, dq, J=3.9, 12.2 Hz), 1.75 (2H, d, J=12.2 Hz), 2.40 (3H, s), 2.40–2.55 (1H, m), 2.55 (3H, s), 2.67 (4H, m), 3.10 (4H, m), 3.27 (2H, d, J=11.7 Hz), 3.90 (2H, d, J=7.8 Hz), 7.18 (1H, d, J=9.3 Hz), 7.36 (2H, d, J=8.3 Hz), 7.41 (2H, d, J=8.3 Hz), 7.86 (1H, dd, J=2.4, 9.3 Hz), 8.09 (1H, d, J=2.4 Hz), 8.27 (1H, s), 9.97 (1H, s).

EXAMPLE 202

1-(4-Chlorophenyl)-N-{3-cyano-4-[4-(3,4,5,6-tetrahydro-2H-thiopyran-4-yl)piperazin-1-yl]phenyl}-5-methylpyrazole-4-carboxamide

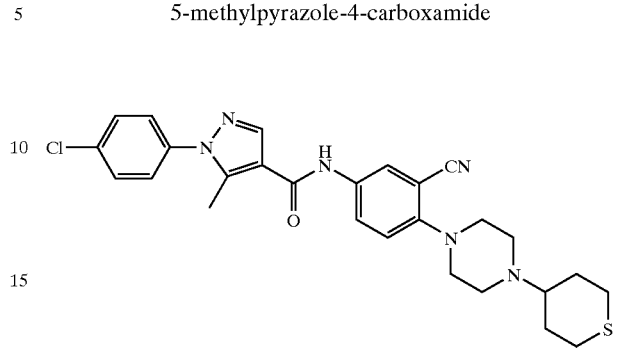

By the reaction and treatment in the same manner as in Example 64 using 1-(4-chlorophenyl)-5-methylpyrazole-4-carboxylic acid (1.3 g) and 5-amino-2-[4-(3,4,5,6-tetrahydro-2H-thiopyran-4-yl) piperazin-1-yl]benzonitrile (1.1 g), the title compound (1.1 g) was obtained, melting point: 281° C.
$^1$H-NMR (400 MHz, DMSO-$d_6$) δ(ppm): 1.58–1.68 (2H, m), 2.07 (2H, d, J=12.2 Hz), 2.41–2.50 (1H, m), 2.56 (3H, s), 2.65 (2H, d, J=11.7 Hz), 2.68 (4H, m), 3.09 (4H, m), 3.33 (2H, m), 7.18 (1H, d, J=8.8 Hz), 7.60 (2H, d, J=8.8 Hz), 7.64 (2H, d, J=8.8 Hz), 7.85 (1H, dd, J=2.4, 8.8 Hz), 8.08 (1H, d, J=2.4 Hz), 8.31 (1H, s), 10.00 (1H, s).

EXAMPLE 203

1-(4-Chlorophenyl)-N-[3-cyano-4-[4-(2-methoxyethyl)piperazin-1-yl]phenyl]-5-methylpyrazole-4-carboxamide

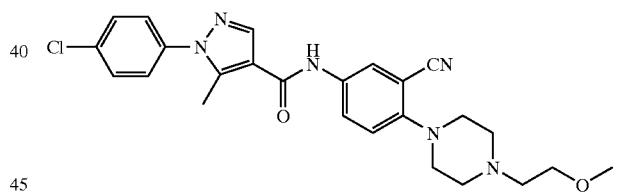

By the reaction and treatment in the same manner as in Example 150 using 1-(4-chlorophenyl)-5-methylpyrazole-4-carboxylic chloride (0.8 g) and 5-amino-2-[4-(2-methoxyethyl)piperazin-1-yl]benzonitrile (0.8 g), the title compound (0.7 g) was obtained, melting point: 207° C.

EXAMPLE 204

1-(4-Chlorophenyl)-N-[3-cyano-4-[4-(4-methoxypiperidin-1-yl)piperidin-1-yl]phenyl]-5-methylpyrazole-4-carboxamide ¼ hydrate

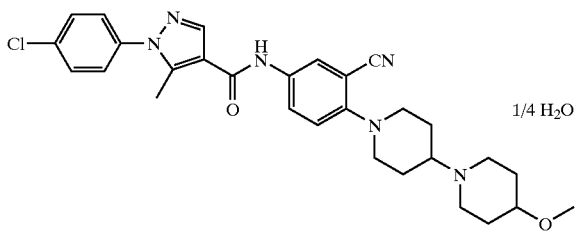

By the reaction and treatment in the same manner as in Example 150 using 1-(4-chlorophenyl)-5-methylpyrazole-4-carboxylic chloride (0.4 g) and 5-amino-2-[4-(4-methoxypiperidin-1-yl)piperidin-1-yl]benzonitrile (0.5 g), the title compound (0.2 g) was obtained, melting point: 245° C. decomposition.

EXAMPLE 205

1-(4-Chlorophenyl)-N-[3-cyano-4-[4-(4-oxopiperidin-1-yl)piperidin-1-yl]phenyl]-5-methylpyrazole-4-carboxamide ¼ hydrate

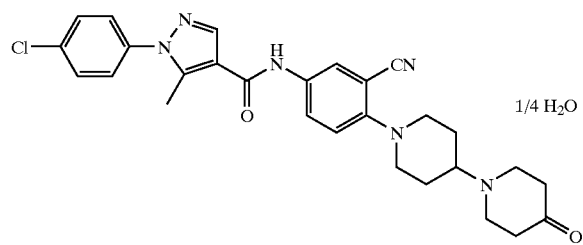

1/4 H₂O

To a solution of oxalyl chloride (0.1 ml) and dimethyl sulfoxide (0.2 ml) in methylene chloride (30 ml) were added under ice-cooling 1-(4-chlorophenyl)-N-[3-cyano-4-[4-(4-hydroxypiperidin-1-yl)piperidin-1-yl]phenyl]-5-methylpyrazole-4-carboxamide synthesized in Example 189 and triethylamine (0.9 ml), and the mixture was stirred at the same temperature for 1 h. To a reaction mixture was added aqueous sodium hydroxide solution. The organic layer was washed with saturated brine and dried over anhydrous sodium sulfate, and the solvent was evaporated under reduced pressure. The residue was purified by silica gel column chromatography (mobile phase: chloroform:methanol=20:1) to give the title compound (0.2 g), melting point: 213° C.

EXAMPLE 206

1-(4-Chlorophenyl)-N-[3-cyano-4-(3-morpholinopropoxy)phenyl]-5-methylpyrazole-4-carboxamide

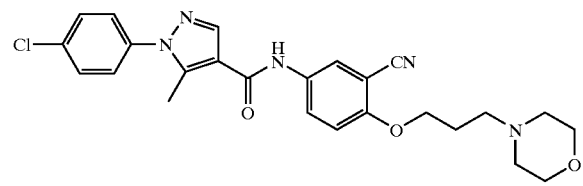

By the reaction and treatment in the same manner as in Example 150 using 1-(4-chlorophenyl)-5-methylpyrazole-4-carboxylic chloride (0.74 g) and 5-amino-2-(3-morpholinopropoxy) benzonitrile (0.76 g), the title compound (0.35 g) was obtained, melting point: 155–157° C.
¹H-NMR (400 MHz, DMSO-dr) δ(ppm): 1.9–1.95 (2H, m), 2.3–2.4 (4H, m), 2.4–2.5 (2H, m), 2.56 (3H, s), 3.55–3.6 (4H, m), 4.17 (2H, t, J=6.3 Hz), 7.28 (1H, d, J=9.2 Hz), 7.60 (2H, d, J=8.8 Hz), 7.64 (2H, d, J=8.8 Hz), 7.90 (1H, dd, J=2.4, 9.2 Hz), 8.07 (1H, d, J=2.4 Hz), 8.31 (1H, s), 10.00 (1H, s)

EXAMPLE 207

N-[3-Cyano-4-(3-morpholinopropoxy) phenyl]-5-methyl-1-(4-trifluoromethylphenyl)pyrazole-4-carboxamide

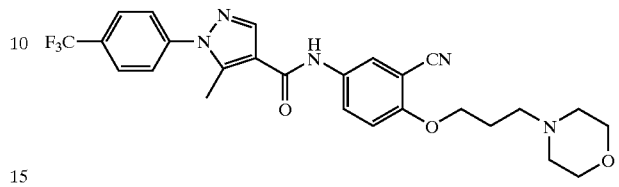

By the reaction and treatment in the same manner as in Example 150 using 5-methyl-1-(4-trifluoromethylphenyl)pyrazole-4-carboxylic chloride (1.0 g) synthesized according to Starting Material Synthesis Example 88 and 5-amino-2-(3-morpholinopropoxy)benzonitrile (0.9 g), the title compound (0.75 g) was obtained, melting point: 172–174° C.
¹H-NMR (400 MHz, DMSO-d₆) δ(ppm): 1.9–1.95 (2H, m), 2.3–2.4 (4H, m), 2.4–2.5 (2H, m), 2.63 (3H, s), 3.55–3.6 (4H, m), 4.17 (2H, t, J=6.3 Hz), 7.29 (1H, d, J=9.3 Hz), 7.84 (2H, d, J=8.3 Hz), 7.90 (1H, dd, J=2.5, 9.3 Hz), 7.95 (2H, d, J=8.3 Hz), 8.07 (1H, d, J=2.5 Hz), 8.36 (1H, s), 10.04 (1H, s)

EXAMPLE 208

1-(4-Chlorophenyl)-N-[3-cyano-4-(2-morpholinoethoxy)phenyl]-5-methylpyrazole-4-carboxamide

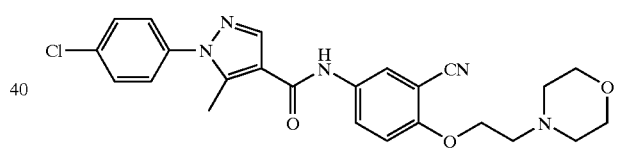

By the reaction and treatment in the same manner as in Example 150 using 1-(4-chlorophenyl)-5-methylpyrazole-4-carboxylic chloride (0.65 g) and 5-amino-2-(2-morpholinoethoxy)benzonitrile (0.95 g), the title compound (1.02 g) was obtained, melting point: 187–189° C.
¹H-NMR (400 MHz, DMSO-d₆) δ(ppm): 2.5–2.6 (4H, m), 2.56 (3H, s), 2.7–2.8 (2H, m), 3.5–3.6 (4H, m), 4.25 (2H, t, J=5.4 Hz), 7.30 (1H, d, J=9.2 Hz), 7.60 (2H, d, J=8.8 Hz), 7.64 (2H, d, J=8.8 Hz), 7.90 (1H, dd, J=2.4, 9.2 Hz), 8.07 (1H, d, J=2.4 Hz), 8.31 (1H, s), 10.00 (1H, s)

EXAMPLE 209

N-[3-Cyano-4-(2-morpholinoethoxy)phenyl]-5-methyl-1-(4-trifluoromethylphenyl)pyrazole-4-carboxamide

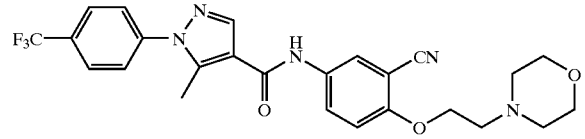

By the reaction and treatment in the same manner as in Example 150 using 5-methyl-1-(4-trifluoromethylphenyl)pyrazole-4-carboxylic chloride (0.74 g) synthesized according to Starting Material Synthesis Example 88 and 5-amino-2-(2-morpholinoethoxy)benzonitrile (0.95 g), the title compound (0.78 g) was obtained, melting point: 191–193° C.

$^1$H-NMR (400 MHz, DMSO-d$_6$) δ(ppm): 2.5–2.6 (4H, m), 2.73 (3H, s), 2.7–2.8 (2H, m), 3.5–3.6 (4H, m), 4.25 (2H, t, J=5.3 Hz), 7.31 (1H, d, J=9.3 Hz), 7.84 (2H, d, J=8.3 Hz), 7.90(1H, dd, J=2.9, 9.3 Hz), 7.95 (2H, d, J=8.3 Hz), 8.07 (1H, d, J=2.9 Hz), 8.36 (1H, s), 10.05 (1H, s)

EXAMPLE 210

1-(4-Chlorophenyl)-N-[3-cyano-4-((4-morpholinopiperidin-1-yl)methyl)phenyl]-5-methylpyrazole-4-carboxamide

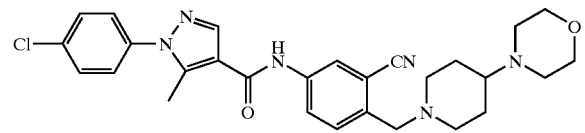

By the reaction and treatment in the same manner as in Example 150 using 1-(4-chlorophenyl)-5-methylpyrazole-4-carboxylic chloride (0.26 g) and 5-amino-2-((4-morpholinopiperidin-1-yl)methyl)benzonitrile (0.3 g), the title compound (0.16 g) was obtained, melting point: 167–168° C.

$^1$H-NMR (400 MHz, DMSO-d$_6$) δ(ppm): 1.3–1.4 (2H, m), 1.7–1.8 (2H, m), 1.95–2.05 (2H, m), 2.1–2.2 (1H, m), 2.4–2.5 (4H, m), 2.57 (3H, s), 2.8–2.9 (2H, m), 3.5–3.6 (6H, m), 7.53 (1H, d, J=8.8 Hz), 7.61 (2H, d, J=8.8 Hz), 7.65 (2H, d, J=8.8 Hz), 7.93 (1H, d, J=8.8 Hz), 8.18 (1H, s), 8.34 (1H, s), 10.14 (1H, s)

EXAMPLE 211

1-(4-Chlorophenyl)-N-[3-cyano-4-(3-hydroxypropylthio)phenyl]-5-methylpyrazole-4-carboxamide ¼ hydrate

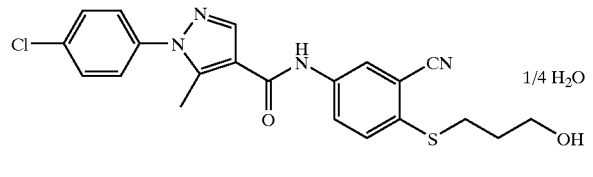

By the reaction and treatment in the same manner as in Example 150 using 1-(4-chlorophenyl)-5-methylpyrazole-4-carboxylic chloride (3.9 g) and 5-amino-2-(3-hydroxypropylthio)benzonitrile (2.9 g), the title compound (1.5 g) was obtained, melting point: 165° C.

EXAMPLE 212

1-(4-Chlorophenyl)-N-[3-cyano-4-(3-morpholinopropylthio)phenyl]-5-methylpyrazole-4-carboxamide

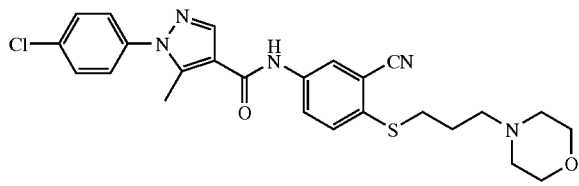

A solution of 1-(4-chlorophenyl)-N-[3-cyano-4-(3-hydroxypropylthio)phenyl]-5-methylpyrazole-4-carboxamide (1.8 g) and methanesulfonyl chloride (0.5 ml) in pyridine (20 ml) was stirred overnight. To the reaction mixture was added aqueous hydrochloric acid solution and the mixture was extracted with ethyl acetate. The organic layer was washed with saturated brine and dried over anhydrous sodium sulfate. The solvent was evaporated under reduced pressure. The residue was purified by silica gel column chromatography (mobile phase: chloroform:methanol=50:1) to give 1-(4-chlorophenyl)-N-[3-cyano-4-(3-methanesulfonyloxypropylthio)phenyl]-5-methylpyrazole-4-carboxamide (1.2 g).

The above compound (0.6 g) and morpholine (0.5 g) were stirred in dimethylformamide (20 ml) at room temperature for 2 h. To the reaction mixture was added aqueous sodium hydroxide solution and the mixture was extracted with ethyl acetate. The organic layer was washed with saturated brine and dried over anhydrous sodium sulfate. The solvent was evaporated under reduced pressure. The residue was dissolved in ethyl acetate. The mixture was acidified with hydrochloric acid-ethanol and crystals were precipitated. The crystals were added to ethyl acetate and aqueous sodium hydroxide solution again, and the mixture was extracted with ethyl acetate. The organic layer was washed with saturated brine and dried over anhydrous sodium sulfate. The solvent was evaporated under reduced pressure. The residue was recrystallized from a mixed solvent of ethyl acetate and hexane to give the title compound (0.2 g), melting point: 105–110° C. (decomposition)

EXAMPLE 213

1-(4-Chlorophenyl)-N-[3-cyano-4-(3-piperidinopropylthio)phenyl]-5-methylpyrazole-4-carboxamide ¼ hydrate

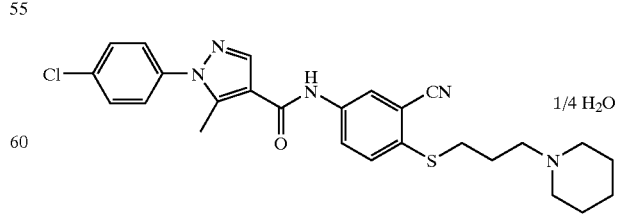

By the reaction and treatment in the same manner as in Example 212 using piperidine instead of morpholine, the title compound was obtained, melting point: 142° C.

In the same manner as in the above-described Starting Material Synthesis Examples and Examples, the following compound can be produced.

EXAMPLE 214

1-(4-Chlorophenyl)-N-[3-cyano-4-(morpholinomethoxy)phenyl]-5-methylpyrazole-4-carboxamide

EXAMPLE 215

1-(4-Fluorophenyl)-N-[3-cyano-4-(morpholinomethoxy)phenyl]-5-methylpyrazole-4-carboxamide

EXAMPLE 216

1-(4-Fluorophenyl)-N-[3-cyano-4-(2-morpholinoethoxy)phenyl]-5-methylpyrazole-4-carboxamide

EXAMPLE 217

1-(4-Fluorophenyl)-N-[3-cyano-4-(3-morpholinopropoxy)phenyl]-5-methylpyrazole-4-carboxamide

EXAMPLE 218

1-(4-Fluorophenyl)-N-[3-cyano-4-(4-morpholinobutoxy)phenyl]-5-methylpyrazole-4-carboxamide

EXAMPLE 219

1-(4-Chlorophenyl)-N-[3-cyano-4-(4-morpholinobutoxy)phenyl]-5-methylpyrazole-4-carboxamide

EXAMPLE 220

1-(4-Fluorophenyl)-N-[3-cyano-4-(morpholinomethylthio)phenyl]-5-methylpyrazole-4-carboxamide

EXAMPLE 221

1-(4-Fluorophenyl)-N-[3-cyano-4-(2-morpholinoethylthio)phenyl]-5-methylpyrazole-4-carboxamide

EXAMPLE 222

1-(4-Fluorophenyl)-N-[3-cyano-4-(3-morpholinopropylthio)phenyl]-5-methylpyrazole-4-carboxamide

EXAMPLE 223

1-(4-Fluorophenyl)-N-[3-cyano-4-(4-morpholinobutylthio)phenyl]-5-methylpyrazole-4-carboxamide

EXAMPLE 224

1-(4-Chlorophenyl)-N-[3-cyano-4-(morpholinomethylthio)phenyl]-5-methylpyrazole-4-carboxamide

EXAMPLE 225

1-(4-Chlorophenyl)-N-[3-cyano-4-(2-morpholinoethylthio)phenyl]-5-methylpyrazole-4-carboxamide 1-(4-Chlorophenyl)-N-[3-cyano-4-(3-morpholinopropylthio)phenyl]-5-methylpyrazole-4-carboxamide

EXAMPLE 227

1-(4-Chlorophenyl)-N-[3-cyano-4-(4-morpholinobutylthio)phenyl]-5-methylpyrazole-4-carboxamide

EXAMPLE 228

1-(4-Chlorophenyl)-N-[3-cyano-4-(2-(4-morpholinopiperidin-1-yl) ethyl) phenyl]-5-ethylpyrazole-4-carboxamide

EXAMPLE 229

1-(4-Chlorophenyl)-N-[3-cyano-4-(3-(4-morpholinopiperidin-1-yl)propyl)phenyl]-5-methylpyrazole-4-carboxamide

EXAMPLE 230

1-(4-chlorophenyl)-N-[3-cyano-4-(4-(4-morpholinopiperidin-1-yl)butyl)phenyl]-5-methylpyrazole-4-carboxamide

EXAMPLE 231

1-(4-Trifluoromethylphenyl)-N-[3-cyano-4-(morpholinomethoxy)phenyl]-5-methylpyrazole-4-carboxamide

EXAMPLE 232

1-(4-Trifluoromethylphenyl)-N-[3-cyano-4-(2-morpholinoethoxy)phenyl]-5-methylpyrazole-4-carboxamide

EXAMPLE 233

1-(4-trifluoromethylphenyl)-N-[3-cyano-4-(3-morpholinopropoxy)phenyl]-5]ethylpyrazole-4-carboxamide

EXAMPLE 234

1-(4-Trifluoromethylphenyl)-N-[3-cyano-4-(4-morpholinobutoxy)phenyl]-5-methylpyrazole-4-carboxamide

EXAMPLE 235

1-(4-Trifluoromethylphenyl)-N-[3-cyano-4-(morpholinomethylthio)phenyl]-5-methylpyrazole-4-carboxamide

EXAMPLE 236

1-(4-Trifluoromethylphenyl)-N-[3-cyano-4-(2-morpholinoethylthio)phenyl]-5-methylpyrazole-4-carboxamide

EXAMPLE 237

1-(4-trifluoromethylphenyl)-N-[3-cyano-4-(3-morpholinopropylthio)phenyl]-5-methylpyrazole-4-carboxamide

EXAMPLE 238

1-(4-Trifluoromethylphenyl)-N-[3-cyano-4-(4-morpholinobutylthio)phenyl]-5-methylpyrazole-4-carboxamide

EXAMPLE 239

N-{3-Cyano-4-[4-(3,4,5,6-tetrahydro-2H-pyran-4-yl)piperazin-1-yl]phenyl}-1-(4-trifluoromethylphenyl)pyrrole-3-carboxamide

EXAMPLE 240

N-[3-Cyano-4-(4-morpholinopiperidin-1-yl)phenyl]-1-(4-trifluoromethylphenyl)pyrrole-3-carboxamide

EXAMPLE 241

N-(3-Cyano-4-[4-(3,4,5,6-tetrahydro-2H-pyran-4-yl)piperazin-1-yl]phenyl}-1-(3,4-dichlorophenyl)pyrrole-3-carboxamide

EXAMPLE 242

N-[3-Cyano-4-(4-morpholinopiperidin-1-yl)phenyl]-1-(3,4-dichlorophenyl)pyrrole-3-carboxamide

EXAMPLE 243

1-(4-Chlorophenyl)-N-{3-ethynyl-4-[4-(3,4,5,6-tetrahydro-2H-pyran-4-yl)piperazin-1-yl]phenyl}-5-methylpyrazole-4-carboxamide

EXAMPLE 244

1-(4-Chlorophenyl)-5-methyl-N-{3-(1-propyne)-4-[4-(3,4,5,6-tetrahydro-2H-pyran-4-yl)piperazin-1-yl]phenyl}pyrazole-4-carboxamide

EXAMPLE 245

1-(4-Chlorophenyl)-5-methyl-N-[3-(1-propyne)-4-(4-morpholinopiperidin-1-yl)phenyl]pyrazole-4-carboxamide

EXAMPLE 246

1-(4-Chlorophenyl)-N-(3-ethenyl-4-[4-(3,4,5,6-tetrahydro-2H-pyran-4-yl)piperazin-1-yl]phenyl}-5-methylpyrazole-4-carboxamide

EXAMPLE 247

1-(4-Chlorophenyl)-N-[3-ethenyl-4-(4-morpholinopiperidin-1-yl)phenyl]-5-methylpyrazole-4-carboxamide

EXAMPLE 248

1-(4-Chlorophenyl)-N-[3-iodo-4-(4-morpholinopiperidin-115 yl) phenyl]-5-methylpyrazole-4-carboxamide

EXAMPLE 249

N-{3-Bromo-4-[4-(3,4,5,6-tetrahydro-2H-pyran-420 yl)piperazin-1-yl]phenyl}-1-(4-chlorophenyl)-5-methylpyrazole-4-carboxamide

EXAMPLE 250

N-{3-Chloro-4-[4-(3,4,5,6-tetrahydro-2H-pyran-4-yl) piperazin-1-yl]phenyl}-1-(4-chlorophenyl)$_p$-5-methylpyrazole-4-carboxamide

EXAMPLE 251

N-{3-Chloro-4-[4-(3,4,5,6-tetrahydro-2H-pyran-4-yl)piperazin-1-yl]phenyl}-1-(4-chlorophenyl)pyrrole-3-carboxamide

EXAMPLE 252

N-{3-Bromo-4-[4-(3,4,5,6-tetrahydro-2H-pyran-4-yl) piperazin-1-yl]phenyl}-1-(4-chlorophenyl)pyrrole-3-carboxamide

EXAMPLE 253

1-(4-Chlorophenyl)-N-[3-cyano-4-(5-morpholinopentyloxy)phenyl]β-5-methylpyrazole-4-carboxamide

EXAMPLE 254

1-(4-Chlorophenyl)-N-[3-cyano-4-(5-morpholinopentyloxy)phenyl] pyrrole-3-carboxamide

EXAMPLE 255

1-(4-Chlorophenyl)-N-[3-cyano-4-(5-morpholinopentylthio)phenyl]-5-methylpyrazole-4-carboxamide

EXAMPLE 256

1-(4-Chlorophenyl)-N-[3-cyano-4-(5-morpholinopentylthio)phenyl]pyrrole-3-carboxamide

EXAMPLE 257

N-[3-Cyano-4-(4-morpholinopiperidin-1-yl)phenyl]-1-(3,4-methylenedioxyphenyl)-5-methylpyrazole-4-carboxamide

EXAMPLE 258

N-[3-Cyano-4-(4-morpholinopiperidin-1-yl)phenyl]-1-(3,4-methylenedioxyphenyl)pyrrole-3-carboxamide

EXAMPLE 259

N-(3-Cyano-4-[4-(3,4,5,6-tetrahydro-2H-pyran-4-yl)piperazin-1-yl]phenyl)-1-(3,4-methylenedioxyphenyl)-5-methylpyrazole-4-carboxamide

EXAMPLE 260

N-{3-Cyano-4-[4-(3,4,5,6-tetrahydro-2H-pyran-4-yl) piperazin-1-yl]phenyl-1-(3,4-methylenedioxyphenyl) pyrrole-3-carboxamide

EXAMPLE 261

1-(4-Chlorophenyl)-N-[3-cyano-4-(2,2-dimethyl-3-morpholinopropoxy)phenyl]-5-methylpyrazole-4-carboxamide

EXAMPLE 262

1-(4-Chlorophenyl)-N-[3-cyano-4-(2,2-dimethyl-3-morpholinopropoxy)phenyl]pyrrole-3-carboxamide

EXAMPLE 263

N-[3-Cyano-4-(2,2-dimethyl-3-morpholinopropoxy) phenyl]-5-methyl-1-(3,4-methylenedioxyphenyl) pyrazole-4-carboxamide

EXAMPLE 264

N-[3-Cyano-4-(2,2-dimethyl-3-morpholinopropoxy) phenyl]-2,5-dimethyl-1-(3,4-methylenedioxyphenyl) pyrrole-3-carboxamide

EXAMPLE 265

N-[3-Cano-4-(4-morpholinopiperidin-1-yl)phenyl]-2,5-dimethyl-1-(3,4-methylenedioxyphenyl)pyrrole-3-carboxamide

EXAMPLE 266

N-[3-Cyano-4-(4-morpholinopiperidin-1-yl)phenyl]-5-methyl-1-(3,4-methylenedioxyphenyl)pyrrole-3-carboxamide

EXAMPLE 267

N-[3-Cyano-4-[4-(3,4,5,6-tetrahydro-2H-pyran-4-yl) piperazin-1-yl]phenyl]-2,5-dimethyl-1-(3,4-methylenedioxyphenyl)pyrrole-3-carboxamide

EXAMPLE 268

N-[3-Chloro-4-(4-morpholinopiperidin-1-yl)phenyl]-2,5-dimethyl-1-(3,4-methylenedioxyphenyl)pyrrole-3-carboxamide

EXAMPLE 269

N-[3-Cyano-4-(4-morpholinopiperidin-1-yl)phenyl]-1-(3,4-dimethoxyphenyl)-S-methylpyrazole-4-carboxamide

EXAMPLE 270

N-[3-Cyano-4-(4-morpholinopiperidin-1-yl)phenyl]-1-(3,4-dimethoxyphenyl)pyrrole-3-carboxamide

EXAMPLE 271

N-[3-Cyano-4-(4-morpholinopiperidin-1-yl)phenyl]-1-(3,4-dimethoxyphenyl)-2,5-dimethylpyrrole-3-carboxamide

EXAMPLE 272

1-(4-Chlorophenyl)-N-[3-cyano-4-(2,2-dimethyl-3-morpholinopropoxy)phenyl]-2,5-dimethylpyrrole-3-carboxamide

EXAMPLE 273

1-(4-Chlorophenyl)-N-[3-cyano-4-(4-morpholinopiperazin-1-yl)phenyl]-2,5-dimethylpyrrole-3-carboxamide

EXAMPLE 274

N-{3-Cyano-4-[4-(2-hydroxyethyl)piperazin-1-yl] phenyl}-1-(3-trifluoromethylphenyl)-5-methylpyrazole-4-carboxamide

EXAMPLE 275

1-(4-Chlorophenyl)-N-(3-cyano-4-[4-(2-hydroxyethyl)piperidin-1-yl]phenyl}-5-methylpyrazole-4-carboxamide

EXAMPLE 276

N-[4-(Piperidin-4-yloxy)-3-cyanophenyl]-1-(4-chlorophenyl)-5-methylpyrazole-4-carboxamide

EXAMPLE 277

N-[4-(1-Methylpiperidin-4-yloxy)-3-cyanophenyl]-1-(4-chlorophenyl)-5-methylpyrazole-4-carboxamide

EXAMPLE 278

N-[4-(1-Benzylpyrrolidin-3-yloxy)-3-cyanophenyl]-1-(4-chlorophenyl)-5-methylpyrazole-4-carboxamide

EXAMPLE 279

N-[4-(3,4,5,6-Tetrahydro-2H-pyran-4-yloxy)-3-cyanophenyl]-1-(4-Chlorophenyl)-5-methylpyrazole-4-carboxamide

EXAMPLE 280

N-[4-(2,3,4,5-Tetrahydrofuran-3-yloxy)-3-cyanophenyl]-1-(4-Chlorophenyl)-5-methylpyrazole-4-carboxamide

EXAMPLE 281

N-[4-(Piperidine-4-yloxy)-3-cyanophenyl]-1-(4-chlorophenyl)pyrrole-3-carboxamide

EXAMPLE 282

N-[4-(1-Methylpiperidin-4-yloxy)-3-cyanophenyl]-1-(4-chlorophenyl)pyrrole-3-carboxamide

EXAMPLE 283

N-[4-(1-Benzylpyrrolidin-3-yloxy)-3-cyanophenyl]-1-(4-chlorophenyl)pyrrole-3-carboxamide

EXAMPLE 284

N-[4-(3,4,5,6-Tetrahydro-2H-pyran-4-yloxy)-3-cyanophenyl]-1-(4-chlorophenyl) pyrrole-3-carboxamide

EXAMPLE 285

N-[4-(2,3,4,5-Tetrahydrofuran-3-yloxy)-3-cyanophenyl]-1-(4-chlorophenyl)pyrrole-3-carboxamide

FORMULATION EXAMPLE

|  | (mg) |
| --- | --- |
| compound of the present invention | 10.0 |
| lactose | 109.6 |
| microcrystalline cellulose | 27.4 |
| light anhydrous silicic acid | 1.5 |
| magnesium stearate | 1.5 |
|  | 150 (per tablet) |

The compound of the present invention (30 g), lactose (328.8 g) and microcrystalline cellulose (82.2 g) are mixed. The mixture is compression formed with a roller compactor to give compressed flakes. The compressed flakes are pulverized in a hammer mill and the pulverizate is passed through a 20-mesh sieve. To the resulting product are added light anhydrous silicic acid (4.5 g) and magnesium stearate (4.5 g), followed by admixing. The mixture is punched with a 7.5 mm diameter pounder to give 3000 tablets weighing 150 mg per tablet.

As regards the pharmacological activity of the compound of the present invention and a pharmaceutically acceptable salt thereof, in vitro proliferation reaction of mouse, rat, dog, monkey or human lymphocytes activated with antigen or mitogen, lymphocyte proliferation reaction dependent on cytokine (e.g., IL-2, IL-4, IL-7, IL-9, IL-13, IL-15 and the like), or production of inflammatory cytokine (e.g., TNF-α, IL-1, IL-6, IL-12, IL-15, IL-18 and the like) derived by lymphocytes, macrophages, dendritic cells and the like upon addition of IL-15, lipopolysaccharide and the like can be tested for evaluation of inhibitory activity. The compound of the present invention and a pharmaceutically acceptable salt thereof show an inhibitory effect in the above-mentioned in vitro test at a concentration of 0.001–100 $\mu$M which is significant as compared to a control group without addition of the compound.

For the in vivo pharmacological activity of the compound of the present invention or a pharmaceutically acceptable salt thereof, type II collagen-induced arthritis is used, which is induced by immunizing a mouse, rat, dog or monkey with type II collagen derived from bovine or suitable mammal together with Freund's complete adjuvant. To be specific, the compound of the present invention or a pharmaceutically acceptable salt thereof is intravenously, intraperitoneally, subcutaneously or orally administered and the inhibitory activity is evaluated. Besides the above-mentioned test, similar evaluation is possible with regard to an autoimmune disease model such as a rat or mouse model with adjuvant arthritis, experimental cerebral meningitis and the like. Using MRL/MpJ-lpr/lpr mouse, (NZBxNZW)F1 mouse and BXSB mouse that spontaneously develop autoimmune diseases similar to systemic lupus erythematosus in human, the therapeutic effect of the compound of the present invention and a pharmaceutically acceptable salt thereof against autoimmune diseases can be evaluated based on manifestation of proteinuria in lupus erythematosus nephritis, production amount of anti-autoantibody such as anti-DNA antibody, rheumatoid factor, anti-erythrocyte antibody, anti-type II collagen antibody and the like, infiltration of activated lymphocytes into inflammation site and proliferation thereof, survival days and the like, as indices. The compound of the present invention and a pharmaceutically acceptable salt thereof show a significant inhibitory effect or therapeutic effect as compared to a control group with medium administration alone, by intravenous, intraperitoneal, subcutaneous or oral administration at 0.1–100 mg/kg body weight in the above-mentioned in vivo pharmacological test. The following Experimental Examples detail such aspect.

EXPERIMENTAL EXAMPLE 1

Effect on Proliferation of Rat Lymphocytes Stimulated with Phorbol-12-Myristate-13-Acetate (PMA) and Calcium Ionophore A23187

As the medium, RPMI1640 medium (Sigma) supplemented with kanamycin sulfate (60 $\mu$g/ml) and penicillin G potassium (100 unit/ml), and fetal calf serum (FCS, Gibco), that underwent inactivation treatment at 56° C. for 30 min, in a proportion of 10% was used for the test. The compound of the present invention or a pharmaceutically acceptable salt thereof was dissolved in dimethyl sulfoxide, diluted with 10% FCS-containing RPMI1640 medium to a desired concentration and used for the test.

Spleen was aseptically removed from 6-week-old male F344 rat or LEW rat (Charles River Japan) and broken up in the RPMI1640 medium with tweezers, after which a single cell suspension of spleen cells was prepared. After haemolysis by hypotonic treatment using a mixture of 0.83% aqueous ammonium chloride solution and Tris-HCl buffer at pH 7.65 at a mixing ratio of 9:1, it was passed through a nylon-wool column to give a nylon non-adhering T cell condensed fraction. A cell suspension prepared using a 10% FCS-containing RPMI1640 medium was added to a flat-bottomed 96 well microtest plate at $5 \times 10^5$ cells/well. The compound of the present invention or a pharmaceutically acceptable salt thereof having a concentration of 0.0001–100 $\mu$M, 10 ng/ml of PMA and 100 ng/ml of A23187 were added and the mixture was cultured at 37° C., under 5% $CO_2$, 95% air for 44 h. After the completion of the culture, tritiated thymidine (specific activity:185 GBq/mmol, Amersham Pharmacia Biotec) was added at 18.5 kBq/well and the mixture was cultured further at 37° C., under 5% $CO_2$, 95% air for 4 h. Then, using a cell harvester, the cells were recovered on a glass fiber filter, and using a plate scintillation counter (Microbeta 1460), the radioactivity taken into the cells was measured, based on which the proliferation of rat lymphocytes induced by the stimulation with PMA and A23187 was determined. That is, percent of inhibition was calculated from the following formula from the average of tritiated thymidine uptake (cpm) into the lymphocytes in the well added with various concentrations of the compound of the present invention.

$$\text{Inhibition}(\%) = \left(1 - \frac{\text{radioactivity (cpm) of well with compound}}{\text{radioactivity (cpm) of well without compound}}\right) \times 100$$

In addition, the concentration ($IC_{50}$) of the compound at which the compound inhibits the radioactivity to 50% of the value of the control group was determined by nonlinear regression based on the dose reaction curve obtained by plotting the average of tritated thymidine uptake (cpm) or percent of inhibition on the axis of ordinates and the concentration on the axis of abscissas.

The compound of the present invention and a pharmaceutically acceptable salt thereof showed a significant and concentration-dependent inhibitory effect in the above-mentioned in vitro test, as compared to the control group without addition of the compound.

EXPERIMENTAL EXAMPLE 2

Effect on IL-2, IL-4, IL-7, IL-9, IL-13 or IL-15-Dependent Proliferation of IL-2-Dependent Mouse CTL-2 Cell, D10.G4.1 cell and HT2 cell.

As the medium, RPMI1640 medium (Sigma) supplemented with kanamycin sulfate (60 μg/ml) and penicillin G potassium (100 unit/ml), and fetal calf serum (FCS, Gibco), that underwent inactivation treatment at 56° C. for 30 min, in a proportion of 10% was used for the test. The compound of the present invention or a pharmaceutically acceptable salt thereof was dissolved in dimethyl sulfoxide, diluted with 10% FCS-containing RPMI1640 medium to a desired concentration and used for the test.

Using IL-2-dependent mouse CTLL-2 cell, D10.G4.1 cell or HT2 cell (purchased from American Type Culture Collection), proliferation dependent on IL-2, IL-4, IL-7, IL-9, IL-13 or IL-15 was measured using tritiated thymidine uptake into the cells as an index.

The CTLL-2 cell, D10.G4.1 cell or HT2 cell was adjusted to a concentration of $10^5$ cells/ml using an RPMI1640 medium containing 10% FCS and $5 \times 10^{-5}$ M of 2-mercaptoethanol, and dispensed to a 96 well microtest plate at $10^4$ cells/well. 0.01–10 ng/ml of recombinant human, monkey or mouse IL-2, IL-4, IL-7, IL-9, IL-13 or IL-15 (Genzyme/Techne) and the compound of the present invention or a pharmaceutically acceptable salt thereof having a concentration of 0.0001–100 μM were added, and the mixture was cultured at 37° C., under 5% $CO_2$, 95% air for 20–92 h. After the completion of the culture, tritiated thymidine (specific activity:185 GBq/mmol, Amersham Pharmacia Biotec) was added at 18.5 kBq/well and the mixture was cultured at 37° C., under 5% $CO_2$, 95% air for 4 h. Then, using a cell harvester, the cells were recovered on a glass fiber filter, and using a plate scintillation counter (Microbeta 1460), the radioactivity taken into the cells was measured, and T cell proliferation dependent on IL-2, IL-4, IL-7, IL-9, IL-13 or IL-15 was measured. That is, percent of inhibition was calculated from the following formula from the average of tritated thymidine uptake (cpm) into the lymphocytes in the well added with various concentrations of the compound of the present invention.

$$\text{Inhibition}(\%) = \left(1 - \frac{\text{radioactivity (cpm) of well with compound}}{\text{radioactivity (cpm) of well without compound}}\right) \times 100$$

In addition, the concentration ($IC_{50}$) of the compound at which the compound inhibits the radioactivity to 50% of the value of the control group was determined by nonlinear regression based on the dose reaction curve obtained by plotting the average of tritated thymidine uptake (cpm) or percent of inhibition on the axis of ordinates and the concentration on the axis of abscissas.

The compound of the present invention and a pharmaceutically acceptable salt thereof showed a significant and concentration-dependent inhibitory effect in the above-mentioned in vitro test, as compared to the control group without addition of the compound.

EXPERIMENTAL EXAMPLE 3

Effect on Production of IL-1, IL-6, IL-12, IL-15, IL-18, TNF-α by Mouse Macrophage or Macrophage-Like Cell Line J774A.1 Cell As the medium, RPMI1640 medium (Sigma) supplemented with kanamycin sulfate (60 μg/ml) and penicillin G potassium (100 unit/ml), and fetal calf serum (FCS, Gibco), that underwent inactivation treatment at 56° C. for 30 min, in a proportion of 10% was used for the test. The compound of the present invention or a pharmaceutically acceptable salt thereof was dissolved in dimethyl sulfoxide, diluted with 10% FCS-containing RPMI1640 medium to a desired concentration and used for the test.

To 7-week-old male C57BL/6 mouse (Charles River Japan) was intraperitoneally administered a 10% proteous peptone (Difco) solution, and intraperitoneally infiltrated cells were harvested 4 days later. The cells were incubated in a 24 well plate for 1 h and, after removing the floating cells, used as macro phages. To the single cell layer (monolayer) of the macrophage obtained above or mouse macrophage-like cell line J774A.1(purchased from American Type Culture Collection) were added 0.1–10 μg/ml of lipopolysaccharide (Difco) or 0.01–10 ng/ml of recombinant human, monkey or mouse IL-15 (Genzyme) and the compound of the present invention or a pharmaceutically acceptable salt thereof having a concentration of 0.0001–100 μM and the mixture was cultured at 37° C., under 5% $CO_2$, 95% air for 12–96 h. After the completion of the culture, the culture supernatant was recovered and IL-1, IL-6, IL-12, IL-15, IL-18, TNF-α produced in the supernatant was quantitatively measured by an enzyme-linked immunosorbent assay (ELISA), and the inhibitory effect of cytokine production was evaluated. The activity of IL-1, IL-6, IL-12, IL-15, IL-18, TNF-α produced in the supernatant was also evaluated by a bioassay using the dependent cells line. The total RNA in the cells was recovered and mRNA of the cytokine was amplified by reverse transcriptase-polymerase chain reaction (RT-PCR). The expression of various cytokine mRNAs was semi-quantitatively determined using hypoxanthine-guanine phosphoribosyltransferase as the control mRNA and used as an index of cytokine production. That is, percent of inhibition was calculated from the following formula from the average of cytokine production or mRNA expression when various concentrations of the compound of the present of invention was added.

$$\text{Inhibition}(\%) = 1 - \left(\frac{\text{cytokine production with compound}}{\text{cytokine production without compound}}\right) \times 100$$

In addition, the concentration ($IC_{50}$) of the compound, at which the compound inhibits the cytokine production to 50% of the value of the control group, was determined by nonlinear regression based on the dose reaction curve obtained by plotting the average of cytokine production or percent of inhibition on the axis of ordinates and the concentration on the axis of abscissas.

The compound of the present invention and a pharmaceutically acceptable salt thereof showed a significant and concentration-dependent inhibitory effect in the above-mentioned in vitro test, as compared to the control group without the addition of the compound.

EXPERIMENTAL EXAMPLE 4

Effect on JAK Phosphorylation

The CTLL-2 cell, D10.G4.1 cell or HT-2 cell, which is a mouse T cells line, was cultured in the presence of a recombinant simian IL-15 or recombinant mouse IL-2 for 24 h. A lysate of the cell obtained by the addition of buffer for lysis was mixed with anti-JAK3 antibody (UBI) or anti-JAK1 antibody (SantaCruz) and a protein agarose, and stirred at 4° C. for 2 h for immunoprecipitation. The immunoprecipitated protein was electrophoresed on 7.5% SDS polyacrylamide gel, transferred onto PVDF membrane filter and subjected to western blotting. That is, after blocking with skim milk, blotting with anti-phosphothyrosine antibody (4G10, UBI), and addition of peroxidase labeled anti-immunoglobulin antibody and substrate for color development were performed to detect a band.

It was clarified that the compound of the present invention or a pharmaceutically acceptable salt thereof inhibited phosphorylation of JAK1 or JAK3 in a concentration-dependent manner in the above-mentioned in vitro test.

EXPERIMENTAL EXAMPLE 5

Effect on Type II Collagen Induced Arthritis in DBA/1J Mouse

An emulsion was prepared by mixing bovine type II collagen (100–200 μg, purchased from Collagen Gizyutsu Kensyukai) with Freund's complete adjuvant (Sigma) containing dead tubercle bacillus H37Ra was given to 6–7 week-old male DBA/1J mice (Charles River Japan) subcutaneously from the root of the tail for immunization twice at 3 week intervals, thereby developing arthritis. The compound of the present invention or a pharmaceutically acceptable salt thereof was suspended or dissolved in 0.5% hydroxypropylmethylcellulose and orally administered repeatedly at the dose of 0.01–100 mg/kg body weight using an oral sound for 6 weeks from the first immunization. This model was evaluated for the symptoms of arthritis in the four limbs according to the following criteria in 0 to 4 scores. The arthritis score of each mouse was expressed by the total of the scores of the four limbs (maximum:16 points), and when the total score was 1 or more, the onset of arthritis was acknowledged.

| score | Symptom |
| --- | --- |
| 0 | No change |
| 1 | edema in only one joint |
| 2 | edema in two or more joints (light edema of whole limb) |
| 3 | severe edema of whole limb |
| 4 | severe edema of whole limb and rigid and immobilized joint |

The thickness of the four limbs of the mouse was measured with vernier calipers and the total score of the four limbs was used as an index of arthritis. Using a soft X-ray photography (OHMIC co.), the four limbs were X rayed to evaluate the level of destruction of the joints.

The score of arthritis, the total of thickness of the four limbs and joint destruction score were expressed by average and standard error of each group (n=5–10). Using the group administered with medium alone as a control, statistical analysis was performed by the non-parametric or parametric Dunnett's method, wherein p value of not more than 0.05 was considered significant.

The compound of the present invention or a pharmaceutically acceptable salt thereof was clarified to have shown significant and dose-dependent improvement in severity of arthritis, swelling of four limbs and joint destruction, and strikingly inhibited the onset and progress of arthritis in the above-mentioned in vivo test by repeat oral administration at 0.1–100 mg/kg body weight, as compared to the control group administered with medium alone.

In contrast, 1-(4-fluorophenyl)-N-(4-trifluoromethylphenyl)-5-methylpyrazole-4-carboxamide described in Bioorganic and Medicinal Chemistry Letters, vol. 8, pp. 2787–2792 (1998) did not improve the severity of developed arthritis, swelling of four limbs or joint destruction by repeat oral administration at 10 mg/kg body weight, and death incidence was confirmed by repeat oral administration at 30 mg/kg body weight.

EXPERIMENTAL EXAMPLE 6

Effect on Lupus Nephritis in Spontaneously Developing Systemic Lupus Erythematosus Model MRL/MpJ-lpr/lpr Mouse and Life Prolonging Effect To male 8–16 week-old MRL/MpJ-lpr/lpr mice (Charles River Japan) was repeat orally administered every day, using an oral sound, 0.01–100 mg/kg body weight of the compound of the present invention or a pharmaceutically acceptable salt thereof suspended or dissolved in 0.5% hydroxypropylmethylcellulose. The survival rate during the administration period was recorded and the blood and urine were sampled with the lapse of time to measure plasma anti-nucleic antibody titer, rheumatoid factor and urinary protein amount. The compound of the present invention and a pharmaceutically acceptable salt thereof were clarified to have shown marked decrease in the manifestation of proteinuria and protein concentration in urine and suppression of the onset of lupus nephritis and improvement of symptoms in MRL/MpJ-lpr/lpr mouse in the above-mentioned in vivo test by repeat oral administration at 0.1–100 mg/kg body weight. In addition, the compound of the present invention and a pharmaceutically acceptable salt thereof were confirmed to have shown a life prolonging effect by a long-term administration to MRL/MpJ-lpr/lpr mouse.

EXPERIMENTAL EXAMPLE 7

Effect on Ovalbumin-Induced Mouse Biphasic Ear Edema

Physiological saline (0.5 ml) containing ovalbumin (10 µg, Sigma) and aluminum hydroxide gel (1 mg) was used to immunize 6–7 week-old male BALB/c mice (Charles River Japan) by intraperitoneally administering twice at 2 week intervals. One week later, ovalbumin (10 µg) was subcutaneously injected to the ear lobe of the mice for a challenge, thereby inducing biphasic ear edema accompanying a biphasic at one hour and 24 hours after the challenge. The compound of the present invention or a pharmaceutically acceptable salt thereof was suspended or dissolved in 0.5% hydroxypropylmethylcellulose and repeat orally administered for 3 weeks from the first immunization at a dose of 0.01–100 mg/kg body weight using an oral sound. The thickness of the ear lobe of the model mice was measured with a dial gauge and used as an index of ear edema.

The thickness of the ear lobe was expressed in average and standard error of each group (n=5–10), and using a group administered with a medium as a control, statistical analysis was performed by the Dunnett's method, wherein p value of not more than 0.05 was considered significant.

The compound of the present invention and a pharmaceutically acceptable salt thereof inhibited the induction of both early phase edema at one hour from the challenge and late phase edema at 24 hours from the challenge significantly and dose-dependently in the above-mentioned in vivo test, by repeat oral administration at 0.1–100 mg/kg body weight, as compared to the control group administered with medium alone suggesting inhibition of allergic reaction involving type 2 helper T cells.

EXPERIMENTAL EXAMPLE 8

Inhibitory Effect on Rat Experimental Autoimmune Cerebral Meningitis

An emulsion (0.1 ml) was prepared by mixing myelin basic protein (100 µg, Sigma) with Freund's complete adjuvant (Sigma) containing dead tubercle bacillus H37Ra and given to immunize 6 week-old female LEW rat intracutaneously from the footpad of the right hind limb. The physical sign after immunization was evaluated according to the following criteria in 6 levels.

| score | Symptom |
| --- | --- |
| 0 | No symptom |
| 1 | Weak tail |
| 2 | Weak hind limb |
| 3 | Paralysis of one hind limb |
| 4 | Paralysis of both hind limbs |
| 5 | incontinence or death |

The compound of the present invention and a pharmaceutically acceptable salt thereof were confirmed to have markedly inhibited the onset and progress of autoimmune cerebral meningitis in the above-mentioned in vivo test by repeat oral administration for 20 days at 0.1–100 mg/kg body weight.

EXPERIMENTAL EXAMPLE 9

Combination Effect Test

According to the method of B. D. Kahan et al. [Transplantation, vol. 55, pp. 849–900 (1993)], test compounds (2 or more) were singly administered respectively. Based on the dose-reaction curve, the effect of combination group was calculated and the combination index was determined. It was defined that, when the combination index was 1, it means additive effect, when the combination index was smaller than 1, it means a synergistic effect, and when the combination index was greater than 1, it means an antagonistic effect.

The compound of the present invention and a pharmaceutically acceptable salt thereof were confirmed to show a synergistic effect in the above-mentioned combination effect test when combined with one or more pharmaceutical agents selected from an antirheumatic drug, an immunosuppressive agent, a steroidal drug and a nonsteroidal anti-inflammatory drug, by which the combination index was smaller than 1.

EXPERIMENTAL EXAMPLE 10

Toxicity Test

In the single administration toxicity test, the test compound was administered to female and male SD rats (3 rats/group) and beagle (1 dog/group), and the toxicity by single administration was evaluated using the incidence of death, general condition and body weight as indices. In the repeat administration toxicity test, the test compound was repeat administered for 2 weeks to female and male SD rats (6 rats/group) and female and male beagle (2 dogs/group), and the toxicity by repeat administration of the test compound was evaluated based on the general condition, body weight, diet taken, haematological test, haemato-biochemical test, weight of organ and biopsy (inclusive of histopathological test) as indices.

EXPERIMENTAL EXAMPLE 11

Evaluation of Bioavailability in Rat

The test compound is intravenously and orally administered to male SD rats (4 per group) and blood is drawn with the lapse of time. The plasma drug concentration is measured by high performance liquid chromatography. The bioavailability (BA) is calculated by the following formula.

$$\frac{\text{AUC upon oral administration}}{\text{AUC upon intravenous administration}} \times \frac{\text{Dose of intravenous administration}}{\text{Dose of oral administration}} \times 100(\%)$$

AUC: area under the plasma concentration-time curve

INDUSTRIAL APPLICABILITY

As is evident from the above-mentioned pharmacological tests, toxicity test and the like, the compound of the present invention and a pharmaceutically acceptable salt thereof show superior inhibitory effect on the proliferation of activated lymphocytes, particularly inhibitory effect on lymphocyte proliferation dependent on IL-2, IL-4, IL-7, IL-9, IL-13 or IL-15 and also inhibit production of IL-15 and inflamatory cytokines induced by IL-15. In addition, since a superior effect is shown in arthritis models and autoimmune disease models, they are useful as agents for the prophylaxis or treatment of various autoimmune diseases.

This application is based on patent application Nos. 33367/1999 and 198473/1999 filed in Japan, the contents of which are hereby incorporated by reference.

The invention claimed is:
1. An amide compound of the formula

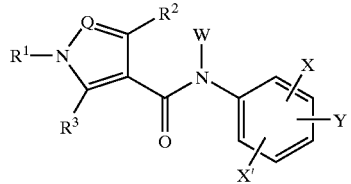

(I)

wherein
$R^1$ is substituted aryl,
$R^2$ and $R^3$ are the same or different and each is hydrogen or alkyl,
Q is nitrogen atom,
W is hydrogen or alkyl,
X is cyano,
X' is hydrogen, and
Y is optionally substituted piperidino,
or a pharmaceutically acceptable salt thereof.

2. The amide compound of claim 1, which has the formula

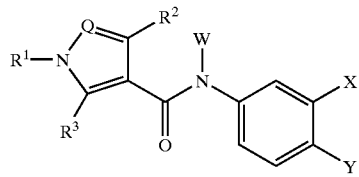

(I-b)

wherein
$R^1$ is substituted aryl,
$R^2$ and $R^3$ are the same or different and each is hydrogen or alkyl,
Q is nitrogen atom,
W is hydrogen or alkyl,
X is cyano,
Y is optionally substituted piperidino,
or a pharmaceutically acceptable salt thereof.

3. An amide compound selected from the group consisting of
N-(3-cyano-4-piperidinophenyl)-1-(4-fluorophenyl)-5-methylpyrazole-4-carboxamide,
N-[3-cyano-4-(4-hydroxypiperidino)phenyl]-1-(4-fluorophenyl)-5-methylpyrazole-4-carboxamide,
1-(4-chlorophenyl)-N-(3-cyano-4-piperidinophenyl)-5-methylpyrazole-4-carboxamide,
1-(4-chlorophenyl)-N-[3-cyano-4-(4-hydroxypiperidin-1-yl)phenyl]-5-methylpyrazole-4-carboxamide,
1-(4-chlorophenyl)-N-[3-cyano-4-(4-morpholinopiperidin-1-yl)phenyl]-5-methylpyrazole- 4-carboxamide,
N-(4-{4-[bis(2-hydroxyethyl)amino]piperidin-1-yl}-3-cyanophenyl)-1-(4-chlorophenyl)-5-methylpyrazole-4-carboxamide,
1-(3,4-dichlorophenyl)-N-[3-cyano-4-(4-morpholinopiperidin-1-yl)phenyl]-5-methylpyrazole-4-carboxamide,
N-[3-cyano-4-(4-morpholinopiperidin-1-yl)phenyl]-1-(3,4-difluorophenyl)-5-methylpyrazole-4-carboxamide,
1-(3-chloro-4-fluorophenyl)-N-[3-cyano-4-(4-morpholinopiperidin-1-yl)phenyl]-5-methylpyrazole-4-carboxamide,
N-[3-cyano-4-(4-morpholinopiperidin-1-yl)phenyl]-1-(4-trifluoromethylphenyl)-5-methylpyrazole-4-carboxamide,
N-{4-[4-bis(2-methoxyethyl)aminopiperidin-1-yl]-3-cyanophenyl}-1-(4-chlorophenyl)-5-methylpyrazole-4-carboxamide,
1-(4-chlorophenyl)-N-{3-cyano-4-[4-(2-hydroxyethyl)piperidin-1-yl]phenyl}-5-methylpyrazole-4-carboxamide,
1-(4-bromophenyl)-N-[3-cyano-4-(4-morpholinopiperidino)phenyl]-5-methylpyrazole-4-carboxamide,
N-[3-cyano-4-(4-morpholinopiperidino)phenyl]-1-(4-fluorophenyl)-5-methylpyrazole-4-carboxamide,
N-[3-cyano-4-(4-morpholinopiperidin-1-yl)phenyl]-1-(4-methylphenyl)-5-methylpyrazole-4-carboxamide,
N-[3-cyano-4-(4-morpholinopiperidin-1-yl)phenyl]-1-(4-iodophenyl)-5-methylpyrazole-4-carboxamide,
N-[3-cyano-4-(4-morpholinopiperidin-1-yl)phenyl]-1-(4-methoxyphenyl)-5-methylpyrazole-4-carboxamide,
1-(4-chlorophenyl)-N-[3-cyano-4-(4-thiomorpholinopiperidin-1-yl)phenyl]-5-methylpyrazole-4-carboxamide,
1-(4-chlorophenyl)-N-[3-cyano-4-(4-methoxymethoxypiperidin-1-yl)phenyl]-5-methylpyrazole- 4-carboxamide,
1-(4-chlorophenyl)-N-[3-cyano-4-[4-(2-methoxyethoxy)piperidin-1-yl]phenyl]-5-methylpyrazole-4-carboxamide,
N-{3-cyano-4-[4-(2-hydroxyethyl)piperidin-1-yl]phenyl}-1 (4-fluorophenyl)-5-methylpyrazole-4-carboxamide,
N-[3-cyano-(4-morpholinopiperidin-1-yl)phenyl]-5-methyl-1-(4-nitrophenyl)pyrazole-4-carboxamide,
1-(3-chlorophenyl)-N-[3-cyano-4-(4-morpholinopiperidino)phenyl]-5-methylpyrazole-4-carboxamide,
N-[3-cyano-4-(4-morpholinopiperidin-1-yl)phenyl]-1-(3,4-methylenedioxyphenyl)-5-methylpyrazole-4-carboxamide, and
N-[3-cyano-4-(4-morpholinopiperidin-1-yl)phenyl]-1-(3,4-dimethoxyphenyl)-5-methylpyrazole-4-carboxamide,
or a pharmaceutically acceptable salt thereof.

4. A pharmaceutical composition comprising the amide compound of claim 1 or a pharmaceutically acceptable salt thereof, and a pharmaceutically acceptable carrier.

5. A method for the treatment of rheumatoid arthritis in a subject, which comprises administering an effective amount of the pharmaceutical composition of claim 4 to the subject.

6. A combination composition comprising an amide compound of the formula

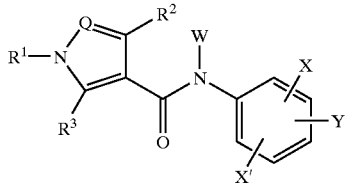

wherein
R¹ is substituted aryl,
R² and R³ are the same or different and each is hydrogen or alkyl,
Q is nitrogen atom,
W is hydrogen or alkyl,
X is cyano,
X' is hydrogen, and
Y is optionally substituted piperidino,
or a pharmaceutically acceptable salt thereof, and one or more pharmaceutical agents selected from an antirheumatic drug, an immunosuppressive agent, a steroidal drug and a nonsteroidal anti-inflammatory drug.

7. The combination composition of claim 6, wherein the antirheumatic drug is selected from a gold compound, penicillamine, bucillamine, lobenzarit, actarit and salazosulfapyridine.

8. The combination composition of claim 6, wherein the immunosuppressive agent is selected from azathioprine, cyclophosphamide, methotrexate, brequinar sodium, deoxyspergualin, mizoribine, 2-morpholinoethyl mycophenolate, cyclosporin, rapamycin, tacrolimus hydrate, leflunomide, OKT-3, anti TNF-α antibody, anti IL-6 antibody and FTY720.

9. The combination composition of claim 6, wherein the steroidal drug is selected from prednisolone, methylprednisolone, dexamethasone and hydrocortisone.

10. The combination composition of claim 6, wherein the nonsteroidal anti-inflammatory drug is selected from aspirin, indomethacin, indomethacin farnesil, diclofenac sodium, alclofenac, amfenac sodium, ibuprofen, ketoprofen, loxoprofen sodium, naproxen, pranoprofen, zaltoprofen, mefenamic acid, flufenamic acid, tolufenamic acid, phenylbutazone, ketophenylbutazone, piroxicam, tenoxicam and ampiroxicam.

11. A method for the treatment of atopic dermatitis in a subject, which comprises administering an effective amount of the pharmaceutical composition of claim 4 to the subject.

12. An amide compound selected from the group consisting of
1-(4-chlorophenyl)-N-[3-cyano-4-(4-morpholinopiperidin-1-yl)phenyl]-5-methylpyrazole-4-carboxamide,
1-(4-chlorophenyl)-N-[3-cyano-4-(4-hydroxypiperidin-1-yl)phenyl]-5-methylpyrazole-4-carboxamide,
N-[3-cyano-4-(4-morpholinopiperidin-1-yl)phenyl]-1-(3,4-difluorophenyl)-5-methylpyrazole-4-carboxamide, and
N-[3-cyano-4-(4-morpholinopiperidino)phenyl]-1-(4-fluorophenyl)-5-methylpyrazole-4-carboxamide.

13. A method for the treatment of cerebral meningitis in a subject, which comprises administering an effective amount of the pharmaceutical composition of claim 4 to the subject.

14. A method for the treatment of multiple sclerosis in a subject, which comprises administering an effective amount of the pharmaceutical composition of claim 4 to the subject.

15. A method for the treatment of systemic lupus erythematodes in a subject, which comprises administering an effective amount of the pharmaceutical composition of claim 4 to the subject.

16. A method for the treatment of lupus nephritis in a subject, which comprises administering an effective amount of the pharmaceutical composition of claim 4 to the subject.

17. A method for the treatment of inflammatory bowel disease in a subject, which comprises administering an effective amount of the pharmaceutical composition of claim 4 to the subject.

18. A method for the treatment of psoriasis in a subject, which comprises administering an effective amount of the pharmaceutical composition of claim 4 to the subject.

* * * * *